(12) United States Patent
Sturino et al.

(10) Patent No.: US 9,399,645 B2
(45) Date of Patent: Jul. 26, 2016

(54) INHIBITORS OF HIV REPLICATION

(71) Applicant: Boehringer Ingelheim International GmbH, Ingelheim am Rhein (DE)

(72) Inventors: Claudio Sturino, Ile-Bizard (CA); Pierre Beaulieu, Rosemère (CA); Patrick Deroy, Blainville (CA); Martin Duplessis, Montréal (CA); Clint James, Candiac (CA); Jean-Eric Lacoste, Laval (CA); Joannie Minville, Terrebonne (CA); Louis Morency, Montréal (CA); Sébastien Morin, Montréal (CA); Bruno Simoneau, Laval (CA); Martin Tremblay, Mont-Royal (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/366,421

(22) PCT Filed: Dec. 19, 2012

(86) PCT No.: PCT/CA2012/050909
§ 371 (c)(1),
(2) Date: Jun. 18, 2014

(87) PCT Pub. No.: WO2013/091096
PCT Pub. Date: Jun. 27, 2013

(65) Prior Publication Data
US 2015/0011531 A1   Jan. 8, 2015

Related U.S. Application Data

(60) Provisional application No. 61/578,008, filed on Dec. 20, 2011.

(51) Int. Cl.
*A61K 45/06* (2006.01)
*A61K 31/519* (2006.01)
*C07D 491/147* (2006.01)
*C07D 491/048* (2006.01)
*A61K 31/5377* (2006.01)

(52) U.S. Cl.
CPC .......... *C07D 491/147* (2013.01); *A61K 31/519* (2013.01); *A61K 31/5377* (2013.01); *A61K 45/06* (2013.01); *C07D 491/048* (2013.01)

(58) Field of Classification Search
CPC ... A61K 31/519; A61K 45/06; C07D 491/147
See application file for complete search history.

(56) References Cited

U.S. PATENT DOCUMENTS 8,349,839 B2 * 1/2013 Sturino ............... C07D 487/04
514/252.01

FOREIGN PATENT DOCUMENTS

| WO | 2007088214 A2 | 8/2007 | |
|----|---------------|--------|---|
| WO | 2010115264 A1 | 10/2010 | |
| WO | WO 2010/115264 | * 10/2010 | ......... C07D 491/048 |

OTHER PUBLICATIONS

International Search Report and Written Opinion for PCT/CA2012/050909 mailed Mar. 19, 2013.

* cited by examiner

*Primary Examiner* — Erich A Leeser
(74) *Attorney, Agent, or Firm* — Michael P. Morris; Atabak R. Royaee

(57) ABSTRACT

Compounds of formula (I) and pharmaceutical compositions thereof: wherein $A^1$ $A^2$ and $A^3$ are each independently selected from the group consisting of N and $CR^3$, wherein $R^1$ is an optionally substituted heterocyclyl or an optionally substituted —$(C_{1-6})$alkyl-heterocyclyl, $R^2$ is an optionally substituted aryl or an optionally subsisted heteroaryl, $R^4$ is an optionally substituted aryl, an optionally substituted heterocyclyl or an optionally substituted heteroaryl, useful as an inhibitor of HIV replication.

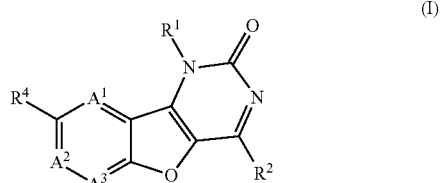

(I)

8 Claims, No Drawings

INHIBITORS OF HIV REPLICATION

RELATED APPLICATIONS

This application claims benefit of U.S. Ser. No. 61/578,008 filed Dec. 20, 2011, which is herein incorporated by reference.

FIELD OF THE INVENTION

The present invention relates to tricyclic compounds which are nucleotide-competing inhibitors of human immunodeficiency virus (HIV) reverse transcriptase activity. In particular, the present invention provides novel inhibitors of HIV replication, pharmaceutical compositions containing such compounds and methods for using these compounds in the treatment of HIV infection.

BACKGROUND OF THE INVENTION

Acquired immune deficiency syndrome (AIDS) is caused by the human immunodeficiency virus, particularly the HIV-1 strain. Most currently approved therapies for HIV infection target the viral reverse transcriptase and protease enzymes, with additional approved drugs targeting the viral integrase enzyme and the viral gp41 protein, to inhibit viral entry. Within the reverse transcriptase inhibitor and protease inhibitor classes, resistance of HIV to existing drugs is a problem. Therefore, it is important to discover and develop new antiretroviral compounds.

Oral dosing is the most common and convenient route of drug administration. It is well recognized that intestinal permeability is an important factor controlling the bioavailability (absorption) of orally administered drugs to enter the general circulation in order to reach the site of action for the compound to exert its effect. The in vitro Caco-2 permeability assay is a system commonly used to model and predict the intestinal permeability of a compound. Studies have demonstrated that compounds with low Caco-2 permeability display low oral bioavailability in humans and other pre-clinical species. By contrast, compounds with high Caco-2 permeability display higher levels of bioavailability in humans and other pre-clinical species (Zheng Yang et. al., *Journal of Pharmaceutical Science*, 2010, Vol 99, No. 4, 2135-2152).

WO 2010/115264 describes compounds that are useful in the treatment of HIV infection.

SUMMARY OF THE INVENTION

The present invention provides a novel series of compounds having inhibitory activity against HIV replication and unexpectedly good in vitro Caco-2 permeability. Further objects of this invention arise for the one skilled in the art from the following description and the examples.

Representative embodiments of the compound aspect of the invention are described below, while other embodiments of the compound aspect of the invention are described throughout the specification, for example under the heading "Preferred Embodiments" beginning at page 12.

Embodiment 1 of the invention provides compounds of formula (I):

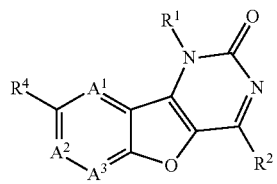

wherein
$R^1$ is heterocyclyl or —$(C_{1-6})$alkyl-heterocyclyl,
  wherein each said heterocyclyl and —$(C_{1-6})$alkyl-heterocyclyl is optionally substituted with 1 to 3 substituents each independently selected from —$(C_{1-6})$alkyl; and wherein each said heterocyclyl contains at least one oxygen atom;
$R^2$ is aryl or heteroaryl, wherein said aryl and heteroaryl are each optionally substituted with 1 to 3 substituents each independently selected from the group consisting of —$(C_{1-6})$alkyl, halo, —$(C_{1-6})$haloalkyl, —$N(R^{21})(R^{22})$, —$O(C_{1-6})$alkyl and heterocyclyl, wherein said heterocyclyl is optionally substituted with 1 or 3 substituents each independently selected from the group consisting of halo, CN, —$(C_{1-6})$alkyl optionally substituted with OH or halo, —$O(C_{1-6})$alkyl and OH;
$R^{21}$ is H or —$(C_{1-6})$alkyl optionally substituted 1 to 3 times with halo;
$R^{22}$ is H, —$(C_{1-6})$alkyl, —$(C_{2-6})$alkenyl or —$(C_{3-7})$cycloalkyl, wherein each said alkyl, alkenyl and cycloalkyl is optionally substituted 1 to 3 times with halo;
$A^1$, $A^2$ and $A^3$ are each independently selected from the group consisting of N and $CR^3$, wherein $R^3$ is independently in each instance selected from the group consisting of H, halo, —CN, —$N(R^{21})(R^{22})$, —$(C_{3-7})$cycloalkyl and —$(C_{1-6})$alkyl, wherein each said alkyl and cycloalkyl is optionally substituted with 1 to 3 substituents each independently selected from the group consisting of —$O(C_{1-6})$alkyl and halo;
$R^4$ is aryl, heterocyclyl or heteroaryl, wherein each said aryl, heterocyclyl and heteroaryl is optionally substituted with 1 to 3 substituents each independently selected from the group consisting of halo, oxo, $R^{41}$ and —C(=O)$R^{41}$;
  each $R^{41}$ is independently —$(C_{1-6})$alkyl, —$(C_{3-7})$cycloalkyl or —$(C_{1-6})$alkyl-$(C_{3-7})$cycloalkyl, wherein each said alkyl and cycloalkyl is optionally substituted with 1 to 3 substituents each independently selected from the group consisting of halo, OH and —$O(C_{1-6})$alkyl;
or a salt thereof.

Embodiment 2 provides a compound of embodiment 1, or a pharmaceutically acceptable salt thereof, wherein $A^1$, $A^2$ and $A^3$ are each independently selected from $CR^3$, wherein $R^3$ is as defined in embodiment 1.

Embodiment 3 provides a compound of embodiment 1, or a pharmaceutically acceptable salt thereof, wherein one of $A^1$, $A^2$ and $A^3$ is N and the remaining two of $A^1$, $A^2$ and $A^3$ are each independently selected from $CR^3$, wherein $R^3$ is as defined in embodiment 1.

Embodiment 4 provides a compound of any one of embodiments 1 to 3, or a pharmaceutically acceptable salt thereof, wherein $R^1$ is heterocyclyl or —$(C_{1-3})$alkyl-heterocyclyl, wherein each said heterocyclyl and —$(C_{1-3})$alkyl-heterocyclyl is optionally substituted with 1 to 2 substituents each independently selected from —$(C_{1-3})$alkyl; and wherein said heterocyclyl is a 5-, 6- or 7-membered heterocycle containing one oxygen atom.

Embodiment 5 provides a compound of any one of embodiments 1 to 4, or a pharmaceutically acceptable salt thereof, wherein R$^1$ is

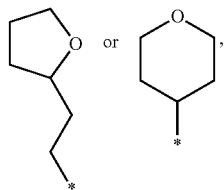

optionally substituted with 1 to 2 substituents each independently selected from —(C$_{1-3}$)alkyl.

Embodiment 6 provides a compound of any one of embodiments 1 to 5, or a pharmaceutically acceptable salt thereof, wherein R$^2$ is a 5- or 6-membered heteroaryl optionally substituted with 1 to 2 substituents each independently selected from the group consisting of —(C$_{1-3}$)alkyl, halo, —(C$_{1-3}$)haloalkyl, —N(R$^{21}$)(R$^{22}$) and —O(C$_{1-3}$)alkyl;
R$^{21}$ is H or —(C$_{1-3}$)alkyl; and
R$^{22}$ is H, —(C$_{1-3}$)alkyl or —(C$_{2-4}$)alkenyl.

Embodiment 7 provides a compound of any one of embodiments 1 to 6, or a pharmaceutically acceptable salt thereof, wherein R$^2$ is a 5- or 6-membered heteroaryl selected from the group consisting of

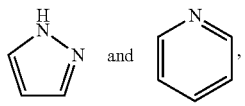

wherein each said heteroaryl is optionally substituted with 1 or 2 substituents independently selected from the group consisting of —(C$_{1-3}$)alkyl, halo, —(C$_{1-3}$)haloalkyl, —N(R$^{21}$)(R$^{22}$) and —O(C$_{1-3}$)alkyl;
R$^{21}$ is H or —(C$_{1-3}$)alkyl; and
R$^{22}$ is —(C$_{1-3}$)alkyl.

Embodiment 8 provides a compound of any one of embodiments 1 to 7, or a pharmaceutically acceptable salt thereof, wherein R$^3$ is independently in each instance selected from the group consisting of H, F, —CN, and —CH$_3$.

Embodiment 9 provides a compound of any one of embodiments 1 to 8, or a pharmaceutically acceptable salt thereof, wherein R$^4$ is a 5- or 6-membered heteroaryl optionally substituted with 1 to 2 substituents each independently selected from the group consisting of halo and —(C$_{1-3}$)alkyl optionally substituted one time with OH or —O(C$_{1-3}$)alkyl.

Embodiment 10 provides a compound of any one of embodiments 1 to 9, or a pharmaceutically acceptable salt thereof, wherein R$^4$ is a 5- or 6-membered heteroaryl selected from the group consisting of

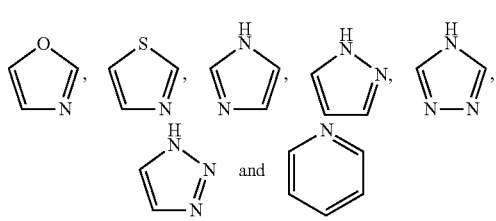

wherein said heteroaryl is optionally substituted with 1 to 2 substituents each independently selected from the group consisting of halo and —(C$_{1-3}$)alkyl optionally substituted one time with OH or —O(C$_{1-3}$)alkyl.

Another aspect of this invention provides a compound of formula (I) or a pharmaceutically acceptable salt thereof, as a medicament.

Still another aspect of this invention provides a pharmaceutical composition comprising a therapeutically effective amount of a compound of formula (I) or a pharmaceutically acceptable salt thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described herein above for the treatment of an HIV infection in a human being having or at risk of having the infection.

A further aspect of the invention involves a method of treating an HIV infection in a human being having or at risk of having the infection, the method comprising administering to the human being a therapeutically effective amount of a compound of formula (I), or a pharmaceutically acceptable salt thereof.

Another aspect of the invention involves a method of treating an HIV infection in a human being having or at risk of having the infection, the method comprising administering to the human being a therapeutically effective amount of a combination of a compound of formula (I) or a pharmaceutically acceptable salt thereof; and one or more pharmaceutically acceptable carriers.

Another aspect of the invention involves a method of treating an HIV infection in a human being having or at risk of having the infection, the method comprising administering to the human being a therapeutically effective amount of a combination of a compound of formula (I) or a pharmaceutically acceptable salt thereof, and at least one other antiviral agent; or a composition thereof.

Also within the scope of this invention is the use of a compound of formula (I) as described herein, or a pharmaceutically acceptable salt thereof, for the treatment of an HIV infection in a human being having or at risk of having the infection.

Another aspect of this invention provides the use of a compound of formula (I) as described herein, or a pharmaceutically acceptable salt thereof, for the manufacture of a medicament for the treatment of an HIV infection in a human being having or at risk of having the infection.

An additional aspect of this invention refers to an article of manufacture comprising a composition effective to treat an HIV infection; and packaging material comprising a label which indicates that the composition can be used to treat infection by HIV; wherein the composition comprises a compound of formula (I) according to this invention or a pharmaceutically acceptable salt thereof.

Still another aspect of this invention relates to a method of inhibiting the replication of HIV comprising exposing the virus to an effective amount of the compound of formula (I), or a salt thereof, under conditions where replication of HIV is inhibited.

Still another aspect of this invention relates to use of a compound of formula (I), or a salt thereof, to inhibit the replication of HIV.

Further included in the scope of the invention are novel intermediates, such as one or more of compounds 29b, 78e, 78g, 81h, 87b, 103f, 115e,

DETAILED DESCRIPTION OF THE INVENTION

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, wherein the alkyl group is bound to the core or to the group to which the substituent is attached. Unless specifically stated otherwise, for groups comprising two or more subgroups, the substituent may be attached to either subgroup.

If a compound of the present invention is depicted in the form of a chemical name and as a formula, in case of any discrepancy, the formula shall prevail.

An asterisk or the designation, ----, may be used in sub-formulas to indicate the bond which is connected to the core molecule as defined.

Unless specifically indicated, throughout the specification and claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as, for instance, hydrates including solvates of the free compounds or solvates of a salt of the compound.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof.

These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography or NMR.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term "halogen" or "halo" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-3}$-alkyl embraces the radicals $H_3C$—, $H_3C$—$CH_2$—, $H_3C$—$CH_2$—$CH_2$— and $H_3C$—$CH(CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "carbocyclyl" or "carbocycle" as used either alone or in combination with another radical, means a mono- or multi-ring ring structure consisting only of carbon containing between one and four rings wherein such rings may be attached together in a pendent manner or may be fused. The term "carbocyclyl" or "carbocycle" refers to fully saturated and aromatic ring systems and partially saturated ring systems. The term "carbocyclyl" or "carbocycle" additionally encompasses spiro systems, and bridged systems.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heterocyclyl" or "heterocycle" means a saturated or unsaturated mono- or polycyclic-ring systems including an aromatic ring system containing one or more heteroatoms selected from N, O or $S(O)_r$ with r=0, 1 or 2 wherein none of the heteroatoms is part of the aromatic ring. The term "heterocyclyl" or "heterocycle" is intended to include all the possible isomeric forms, spiro systems, and bridged systems. Thus, the term "heterocyclyl" or "heterocycle" includes the following exemplary structures which are not depicted as radicals as each form may be attached through a covalent bond to any atom so long as appropriate valences are maintained:

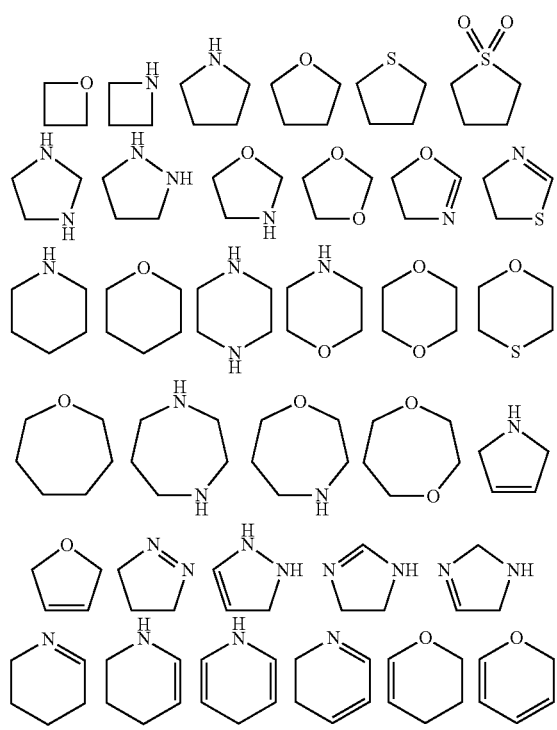

The term "heteroaryl" means a mono- or polycyclic-ring systems containing one or more heteroatoms selected from N, O or $S(O)_r$ with r=0, 1 or 2 wherein at least one of the heteroatoms is part of an aromatic ring. The term "heteroaryl" is intended to include all the possible isomeric forms. Thus, the term "heteroaryl" includes the following exemplary structures which are not depicted as radicals as each form may be attached through a covalent bond to any atom so long as appropriate valences are maintained:

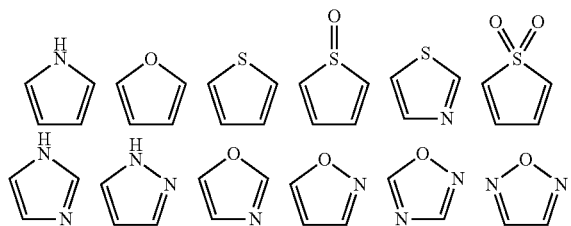

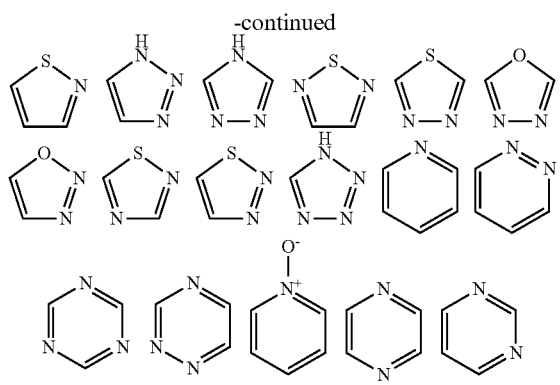

Many of the terms given above may be used repeatedly in the definition of a formula or group and in each case have one of the meanings given above, independently of one another.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV-1 from mother to baby, by administration to the mother before giving birth and to the child within the first days of life.

The term "antiviral agent" as used herein is intended to mean an agent that is effective to inhibit the formation and/or replication of a virus in a human being, including but not limited to agents that interfere with either host or viral mechanisms necessary for the formation and/or replication of a virus in a human being.

PREFERRED EMBODIMENTS

In the following preferred embodiments, groups and substituents of the compounds of Formula (I) according to this invention are described in detail.

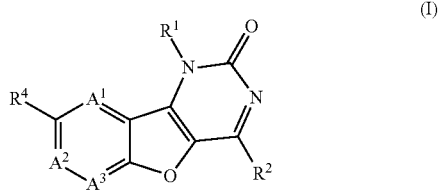

Any and each individual definition as set out herein may be combined with any and each individual definition as set out herein.

Core:

Core-A: $A^1$, $A^2$ and $A^3$ are each independently selected from the group consisting of N and $CR^3$, wherein $R^3$ is as defined herein.

Core-B: $A^1$, $A^2$ and $A^3$ are each independently selected from $CR^3$, wherein $R^3$ is as defined herein.

Core-C: One of $A^1$, $A^2$ and $A^3$ is N and the remaining two of $A^1$, $A^2$ and $A^3$ are each independently selected from $CR^3$, wherein $R^3$ is as defined herein.

It will be apparent to the skilled person that, when $A^1$, $A^2$ and $A^3$ are each independently selected from N and $CR^3$, compounds of, at least, the following formulas Ia to Id are contemplated, wherein $R^3$ is as defined herein. Where more than one instance of $R^3$ occurs in a formula, $R^3$ at one instance can be the same as or different than $R^3$ at any other instance.

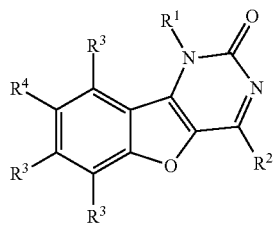

Ia

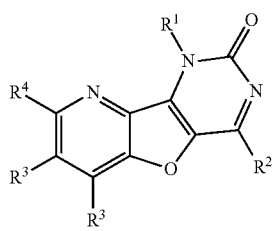

Ib

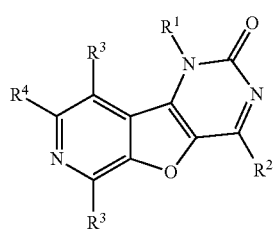

Ic

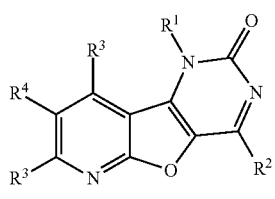

Id $R^1$:
$R^1$-A: $R^1$ is heterocyclyl or —$(C_{1-6})$alkyl-heterocyclyl, wherein each said heterocyclyl and —$(C_{1-6})$alkyl-heterocyclyl is optionally substituted with 1 to 3 substituents each independently selected from —$(C_{1-6})$alkyl; and wherein each said heterocyclyl contains at least one oxygen atom.

$R^1$-B: $R^1$ is heterocyclyl or —$(C_{1-3})$alkyl-heterocyclyl, wherein each said heterocyclyl and —$(C_{1-3})$alkyl-heterocyclyl is optionally substituted with 1 to 2 substituents each independently selected from —$(C_{1-3})$alkyl; and wherein said heterocyclyl is a 5-, 6- or 7-membered heterocycle containing one oxygen atom.

$R^1$-C: $R^1$ is

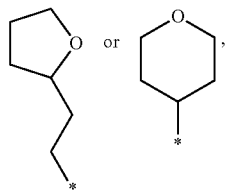

optionally substituted with 1 to 2 substituents each independently selected from —$(C_{1-3})$alkyl.

$R^2$:
$R^2$-A: $R^2$ is aryl or heteroaryl, wherein said aryl and heteroaryl are each optionally substituted with 1 to 3 substituents each independently selected from the group consisting of —$(C_{1-6})$alkyl, halo, —$(C_{1-6})$haloalkyl, —$N(R^{21})(R^{22})$, —$O(C_{1-6})$alkyl and heterocyclyl, wherein said heterocyclyl is optionally substituted with 1 or 3 substituents each independently selected from the group consisting of halo, CN, —$(C_{1-6})$alkyl optionally substituted with OH or halo, —$O(C_{1-6})$alkyl and OH;
$R^{21}$ is H or —$(C_{1-6})$alkyl optionally substituted 1 to 3 times with halo; and
$R^{22}$ is H, —$(C_{1-6})$alkyl, —$(C_{2-6})$alkenyl or —$(C_{3-7})$cycloalkyl, wherein each said alkyl, alkenyl and cycloalkyl is optionally substituted 1 to 3 times with halo.

$R^2$-B: $R^2$ is a 5- or 6-membered heteroaryl optionally substituted with 1 to 2 substituents each independently selected from the group consisting of —$(C_{1-3})$alkyl, halo, —$(C_{1-3})$haloalkyl, —$N(R^{21})(R^{22})$ and —$O(C_{1-3})$alkyl;
$R^{21}$ is H or —$(C_{1-3})$alkyl; and
$R^{22}$ is H, —$(C_{1-3})$alkyl or —$(C_{2-4})$alkenyl.

$R^2$-C: $R^2$ is a 5- or 6-membered heteroaryl selected from the group consisting of

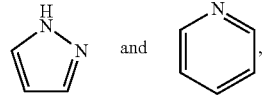

wherein each said heteroaryl is optionally substituted with 1 or 2 substituents independently selected from the group consisting of —$(C_{1-3})$alkyl, halo, —$(C_{1-3})$haloalkyl, —$N(R^{21})(R^{22})$ and —$O(C_{1-3})$alkyl;
$R^{21}$ is H or —$(C_{1-3})$alkyl; and
$R^{22}$ is —$(C_{1-3})$alkyl.

$R^3$:
$R^3$-A: $R^3$ is independently in each instance selected from the group consisting of H, halo —CN, —$N(R^{21})(R^{22})$, —$O(C_{1-6})$alkyl, —$(C_{3-7})$cycloalkyl and —$(C_{1-6})$alkyl, wherein each said alkyl and cycloalkyl is optionally substituted with 1 to 3 substituents each independently selected from the group consisting of —$O(C_{1-6})$alkyl and halo;
$R^{21}$ is H or —$(C_{1-6})$alkyl optionally substituted 1 to 3 times with halo; and
$R^{22}$ is H, —$(C_{1-6})$alkyl, —$(C_{2-6})$alkenyl or —$(C_{3-7})$cycloalkyl, wherein each said alkyl, alkenyl and cycloalkyl is optionally substituted 1 to 3 times with halo.

$R^3$-B: $R^3$ is independently in each instance selected from the group consisting of H, halo, —CN, —$O(C_{1-6})$alkyl and —$(C_{1-6})$alkyl optionally substituted with —$O(C_{1-6})$alkyl.

$R^3$-C: $R^3$ is independently in each instance selected from the group consisting of H, F, —CN, and —$CH_3$.

$R^4$:
$R^4$-A: $R^4$ is aryl, heterocyclyl or heteroaryl, wherein each said aryl, heterocyclyl and heteroaryl is optionally substituted with 1 to 3 substituents each independently selected from the group consisting of halo, oxo, $R^{41}$ and —$C(=O)R^{41}$; each $R^{41}$ is independently —$(C_{1-6})$alkyl, —$(C_{3-7})$cycloalkyl or —$(C_{1-6})$alkyl-$(C_{3-7})$cycloalkyl, wherein each said alkyl and cycloalkyl is optionally substituted with 1 to 3 substituents each independently selected from the group consisting of halo, OH and —$O(C_{1-6})$alkyl.

$R^4$-B: $R^4$ is heteroaryl optionally substituted with 1 to 2 substituents each selected from the group consisting of halo, —(C$_{3-7}$)cycloalkyl, —(C$_{1-6}$)alkyl-(C$_{3-7}$)cycloalkyl and —(C$_{1-6}$)alkyl optionally mono-substituted with OH or —O(C$_{1-6}$)alkyl.

R$^4$-C: R$^4$ is a 5- or 6-membered heteroaryl optionally substituted with 1 to 2 substituents each independently selected from the group consisting of halo and —(C$_{1-3}$)alkyl optionally mono-substituted with OH or —O(C$_{1-3}$)alkyl.

R$^4$-D: R$^4$ is a 5- or 6-membered heteroaryl selected from the group consisting of

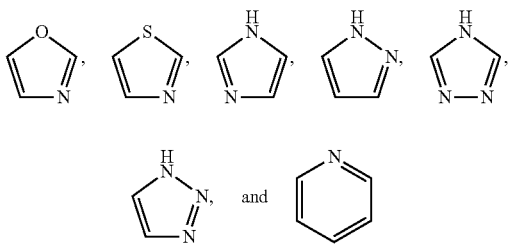

wherein each said heteroaryl is optionally substituted with 1 to 2 substituents each independently selected from the group consisting of halo and —(C$_{1-3}$)alkyl optionally mono-substituted with OH or —O(C$_{1-3}$)alkyl.

Representative embodiments 1-10 of the compounds aspects of the present invention are defined above. Examples of further subgeneric embodiments of the invention are set forth in the following table, wherein each substituent group of each embodiment is defined according to the definitions set forth above:

| Embodiment | Core | R$^1$ | R$^2$ | R$^3$ | R$^4$ |
|---|---|---|---|---|---|
| E11 | Core-A | R$^1$-A | R$^2$-B | R$^3$-A | R$^4$-C |
| E12 | Core-A | R$^1$-A | R$^2$-B | R$^3$-B | R$^4$-C |
| E13 | Core-A | R$^1$-B | R$^2$-B | R$^3$-B | R$^4$-C |
| E14 | Core-A | R$^1$-C | R$^2$-C | R$^3$-C | R$^4$-D |
| E15 | Core-B | R$^1$-B | R$^2$-B | R$^3$-B | R$^4$-C |
| E16 | Core-B | R$^1$-C | R$^2$-C | R$^3$-B | R$^4$-B |
| E17 | Core-C | R$^1$-B | R$^2$-B | R$^3$-B | R$^4$-C |
| E18 | Core-C | R$^1$-B | R$^2$-C | R$^3$-B | R$^4$-B |
| E19 | Core-C | R$^1$-B | R$^2$-B | R$^3$-A | R$^4$-D |
| E20 | Core-C | R$^1$-C | R$^2$-C | R$^3$-C | R$^4$-D |

Examples of most preferred compounds according to this invention are each single compound referred to as Compound 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102 and 1103.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Combination Therapy

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen. Therefore, according to one embodiment, the pharmaceutical composition of this invention additionally comprises one or more antiviral agents.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being. Such agents can be selected from:

an HIV non-catalytic site integrase inhibitor selected from BI 224436 (Boehringer Ingelheim; Gilead Sciences);

an HIV integrase strand transfer inhibitor (INSTI) selected from the group consisting: raltegravir (ISENTRESS®; Merck); elvitegravir (Gilead); soltegravir (GSK; ViiV); and GSK 1265744 (GSK; ViiV);

an HIV nucleoside reverse transcriptase inhibitor (NRTI) selected from the group consisting of: abacavir (ZIAGEN®; GSK); didanosine (VIDEX®; BMS); tenofovir (VI READ®; Gilead); emtricitabine (EMTRIVA®; Gilead); lamivudine (EPIVIR®; GSK/Shire); stavudine (ZERIT®; BMS); zidovudine (RETROVIR®; GSK); elvucitabine (Achillion); and festinavir (Oncolys);

a non-nucleoside reverse transcriptase inhibitor (NNRTI) selected from the group consisting of: nevirapine (VIRAMUNE®; Boerhringer Ingleheim); efavirenz (SUSTIVA®; BMS); etravirine (INTELENCE®; J&J); rilpivirine (TMC278, R278474; J&J); fosdevirine (GSK/ViiV); and lersivirine (Pfizer/ViiV);

an HIV protease inhibitor selected from the group consisting of: atazanavir (REYATAZ®; BMS); darunavir (PREZISTA®; J&J); indinavir (CRIXIVAN®; Merck); lopinavir (KELETRA®; Abbott); nelfinavir (VIRACEPT®; Pfizer); saquinavir (INVIRASE®; Hoffmann-LaRoche); tipranavir (APTIVUS®; Boehringer Ingelheim); ritonavir (NORVIR®; Abbott); and fosamprenavir (LEXIVA®; GSK/Vertex);

an HIV entry inhibitor selected from: maraviroc (SELZENTRY®; Pfizer); enfuvirtide (FUZEON®; Trimeris); and BMS-663068 (BMS); and an HIV maturation inhibitor selected from: bevirimat (Myriad Genetics).

Furthermore, a compound according to the invention can be used with at least one other compound according to the invention or with one or more antifungal or antibacterial agents (including but not limited to fluconazole).

EXPERIMENTAL

Abbreviations or symbols used herein include:
Ac: acetyl; AcOH: acetic acid; $Ac_2O$: acetic anhydride; BOC or Boc: tert-butyloxycarbonyl; Bn: benzyl; Bu: butyl; dba: dibenzylidene acetone; DCC: N,N' dicyclohexylcarbodiimide; DCM: dichloromethane; DIAD: diisopropyl azodicarboxylate; DMA: dimethylacetamide; DMAP: 4-(N,N-dimethylamino)pyridine; DMEM: Dulbecco's modified Eagle's medium; DMF: N,N-dimethylformamide; DMSO: dimethylsulfoxide; dppf: 1,1'-bis(diphenylphosphino)ferrocene; $EC_{50}$: 50% effective concentration; EDCI: 1-[3-(dimethylamino)propyl]-3-ethylcarbodiimide hydrochloride; Et: ethyl; $Et_2O$: diethyl ether; EtOAc: ethyl acetate; EtOH: ethanol; HATU: 2-(1H-7-azabenzotriazol-1-yl)-1,1,3,3-tetramethyl uronium hexafluorophosphate methanaminium; Hex: hexanes; HPLC: high performance liquid chromatography; HSS: high strength silica; $^iPr$ or i-Pr: 1-methylethyl (isopropyl); mCPBA: meta-chloroperoxybenzoic acid; Me: methyl; MeCN: acetonitrile; MeOH: methanol; MsOH: methanesulfonic acid; MsCl: methanesulfonyl chloride; MS: mass spectrometry; MTBE: methyl-tert-butyl ether; NBS: N-bromosuccinimide; NMP: N-methylpyrrolidone; NMR: nuclear magnetic resonance spectroscopy; OBD: optimum bed density; Ph: phenyl; Pr: propyl; Pro: proline; RT: room temperature (approximately 18° C. to 25° C.); SM: starting material; S-Phos: 2-dicyclohexylphosphino-2',6'-dimethoxybiphenyl; tert-Bu or t-Bu: 1,1-dimethylethyl (tert-butyl or t-butyl); TEA: triethylamine; TFA: trifluoroacetic acid; THF: tetrahydrofuran; TLC: thin layer chromatography; TMS: trimethylsilyl; $t_R$: retention time; Ts: tosyl; UPLC-MS: ultra performance liquid chromatography mass spectrometry.

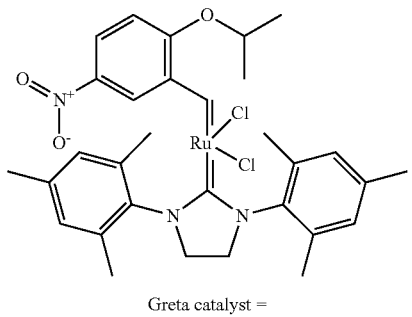

Greta catalyst =

General Procedures

The synthesis of compounds of formula (I) according to this invention is conveniently accomplished following the general procedures outlined below and as indicated in the examples.

General Procedure A (Mitsunobu)

The carbamate (1 equivalent), $PPh_3$ (2 equivalents) and alcohol (1.2 equivalents) are dissolved in THF (0.2 mol/L), cooled to RT and DIAD (2 equivalents) is added dropwise to the mixture. After stirring at 0° C. for 30 min, the solution is warmed to RT and is stirred at RT for 18 h. The solution is concentrated and the resulting residue purified by chromatography using EtOAc in hexanes or MeOH in DCM to give the desired product.

General Procedure B (Saponification)

The starting ester (1 equivalent) is dissolved either in THF (0.6 mol/L) and MeOH (0.6 mol/L) or EtOH, then an aqueous NaOH solution 5M (1 equivalent) is added under stirring. After stirring for 10 min, 10% citric acid solution is added to neutralize the solution. The mixture is extracted twice with EtOAc or DCM. The organic layers are washed with brine, dried ($Na_2SO_4$), filtered and concentrated to give the desired product.

General Procedure C (Weinreb Amide Formation from Acid)

The acid (1 equivalent) and the amine salt (1.2 equivalent) are dissolved in DMF (0.2 mol/L) and the base (2.5 equivalent) is added. The solution is cooled to 0° C. and HATU (1.5 equivalent) is added and stirred for 18 hours (h) while slowly being warmed to RT. The solution is poured into $H_2O$ and extracted with EtOAc. The combined organic extracts are washed with $H_2O$, brine, dried ($Na_2SO_4$) and concentrated. The resulting crude oil is purified by chromatography using EtOAc in hexanes or MeOH in DCM to give the desired product.

General Procedure D1 (Suzuki Cross-Coupling)

To a solution of the starting material (1 equivalent), the boronic acid or ester (1.5 to 3 equivalents), $NaHCO_3$ (2 to 3 equivalents) in degassed dioxane/$H_2O$ (4:1, 0.1 mol/L) is added $PdCl_2(dppf)$ (0.05 to 0.01 equivalent). The mixture is heated at 80° C. for 16 h or in the microwave at 130 to 150° C. for 30 to 50 min and cooled to RT. The reaction mixture is poured into $H_2O$/EtOAc and the layers separated. The aqueous phase is extracted with EtOAc and the combined organic layers are washed with $H_2O$, brine, dried ($Na_2SO_4$) and concentrated under vacuum. The residue is purified by column chromatography using EtOAc in hexanes or MeOH in DCM to give the desired product.

General Procedure D2 (Suzuki Cross-Coupling)

To a solution of the starting material (1 equivalent), the boronic acid or ester (1.5 to 3 equivalents), $K_2CO_3$ (2.5 to 3.0 equivalents) and CsF (2.5 equivalents) in degassed dioxane/$H_2O$ (4:1, 0.1 mol/L) is added $PdCl_2(dppf)$ (0.05 to 0.1 equivalent). The mixture is heated in the microwave at 120-135° C. for 20-30 min and cooled to RT. The resulting residue is purified by chromatography using EtOAc in hexanes or MeOH in DCM or purified by preparative HPLC.

General Procedure D3 (Suzuki Cross-Coupling)

To a solution of the starting material (1 equivalent), the boronic acid or ester (1.2 to 2 equivalents), $Na_2CO_3$ (2M in water, 2.5 equivalents) in degassed dimethylformamide (0.2 M) is added $PdCl_2(PPh_3)_2$ (0.1 equivalent). The mixture is heated in the microwave at 120° C. for 10 min and cooled to RT. The resulting residue is purified by chromatography using EtOAc in hexanes or MeOH in DCM or purified by preparative HPLC.

General Procedure D4 (Stille Cross-Coupling)

To a solution of the SM (1 equivalent) and the stannane (1.5 to 3 equivalents) in degassed DMF or toluene (0.1 mol/L) is added a palladium catalyst (0.05 to 0.02 equivalent). The mixture is heated at 80° C. for 16 h in an oil bath or in a microwave at 120 to 150° C. for 30 min and cooled to RT. The reaction mixture is poured into $H_2O$/EtOAc and the layers separated. The aqueous phase is extracted with EtOAc and the combined organic layers are washed with $H_2O$, brine, dried ($Na_2SO_4$) and concentrated under vacuum. The residue is purified by column chromatography using EtOAc in hexanes or MeOH in DCM to give the desired product. In cases where the coupling is the last step in the synthesis, the product is also optionally purified by preparative HPLC.

General Procedure E (C4 Addition)

To solution of the SM (1 equivalent) in THF (0.1 mol/L) is added the arylhalide or heteroarylhalide (4 equivalents). The solution is cooled to −78° C., a solution of n-butyllithium (2 to 3 equivalents) is added dropwise and the reaction is stirred for 20 min. The reaction mixture is quenched using one of the following methods:
  a) Acidified with AcOH in THF (10%). The mixture is warmed up to RT, silica gel is added and the volatiles are evaporated.
  b) Poured in $H_2O$/EtOAc and the layers are separated. The aqueous phase is extracted with EtOAc and the combined organic layers are washed with saturated aqueous $NaHCO_3$, $H_2O$, brine, dried ($Na_2SO_4$) and concentrated under vacuum.
  c) Poured into $NH_4Cl$ (saturated) and extracted with DCM or EtOAc.

The solid residue is purified by chromatography using EtOAc in hexanes or MeOH in DCM to give the desired product.

General Procedure F (Cyclization)

The SM (1 equivalent) is dissolved in DMSO or NMP (0.1 mol/L), ammonium acetate (120 mmol) is added and the slurry is heated at 130° C. for 4 h while adding more ammonium acetate every hour (if needed to promote the cyclization). The solution is then cooled to RT and the product is purified by one or a combination of these methods:
  a) Neutralization with NaOH 5 or 10N. The aqueous phase is extracted with DCM and the combined organic extracts are washed with brine, dried ($Na_2SO_4$) and concentrated.
  b) By preparative HPLC.
  c) By precipitation following the addition of water and filtration of the suspension.
  d) By trituration in EtOAc, MeCN, DCM, $Et_2O$, hexanes or a combination thereof.
  e) By partition between DCM and water followed by DCM extractions.

General Procedure G (Alkylation of N1)

To a solution of the carbamate (1 equivalent) and the electrophile (mesylate, tosylate, iodide or bromide) (1.3 equivalents) in DMSO (1 mol/L), is added $Cs_2CO_3$ (2.3 equivalents). The reaction mixture is stirred at RT for 24 h. The solution is poured into HCl 1N and extracted with EtOAc. The combined organic extracts are washed with brine, dried ($Na_2SO_4$) and concentrated. The resulting residue is purified by chromatography using EtOAc in hexanes or MeOH in DCM to give the desired product.

General Procedure H (SNAr Followed by Cyclization)

In a sealed tube, the SM (1 equivalent) and the amine (2 to 5 equivalents) are dissolved in DMSO (0.1 mol/L) and heated at 100° C. for 1 h. Ammonium acetate (120 mmol) is added and the slurry is heated at 130° C. for 4 h while adding more ammonium acetate every hour (if needed to promote the cyclization). The solution is then cooled to RT and the product can be purified by one or a combination of these methods:
  a) By preparative HPLC.
  b) By precipitation following the addition of water and filtration of the suspension.
  c) By trituration in EtOAc, MeCN, DCM, $Et_2O$, hexanes or a combination thereof.

General Procedure I (Weinreb Amide from Ester)

A solution of N,O-dimethylhydroxylamine hydrochloride (2.2 equivalents) in THF (0.8 mol/L) at −60° C. is treated with a solution of n-butyllithium (4.1 equivalents). The mixture is stirred for 15 min and a solution of the ester (1 equivalent) in THF (0.6 mol/L) is added dropwise. The reaction mixture is stirred for 30 min and then AcOH in THF (10%) followed by a saturated aqueous solution of $NH_4Cl$ is added. The layers are separated. The aqueous phase is extracted with EtOAc and the combined organic layers are washed with saturated aqueous $NaHCO_3$, $H_2O$, brine, dried ($Na_2SO_4$) and concentrated under vacuum. The residue is purified by column chromatography using EtOAc in hexanes or MeOH in DCM to give the desired product.

General Procedure J (Synthesis of Substituted Pyrans)

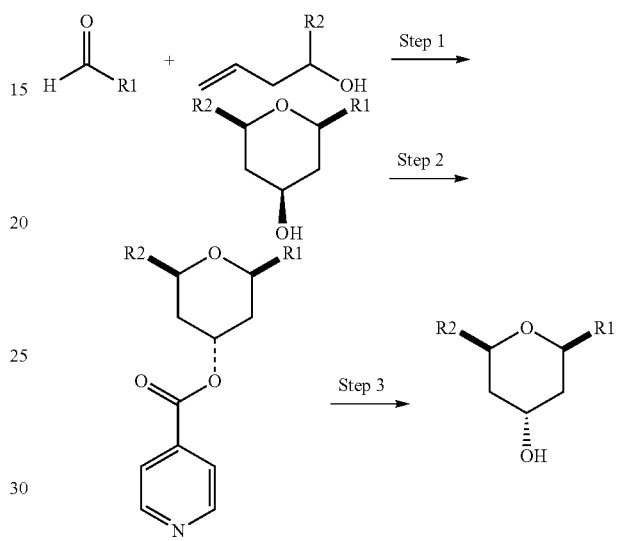

Step 1

A mixture of the aldehyde (1 equivalent) and homoallylic alcohol (1 equivalent) are treated with 20% $H_2SO_4$ and heated at 80° C. in a sealed tube for 3 h (or RT overnight). The reaction mixture is cooled if necessary, neutralized with NaOH (aq) or $NH_3$ (aq) and extracted with EtOAc. The organic layer is dried ($Na_2SO_4$) and concentrated and the residue purified by flash chromatography or distillation.

Step 2

A solution of the alcohol (1 equivalent), $PPh_3$ (1.5-5 equivalent), and acid (typically, p-toluic acid, p-nitrobenzoic acid or isonicotinic acid, 1.1 to 1.5 equivalent are used) is cooled to 0° C. and treated with DIAD (1.5-5 equivalent). The mixture is allowed to stir at RT overnight and is then concentrated and purified by flash chromatography. In cases where isonicotinic acid is used, the product is purified by acid-base extraction.

Step 3

The ester obtained in step 2 (1 equivalent) is dissolved in THF, MeOH, $H_2O$ (3:1:1) and treated with LiOH (10 equivalent) at RT. The mixture is allowed to stir at RT until the reaction is complete (as indicated by TLC or HPLC). The reaction mixture is then concentrated to remove the volatile solvents, diluted with a small amount of $H_2O$ and extracted with $Et_2O$. The organic phase is washed with brine, dried ($Na_2SO_4$) and concentrated. The residue is purified by flash chromatography or distillation.

General Procedure K

Salt forms of the compounds may be prepared according to standard methods known to a person skilled in the art. For example, the TFA or MsOH salt form of the compounds of the invention may be prepared according to the methods:
  a) TFA salt: Lyophlization after the preparative HPLC using TFA/$H_2O$/MeCN.
  b) MsOH salt: Solubilization of the product in MeCN/$H_2O$, then addition of 1 to 2 equivalents of MsOH followed by lyophilization.

Other procedures by which compounds of the invention may be prepared are well known in the art or are set forth in the examples below. Further, it is appreciated that, in the above general procedures and examples, the skilled in the art could make certain changes or modifications, and these equivalents would still be within the scope of the general procedures or examples described in the application. For example, general procedure A (Mitsunobu reaction) may be performed by mixing the carbamate, $PPh_3$ and alcohol in an aprotic solvent, such as THF or DCM, preferably at 0° C. and adding dropwise an appropriate azocarboxylate, such as DEAD or DIAD. The general procedure C (Weinreb amide formation from an acid) may be performed by dissolving the appropriate acid, such as N,O-dimethylhydroxylamine hydrochloride, in an appropriate solvent such as DMF, THF or DCM, and a base, such as $Et_3N$, $Et_2iPrN$ or other non nucleophilic organic bases. After preferably cooling down the reaction mixture at 0° C., the peptide coupling agent is added, such as TBTU, HATU, DCC or other derivatives. The general procedures D1, D2 and D3 (Suzuki cross-coupling) may be performed by dissolving the starting material, boronic acid or analogue and base in a preferably degassed organic solvent, such as dioxane, THF, DMF or a mixture with water. The palladium catalyst may be selected from, for example, $PdCl_2$(dppf), $Pd(PPh_3)_4$, $PdCl_2(PPh_3)_2$ or $Pd(tBu_3P)_2$ or derivatives. The general procedure D4 (Stille cross-coupling) may be performed by dissolving the starting material and stanane in a preferably degassed organic solvent, such as DMF, DMA or dioxane. The palladium catalyst may be selected from, for example, $PdCl_2$(dppf), $Pd(PPh_3)_4$, $PdCl_2(PPh_3)_2$ or $Pd(tBu_3P)_2$ or derivatives. The general procedure E (C4 addition) may be performed by adding an appropriate arylhalide or heteroarylhalide to solution of the SM in THF. The solution is cooled to −78° C., a solution of n-butyllithium is added and the reaction is stirred until desired conversion. The general procedure F (cyclization) may be performed by a person skilled in the art by dissolved the SM in DMSO or NMP, adding ammonium acetate and heating until the desired conversion. More ammonium acetate can be added or gaseous ammonia can bubbled to the reaction mixture to promote the cyclization. The general procedure G (alkylation of N1) may be performed by a person skilled in the art by dissolving the carbamate and the desired electrophile (mesylate, tosylate, iodide or bromide) in an appropriate solvent such as DMSO, acetone, DMF or THF and addition of an organic or inorganic base such as NaH, $Cs_2CO_3$, $Et_3N$ or DBU. The reaction is stirred until desired conversion at RT or by heating. The General procedure H (SNAr followed by cyclization) may be performed by a person skilled in the art by dissolving the starting material and the appropriate amine in a suitable solvent such as DMSO, DMF, MeOH or THF. Ammonium acetate is added and the slurry is heated until desired conversion. Additional ammonium acetate or gaseous ammonia may be added to the reaction mixture to promote the cyclization. The general procedure I (Weinreb amide from ester) may be performed by a person skilled in the art by treating a solution of an appropriate acid, such as N,O-dimethylhydroxylamine hydrochloride in THF, with n-butyllithium. A solution of the ester in an appropriate solvent, such as THF, is added and the reaction is stirred until desired conversion.

EXAMPLES

Other features of the present invention will become apparent from the following non-limiting examples which illustrate, by way of example, the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. The reactants used in the examples below may be obtained either as described herein, or if not described herein, are themselves either commercially available or may be prepared from commercially available materials by methods known in the art. Flash chromatography is carried out on silica gel ($SiO_2$) according to the procedure of W. C. Still et al., J. Org. Chem., (1978), 43, 2923; or using Teledeyne Isco Flash Combiflash Companion or Rf instrument. Mass spectral analyses are recorded using electrospray mass spectrometry. Preparative HPLC is performed using a Waters instrument, using one of the four conditions outlined below:

Sunfire Prep C18 column, OBD, 5 μm, 30×75 mm, 120 Å, elution with a gradient of $MeCN/H_2O$ containing 0.06% TFA, 60 mL/min.

Sunfire Prep C18 column, OBD, 5 μm, 19×50 mm, 120 Å, elution with a gradient of $MeCN/H_2O$ containing 0.06% TFA, 30 mL/min.

Sunfire Prep C18 column, OBD, 5 μm, 19×50 mm, 120 Å at RT or 45° C., elution with a gradient of MeOH or MeCN/Ammonium formate 10 mM in $H_2O$, pH 3.8, 30 mL/min.

X-Bridge Prep C18 column, OBD, 5 μm, 19×50 mm, 120 Å at RT or 45° C., elution with a gradient of MeOH or MeCN/Ammonium bicarbonate 10 mM in $H_2O$, pH 10, 30 mL/min.

Analytical HPLC and UPLC-MS are carried out under standard conditions using one of four columns (Sunfire C18, CombiScreen ODS-AQ, HSS C18 or BEH C18) with the specific conditions shown below:

Column: Sunfire C18, 3.5 μm, 4.6×30 mm

Eluent A: $H_2O$+0.06% or 0.1% TFA

Eluent B: MeCN+0.06% or 0.1% TFA

Gradient: Linear 2% B for 0.6 min, 2% to 50% B in 4.9 min, 50% to 100% B in 1.8 min, isocratic at 100% B for 0.6 min Column: CombiScreen ODS-AQ, S-5 μm, 12 nm, 4.6×50 mm Eluent A: $H_2O$+0.1% TFA Eluent B: MeCN+0.1% TFA Gradient: Linear 5% B for 0.5 min, 5% to 50% B in 5.5 min, 50% to 100% B in 4.5 min, isocratic at 100% B for 1.0 min Column: HSS C18, 1.8 μm, 2.1×30 mm Eluent A: Ammonium formate 10 mM in $H_2O$, pH 3.8

Eluent B: MeOH

Gradient: 5% to 100% B in 2.3 min, isocratic at 100% B for 0.7 min

Column: HSS C18, 1.8 μm, 2.1×30 mm

Eluent A: $H_2O$+0.06% TFA

Eluent B: MeCN

Gradient: 5% to 100% B in 2.2 min, isocratic at 100% B for 0.8 min

Column: BEH C18, 1.7 μm, 2.1×30 mm at 25° C. or 45° C.

Eluent A: Ammonium bicarbonate 10 mM in $H_2O$, pH 10.0

Eluent B: MeOH or MeCN

Gradient: 5% to 100% B in 2.2 min, isocratic at 100% B for 0.8 min

Column: BEH C18, 1.7 μm, 2.1×30 mm at 25° C. or 45° C.

Eluent A: Ammonium bicarbonate 10 mM in $H_2O$, pH 10.0

Eluent B: MeOH or MeCN

Gradient: 5% to 100% B in 2.2 min, isocratic at 100% B for 0.8 min

Example 1

Synthesis of Intermediate 1e

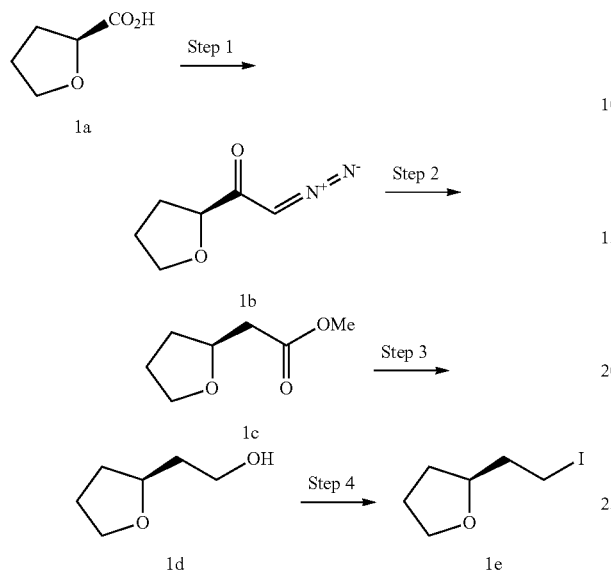

Step 1
A solution of 1a (40.0 g, 344.8 mmol, TCI) in THF (800 mL) is cooled to −25° C. and treated with TEA (62.4 mL, 448.2 mmol). EtOCOCl (42.4 mL, 448.2 mmol) is then added dropwise at the same temperature. The mixture is stirred for 30 min, then filtered. The filtrate is cooled to 0° C. and treated with an excess of diazomethane in ether. The mixture is allowed to stir while warming to RT overnight. The solution is treated with HOAc and then concentrated to approximately one-half its volume. The mixture is poured into water (1 L) and extracted with EtOAc (500 mL×2). The combined organic layers are washed with saturated $NaHCO_3$ and brine, dried ($Na_2SO_4$) and concentrated in vacuo to give diazoketone 1b, which is used as such in the next step.

Step 2
A solution of diazoketone 1b (40.0 g, 285.7 mmol) in MeOH (500 mL) is cooled to 0° C. and treated with a solution of silver benzoate (6.5 g, 28.6 mmol) in TEA (67 mL). The mixture is protected from light and stirred while warming to RT. The crude reaction mixture is filtered through a Celite pad and concentrated in vacuo. The residue is distilled in vacuum (60° C., 20 mmHg) to afford ester 1c ((S)-(tetrahydro-furan-2-yl)-acetic acid methyl ester).

Step 3
A solution of ester 1c (22.0 g, 152.8 mmol) in THF (220 mL) at 0° C. is treated portionwise with a solution of $LiAlH_4$ (11.6 g, 305.6 mmol) in THF (260 mL) under a nitrogen atmosphere. The mixture is stirred at 0° C. for 30 min and then the cooling bath is removed. Stirring is continued for 3 h and the solution is re-cooled to 0° C. and treated with 5 M NaOH (48.5 mL). The solid is filtered, washed with THF and the combined filtrates are concentrated in vacuo to give alcohol 1d, which is used as such in the next step.

Step 4
To a stirring solution of alcohol 1d (20.0 g, 172.4 mmol) in THF (1 L) and MeCN (400 mL) are added $PPh_3$ (67.6 g, 258.0 mmol), imidazole (17.5 g, 258.0 mmol) and $I_2$ (65.5 g, 258.0 mmol) at 25° C. The mixture is stirred at 25° C. for 2 h, and then the solvent is evaporated in vacuo. The precipitate is filtered off and the filtrate is concentrated under reduced pressure. The residue is purified on silica gel (1-2.5% EtOAc in petroleum ether) to afford intermediate 1e.

Example 2

Preparation of Intermediate racemic 2a (2-(tetrahydro-furan-2-yl)-ethanol)

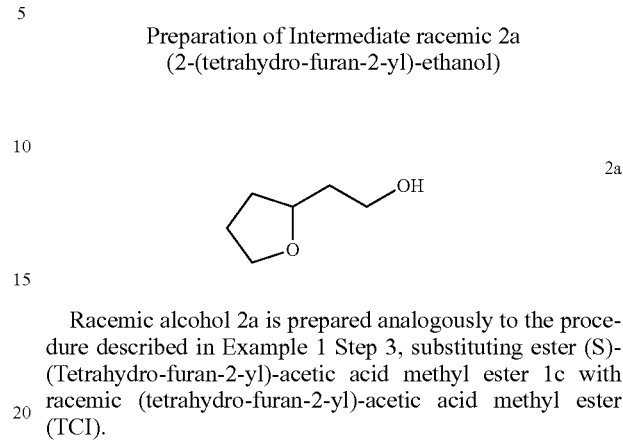

Racemic alcohol 2a is prepared analogously to the procedure described in Example 1 Step 3, substituting ester (S)-(Tetrahydro-furan-2-yl)-acetic acid methyl ester 1c with racemic (tetrahydro-furan-2-yl)-acetic acid methyl ester (TCI).

Example 3

Synthesis of Intermediate racemic 3e (2-ethyl-tetrahydropyran-4-ol)

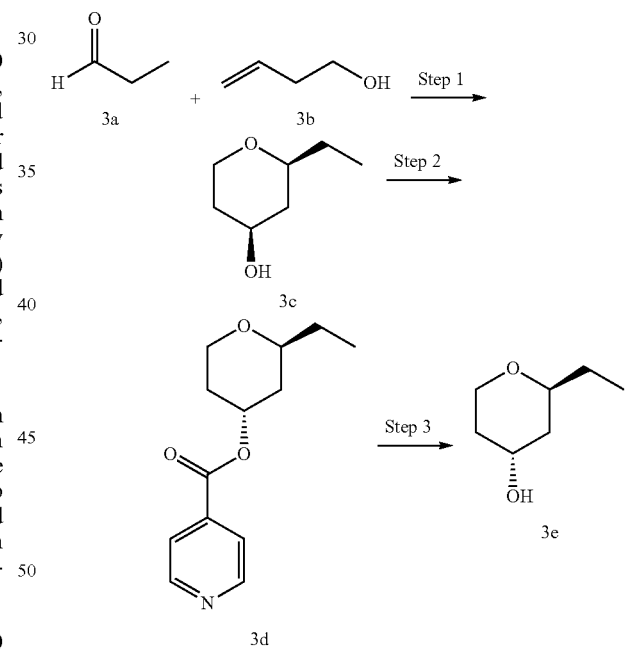

Step 1
To 25% $H_2SO_4$ (1 L, separated into four flasks) cooled to 0° C. in an ice bath is added a neat mixture of 3-butenol 3b (160 g, 2.2 mmol, Aldrich) and propionaldehyde 3a (134 g, 2.3 mmol, Aldrich) dropwise. After complete addition, the mixture is allowed to stir at this temperature for 30 min and then the cooling bath is removed. The mixture is allowed to stir at RT overnight and then neutralized with 10 M NaOH (pH ~8). The basified layer is extracted with $Et_2O$ (4×). The ether layers are combined and dried ($MgSO_4$) and concentrated in vacuo. The aqueous phase is saturated with NaCl, filtered and extracted with DCM (6×). The DCM layers are combined, dried ($MgSO_4$) and concentrated in vacuo. The organic layers are combined and distilled under vacuum and the fraction boiling at 75-80° C. (ca. 2 mmHg) is collected to afford 3c.
Step 2

A mixture of isonicotinic acid (114.4 g, 0.93 mol), PPh₃ (333.2 g, 1.27 mol) and alcohol 3c (110 g, 0.85 mol), in THF (1.1 L) is treated with DIAD (249.5 mL, 1.3 mol) dropwise at 0° C. After stirring for 30 min, the cooling bath is removed and the mixture is stirred at RT for 2 h. The mixture is filtered and then concentrated. The residue is triturated with Et₂O and the ether layers are extracted with 30% HCl. The combined aqueous phases are washed with Et₂O (2×) and EtOAc (2×) and then neutralized with Na₂HPO₄ to about pH 6. The neutralized aqueous phase is extracted with Et₂O (5×) and then DCM (3×). The combined ether layers are dried (MgSO₄) and concentrated in vacuo. The DCM layers are combined and dried (MgSO₄), concentrated in vacuo and combined with the product resulting from the ether extractions to afford ester 3d.
Step 3

A solution of ester 3d (271.1 g, 1.15 mmol) in THF (2.1 L) is treated with LiOH—H₂O (490.4 g, 11.7 mol) in H₂O (0.7 L) and then MeOH (0.7 L). The mixture is allowed to stir overnight, and then concentrated. The residue is poured into H₂O-EtOAc and the layers separated. The aqueous phase is extracted with EtOAc. The combined organic layers are washed (H₂O, brine), dried (Na₂SO₄) and concentrated in vacuo. The residue is distilled in vacuo to afford intermediate 3e.

Example 4

Preparation of Intermediate racemic 4a
(2-propyl-tetrahydropyran-4-ol)

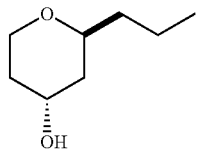

Intermediate 4a is prepared analogously to the procedure described in Example 3 wherein propionaldehyde 3a is replaced with butyraldehyde (Aldrich) in Step 1 and the reaction is carried out at 80° C. for 3 h in a sealed reaction vessel. In Step 2, isonicotinic acid is replaced with p-toluic acid (Aldrich) and the product is purified by flash chromatography (hexane-EtOAc).

Example 5

Preparation of Intermediate racemic 5a
(2,6-dimethyl-tetrahydropyran-4-ol)

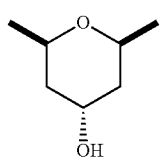

Intermediate 5a is prepared analogously to the procedure described in Example 4 wherein butyraldehyde is replaced with acetaldehyde (Aldrich) and buten-3-ol is replaced with 4-penten-3-ol (TCI-US) in Step 1.

Example 6

Preparation of Intermediate racemic 6a
(2-ethyl-6-methyl tetrahydropyran-4-ol)

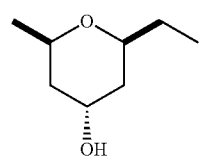

Intermediate 6a is prepared analogously to the procedure described in Example 4 wherein buten-3-ol is replaced with 4-penten-3-ol (TCI-US) in Step 1.

Example 7

Preparation of Intermediate 7c
((2S,4R)-2-ethyl-tetrahydropyran-4-ol)

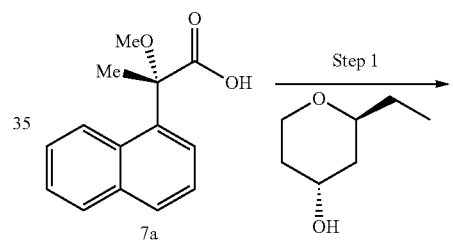

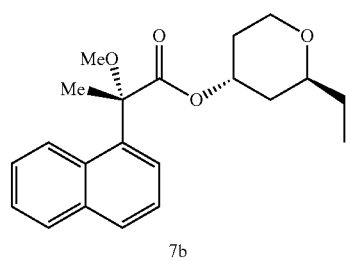

Step 1

To a solution of S-acid 7a (150 g, 0.65 mol, prepared analogously to the method described in: Harada et al, *Chirality,* 2004, 569), DCC (208 g, 1 mol), DMAP (40.6 g, 0.33 mol), and 10-camphorsulfonic acid (16.3 g, 0.07 mol) in DCM (2 L) is added racemic 3e (85 g, 0.65 mol). The mixture is stirred at RT overnight. Water (1 L) is added and stirring is continued for 1 h. The mixture is filtered with Celite, which is washed with EtOAc. The combined organic layers are evaporated under reduced pressure, and the residue is purified by HPLC on silica gel (7% EtOAc/petroleum ether) to afford 7b.

Step 2

To a solution of ester 7b (70 g, 0.20 mol) in MeOH (1.0 L) is added NaOMe (200 g, 3.7 mol) with stirring. The reaction mixture is heated to reflux and allowed to stir overnight. Water (0.5 L) is added to the solution and the mixture is stirred at reflux for another 3 h. After removal of the organic solvent under reduced pressure, the mixture is extracted with methyl-tert-butyl ether (2×). The combined organic layers are dried and concentrated in vacuo to afford 7c.

Example 8

Preparation of Intermediate 8a
((2S,4R)-2-propyl-tetrahydropyran-4-ol)

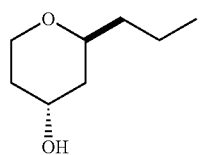

8a

Intermediate 8a is prepared analogously to the procedure described in Example 7 wherein 3e is replaced with 4a.

Example 9

Synthesis of Intermediate 9f1
((2S,4R)-2-ethyl-oxepan-4-ol)

Step 1

To a solution of 9a (4.5 g, 34 mmol, Aldrich) and trichloroacetimidate (13.7 g, 68 mmol, Aldrich) in DCM (39 mL) and hexanes (78 mL) is added triflic acid (0.6 mL, 6.8 mmol) dropwise. The mixture is stirred at RT for 48 h, quenched by addition of excess TEA and concentrated under vacuum. The crude material is purified by chromatography (0-20% EtOAc in hexanes) to afford ether 9b.

Step 2

To ester 9b (4.58 g, 24.6 mmol) dissolved in DCM (240 mL) is added Dibal-H (1M in DCM, 27 mL, 27 mmol) dropwise. The mixture is stirred at −78° C. for 30 min. MeOH is added and the mixture is warmed to RT. Sodium potassium tartrate solution is added and the mixture is stirred for 15 h. Water is added and the product is extracted with DCM, dried ($Na_2SO_4$) and concentrated. The crude aldehyde 9c is used as such for the next step.

Step 3

To aldehyde 9c (3.5 g, 24.6 mmol) in THF (240 mL) at −78° C. is added vinylmagnesium bromide (0.7 M in THF, 70 mL, 49 mmol) over 30 min. The mixture is kept at −78° C. for 30 min and then warmed to 0° C. for 30 min. The reaction mixture is quenched with $NH_4Cl$, extracted with EtOAc, dried ($Na_2SO_4$) and concentrated. The crude product 9d is used as such for the next step.

Step 4

To a DCM (2500 mL) solution of diene 9d (4.2 g, 24.6 mmol) purged with $N_2$ is added the Grela catalyst (771 mg, 1.15 mmol). The reaction mixture is allowed to stir for 10 min. Ethyl vinylether is added and stirred for 15 min. The volatiles are removed in vacuo and the crude material is purified by chromatography (20-60% EtOAc in hexanes) to afford 9e.

Step 5

To a DCM (150 mL) solution of alkene 9e (2.2 g, 15.4 mmol) at 0° C. is added [(1,2,5,6-η)-1,5-cyclobutadiene](pyridine)(tricyclohexylphosphine)iridium(I) hexafluorophosphate Crabtree's catalyst (554 mg, 0.7 mmol). The flask is then purged (3×) with hydrogen. This solution is stirred at 0° C. for 1 h, then warmed to RT and stirred for 2 h. The volatiles

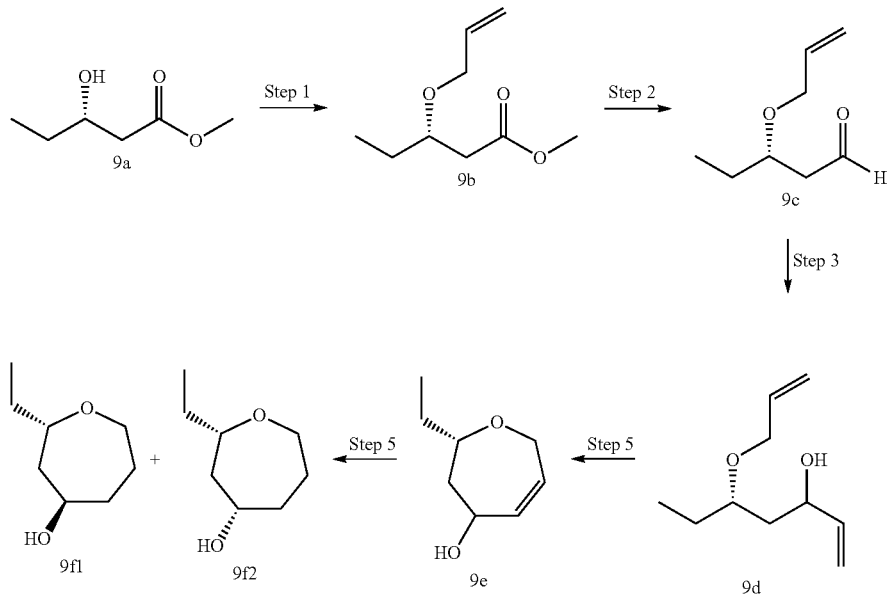

are removed and the residue is purified by flash chromatography (20-60% EtOAc in hexanes) to afford trans-isomer 9f1 and the cis-isomer 9f2.

Example 10

Synthesis of Intermediate racemic 10e (5-ethyl-tetrahydro-furan-3-ol)

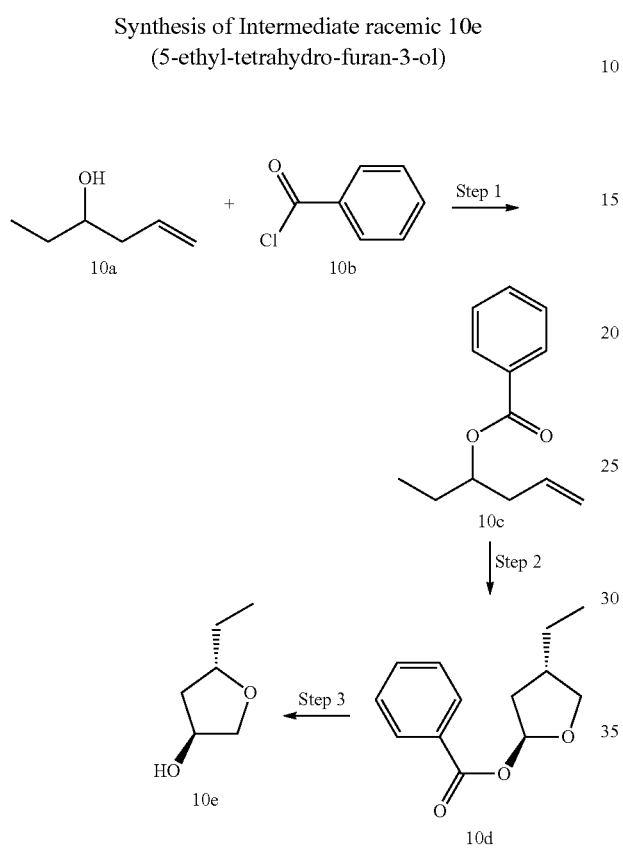

Step 1

5-hexen-3-ol 10a (10 g, 99.8 mmol, Pfaltz-Bauer) is dissolved in pyridine (65 mL) and cooled to 0° C. Benzoyl chloride 10b (13.9 mL, 119.8 mmol) is added and stirred at RT for 15 h. The reaction mixture is concentrated, quenched with 1N HCl, extracted with EtOAc, dried (MgSO$_4$), filtered and concentrated. Purification by chromatography (0-20% EtOAc in hexanes) affords alkene 10c.

Step 2

Alkene 10c (7.1 g, 34.8 mmol) is dissolved in DCM (400 mL) and cooled to 0° C. mCPBA (15.6 g, 70 mmol) is added followed by boron trifluoride diethyl etherate (8.6 mL, 70 mmol). The mixture is stirred at RT for 15 h, then quenched by adding saturated sodium bicarbonate. This mixture is extracted with DCM, dried (MgSO$_4$), filtered and volatiles are evaporated. Purification by flash chromatography (0-10% EtOAc in hexanes) affords trans-isomer 10d.

Step 3

Ester 10d (4 g, 18.2 mmol) is dissolved in MeOH (120 mL) and water (40 mL). LiOH (1.7 g, 71 mmol) is added. The reaction mixture is stirred for 72 h, then concentrated. Water is added and the mixture is extracted with Et$_2$O. The organic phase is dried (MgSO$_4$), filtered and concentrated to provide intermediate 10e, which is used as such in subsequent reactions.

Example 11

Preparation of Intermediate 11b

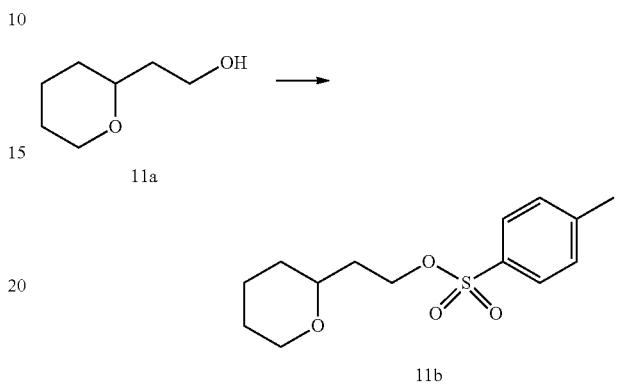

To a solution of alcohol 11a (3.77 g, 29.0 mmol, Chembridge-BB) in DCM (60 mL) is added TEA (5.65 mL, 40.5 mmol) followed by TsCl (6.63 g, 34.8 mmol) and DMAP (60 mg). The resulting mixture is stirred at RT overnight. The solution is washed with H$_2$O, brine, dried (Na$_2$SO$_4$) and concentrated. Silica gel is added, then the mixture concentrated and purified by chromatography (0-30% EtOAc in hexanes) to afford intermediate 11b.

Example 12

Preparation of Intermediate 12d

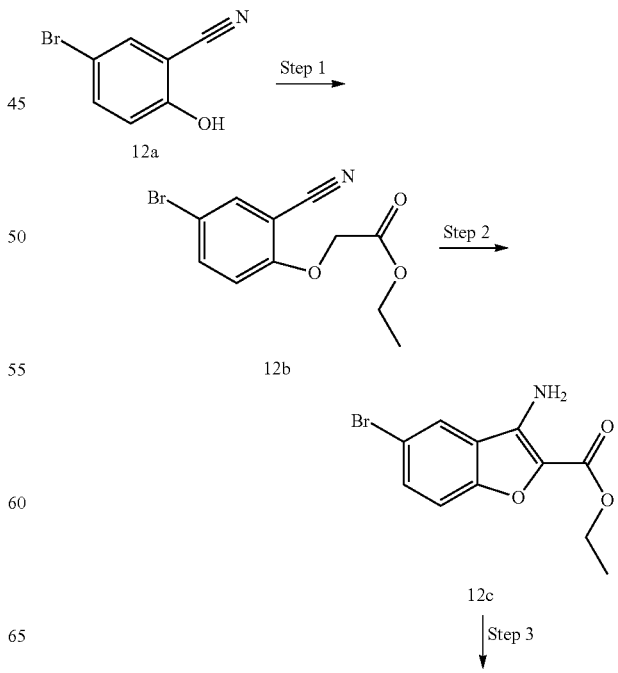

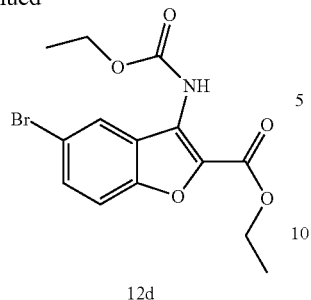

12d

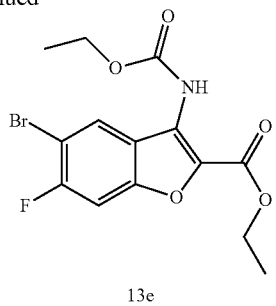

13e

Step 1

A suspension of phenol 12a (25.0 g, 126.3 mmol, Appollo), ethyl bromoacetate (31.6 g, 189.4 mmol) and sodium carbonate (20.1 g, 189.4 mmol) in acetone (900 mL) is stirred at reflux overnight. The mixture is quenched with 1N HCl, extracted with EtOAc, washed with brine, dried (Na$_2$SO$_4$), filtered and concentrated to provide ether 12b, which is used as such in subsequent steps.

Step 2

Ether 12b (31 g, 109.1 mmol) is added to a solution of NaOEt in EtOH (prepared from 2.51 g, 109.1 mmol of sodium and 900 mL EtOH) and the resulting solution is allowed to stir RT for 30 min. The solid is filtered and dried to provide 12c, which is used as such in subsequent steps.

Step 3

A solution of amine 12c (25 g, 88.0 mmol) in PhMe (700 mL) and MeCN (500 mL) is treated with EtOCOCl (71.2 mL, 748 mmol). The mixture is heated at 100° C. for 6 h and cooled to RT. The solid is filtered and washed with hexane to afford intermediate 12d.

Example 13

Preparation of Intermediate 13e

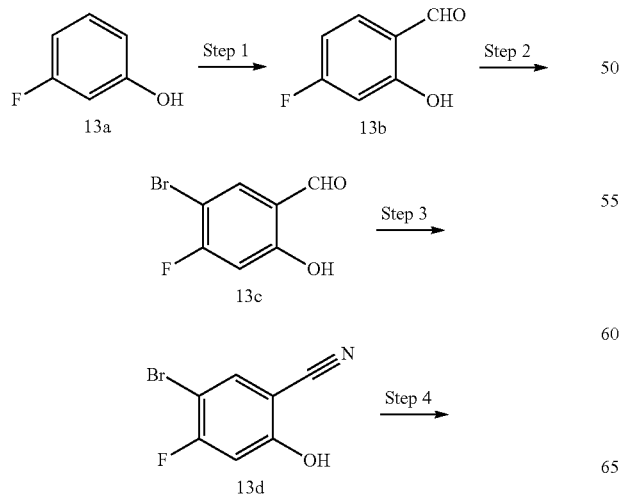

Step 1

To a mixture of phenol 13a (60 mL, 612 mmol) and anhydrous MgCl$_2$ (169.2 g, 4.7 mol) in anhydrous MeCN (3 L) is added anhydrous TEA (402 mL, 2.3 mol) and paraformaldehyde (406.8 g, 4.5 mol). The mixture is heated to reflux for 5 h. After cooling to RT, HCl (5%, 3 L) is added and the mixture is extracted with EtOAc. The combined organic extracts are washed with HCl (5%, 500 mL×3) and brine and dried (Na$_2$SO$_4$). The solvent is evaporated under reduced pressure to afford aldehyde 13b.

Step 2

To a solution of phenol 13b (80.0 g, 571.4 mmol) in AcOH (500 mL) is added Br$_2$ (89.7 g, 571.4 mmol) dropwise with stirring at RT for 2 h. The solution is poured into water (500 mL), and extracted with EtOAc (500 mL×2). The combined organic layers are washed with brine and dried (Na$_2$SO$_4$). The solvent is concentrated in vacuo to afford crude bromo-phenol 13c, which is used as such in the next step.

Step 3

A mixture of crude aldehyde 13c (150.0 g) and hydroxylamine-O-sulfonic acid (130.5 g, 1.2 mol) are suspended in water (2 L) and then heated to 60° C. for 8 h. After cooling, the mixture is diluted with water (2 L) and then cooled in an ice bath. The precipitate is collected by simple filtration and dried under vacuum to afford crude nitrile 13d.

Step 4

The crude nitrile 13d is transformed to intermediate 13e analogously to the procedure described in Example 12, Steps 1 to 3.

Example 14

Preparation of Intermediate 14a

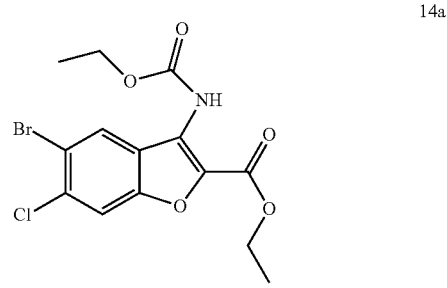 [SMILES: CCOC(=O)Nc1c(C(=O)OCC)oc2cc(Cl)c(Br)cc12]

14a

Intermediate 14a is prepared analogously to the procedure described in Example 13 (Steps 1, 3 and 4) starting from 4-bromo-3-chlorophenol.

Example 15

Preparation of Intermediate 15d

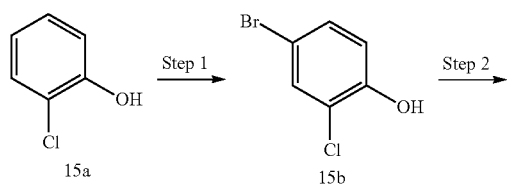

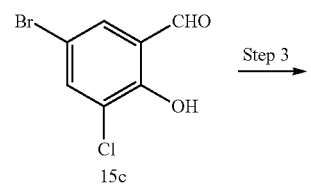

Step 1

To a solution of 2-chlorophenol 15a (70.0 g, 0.57 mol) in AcOH (200 mL) is added $Br_2$ (91.5 g, 0.57 mol) dropwise with stirring at RT for 2 h. The solution is poured into water (500 mL), and extracted with EtOAc (500 mL×2). The combined organic layers are washed with brine and dried ($Na_2SO_4$). The solvent is concentrated in vacuo to afford crude bromide 15b.

Step 2

To a solution of crude bromide 15b (116.5 g, 0.56 mol) in trifluoroacetic acid (400 mL) is added hexamethylenetetramine (157.6 g, 1.12 mol) in three portions over 20 min under $N_2$. The mixture is stirred at RT for 20 min, and then at 90° C. overnight. After being cooled to RT, water (650 mL) and a 50% aqueous solution of sulfuric acid (303 mL) are sequentially added. The mixture is stirred at RT for 2 h. The precipitate is collected by filtration and air dried to give crude aldehyde 15c.

Step 3

Crude aldehyde 15c is elaborated to intermediate 15d analogously to the method described in Example 13 (Steps 3 and 4).

Example 16

Preparation of Intermediate 16a

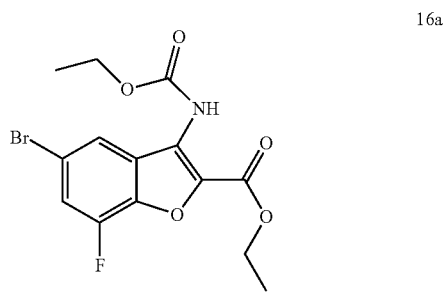 [SMILES: CCOC(=O)Nc1c(C(=O)OCC)oc2c(F)cc(Br)cc12]

Intermediate 16a is prepared analogously to the procedure described in Example 15 (Steps 2 and 3) starting from 4-bromo-2-fluorophenol.

Example 17

Preparation of Intermediate 17d

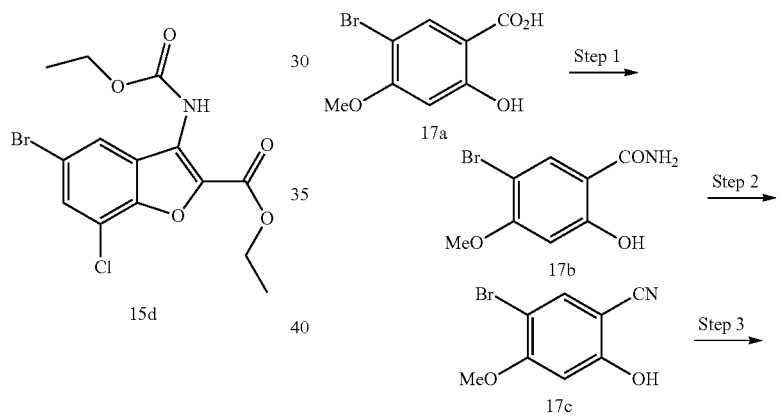

Step 1

Acid 17a (1.00 g, 4.05 mmol, Aldrich) is dissolved in DCM under $N_2$ at 0° C. Oxalyl chloride (0.88 mL, 10.1 mmol) is added, followed by 3 drops of DMF. The solution is allowed to warm to RT and concentrated. The residue is dissolved in THF at 0° C. and $NH_3(g)$ is bubbled through the solution until it turns yellow. The solution is concentrated, diluted with $H_2O$ and EtOAc and the layers separated. The aqueous phase is extracted with EtOAc and the combined organic extracts are washed with brine, dried ($Na_2SO_4$) and concentrated to give crude amide 17b.

31

Step 2

Thionyl chloride (3.97 mL, 54.7 mmol) is added to DMF (20 mL) at 0° C. and the solution is stirred for 20 min. Crude amide 17b (2.69 g, 10.9 mmol) is added and the solution is stirred at RT for 1 h. The solution is diluted with EtOAc/H$_2$O and the aqueous phase is extracted with EtOAc. The combined organic extracts are washed with H$_2$O and brine and dried (Na$_2$SO$_4$). The residue is triturated (DCM) to afford nitrile 17c, which is used as such in the next step.

Step 3

Nitrile 17c is converted to intermediate 17d analogously to the procedure described in Example 12.

Example 18

Preparation of Intermediate 18c

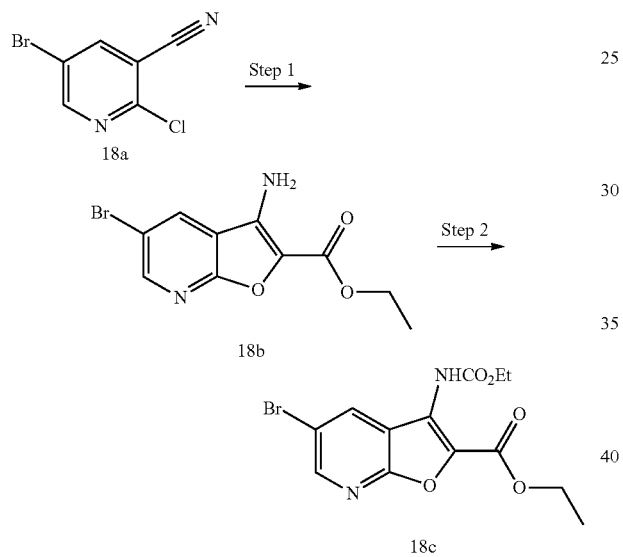

Step 1

Ethylglycolate (19.6 mL, 206.9 mmol) is dissolved in DMF (270 mL) and cesium carbonate (224.2 g, 413.9 mmol) is added portionwise at RT. The reaction mixture is stirred for 15 min, then 18a (45 g, 206.9 mmol, Combi-Blocks) is added and the reaction mixture is heated for 2 h at 80° C. The mixture is cooled to RT, ice cold water is added and the solution is filtered. The filtrate is diluted with EtOAc and is washed with water, then with brine. The organic layer is dried and concentrated. The residue is purified by flash column chromatography (20-30% EtOAc in petroleum ether) to afford 18b.

Step 2

Amine 18b (21 g, 73.7 mmol) is dissolved in a mixture of MeCN (195 mL) and toluene (315 mL). Ethylchloroformate (24 g, 220.98 mmol) is added and the solution is refluxed for 18 h. The solvents are evaporated under vacuum and the residue is triturated in MeCN and filtered to give intermediate 18c.

32

Example 19

Preparation of Intermediate 19f

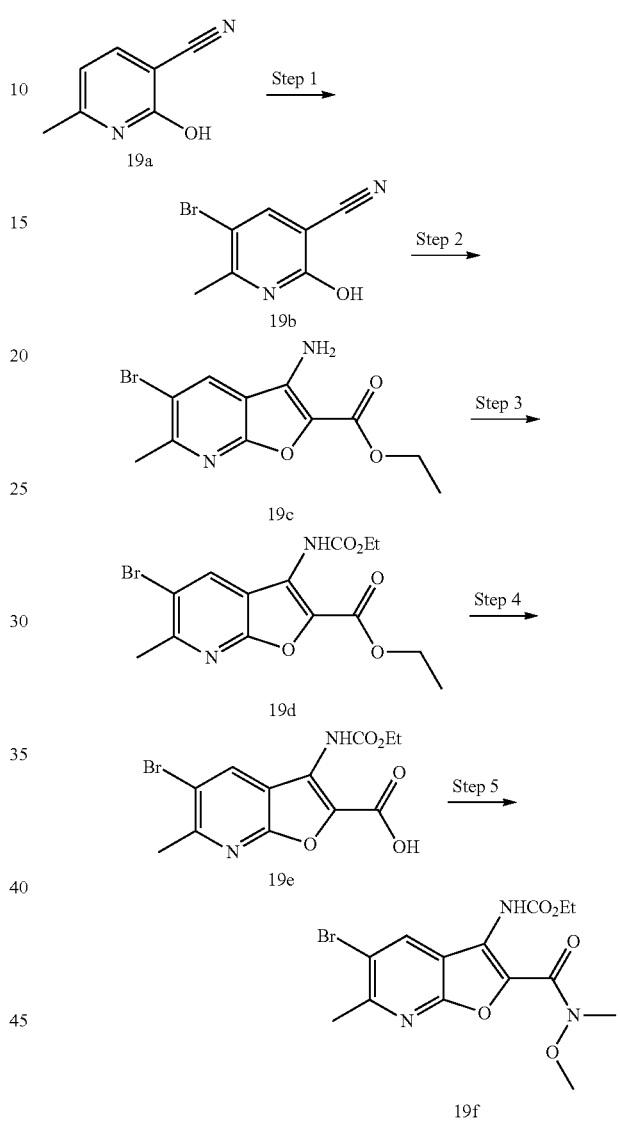

Step 1

To hydroxy-pyridine 19a (13.4 g, 101.2 mmol, Lancaster) suspended in DCE (200 mL) is added NBS (18.7 g, 105.2 mmol), which is then refluxed for 1 h. The solution is cooled to RT, filtered and the solid that is collected is rinsed with H$_2$O, DCM and dried to give bromo-pyridine 19b.

Step 2

Hydroxy-pyridine 19b (69 g, 0.32 mol) and bromoethyl acetate (64.9 g, 0.39 mol) are dissolved in DMF (500 mL) and heated at 70° C. for 18 h. The solution is cooled to RT, then water is added. The aqueous phase is extracted with EtOAc. The combined organic extracts are washed with H$_2$O, brine, dried (Na$_2$SO$_4$) and concentrated. The residue is purified by chromatography (0 to 10% EtOAc in petroleum ether) to provide ester 19c.

Step 3

To amine 19c (30 g, 0.100 mol) suspended in toluene (30 mL) is added ethylchloroformate (21.8 g, 0.200 mol), which is then refluxed for 18 h. The solvents are evaporated under vacuum and the residue is purified by chromatography (0 to 2% EtOAc in petroleum ether) to afford carbamate 19d.

Step 4

According to general procedure B, ester 19d (12 g, 32.3 mmol) is coverted to acid 19e.

Step 5

According to general procedure B, acid 19e (10.7 g, 31.2 mmol) is transformed to intermediate 19f wherein the purification is by addition of water and filtration.

Example 20

Preparation of Intermediate 20d

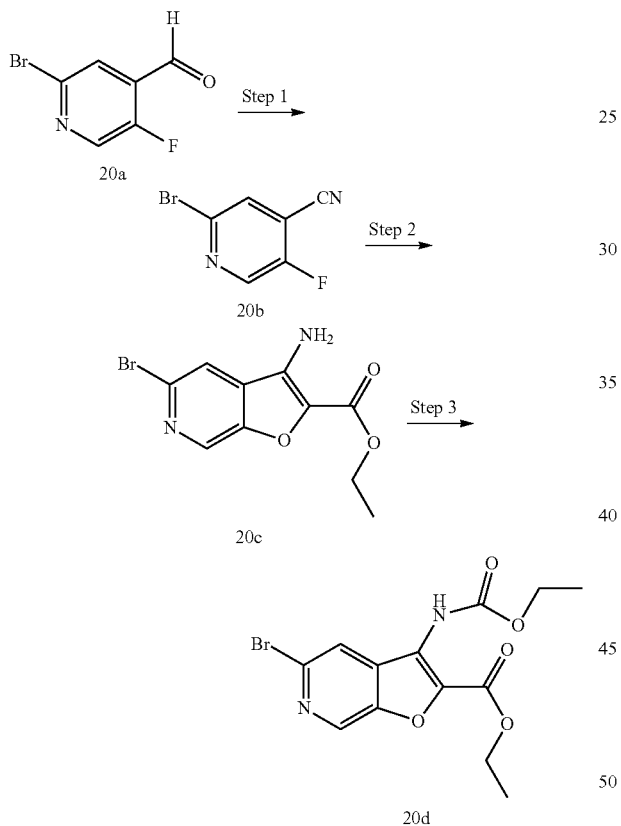

Step 1

To a solution of aldehyde 20a (100 g, 735 mmol, Frontier) in isopropyl alcohol (2000 mL) is added hydroxyl amine hydrochloride (204 g, 2941 mmol). The solution is heated to reflux for 2 h, then cooled to RT and the solvent is removed in vacuo. The residue is dissolved in EtOAc and the solution is washed with sodium bicarbonate solution. The organic layer is dried ($MgSO_4$) to obtain the corresponding oxime. Cyanuric chloride (180 g, 978 mmol) is added portionwise to DMF (1500 mL) at 0° C. while maintaining the temperature below 25° C. until cyanuric chloride completely consumed (~1 h). The obtained oxime is added to the solution of DMF at the same temperature and stirred for 1 h. The reaction mixture is quenched by adding water, extracted with EtOAc and washed with a $NaHCO_3$ solution and brine. The organic layer is dried ($MgSO_4$) and concentrated to give cyanide 20b.

Step 2

To a solution of ethyl glycolate (95 mL, 900 mmol) in MeCN (1500 mL) at 0° C. is added NaH (40 g, 1666 mmol) portionwise. The reaction mixture is stirred for 5 min, then fluoropyridine 20b (100 g, 500 mmol) is added. Stirring is continued for 1.5 h at 0° C. The mixture is quenched with ice water, diluted with HCl 10% and extracted with EtOAc. The organic layer is dried ($Na_2SO_4$) and concentrated to give crude 20c, which is used as such in the next step.

Step 3

Crude amine 20c (150 g, 526 mmol) is dissolved in a mixture of MeCN (230 mL) and toluene (1500 mL). Ethylchloroformate (259 mL, 2630 mmol) is added and the solution is refluxed for 18 h. The solvents are evaporated under vacuum. The residue is triturated in $Et_2O$/hexanes (10:1) and filtered to give intermediate 20d.

Example 21

Preparation of Intermediate 21f

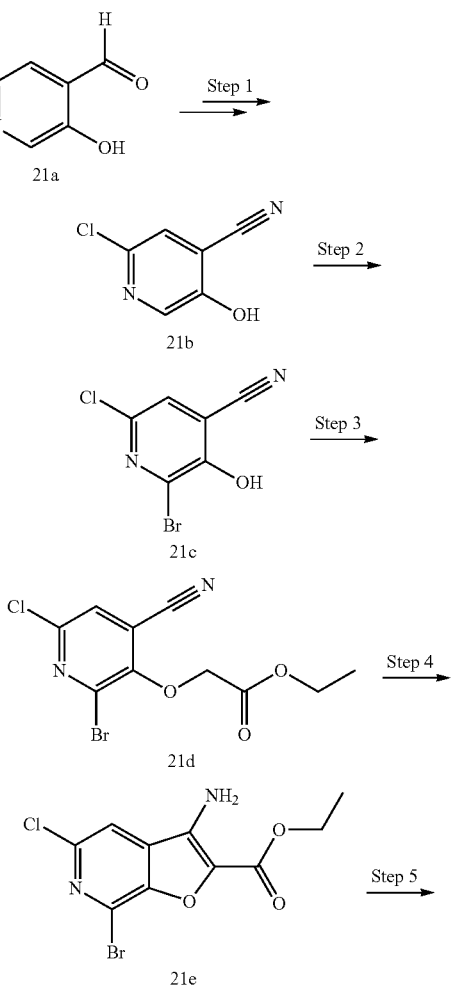

35

-continued

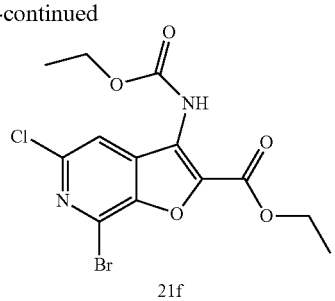

21f

Step 1

To a solution of aldehyde 21a (4.4 g, 27.9 mmol, Anichem) in isopropyl alcohol (180 mL) is added hydroxylamine hydrochloride (5.8 g, 83.8 mmol). The solution is heated to reflux for 1 h, then cooled to RT and the solvent is removed in vacuo. The residue is diluted with EtOAc, washed with sodium bicarbonate solution and dried ($Na_2SO_4$) to obtain the corresponding oxime. Cyanuric chloride (9.1 g, 49.3 mmol) is added portionwise to DMF (40 mL) at 0° C. while maintaining the temperature below 25° C. until cyanuric chloride completely consumed (~1 h). The obtained oxime is added to the solution of DMF at the same temperature and stirred for 1 h. The reaction mixture is quenched by adding water, extracted with EtOAc and washed with $NaHCO_3$ solution and brine. The organic layer is dried ($Na_2SO_4$) and concentrated to give cyanide 21b.

Step 2

Pyridine 21b (3.7 g, 23.9 mmol) is suspended in DCE (48 mL) and NBS (4.5 g, 25.1 mmol) is added. The reaction mixture is stirred at RT for 1 h, then concentrated to provide crude bromo-pyridine 21c, which is used as such in the next step.

Step 3

To a stirred solution of crude hydroxy-pyridine 21c (4.92 g, 21.1 mmol) in acetone is added potassium carbonate (4.36 g, 31.6 mmol) and ethyl bromoacetate (3.5 mL, 31.6 mmol). The mixture is refluxed for 1 h, then quenched with water and extracted with EtOAc. The combined organic layers are washed with brine, dried ($Na_2SO_4$), filtered and concentrated to provide crude ester 21d, which is used as such in the next step.

36

Step 4

To a stirred solution of crude ether 21d (6.7 g, 21.1 mmol) in DMF (12 mL) is added cesium carbonate (5.15 g, 15.8 mmol). The reaction mixture is heated to 70° C. for 1 h, then added to a stirring 1 M solution of HCl in water. The acidic aqueous layer is decanted and the residue is triturated in EtOAc and filtered. The filtrate is dried ($Na_2SO_4$), filtered and concentrated. The residue is suspended in EtOAc, then the solution is filtered to give 21e.

Step 5

To amine 21e (2.2 g, 6.89 mmol) dissolved in toluene (20 mL) is added ethylchloroformate (3.29 mL, 34.4 mmol). The solution is refluxed for 18 h, then cooled to RT and $Et_2O$ is added. The suspension is filtered and the residue is triturated with $Et_2O$ to give intermediate 21f.

Example 22

Preparation of Intermediate 22e

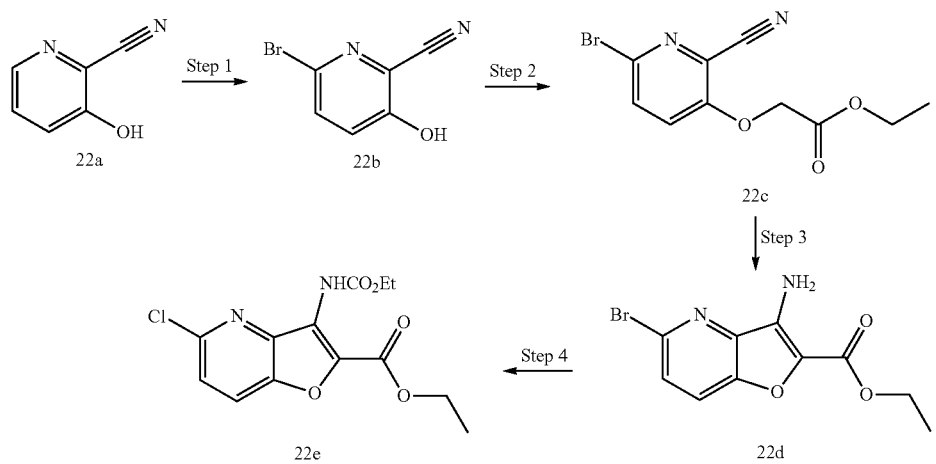

Step 1

To a mixture of pyridine 22a (42.0 g, 0.350 mol) in MeCN (800 mL) and $H_2O$ (160 mL) is added 1-bromo-pyrrolidine-2,5-dione (68 g, 0.385 mol) portionwise at 0° C. with stirring over 2 h. The solution is then stirred at 0° C. for 5 h. The solution is diluted with EtOAc (2000 mL), washed with water (1000 mL) and brine (1000 mL). The organic layer is separated, dried and concentrated to afford crude bromo-pyridine 22b.

Step 2

A mixture of crude hydroxy-pyridine 22b (30.0 g, 0.151 mol), bromo-acetic acid ethyl ester (16.9 ml, 0.151 mol) and $K_2CO_3$ (41.7 g, 0.301 mol) in acetone (1000 mL) is heated to reflux for 5 h. The mixture is cooled to RT, poured into water (800 mL) and extracted with EtOAc (500 mL×2). The combined organic layers are washed with brine, dried ($Na_2SO_4$). The solvent is evaporated and the residue is purified by column to afford ester 22c.

Step 3

To a mixture of sodium ethanolate (6 g, 0.088 mol) in EtOH (500 mL) is added ether 22c (25.0 g, 0.088 mol). The mixture is stirred for 3 h. The mixture is quenched by the addition of saturated $NH_4Cl$ (500 mL) in an ice bath and extracted with EtOAc (500 mL×2). The combined organic layers are washed with brine and dried ($Na_2SO_4$). The solvent is evaporated in vacuo to afford 22d.

Step 4

A solution of amine 22d (25.0 g, 0.088 mol) and ethylchloroformate (82.7 mL, 0.877 mol) in toluene (800.0 mL) and $Na_2CO_3$ (37.2 g, 0.351 mol) is heated to reflux overnight. The mixture is evaporated to dryness and the residue is recrystallized to afford intermediate 22e.

Example 23

Preparation of Compound 1001

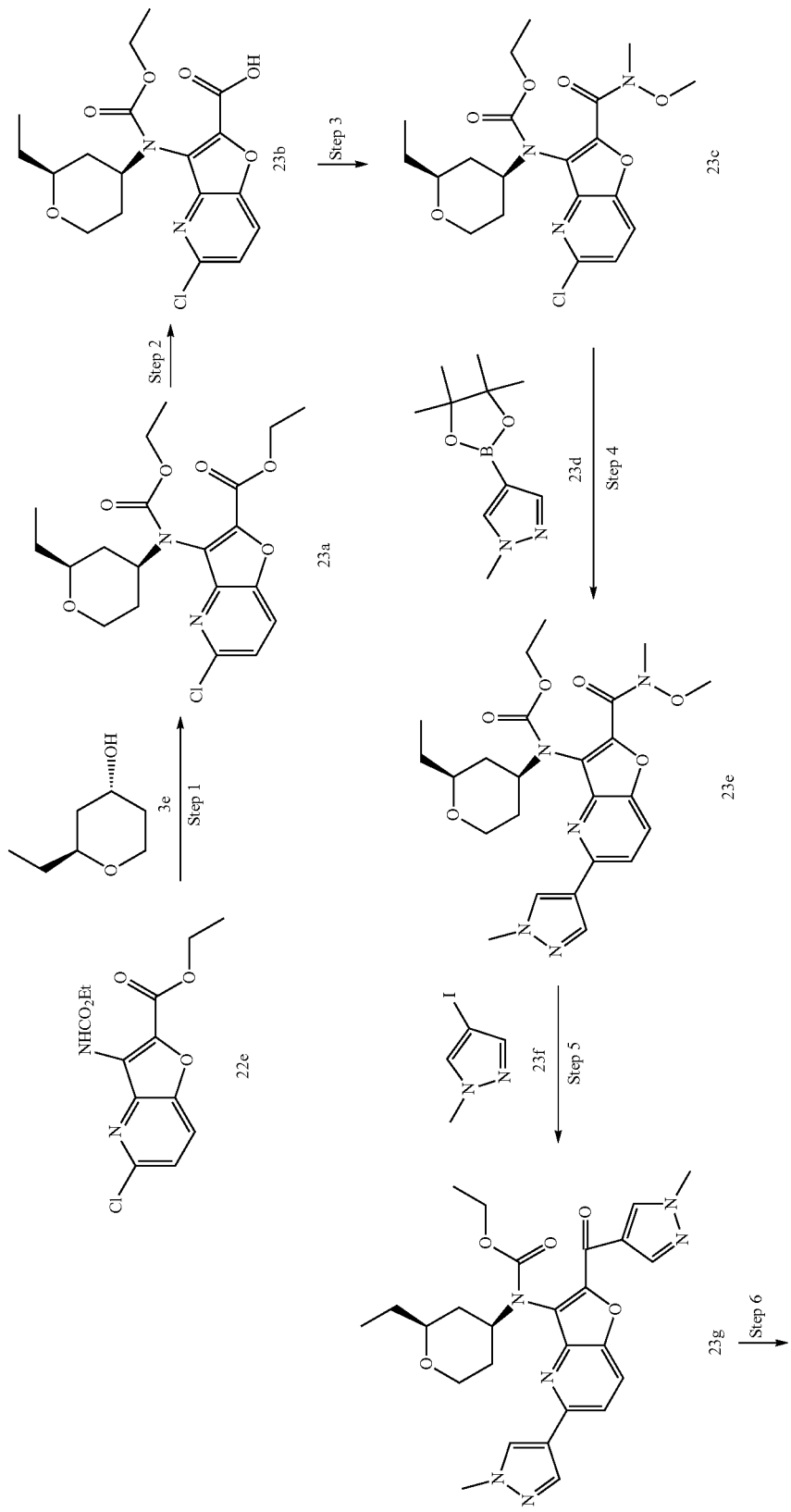

-continued
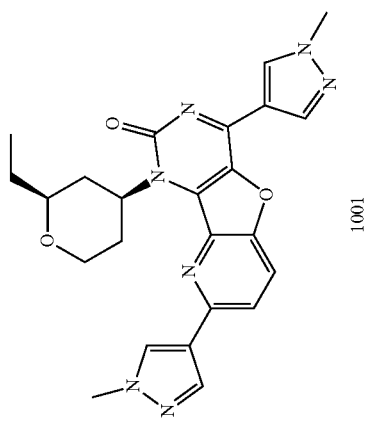
1001

Step 1

According to general procedure A, carbamate 22e (1.06 g, 4.1 mmol) is used with 3e to give 23a. Purification is by chromatography (10 to 60% EtOAc in hexanes).

Step 2

According to general procedure B, crude ester 23a (3.5 g) is used to give crude acid 23b.

Step 3

According to general procedure C, crude acid 23b (3.4 g) is used to give Weinreb amide 23c. Purification is by chromatography (60-100% EtOAc in hexanes).

Step 4

According to general procedure D1, arylchloride 23c (1.33 g, 3.0 mmol) is used with boronate ester 23d (Frontier) to give pyrazole 23e. Purification is by chromatography (50-100% EtOAc in hexanes).

Step 5

According to general procedure E, Weinreb amide 23e (642 mg, 1.32 mmol) is used with pyrazole 23f (Aldrich) to give ketone 23g. Purification is by chromatography (0-10% MeOH in DCM).

Step 6

According to general procedure F, ketone 23g (678 mg, 1.33 mmol) is used to give compound 1001. Purification is by precipitation and trituration.

Example 24

Preparation of Compound 1002

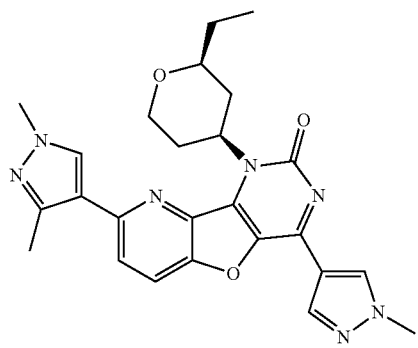 [SMILES: CC[C@H]1C[C@@H](n2c(=O)nc(-c3cnn(C)c3)c3oc4ccc(-c5cn(C)nc5C)nc4c32)CCO1]

Compound 1002 is prepared analogously to the procedure described in Example 23, with 24a replacing 23d in Step 4. Purification is by precipitation and trituration.

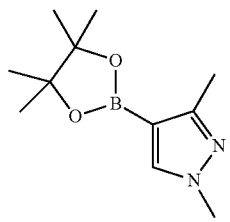

24a

Preparation of Intermediate 24a

Into a dry flask under $N_2$ is added dry diethyl ether (150 mL) and 1,3-dimethyl-4-bromopyrazole (5g, 28.6 mmol, Combi-Blocks). The mixture is cooled to −78° C. in a dry ice/acetone bath. To this solution is added t-BuLi (37 mL, 62.9 mmol, 1.7 M in pentane) over 5 min, which is allowed to stir for 30 min at −78° C. 2-isopropoxy-4,4,5,5-tetramethyl-1,3,2-dioxaborolane (6.4 mL, 31.4 mmol) is added in one portion via syringe. Stirring is continued at −78° C. for 15 min. The reaction mixture is allowed to warm to RT and is then stirred for 30 min. The reaction mixture is poured into saturated $NH_4Cl$, then extracted with EtOAc (3×). The combined organic layers are dried ($Na_2SO_4$), filtered and evaporated under reduced pressure. The residue is dissolved in hexanes (6 mL). The solvent is evaporated under reduced pressure and then dried under high vacuum for 48 h to provide boronate ester 24a.

Example 25

Preparation of Compound 1003

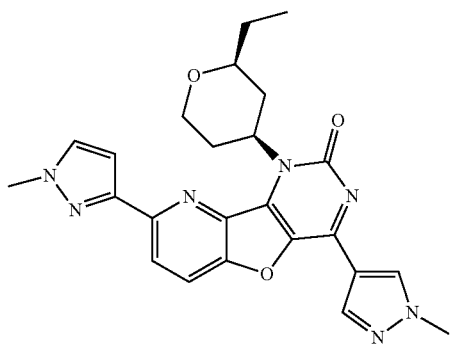

Compound 1003 is prepared analogously to the procedure described in Example 23, with 25a (Milestone) replacing 23d in Step 4. The residue is purified by preparative HPLC to provide compound 1003 as a TFA salt.

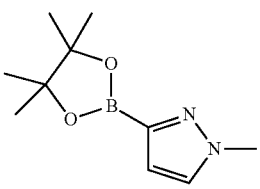

25a

Example 26

Preparation of Compound 1004

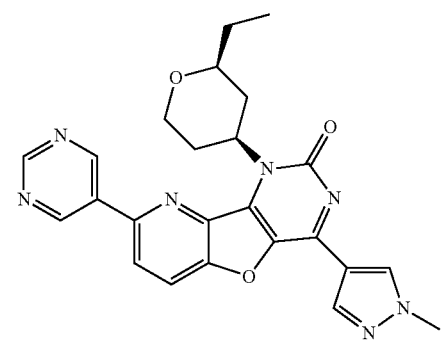

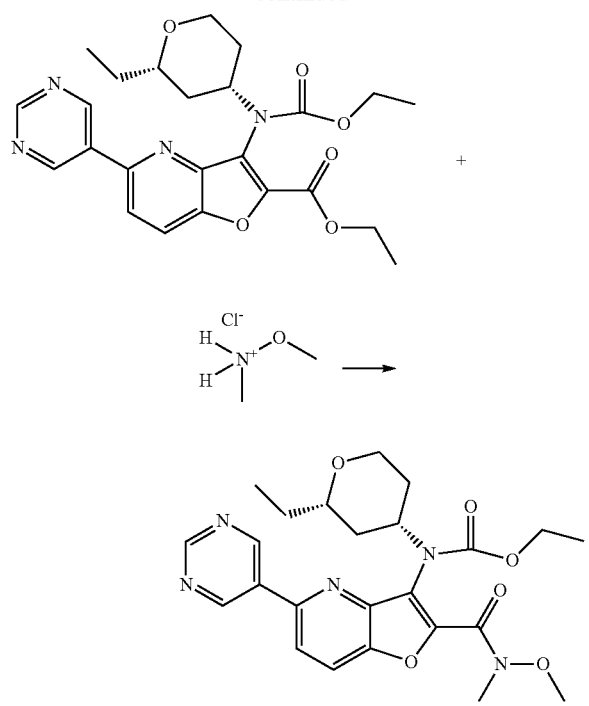

Compound 1003 is prepared analogously to the procedure described in Example 23 (Steps 1, 4, 5 and 6). The amide intermediate is prepared according to general protocol D3 replacing 23d with pyrimidine-5-boronic acid (Synthonix). The Weinreb amide is synthesized according to general procedure I and is elaborated to the final inhibitor according to Steps 5 and 6 of Example 23. The product is purified preparative HPLC. and isolated as aTFA salt.

Example 27

Preparation of Compound 1005

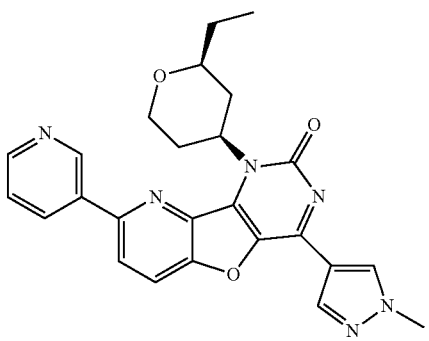 [SMILES: CC[C@H]1C[C@@H](n2c(=O)nc(-c3cnn(C)c3)c3oc4ccc(-c5cccnc5)nc4c32)CCO1]

Compound 1005 is prepared analogously to the procedure described in Example 26 Step 4 is performed according to the general procedure D3 replacing pyrimidine-5-boronic acid with 2-methylpyridine-5-boronic acid hydrate. The order of Steps 4 and 5 are inverted. The product is purified by preparative HPLC.

Example 28

Preparation of Compound 1006

Compound 1006 is prepared analogously to the procedure described in Example 26, wherein Step 4 is performed according to general procedure D3 by replacing pyrimidine-5-boronic acid with 3-pyridineboronic acid (Aldrich). The product is purified by preparative HPLC.

Example 29

Preparation of Compound 1007

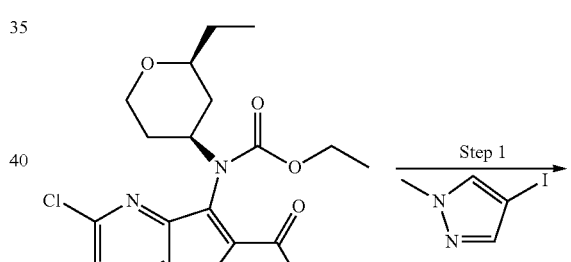

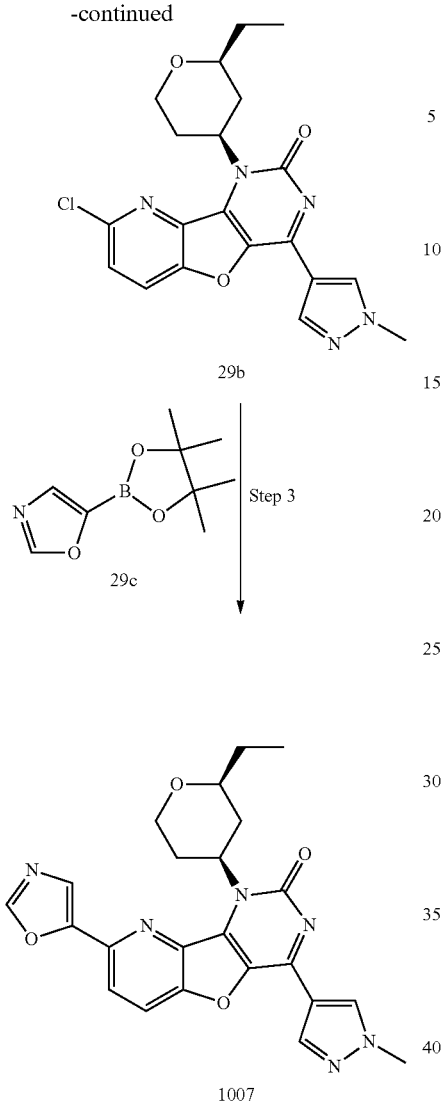

Step 1

According to general procedure E, Weinreb amide 23c (320 mg, 0.73 mmol) is used with pyrazole 23f to afford ketone 29a. Purification is by chromatography (0-6% MeOH in DCM).

Step 2

According to general procedure F, ketone 29a (75 mg, 0.16 mmol) is transformed to arylchloride 29b wherein the purification is performed by precipitation and trituration. The crude arylchloride 29b is used as such without further purification.

Step 3

According to general procedure D3, crude arylchloride 29b (31 mg, 0.08 mmol) is transformed to compound 1007. The product is purified by preparative HPLC and isolated as its TFA salt.

Example 30

Preparation of Compound 1008

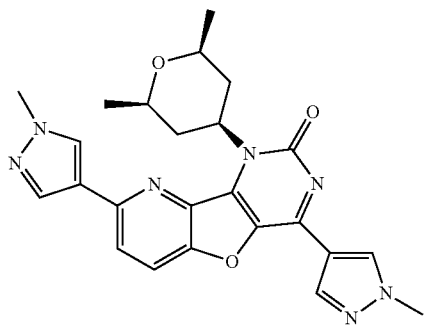 [SMILES: C[C@@H]1C[C@H](n2c(=O)nc(-c3cnn(C)c3)c3oc4ccc(-c5cnn(C)c5)nc4c32)C[C@H](C)O1]

Compound 1008 is prepared analogously to the procedure described in Example 23, replacing 3e with 5a in Step 1. The ester obtained is converted directly to the ketone according to General Procedure E using 1-methyl-4-bromopyrazole (Aldrich). Compound 1008 is obtained after purification by preparative HPLC and conversion to its methanesulfonic acid salt according to General Procedure K.

Example 31

Preparation of Compound 1009

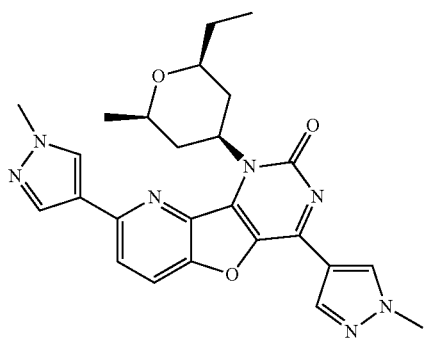 [SMILES: CC[C@H]1C[C@@H](n2c(=O)nc(-c3cnn(C)c3)c3oc4ccc(-c5cnn(C)c5)nc4c32)C[C@@H](C)O1]

Compound 1009 is prepared analogously to the procedure described in Example 23, replacing 3e with 6a. The ester obtained is converted directly to the ketone according to General Procedure E using 1-methyl-4-bromopyrazole (Aldrich). Compound 1009 is obtained after purification by preparative HPLC and conversion to its methanesulfonic acid salt according to General Procedure K.

Example 32

Preparation of Compound 1010

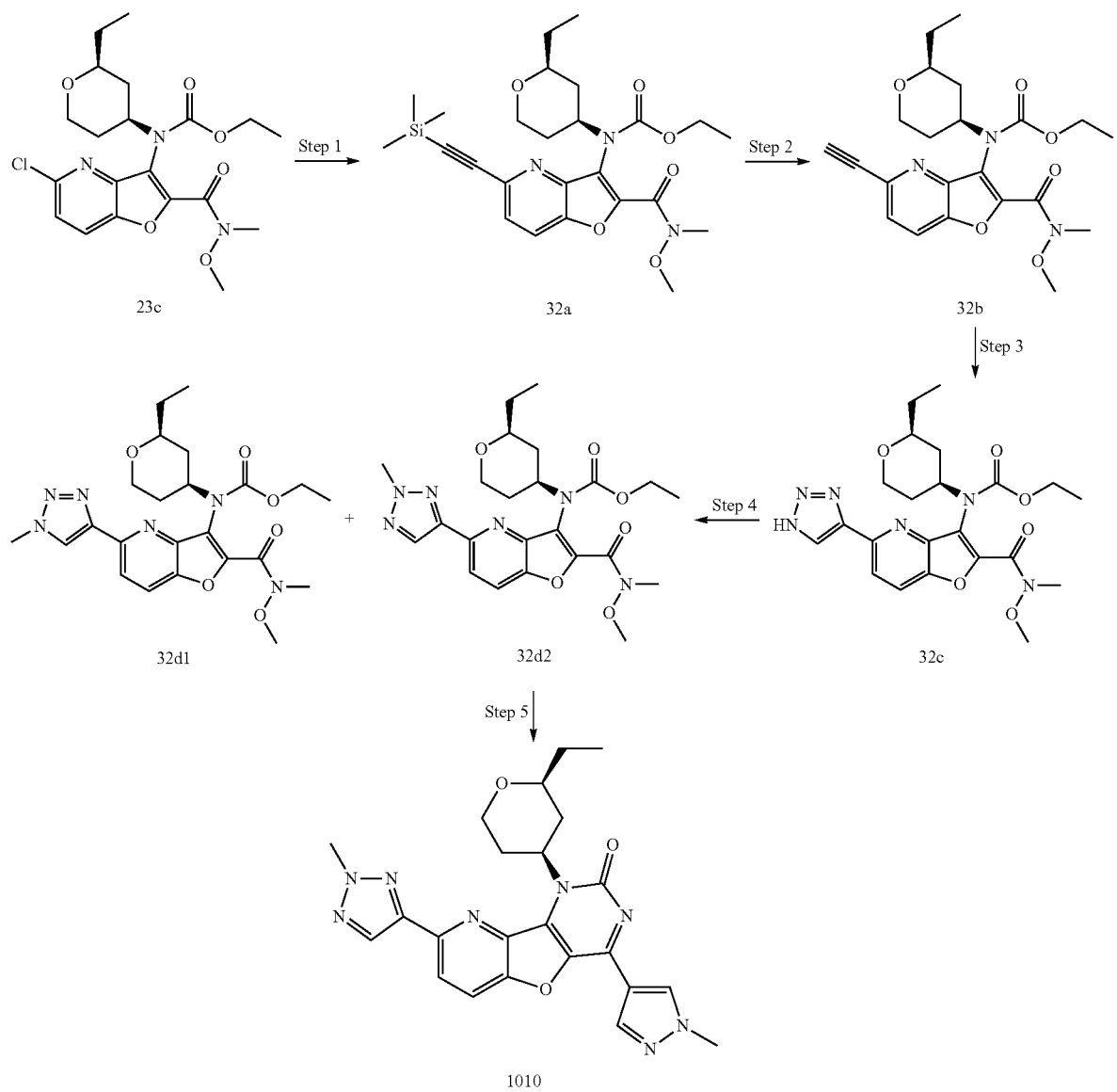

Step 1

A solution of arylchloride 23c (783 mg, 1.78 mmol) in DMF (20 mL) is degassed by bubbling argon for 15 min. Diethylamine (0.921 mL, 8.9 mmol) and TMS-acetylene (1.5 mL, 10.7 mmol) are added followed by CuI (68 mg, 0.36 mmol) and trans-dichlorobis(triphenylphosphine)palladium (II) (Strem, 250 mg, 0.36 mmol). Argon is bubbled for 5 min, then the system is sealed and heated to 115° C. for 3.5 h. The reaction mixture is allowed to cool to RT, then poured into EtOAc and washed with water. The organic extracts are washed with brine, dried ($Na_2SO_4$), filtered and concentrated. Purification by chromatography (60-80% EtOAc in hexanes) affords silyl-acetylene 32a.

Step 2

Silyl-acetylene 32a (600 mg, 1.2 mmol) is dissolved in MeOH (15 mL) and treated with potassium carbonate (33 mg, 0.24 mmol). After 15 min at RT, the mixture is concentrated, diluted with EtOAc and successively washed with water and brine. The organic extracts are dried ($Na_2SO_4$), filtered and concentrated. Purification by chromatography (30-80% EtOAc in hexanes) affords acetylene 32b.

Step 3

Acetylene 32b (375 mg, 0.87 mmol) and sodium azide (113 mg, 1.75 mmol) are suspended in $H_2O$ (5 mL)/tBuOH (5 mL) and copper (42 mg, 0.66 mmol) and 1M solution of $CuSO_4$ (0.17 mL, 0.18 mmol) are added. The solution is heated in the microwave (120° C., 20 min), then diluted with EtOAc and water. Brine is added and the aqueous layer is extracted with EtOAc. The combined organic layers are washed with brine, dried ($Na_2SO_4$), filtered and concentrated to afford crude triazole 32c, which is used as such for the next step.

Step 4

To a solution of crude triazole 32c (361 mg, 0.76 mmol) in acetone (15 mL), is added MeI (0.48 mL, 7.6 mmoL) followed by Cs$_2$CO$_3$ (622 mg, 1.9 mmol). The reaction mixture is heated at 60° C. for 1 h, then silica gel is added. The solvent is removed and the residue is purified by chromatography (60-100% EtOAc in hexanes) to afford triazoles 32d1 and 32d2.

Step 5

Weinreb amide 32d2 is converted to compound 1010 analogously to the procedure described in Example 23, Steps 5 and 6. Purification is by precipitation and trituration.

Example 33

Preparation of Compound 1011

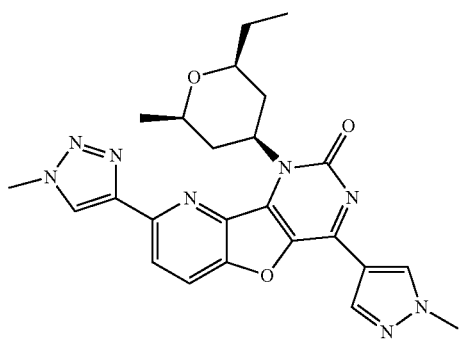

Compound 1011 is prepared analogously to the procedure described in Example 32 replacing 3e with 5a in the preparation of the starting material in Step 1 and the regioisomer analogous to 32d1 is elaborated and cyclized to the final product. The product is purified by precipitation and trituration.

Example 34

Preparation of Compound 1012

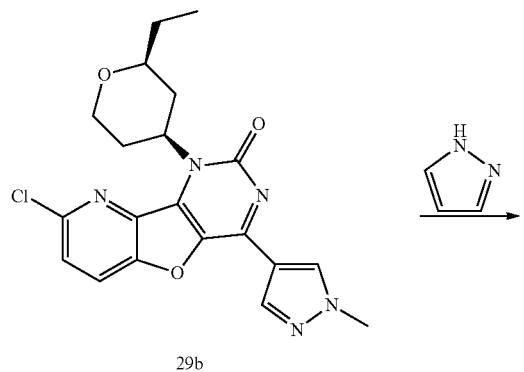
29b

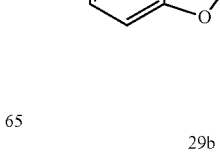

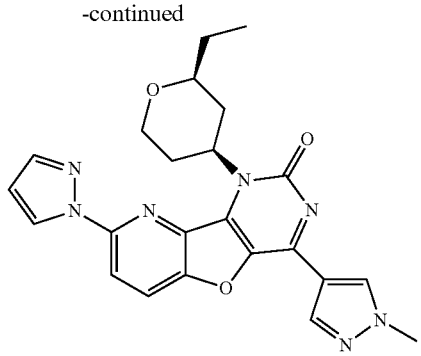
1012

To a solution of chloropyridine 29b (50 mg, 0.12 mmol) in DMF (0.5 mL) is added pyrazole (Aldrich, 49 mg, 0.73 mmol) followed by K$_2$CO$_3$ (50 mg, 0.36 mmol). The mixture is heated in the microwave at 140° C. for 40 min, and then water is added. The solid is filtered and triturated with Et$_2$O and EtOAc. The residue is purified by trituration to obtain compound 1012.

Example 35

Preparation of Compound 1013

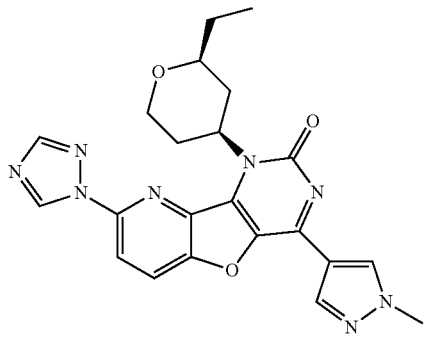 [SMILES: CC[C@H]1C[C@@H](n2c(=O)nc(-c3cnn(C)c3)c3oc4ccc(-n5cncn5)nc4c32)CCO1]

Compound 1013 is prepared analogously to the procedure described in Example 34, replacing pyrazole with 1,2,4-triazole (Aldrich). Purification is by precipitation and trituration.

Example 35a

Preparation of Compound 1014

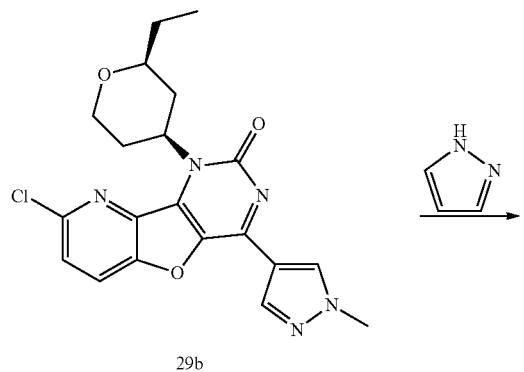
29b

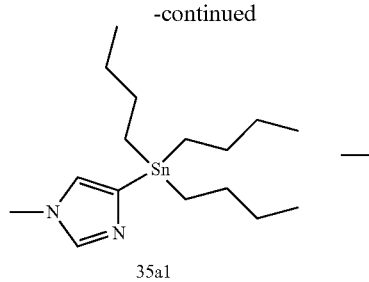

35a1

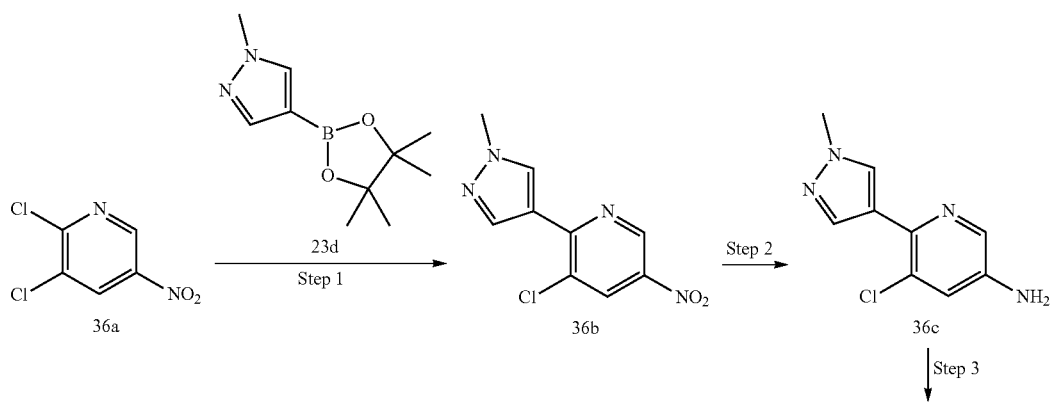

1014

To a solution of 29b (100 mg, 0.242 mmol) and stannane 35a1 (119 μL, 0.362 mmol, Aldrich) in DMF (1.4 mL) is added Pd(dppf)Cl$_2$-DCM complex (9.9 mg, 0.012 mmol). The mixture is heated in the microwave (120° C., 20 min.), then the solution is diluted with DCM (20 mL). The organic phase is washed with H$_2$O (50 mL) (filtered over celite to remove suspension), brine (50 mL), dried (MgSO$_4$) and concentrated. The crude product is purified by preparative HPLC. The fractions containing the product are concentrated to remove acetonitrile and treated with saturated aqueous NaHCO$_3$ (100 mL). The aqueous phase is extracted with DCM (2× 150 mL). The combined organic phases are dried (MgSO$_4$), filtered and evaporated to obtain compound 1014.

Example 36

Preparation of Compound 1015

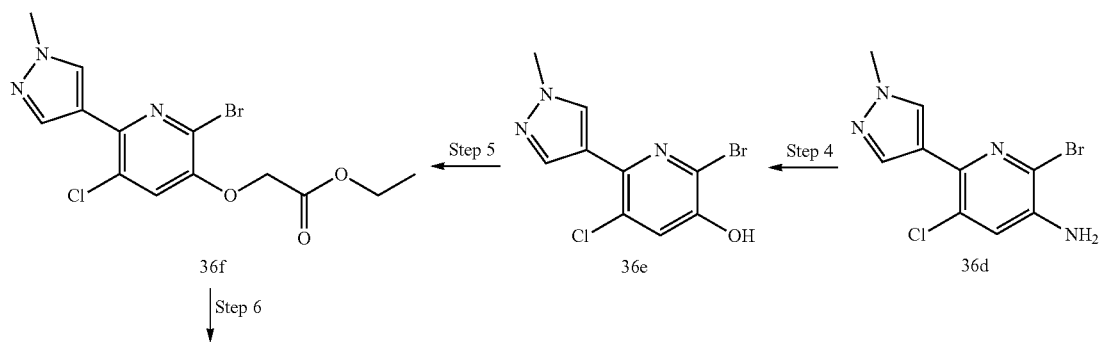

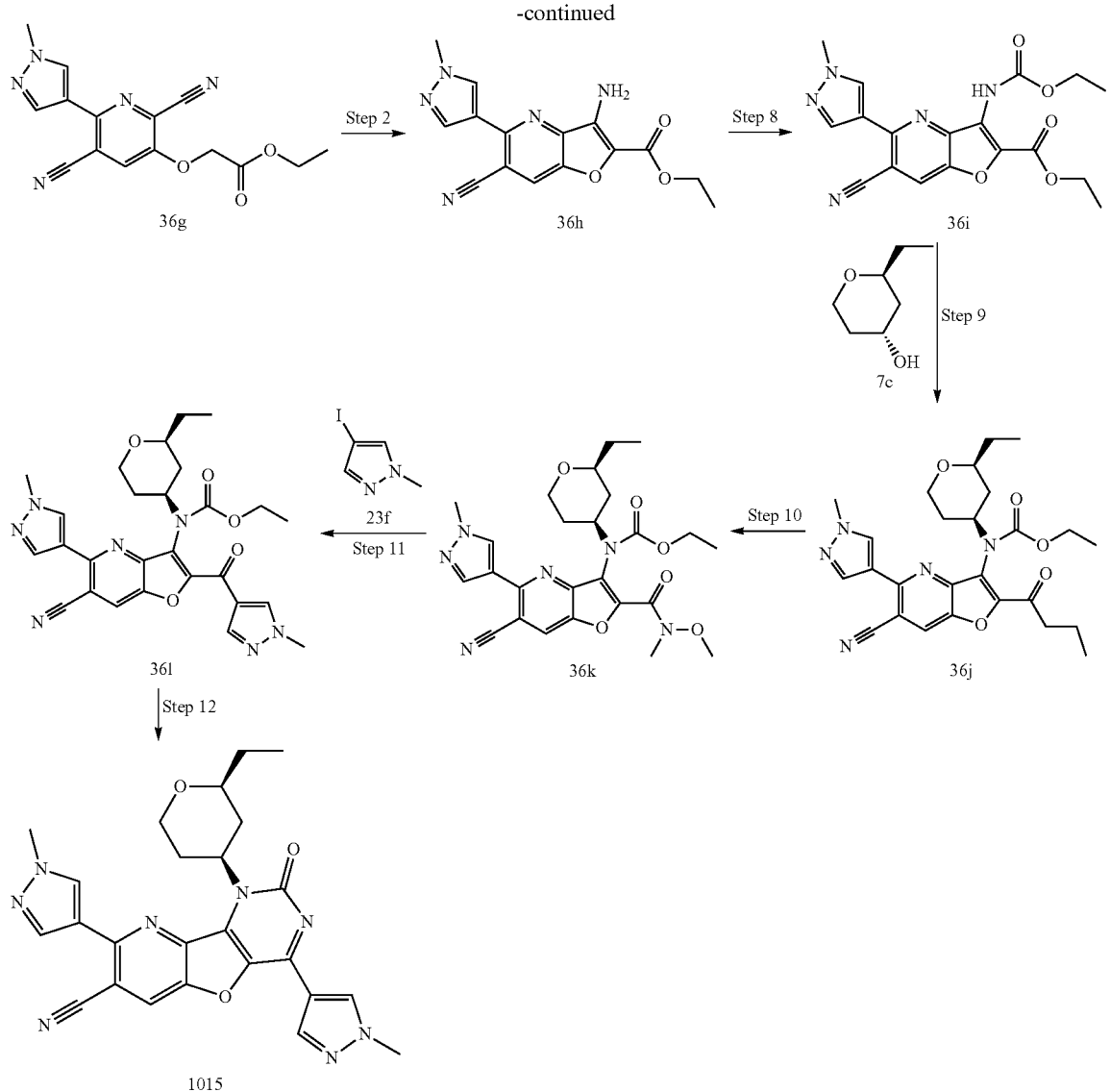

Step 1

A mixture of chloropyridine 36a (150 g, 0.78 mol), 23d (177.9 g, 0.855 mol), Pd(dppf)Cl$_2$ (17 g, 0.023 mol) and Na$_2$CO$_3$ (972 mL, 1.943 mol) in MeCN (1200 mL) is heated to 80° C. overnight. The mixture is poured into H$_2$O (1500 mL) and extracted with EtOAc (500 mL×2). The combined organic layers are washed with brine and dried (Na$_2$SO$_4$). The solvent is evaporated in vacuo to afford pyrazole 36b.

Step 2

Fe (533 g, 9.56 mol) is added to a solution of nitropyridine 36b (570 g, 2.39 mol) in acetic acid (1000 mL). The mixture is kept at RT overnight, and then EtOAc is added. The mixture is filtered and the filtrate is washed with water and brine and dried (Na$_2$SO$_4$). The organic layer is evaporated in vacuo and the residue is purified by chromatography to afford aminopyridine 36c.

Step 3

To a solution of pyridine 36c (280 g, 1.342 mol) in acetic acid (2400 mL) is added Br$_2$ (362 g, 2.01 mol) dropwise at RT for 1.5 h. The mixture is neutralized with NaOH (10 N) and Na$_2$CO$_3$. The mixture is extracted with DCM. The organic phase is dried (Na$_2$SO$_4$) and evaporated to afford bromopyridine 36d.

Step 4

Aminopyridine 36d (226 g, 0.79 mol) is dissolved in H$_2$SO$_4$ (1850 g, 18.86 mol) and H$_2$O (439 g, 24.37 mol). The mixture is cooled to 0° C. and then treated with NaNO$_2$ (65.07 g, 0.94 mol) at 0° C. The temperature is gradually increased to RT, stirred for 1 h, then the solution is heated to 80° C. for 1.5 h. The solution is cooled to 0° C. and then neutralized with NaOH (10 N) until approximately pH=9. The solution is mildly acidified back to pH 6 with sodium dihydrogen phosphate. The solid is filtered under suction, collected and dried under high vacuum to afford crude hydroxypyridine 36e.

Step 5

A solution of hydroxypyridine 36e (152 g, 0.527 mol), ethylbromoacetate (141 g, 0.843 mol) and Na$_2$CO$_3$ (184.3 g, 1.738 mol) in acetone (2000 mL) is refluxed for 6 h. The aqueous phase is extracted with DCM. The combined organic extracts are washed with brine, dried over Na$_2$SO$_4$ and concentrated in vacuo. Purification by chromatography (1-50% EtOAc in petroleum ether) yields ester 36f.

Step 6

Halopyridine 36f (167.4 g, 0.45 mol), Zn(CN)$_2$ (115.4 g, 0.983 mol) and dppf (19.8 g, 0.036 mol) is added to DMF (700 mL). The mixture is purged with N$_2$ and then Pd$_2$dba$_3$ (16.4 g, 0.018 mol) is added. The reaction mixture is heated at 130° C. for 12 h. Water is added to the reaction mixture. A precipitate is formed that is extracted with EtOAc. The organic layers are combined and washed with brine, dried (Na$_2$SO$_4$), filtered and evaporated in vacuo. The residue is purified by chromatography (1-50% EtOAc in petroleum ether) to yield nitrile 36g.

Step 7

Ether 36g (58 g, 0.186 mol) is dissolved in DMF (130 mL), and then Cs$_2$CO$_3$ (32 g, 0.099 mol) is added. The mixture is heated to 60° C. under vigorous stirring for 1.5 h, cooled and water is added to the solvent. The solid is filtered and washed with water. The water phase is extracted with EtOAc. The organic later is washed with water, dried (Na$_2$SO$_4$), filtered and evaporated in vacuo to afford 36h.

Step 8

Amine 36h (20 g, 0.064 mol) in toluene (260 mL) and MeCN (130 mL) is treated with ethylchlorformate (139 g, 1.285 mol). The reaction mixture is heated to reflux overnight, then cooled to 0° C. The residue is filtered, washed with MeOH and dried under high vacuum to afford carbamate 36i.

Step 9

According to general procedure A, carbamate 36i (9.8 g, 75.3 mmol) is used with 7c to afford 36j after purification by chromatography (20 to 100% EtOAc in hexanes).

Step 10

According to general procedure I, ester 36j (5.7 g) is used to afford the Weinreb amide 36k.

Step 11

According to general procedure E, Weinreb amide 36k (1.87 g, 3.66 mmol) is used with pyrazole 23f to give ketone 36l after purification by chromatography (50-100% EtOAc in hexanes).

Step 12

A mixture of ketone 36l (5 g, 9.4 mmol) and ammonium acetate (47 g, 611 mmol) in NMP (36 mL) is degassed with nitrogen for 10 min then warmed to 130° C. NH$_3$ gas is then bubbled through the system for 45 min. The mixture is quenched with water (400 mL) and DCM (500 mL). The water layer is further extracted with DCM (2×150 mL). The combined DCM layers are washed with water (300 mL×2), brine and dried (Na$_2$SO$_4$). The mixture is concentrated. Treatment with activated charcoal (SX-Ultra) and trituration with DCM affords compound 1015.

Example 37

Preparation of Compound 1016

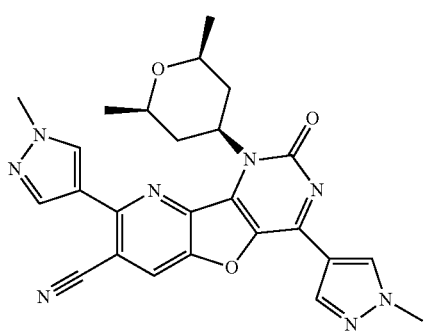 [SMILES: C[C@@H]1C[C@H](n2c(=O)nc(-c3cnn(C)c3)c3oc4cc(C#N)c(-c5cnn(C)c5)nc4c32)C[C@H](C)O1]

Compound 1016 is prepared analogously to the procedure described in Example 36, replacing 7c with 5a in Step 9. Step 12 is performed analogously to the procedure described in general procedure F wherein the ketone (165 mg, 0.31 mmol) is used to give compound 1016 after purification by preparative HPLC.

Example 38

Preparation of Compound 1017

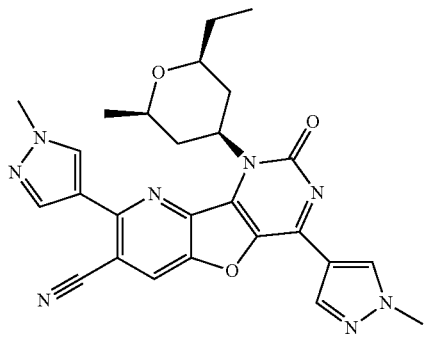 [SMILES: CC[C@H]1C[C@@H](n2c(=O)nc(-c3cnn(C)c3)c3oc4cc(C#N)c(-c5cnn(C)c5)nc4c32)C[C@@H](C)O1]

Compound 1017 is prepared analogously to the procedure described in Example 37, replacing 5a with 6a in Step 9. Purification is by preparative HPLC.

Example 39

Preparation of Compound 1018

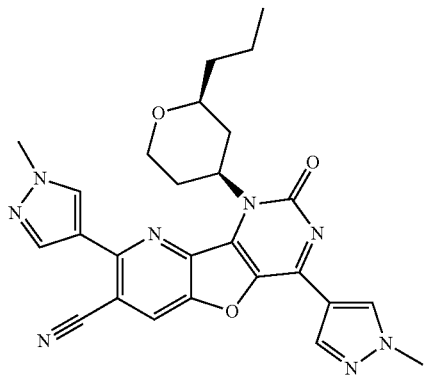 [SMILES: CCC[C@H]1C[C@@H](n2c(=O)nc(-c3cnn(C)c3)c3oc4cc(C#N)c(-c5cnn(C)c5)nc4c32)CCO1]

Compound 1018 is prepared analogously to the procedure described in Example 37, replacing 5a with 8a in Step 9. Step 10 is omitted and the pyrazole is added directly on the ester at Step 11. Purification is by trituration.

Example 40

Preparation of Compound 1019

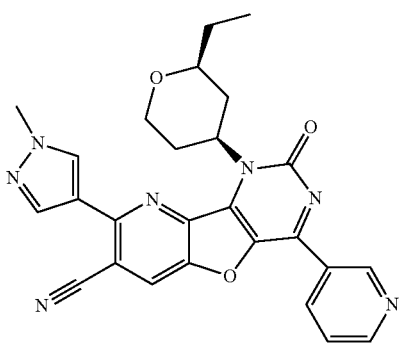 [SMILES: CC[C@H]1C[C@@H](n2c(=O)nc(-c3cccnc3)c3oc4cc(C#N)c(-c5cnn(C)c5)nc4c32)CCO1]

Compound 1019 is prepared analogously to the procedure described in Example 36, replacing pyrazole 23f with 3-iodopyridine (Aldrich) in Step 11. Step 10 is omitted and the pyridine is added directly on the ester at Step 11. Purification is by preparative HPLC.

Example 41

Preparation of Compound 1020

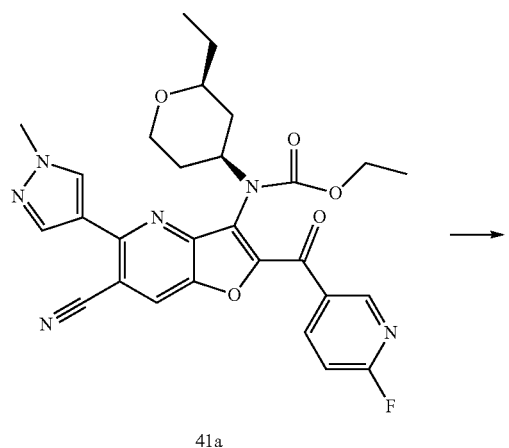

41a

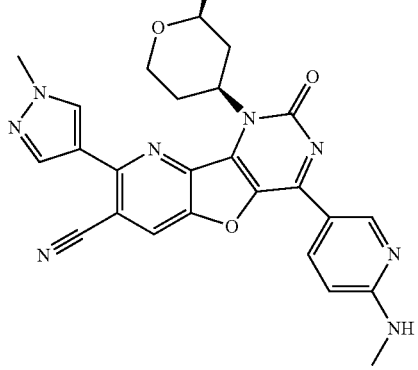

1020

A solution of fluoropyridine 41a (prepared analogously to the procedure described in Example 40, replacing pyrazole 23f with 5-bromo-2-fluoropyridine 41 b (Matrix) in Step 11) (140 mg, 0.26 mmol) in DMSO (1 mL) and methylamine solution (2M in THF, 0.38 mL, 0.77 mmol) in THF for 45 min. Ammonium acetate (400 mg, 5.2 mmol) is added, then the solution is heated to 135° C. Purification by preparative HPLC affords compound 1020.

Example 42

Preparation of Compound 1021

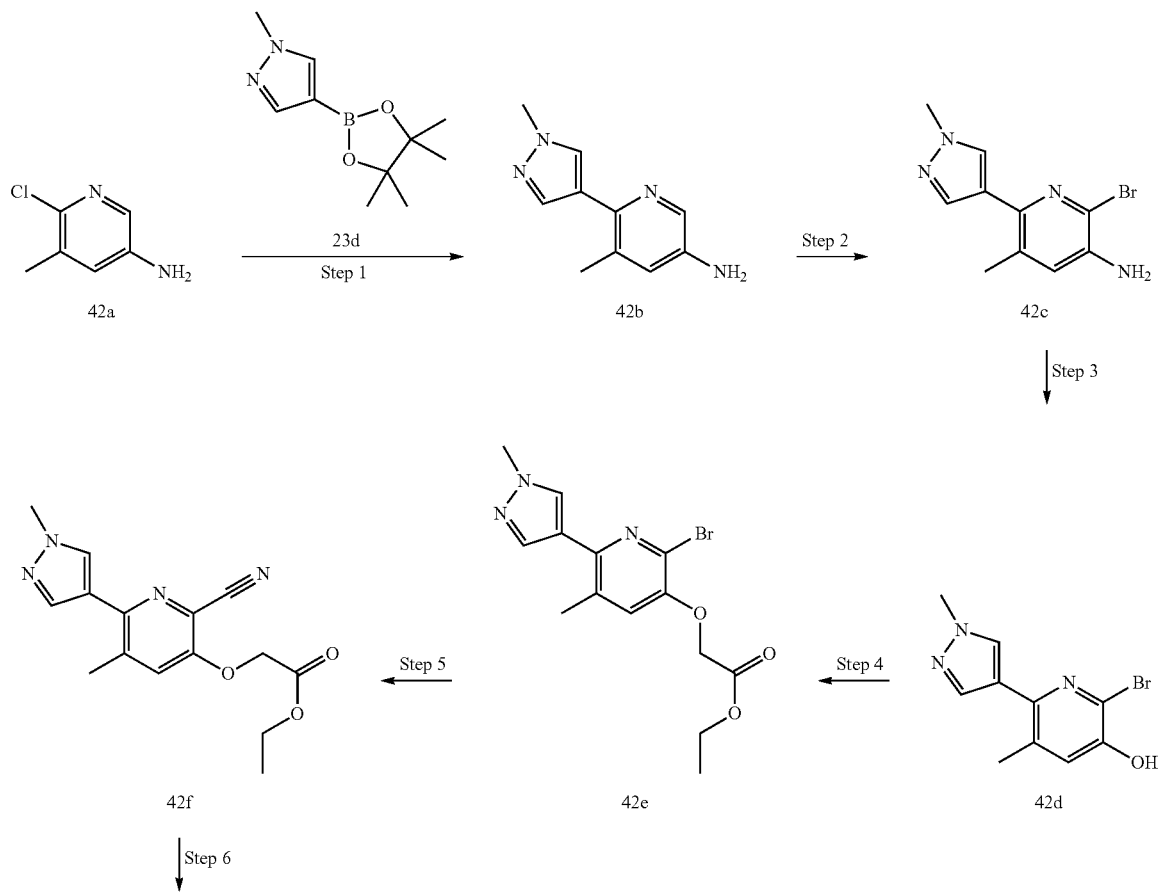

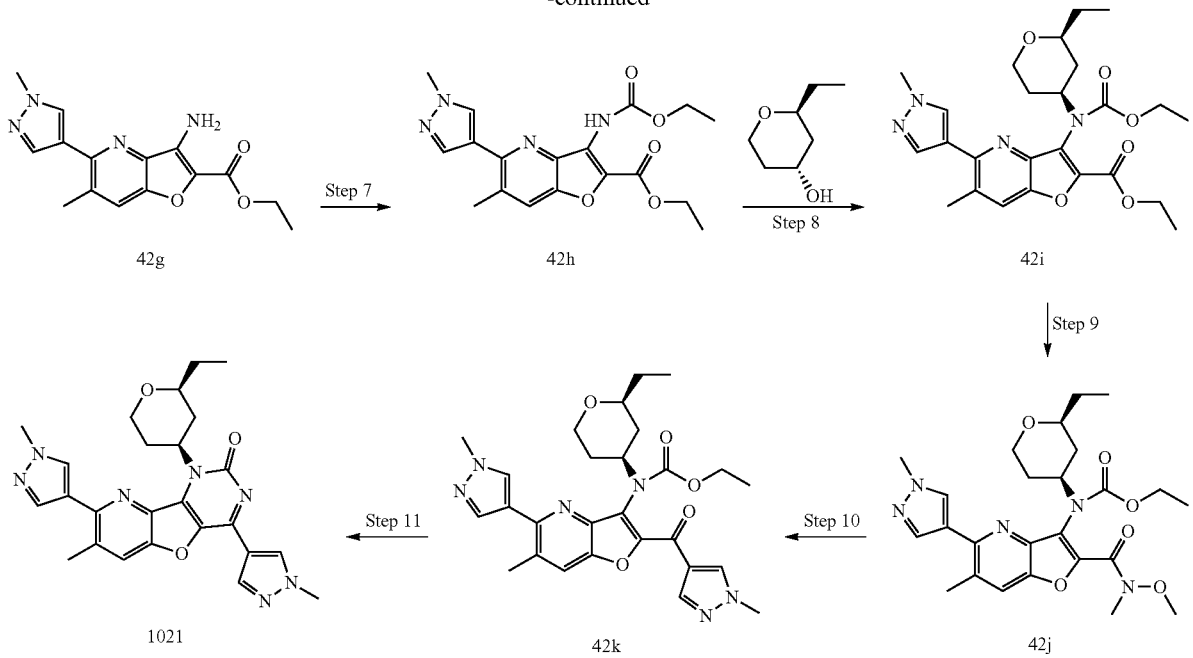

Step 1

Chloropyridine 42a (Parkway, 2.8 g, 19.6 mmol), boronate ester 23d (5g, 24 mmol), S-Phos (400 mg, 0.97 mmol) and palladium acetate (108 mg, 0.48 mmol) are mixed in a round bottom flask. MeCN and a sodium carbonate solution (2 M in water, 40 mL, 81 mmol) are added. Argon is bubbled through the solution for 5 min. The reaction mixture is stirred and heated at 100° C. for 24 h, and then cooled to RT. NaHCO$_3$ (saturated) is added and the mixture is extracted with EtOAc. The organic phase is washed with brine, dried (Na$_2$SO$_4$), filtered and evaporated. Purification by chromatography (0% to 10% MeOH in DCM) affords pyrazole 42b.

Step 2

To a suspension of aminopyridine 42b (3.1g, 16.5 mmol) in acetic acid (20 mL) is added bromine (1.3 ml, 24.7 mmol) dropwise with vigorous magnetic stirring. The mixture is stirred at RT for 2 h, neutralized with sodium bicarbonate (aqueous, saturated+solid) and extracted with EtOAc. The organic phase is evaporated without any drying to afford 42c, which is used as such for the next step.

Step 3

Aniline 42c (4.8g, 18 mmol) is suspended in sulfuric acid (23 mL) and then water (10 mL) is added. The suspension is sonicated and cooled to 0° C., then treated with solid NaNO$_2$ at 0° C. The temperature is gradually increased to RT, then the mixture is stirred for 1 h. The solution is heated to 80° C. for 1.5 h and then cooled to 0° C. The mixture is neutralized with NaHCO$_3$, extracted with EtOAc, washed with brine, dried (Na$_2$SO$_4$), filtered and evaporated to afford hydroxy-pyridine 42d, which is used as such for the next step.

Step 4

A solution of hydroxy-pyridine 42d (1.5g, 5.6 mmol), ethylbromoacetate (0.95 mL, 8.4 mmol) and Na$_2$CO$_3$ (0.93 mg, 8.8 mmol) is refluxed (75° C.) in acetone (35 mL) for 6 h. The solution is concentrated, then diluted with H$_2$O/DCM. The aqueous phase is extracted with DCM. The combined organic extracts are washed with brine, dried (MgSO$_4$) and concentrated. Purification by chromatography (20-100% EtOAc in hexanes) afford affords ester 42e.

Step 5

A microwave vessel is charged with bromopyridine 42e (911 mg, 2.6 mmol), Zn(CN)$_2$ (393 mg, 3.34 mmol), 1,1'-bis (diphenylphosphino)ferrocene (143 mg, 0.26 mmol) and DMF (10 mL). The solution is then purged with Ar and sonicated prior to the addition of tris(dibenzylideneacetone) dipalladium (118 mg, 0.13 mmol). The mixture is heated at 130° C. for 30 min in a microwave. Water is added and the mixture is extracted with DCM. The organic extracts are washed with brine, dried (MgSO$_4$), filtered, and evaporated to afford cyanopyridine 42f, which is used as such for the next step.

Step 6

Cyanopyridine 42f (655 mg, 2.18 mmol) is dissolved in DMF (3.5 mL), and cesium carbonate (355 mg, 1.1 mmol) is added. The mixture is heated to 60° C. under vigorous stirring for 1.5 h. Citric acid (10% in water) is added then the mixture is extracted with DCM (3×). The organic extracts are washed with brine, dried (MgSO$_4$), filtered and evaporated to afford 42g, which is used as such for the next step.

Step 7

A suspension of amine 42g (544 mg, 1.8 mmol) in toluene (15 mL) and MeCN (3 mL) is treated with ethyl chloroformate (4.15 mL, 44 mmol) and potassium carbonate (2.5g, 18 mmol). The reaction mixture is stirred at 110° C. overnight. The solution is then cooled to RT. Water is added, followed by EtOAc. The organic layer is separated, washed with brine, dried (MgSO$_4$), filtered. Silica is added and dry packed. Purification by chromatography (10-100% EtOAc in hexanes) affords 42h.

Step 8

According to general procedure A, carbamate 42h (350 mg, 0.94 mmol) is used with alcohol 3e to give 42i after purification by chromatography (10 to 100% EtOAc in hexanes).

63

Step 9

According to general procedure B, ester 42i (344 mg, 0.71) is used to give an acid intermediate, which is treated according to general procedure C, to provide Weinrib amide 42j. Purification is by chromatography (20-100% EtOAc in hexanes).

Step 10

According to general procedure E, amide 42j (150 mg, 0.3 mmol) is used with pyrazole 23f to give ketone 42k. Purification is by chromatography (0-10% MeOH in DCM).

Step 11

According to general procedure F, ketone 42k (120 mg, 0.231 mmol) is used to afford compound 1021. Purification is by precipitation and trituration.

Example 43

Preparation of Compound 1022

64

Step 1

Bromopyridine 36f is dissolved in DMF (59 mL) then CuCN (2.6 g, 29 mmol) is added. The reaction mixture is heated to 140° C. for 2 h and then cooled to RT. The reaction mixture is taken up in a solution of 4:1:3 (NH$_4$Cl (aqueous, saturated):30% NH$_4$OH:water (540 mL)) and stirred for 10 min. The residue is filtered, washed with water and ether to afford nitrile 43a.

Step 2

Ether 43a (4.1 g, 12.8 mmol) is dissolved in anhydrous DMF (23 mL) then cesium carbonate (2g, 6.4 mmol) is added. The mixture is heated to 60° C. and stirred for 1.5 h, then cooled to RT and 10% citric acid is added. The product is extracted with DCM (3×). The combined organic layers are washed with brine, dried (MgSO$_4$) and concentrated to afford aryl 43b, which is used as such for the next step.

Step 3

A suspension of amine 43b (3.4 g, 10.6 mmol) in toluene (30 mL) and MeCN (10 mL) is treated with ethyl chlorofor-

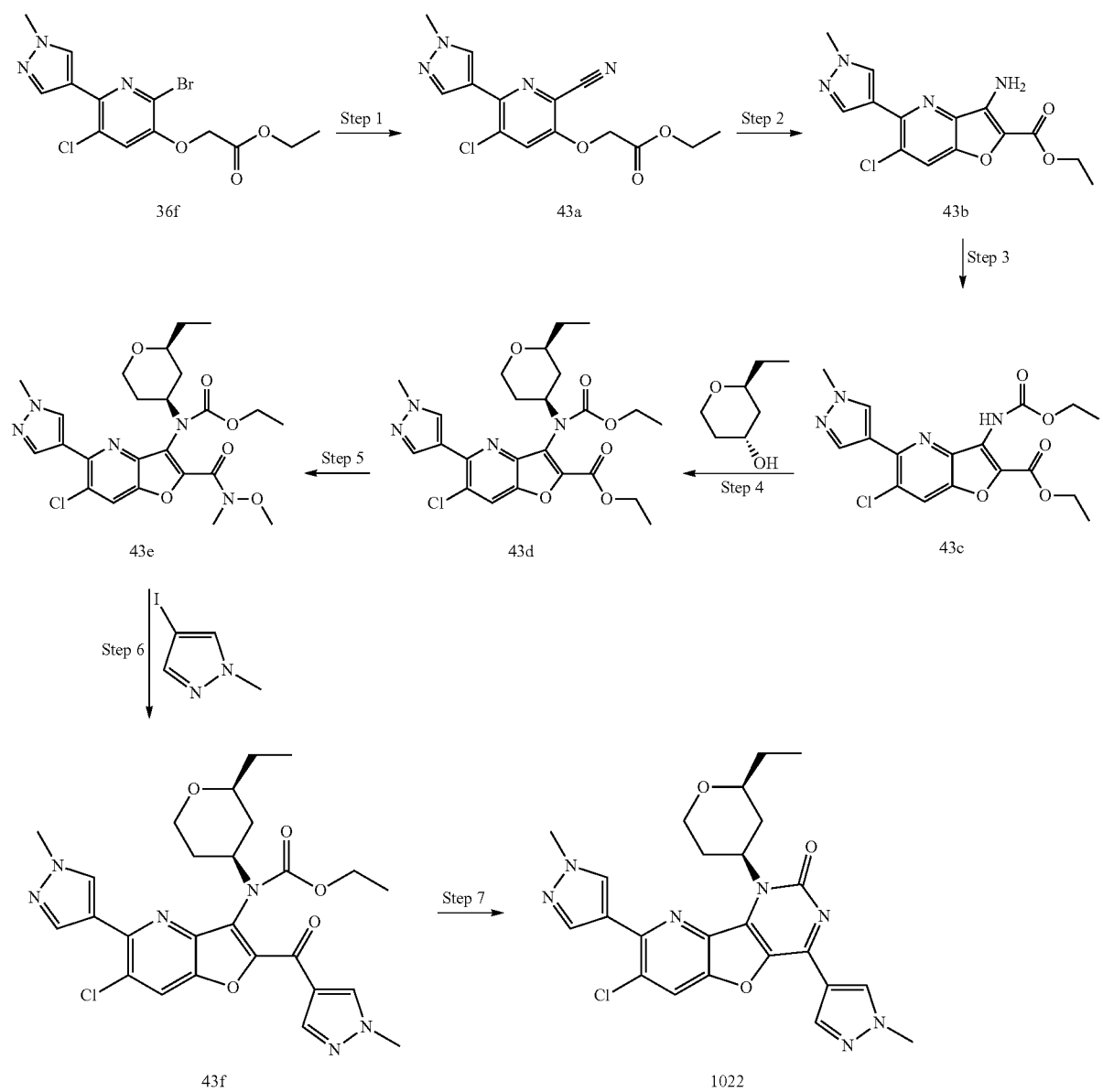

mate (12.1 mL, 127.2 mmol), and then stirred at 110° C. for 15 h. The reaction mixture is cooled to RT, evaporated under reduced pressure until a solid is formed. Purification by trituration affords carbamate 43c.

Step 4

According to general procedure A, carbamate 43c (320 mg, 0.82 mmol) is used with racemic 3e to afford 43d after purification by chromatography (10 to 70% EtOAc in hexanes).

Step 5

According to general procedure I, ester 43d (3.6 g, 7.1 mmol) is transformed to Weinreb amide 43e.

Step 6

According to general procedure E, Weinreb amide 43e (200 mg, 0.39 mmol) is used with pyrazole 23f to give ketone 43f after purification by chromatography (0-6% MeOH in DCM).

Step 7

According to general procedure F, ketone 43f (177 mg, 0.33 mmol) is transformed to compound 1022 after purification by preparative HPLC.

Example 44

Preparation of Compound 1023

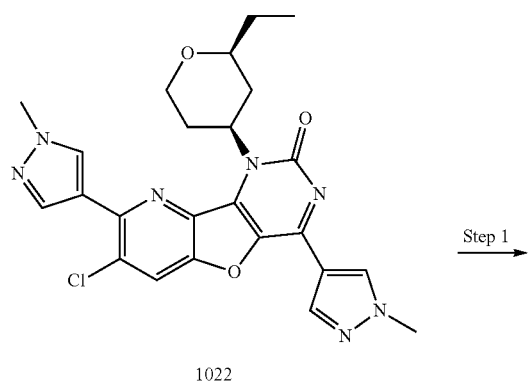

1022

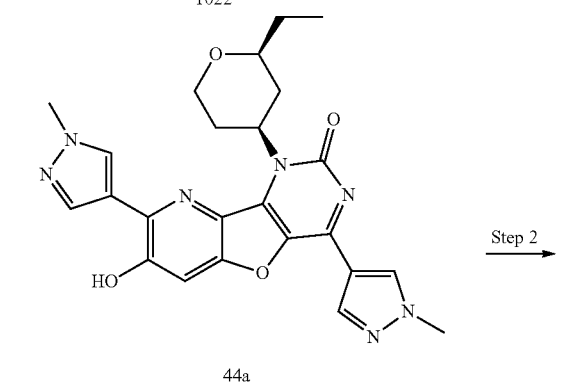

44a

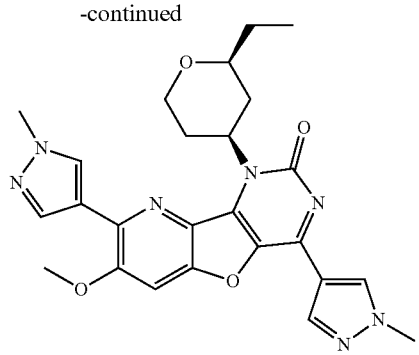

1023

Step 1

A mixture of $Pd_2(dba)_3$ (27 mg, 0.029 mmol), 2-di-tert-butylphosphino-3,4,5,6-tetramethyl-2',4',6'-triisopropyl-1,1'-biphenyl (57 mg, 0.12 mmol) and KOH (99 mg, 1.76 mmol) is flushed with Ar(g) for 3 min and then compound 1022 (140 mg, 0.28 mmol), dioxane (2.5 mL) and water (1.2 mL) are added. Ar(g) is bubbled into the reaction vessel under sonication (10 min) and the solution is heated to 100° C. in a pre-heated oil bath for 16 h. The mixture is allowed to cool to RT, neutralized with HCl (1N) and water is added. The product is extracted with DCM (3×) and EtOAc (3×). The organic layers are combined, washed with brine, dried ($Na_2SO_4$), filtered and concentrated to afford crude hydroxy-pyridine 44a.

Step 2

Crude hydroxy-pyridine 44a (146 mg, 0.30 mmol) is dissolved in anhydrous DMF (2 mL) and to the solution is added $K_2CO_3$ (84.8 mg, 0.61 mmol) followed by MeI (0.195 mL, 0.071 mmol). The solution is stirred for 2 h at RT, taken up in DCM (100 mL) and washed with brine (4×). The organic layer is dried ($Na_2SO_4$), filtered and concentrated. Purification by preparative HPLC affords compound 1023.

Example 45

Preparation of Compound 1024

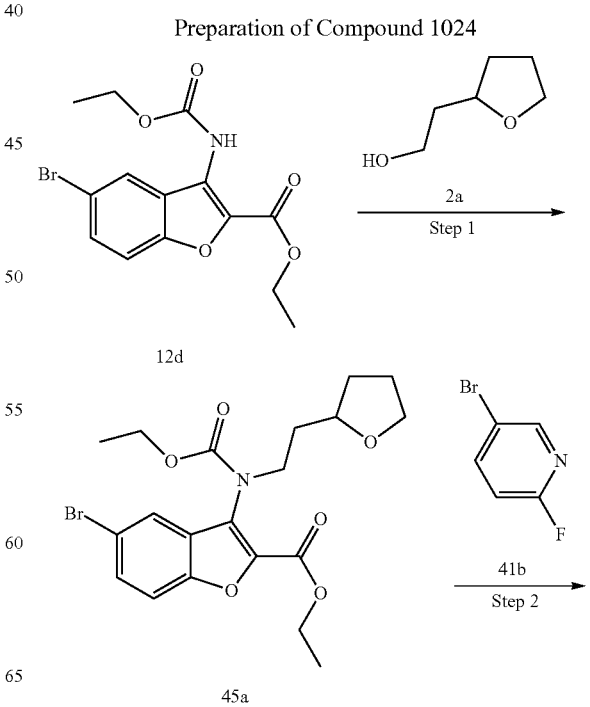

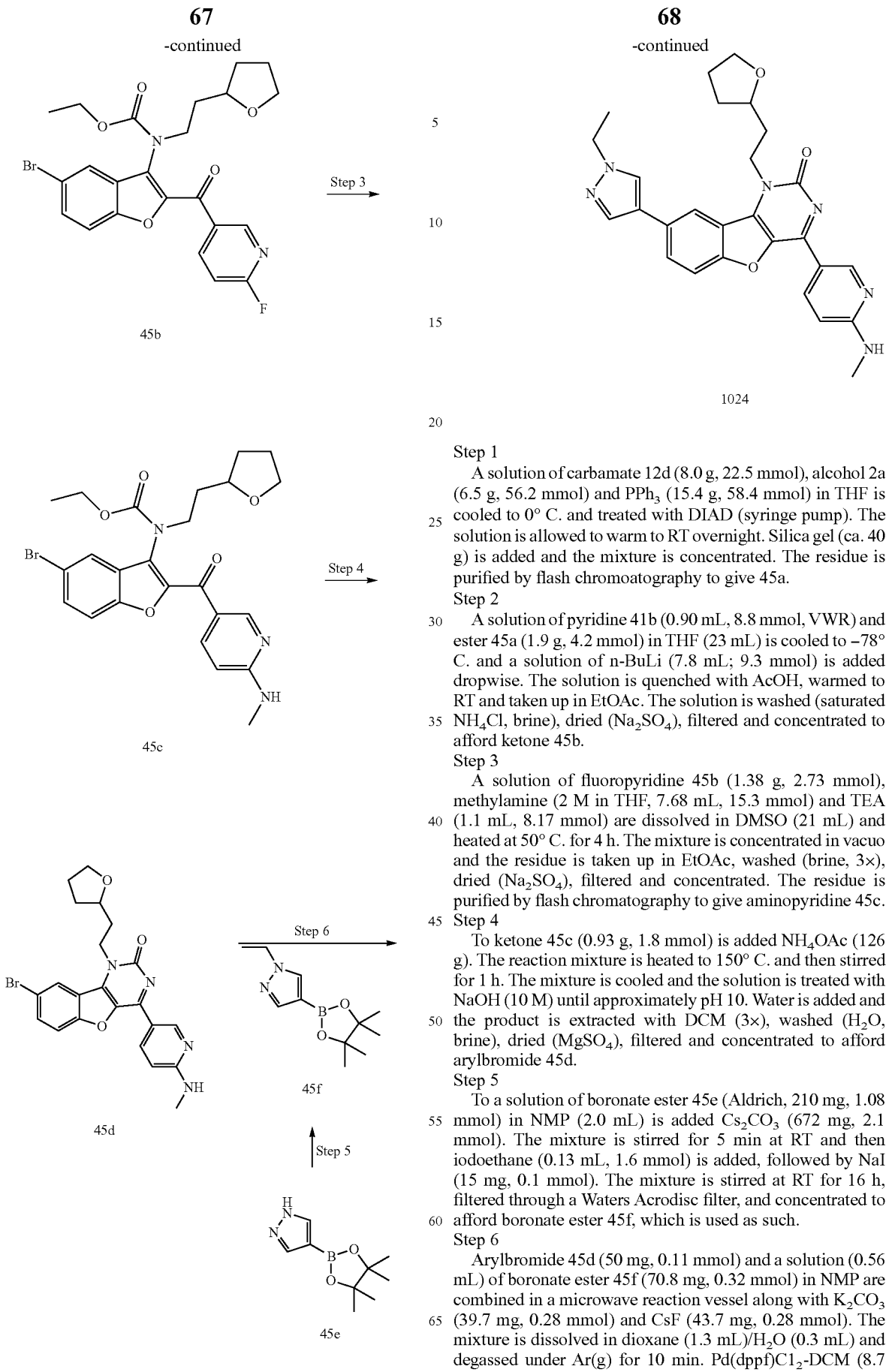

Step 1

A solution of carbamate 12d (8.0 g, 22.5 mmol), alcohol 2a (6.5 g, 56.2 mmol) and PPh₃ (15.4 g, 58.4 mmol) in THF is cooled to 0° C. and treated with DIAD (syringe pump). The solution is allowed to warm to RT overnight. Silica gel (ca. 40 g) is added and the mixture is concentrated. The residue is purified by flash chromoatography to give 45a.

Step 2

A solution of pyridine 41b (0.90 mL, 8.8 mmol, VWR) and ester 45a (1.9 g, 4.2 mmol) in THF (23 mL) is cooled to −78° C. and a solution of n-BuLi (7.8 mL; 9.3 mmol) is added dropwise. The solution is quenched with AcOH, warmed to RT and taken up in EtOAc. The solution is washed (saturated NH₄Cl, brine), dried (Na₂SO₄), filtered and concentrated to afford ketone 45b.

Step 3

A solution of fluoropyridine 45b (1.38 g, 2.73 mmol), methylamine (2 M in THF, 7.68 mL, 15.3 mmol) and TEA (1.1 mL, 8.17 mmol) are dissolved in DMSO (21 mL) and heated at 50° C. for 4 h. The mixture is concentrated in vacuo and the residue is taken up in EtOAc, washed (brine, 3×), dried (Na₂SO₄), filtered and concentrated. The residue is purified by flash chromatography to give aminopyridine 45c.

Step 4

To ketone 45c (0.93 g, 1.8 mmol) is added NH₄OAc (126 g). The reaction mixture is heated to 150° C. and then stirred for 1 h. The mixture is cooled and the solution is treated with NaOH (10 M) until approximately pH 10. Water is added and the product is extracted with DCM (3×), washed (H₂O, brine), dried (MgSO₄), filtered and concentrated to afford arylbromide 45d.

Step 5

To a solution of boronate ester 45e (Aldrich, 210 mg, 1.08 mmol) in NMP (2.0 mL) is added Cs₂CO₃ (672 mg, 2.1 mmol). The mixture is stirred for 5 min at RT and then iodoethane (0.13 mL, 1.6 mmol) is added, followed by NaI (15 mg, 0.1 mmol). The mixture is stirred at RT for 16 h, filtered through a Waters Acrodisc filter, and concentrated to afford boronate ester 45f, which is used as such.

Step 6

Arylbromide 45d (50 mg, 0.11 mmol) and a solution (0.56 mL) of boronate ester 45f (70.8 mg, 0.32 mmol) in NMP are combined in a microwave reaction vessel along with K₂CO₃ (39.7 mg, 0.28 mmol) and CsF (43.7 mg, 0.28 mmol). The mixture is dissolved in dioxane (1.3 mL)/H₂O (0.3 mL) and degassed under Ar(g) for 10 min. Pd(dppf)Cl₂-DCM (8.7

Example 46

Preparation of Compound 1025

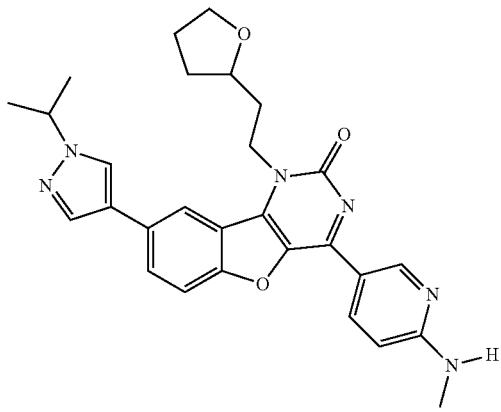 [SMILES: CNc1ccc(-c2nc(=O)n(CCC3CCCO3)c3c2oc2ccc(-c4cnn(C(C)C)c4)cc23)cn1]

Compound 1025 is prepared analogously to the procedure described in Example 45, replacing boronate ester 45f with 1-isopropyl-pyrazole-4-boronic acid pinacol ester (Boron Molecular) in step 6.

Example 47

Preparation of Compound 1026

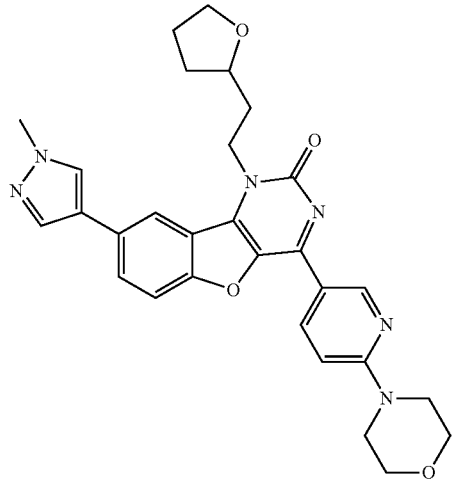 [SMILES: Cn1cc(-c2ccc3oc4c(-c5ccc(N6CCOCC6)nc5)nc(=O)n(CCC5CCCO5)c4c3c2)cn1]

Compound 1026 is prepared analogously to the procedure described in Example 45. Methylamine is replaced with morpholine (Aldrich) in step 3 and boronate ester 45f is replaced with with boronate ester 23d (Frontier) in step 6.

Example 48

Preparation of Compound 1027

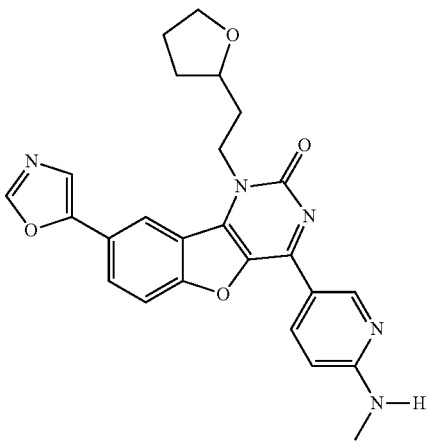 [SMILES: CNc1ccc(-c2nc(=O)n(CCC3CCCO3)c3c2oc2ccc(-c4cnco4)cc23)cn1]

Compound 1027 is prepared analogously to the procedure described in Example 45, replacing boronate ester 45f with boronate ester 29c (Boropharm) in step 6.

Example 49

Preparation of Compound 1028

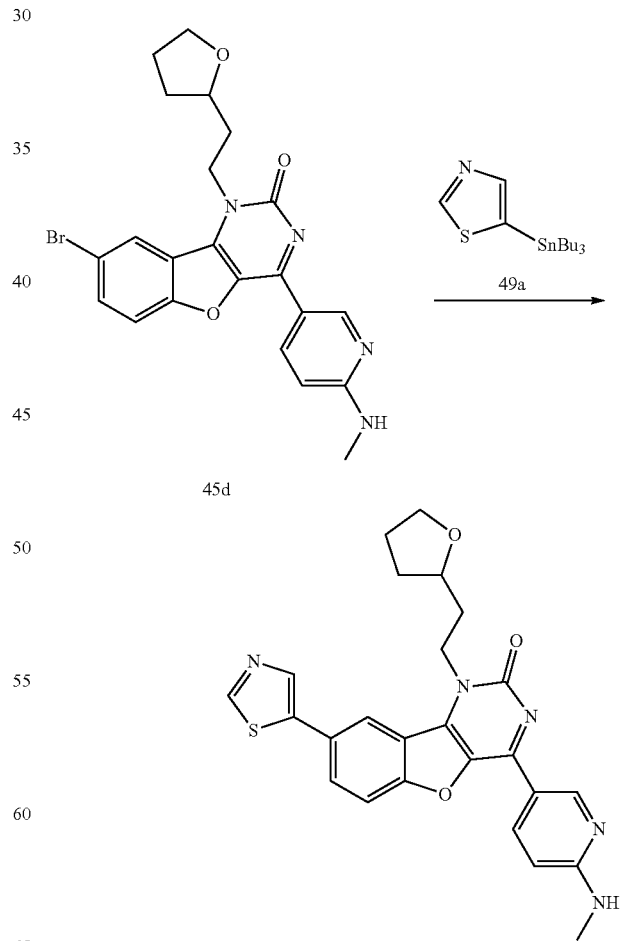

According to general procedure D2, arylbromide 45d (50 mg, 0.11 mmol) is treated with thiazole 49a (79 mg, 0.21 mmol, Synthonix). The mixture is heated in the microwave for 20 min at 120° C. Purification by preparative HPLC affords compound 1028.

Example 50

Preparation of Compound 1029

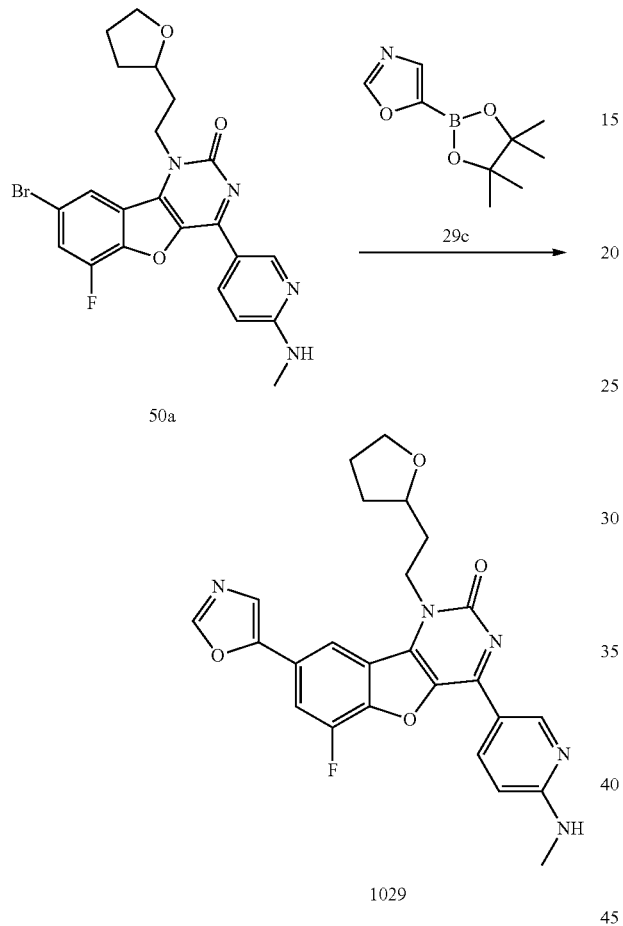

According to general procedure D1, arylbromide 50a (50 mg, 0.1 mmol) is converted to compound 1029 after purification by preparative HPLC.

Preparation of Arylbromide 50a

Arylbromide 50a is prepared analogously to the procedure described in Example 45 (Steps 1 to 4), replacing carbamate 12d with carbamate 16a.

Example 51

Preparation of Compound 1030

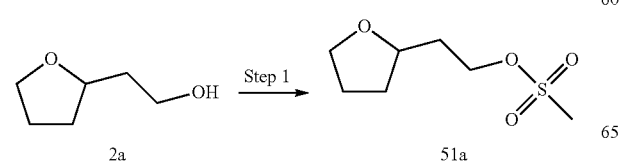

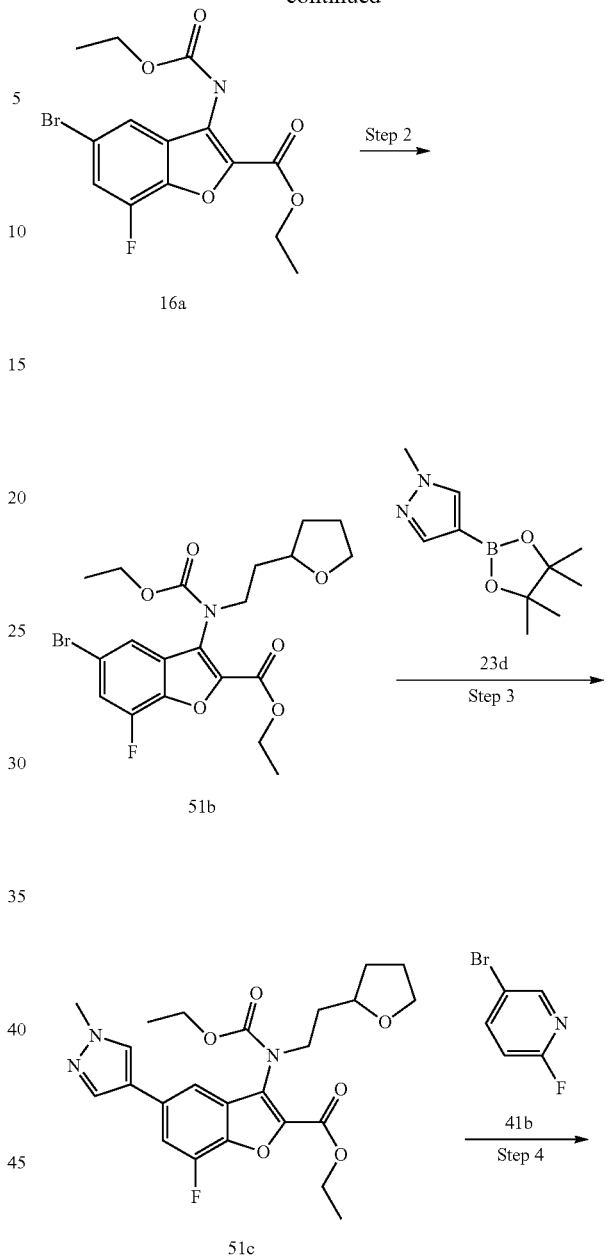

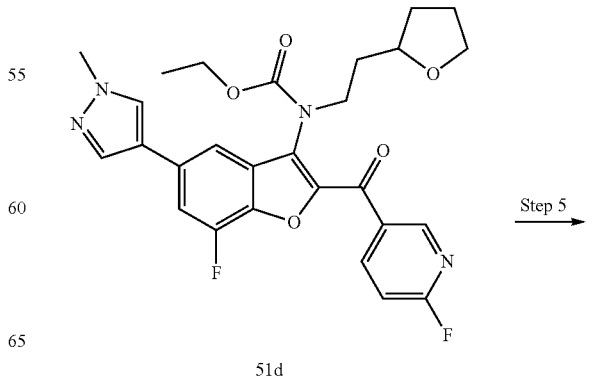

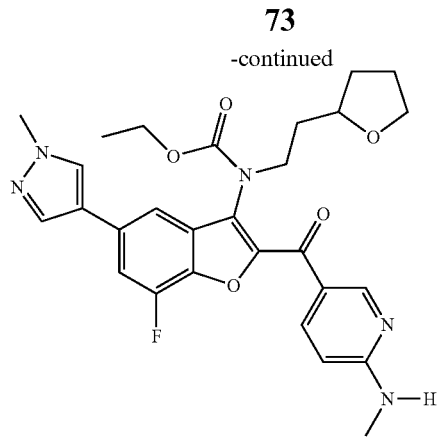

51e

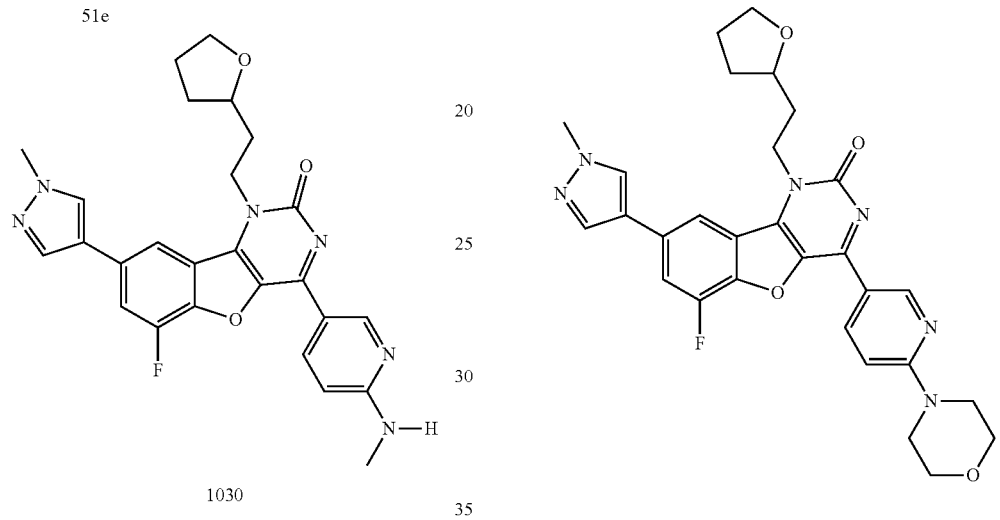

1030

0.19 mL, 0.19 mmol) to afford crude aminopyridine 51e, which is used as such in the next step.

Step 6

According to general procedure F, a DMSO solution of crude ketone 51e (0.095 mmol) is treated with NH₄OAc (300 mg, 0.063 mmol). The residue is purified by preparative HPLC to provide compound 1030.

Example 52

Preparation of Compound 1031

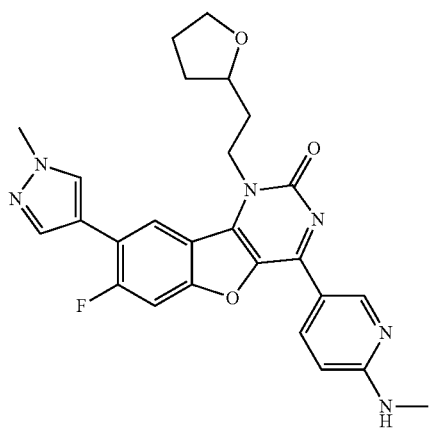 [SMILES: CNc1ccc(-c2nc(=O)n(CCC3CCCO3)c3c2oc2cc(F)c(-c4cnn(C)c4)cc23)cn1]

Compound 1031 is prepared analogously to the procedure described in Example 51 replacing MeNH₂ with morpholine (Aldrich) in Step 5 to provide compound 1031.

Example 53

Preparation of Compound 1032

Step 1

To an ice cooled stirring solution of alcohol 2a (5.0 g, 43.0 mmol) and TEA (11.4 mL, 81.8 mmol) in dry DCM (50 mL) is added MsCl (4.3 mL, 56.0 mmol) dropwise over 15 min. The mixture is allowed to warm to RT over 1 h. The reaction is treated with aqueous NaHCO₃ (saturated) and the layers separated. The aqueous layer is extracted with DCM. The combined organic layers are washed with brine, dried (MgSO₄), filtered and concentrated to provide crude mesylate 51a, which is used as such in the next step.

Step 2

According to general procedure G, carbamate 16a (3.3 g, 8.9 mmol) is treated with mesylate 51a (2.3 g, 11.6 mmol) and Cs₂CO₃ (6.4 g, 19.6 mmol) in DMSO (15 mL). Purification by flash chromatography affords 51 b.

Step 3

According to general procedure D2, arylbromide 51b (1.6 g, 3.4 mmol) is treated with PdCl₂dppf (276 mg, 0.3 mmol), boronate 23d (1.4 g, 6.8 mmol) and NaHCO₃ (854 mg, 10.2 mmol) in dioxane (30 mL) and H₂O (6 mL). Purification by flash chromatography affords 51c.

Step 4

According to general procedure E, ester 51c (1.5 g, 3.2 mmol) is treated with pyridine 41b (954 mg, 5.4 mmol, Matrix Scientific) and BuLi (1.86 mL, 4.5 mmol) in THF (25 mL). Purification by flash chromatography affords ketone 51d.

Step 5

According to general procedure H, fluoropyridine 51d (50 mg, 0.095 mmol) is treated with a solution of MeNH₂ (THF, Compound 1032 is prepared analogously to the procedure described in Example 51 replacing 16a with 13e. The residue is purified by preparative HPLC to provide compound 1032.

Example 54

Preparation of Compound 1033

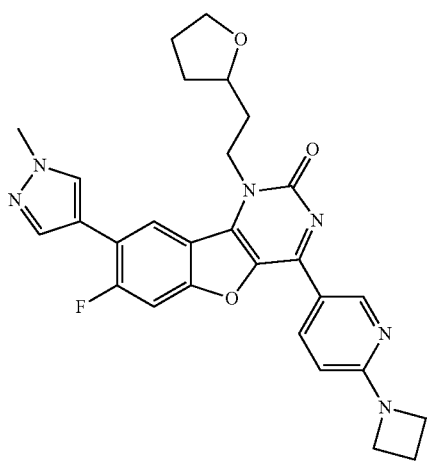 [SMILES: Cn1cc(-c2cc3c(cc2F)oc2c(-c4ccc(N5CCC5)nc4)nc(=O)n(CCC4CCCO4)c23)cn1]

Compound 1033 is prepared analogously to the procedure described in Example 53 replacing MeN H$_2$ with azetidine (Apollo) in Step 5. The residue is purified by preparative HPLC to provide compound 1033.

Example 55

Preparation of Compound 1034

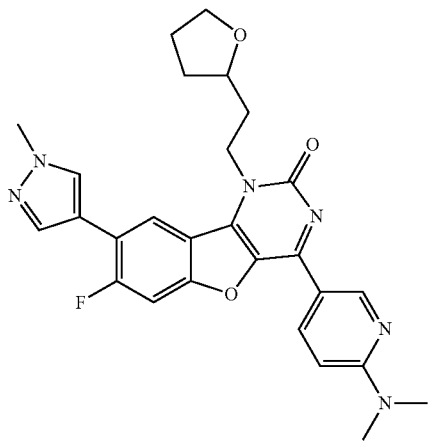 [SMILES: CN(C)c1ccc(-c2nc(=O)n(CCC3CCCO3)c3c2oc2cc(F)c(-c4cnn(C)c4)cc23)cn1]

Compound 1034 is prepared analogously to the procedure described in Example 53 replacing MeN H$_2$ with dimethylamine (Adrich) in Step 5. The product is purified by preparative HPLC to provide compound 1034.

Example 56

Preparation of Compound 1035

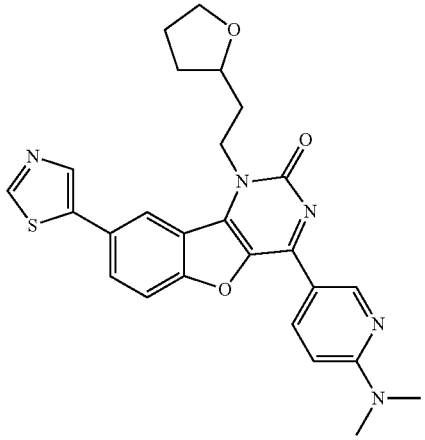 [SMILES: CN(C)c1ccc(-c2nc(=O)n(CCC3CCCO3)c3c2oc2ccc(-c4cncs4)cc23)cn1]

Compound 1035 is prepared analogously to the procedure described in Example 53, replacing 13e with 12d in Step 2. Step 3 is conducted with thiazole 49a under the conditions of general procedure D2. The final product is purified by preparative HPLC and lyophyllized to give compound 1035 as a TFA salt.

Example 57

Preparation of Compound 1036

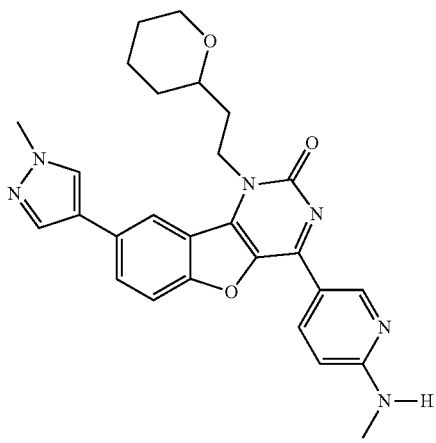 [SMILES: CNc1ccc(-c2nc(=O)n(CCC3CCCCO3)c3c2oc2ccc(-c4cnn(C)c4)cc23)cn1]

Compound 1036 is prepared analogously to the procedure described in Example 51, replacing 51a and 16a with 11 b and 12d, respectively, in Step 2.

Example 58

Preparation of Compound 1037

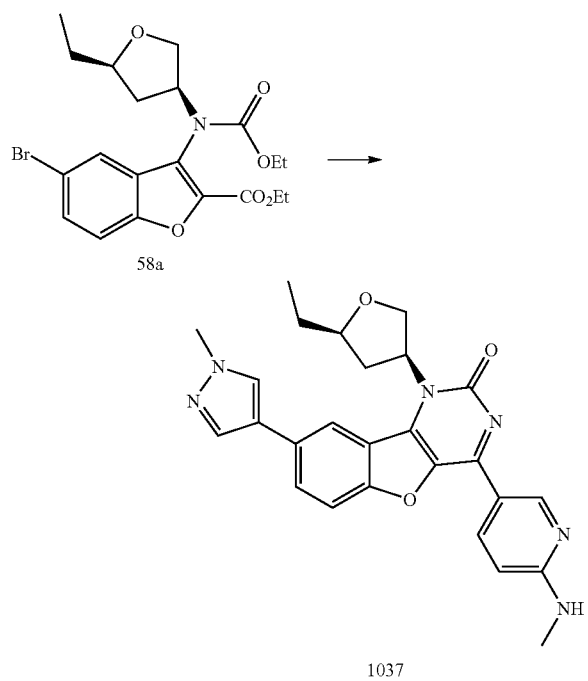

Compound 1037 is prepared analogously to the procedure described in Example 57 (Steps 3 to 6).

Preparation of 58a 58a is prepared analogously to the procedure described in Example 45 (Step 1) substituting 2a with racemic 10e.

Example 59

Preparation of Compound 1038

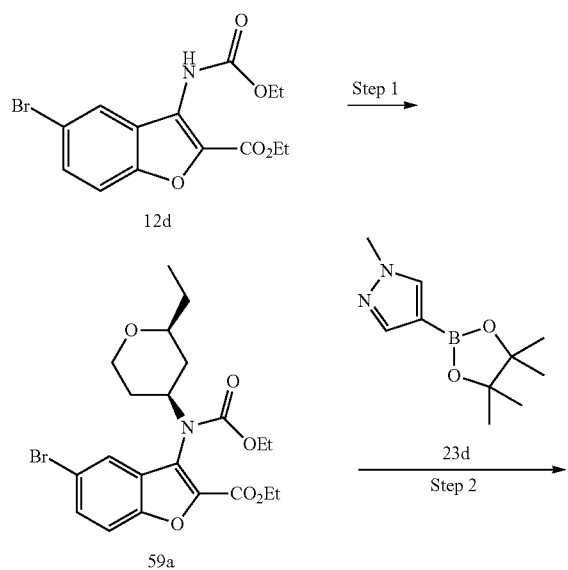

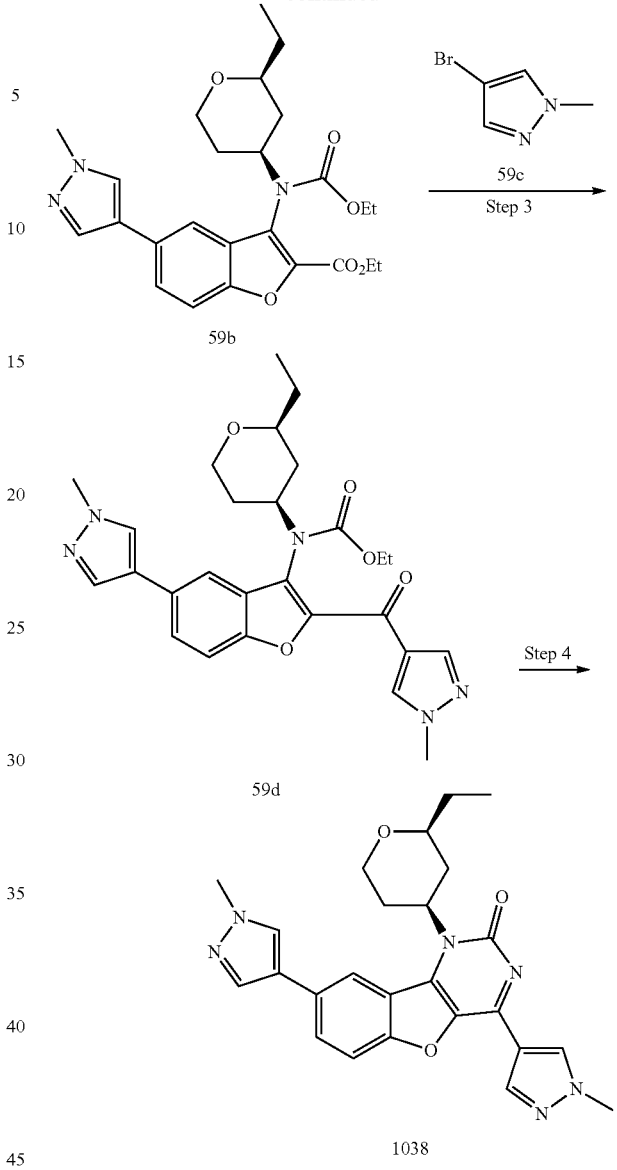

Step 1
According to general procedure A, carbamate 12d (0.91 g, 2.56 mmol) is treated with racemic 3e (0.50 g, 3.84 mmol), PPh$_3$ (1.35 g, 5.12 mmol) and DIAD (1.01 mL, 5.12 mmol) in THF (55 mL) to obtain 59a after purification by flash chromatography (25% EtOAc in hexanes).

Step 2
According to general procedure D1, arylbromide 59a (0.25 g, 0.53 mmol) is treated with 23d (0.26 g, 1.23 mmol, Frontier), PdCl$_2$dppf (43.6 mg, 0.053 mmol) and NaHCO$_3$ (0.135 g, 1.60 mmol) in dioxane (9 mL) and H$_2$O (3 mL). Standard workup and purification by flash chromatography affords pyrazole 59b.

Step 3
According to general procedure E, ester 59b (95.5 mg, 0.20 mmol) is treated with pyrazole 59c (49.1 mg, 0.31 mmol, Aldrich) and BuLi (0.13 mL, 0.31 mmol) in THF (5.5 mL). The mixture is subjected to a standard work-up to afford crude ketone 59d, which is used as such in the next step.

Step 4
According to general procedure F, crude ketone 59d is treated with DMSO (0.8 mL) and NH$_4$OAc (550 mg). The mixture is subjected to a standard work-up and purification by preparative HPLC to afford compound 1038.

Example 60

Preparation of Compound 1039

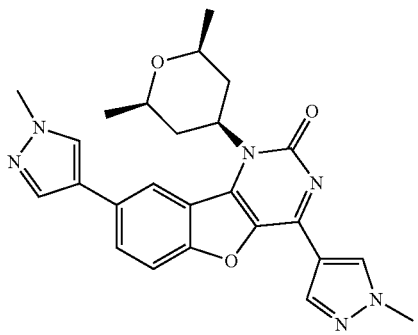 [SMILES: C[C@@H]1C[C@H](n2c(=O)nc(-c3cnn(C)c3)c3oc4ccc(-c5cnn(C)c5)cc4c32)C[C@H](C)O1]

Compound 1039 is prepared analogously to the procedure described in Example 59 substituting 3e with 5a. Purification by preparative HPLC affords compound 1039.

Example 61

Preparation of Compound 1040

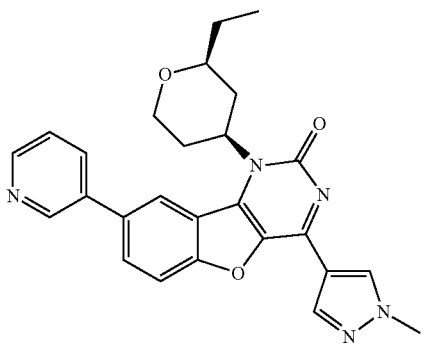 [SMILES: CC[C@H]1C[C@@H](n2c(=O)nc(-c3cnn(C)c3)c3oc4ccc(-c5cccnc5)cc4c32)CCO1]

Compound 1040 is prepared analogously to the procedure described in Example 59 substituting 23d with 3-pyridylboronic acid (Aldrich) using the conditions of general procedure D4. Purification by preparative HPLC affords compound 1040 as its TFA salt.

Example 62

Preparation of Compound 1041

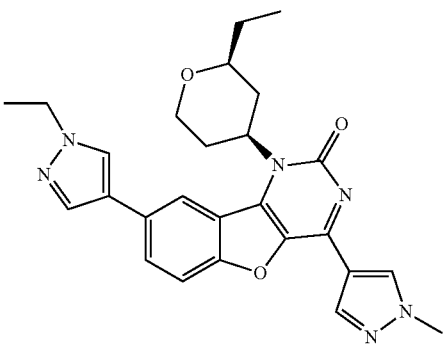 [SMILES: CC[C@H]1C[C@@H](n2c(=O)nc(-c3cnn(C)c3)c3oc4ccc(-c5cnn(CC)c5)cc4c32)CCO1]

Compound 1041 is prepared analogously to the procedure described in Example 59 substituting 23d with 1-ethyl-pyrazole-4-boronic acid (Aldrich) using general procedure D1. Purification by preparative HPLC affords compound 1041.

Example 63

Preparation of Compound 1042

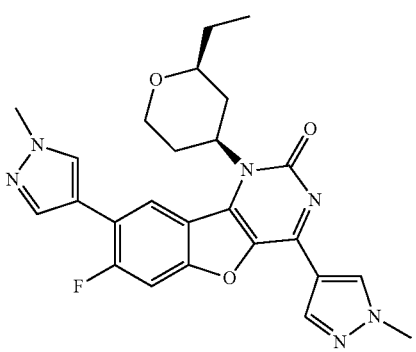 [SMILES: CC[C@H]1C[C@@H](n2c(=O)nc(-c3cnn(C)c3)c3oc4cc(F)c(-c5cnn(C)c5)cc4c32)CCO1]

Compound 1042 is prepared analogously to the procedure described in Example 59 replacing 12d with 13e in Step 1. Purification by preparative HPLC affords compound 1042.

Example 64

Preparation of Compound 1043

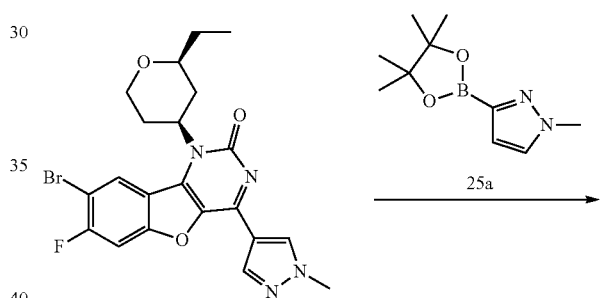

64a

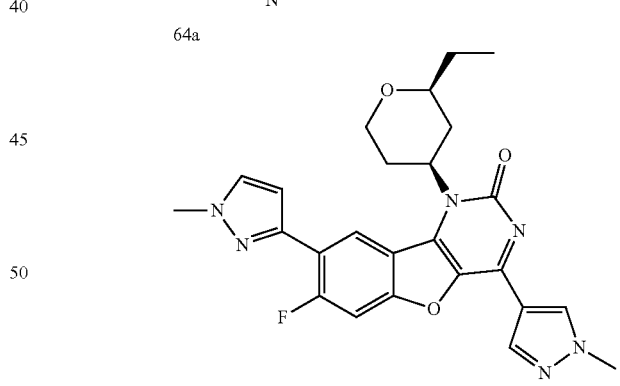

1043

Arylbromide 64a is prepared analogously to the procedure described in Example 63, Steps 1, 3 and 4. In step 3, pyrazole 23f is used for the ketone formation. Compound 1043 is prepared using the conditions of general procedure D2, substituting K$_2$CO$_3$ by NaHCO$_3$. Arylbromide 64a (90.0 mg, 0.13 mmol) is treated with 25a (83.9 mg, 0.40 mmol), NaHCO$_3$ (22.3 mg, 0.27 mmol) and CsF (60.6 mg, 0.40 mmol) and PdCl$_2$dppf (10.9 mg, 0.013 mmol) in dioxane-H$_2$O (4:1, 1.5 mL). The mixture is heated in the microwave at 120° C. for 20 min. The residue is purified by preparative HPLC to provide compound 1043.

Example 65

Preparation of Compound 1044

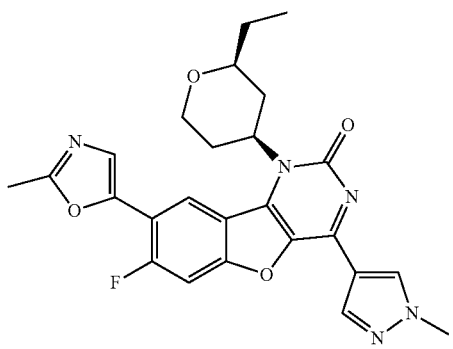

Compound 1044 is prepared analogously to the procedure described in Example 64 replacing 25a with 65a (Boropharm). Purification by preparative HPLC affords compound 1044.

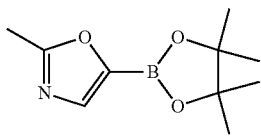

65a

Example 66

Preparation of Compound 1045

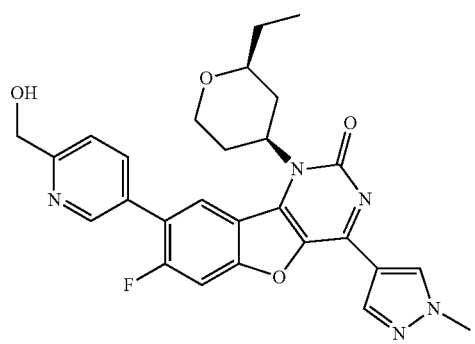 [SMILES: CC[C@H]1C[C@@H](n2c(=O)nc(-c3cnn(C)c3)c3oc4cc(F)c(-c5ccc(CO)nc5)cc4c32)CCO1]

Compound 1045 is prepared analogously to the procedure described in Example 64 replacing 25a with 66a (2-hydroxymethyl-pyridine-5-boronic acid pinacol ester). Purification by preparative HPLC affords compound 1045.

Preparation of 66a

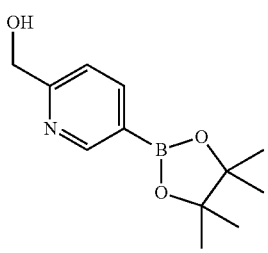

66a

A solution of 5-bromo-2-hydroxymethylpyridine (Biofine) (75 mg, 0.4 mmol), bis-pinacolatodiboron (121.6 mg, 0.48 mmol), KOAc (117.4 mg, 1.2 mmol), PdCl$_2$dppf (32.6 mg, 0.04 mmol) and dioxane (3 mL) are combined in a microwave vial and the mixture is degassed by bubbling N$_2$ through the solution. The vial is capped and then heated in an oil bath at 130° C. for 30 min to provide crude 66a, which is used as such in subsequent steps.

Example 67

Preparation of Compound 1046

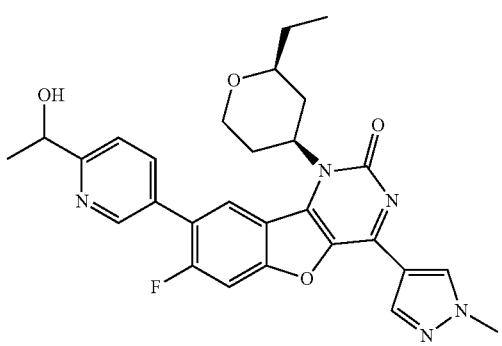 [SMILES: CC[C@H]1C[C@@H](n2c(=O)nc(-c3cnn(C)c3)c3oc4cc(F)c(-c5ccc(C(C)O)nc5)cc4c32)CCO1]

Compound 1046 is prepared analogously to the procedure described in Example 66 replacing boronate ester 66a with 67a. Purification by preparative HPLC affords compound 1046.

Preparation of 67a

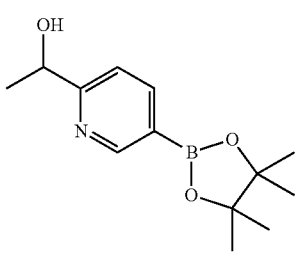

67a

Boronate ester 67a is prepared ananlogously to the procedure described in Example 66 for the preparation of boronate ester 66a with 5-bromo-2-hydroxymethylpyridine replaced by (1-(5-bromo-pyridin-2-yl)-ethanol).

Preparation of (1-(5-bromo-pyridin-2-yl)-ethanol)

Step a.

A solution of 5-bromo-pyridine-2-carboxylic acid (15.0 g, 74.3 mmol, Alfa), DIPEA (38.8 mL, 222.8 mmol), HOAt (1.01 g, 7.43 mmol), EDCI (21.4 g, 111.4 mmol) in DMF (150 mL) is treated with N-methyl-O-methylhydroxylamine hydrochloride (7.24 g, 74.3 mmol). The mixture is stirred at RT for 48 h, then water (100 mL) is added. The mixture is concentrated on high vaccum to about 50 mL and diluted with 300 mL of toluene. The layers are separated and the organic phase is washed with water (100 mL), 0.1 N HCl (100 mL) and 1.0 N NaOH (100 mL). The organic layer is dried (MgSO$_4$) and concentrated to provide 67a1, which is used as such in the next step.

Step b.

Amide 67a1 (919.0 g, 40.8 mmol) is dissolved in THF (100 mL) and cooled to −78° C. The mixture is treated with MeLi (31.6 mL, 44.9 mmol) and stirred at this temperature for 1 h. The reaction is quenched with saturated NH$_4$Cl and the solvent is evaporated. The residue is basified with saturated NaHCO$_3$ and extracted with EtOAc (2×). The combined organic layers are dried (MgSO$_4$), filtered and concentrated. The residue is purified by flash chromatography to obtain 67a2.

Step c.

Sodium borohydride (102.1 mg, 2.70 mmol) is added portionwise to a solution of ketone 67a2 in MeOH (2.5 mL) at 0° C. The solution is stirred at RT for 2 h and the solvent is removed under reduced pressure. The residue is partitioned between DCM and water. The layers are separated and the aqueous layer is extracted with DCM (3×). The combined organic layers are washed with brine, dried (Na$_2$SO$_4$), filtered and concentrated to afford crude 1-(5-bromo-pyridin-2-yl)-ethanol, which is used as such in subsequent steps.

Example 68

Preparation of Compound 1047

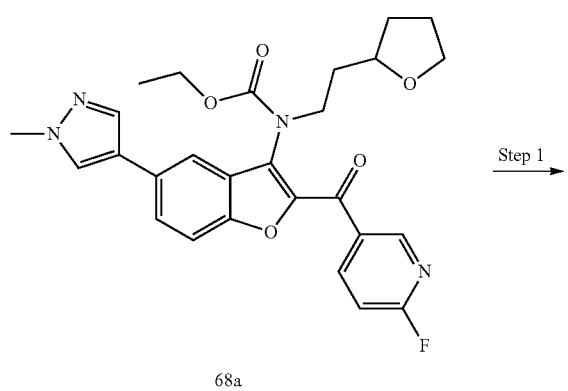
68a

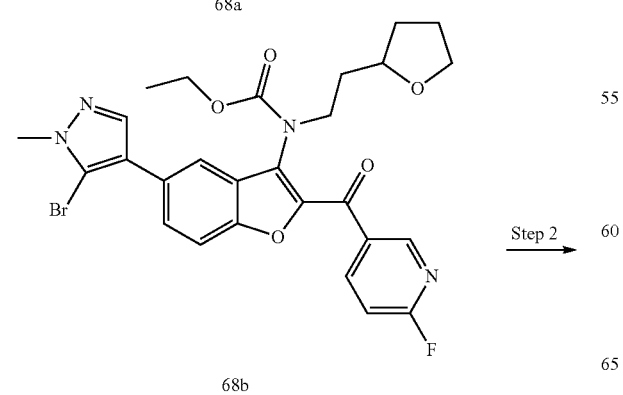
68b

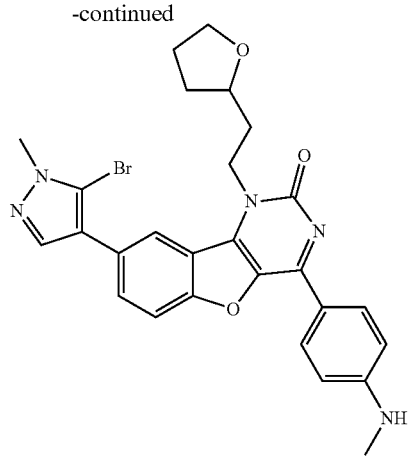
1047

Step 1

A solution of ketone 68a (180 mg, 0.36 mmol, prepared analogously to the procedure described in Example 51 (Steps 1 to 4), replacing 16a with 12d) and Na$_2$CO$_3$ (113 mg, 1.1 mmol), HOAc (8 mL) is treated with Br$_2$ (36 µL, 0.71 mmol). The reaction mixture is treated with aqueous sodium thiosulfate and extracted with EtOAc. The organic layer is dried (MgSO$_4$) and concentrated in vacuo. The crude material is purified by flash chromatography to provide brominated pyrazole 68b.

Step 2

Ketone 68b is converted to compound 1047 analogously to the procedure described in Example 51 (Steps 5 and 6). The crude product obtained in step 6 is diluted with H$_2$O, filtered, washed with Et$_2$O and dried to provide compound 1047.

Example 69

Preparation of Compound 1048

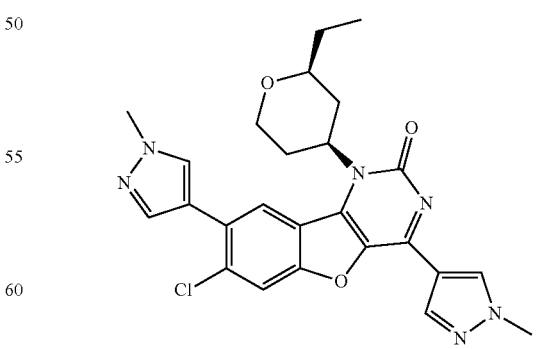

Compound 1048 is prepared analogously to the procedure described in Example 59 replacing 12d with 14a. Purification by preparative HPLC provides compound 1048.

Example 70

Preparation of Compound 1049

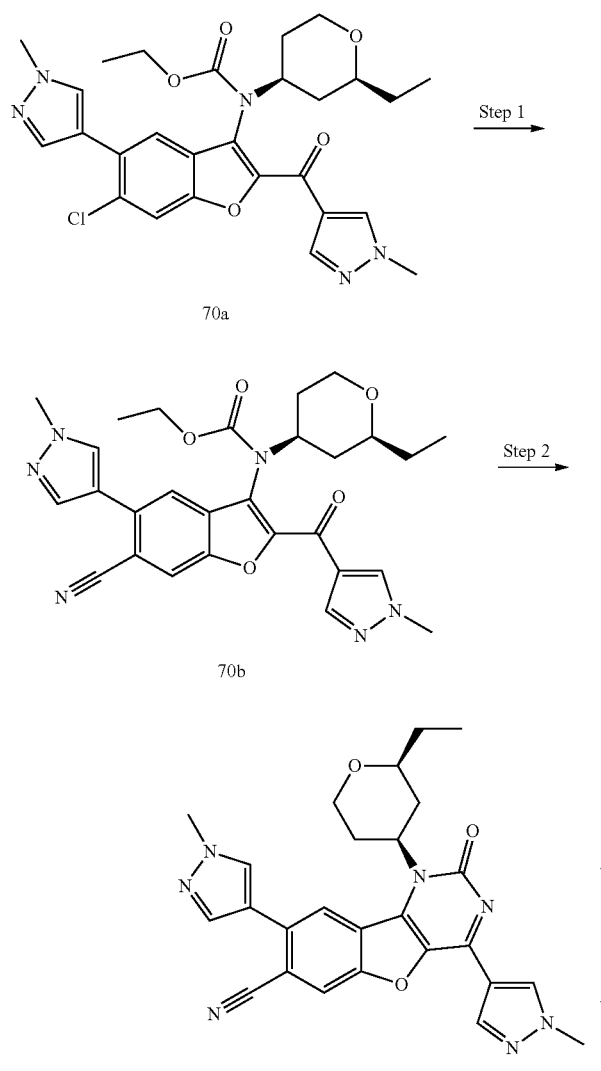

Example 71

Preparation of Compound 1050

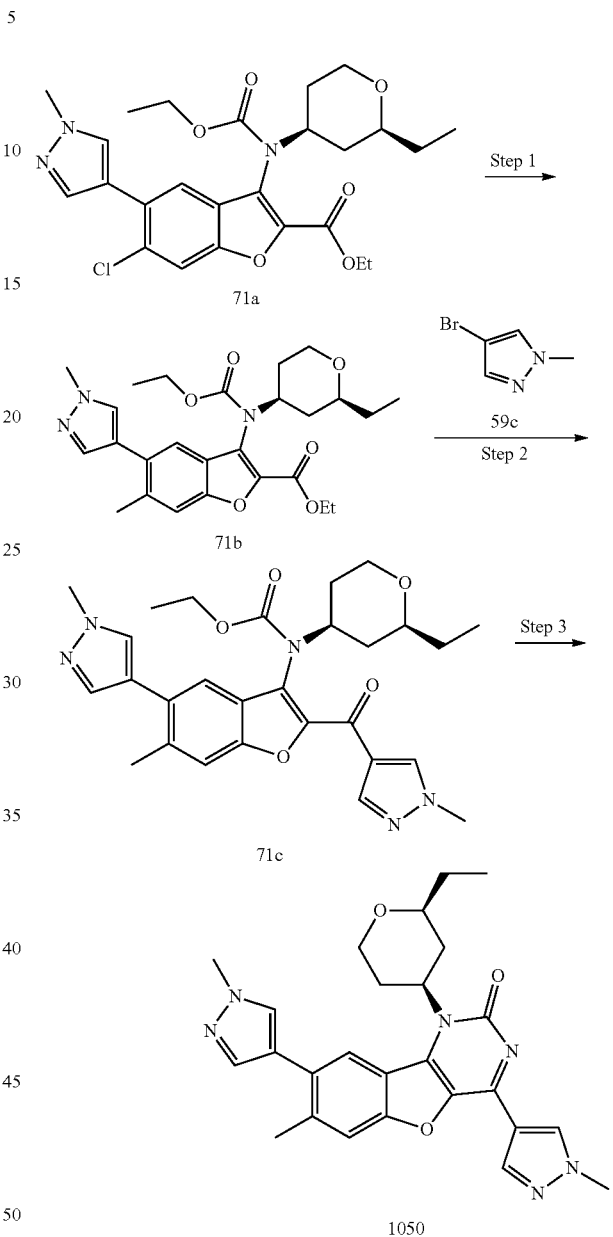

Step 1

A solution of 70a (170 mg, 0.32 mmol, prepared analogously to the procedure described in Example 69, Steps 1-3) and $Zn(CN)_2$ (184.8 mg, 1.57 mmol, Lancaster) in degassed DMA is treated with $Pd((PtBu)_3)_2$ (Strem). The mixture is heated at 130° C. in the microwave for 30 min. The solution is diluted with EtOAc, washed ($H_2O$, brine), dried ($Na_2SO_4$) and concentrated to afford crude nitrile 70b, which is used as such in the next step.

Step 2

Crude ketone 70b is dissolved in DMSO, treated with ammonium acetate and the solution is heated at 130° C. for 2 h. The residue is purified by preparative HPLC to afford compound 1049.

Step 1

A solution of arylchloride 71a (100 mg, 0.20 mmol, prepared analogously to the procedure described in Example 69 Steps 1 and 2), $MeB(OH)_2$ (Aldrich) (59.4 mg, 0.10 mmol) and CsF (90.4 mg, 0.60 mmol) in degassed dioxane (2 mL) and $H_2O$ (1 mL) is treated with $Pd(PtBu_3)_2$ (Strem). The mixture is heated at 120° C. for 20 min in the microwave. The residue is purified by preparative HPLC to afford 71b.

Step 2

Ester 71b is transformed to ketone 71c analogously to the procedure described in Example 69, Step 3.

Step 3

Ketone 71c is transformed to compound 1050 analogously to the procedure described in Example 69, Step 4.

Example 72

Preparation of Compound 1051

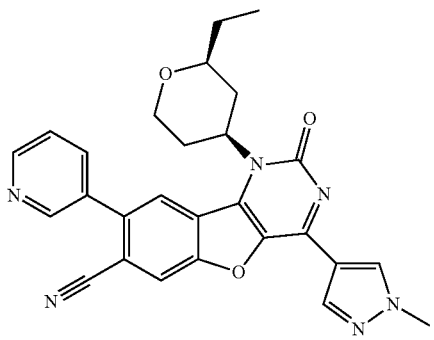 [SMILES: CC[C@H]1C[C@@H](n2c(=O)nc(-c3cnn(C)c3)c3oc4cc(C#N)c(-c5cccnc5)cc4c32)CCO1]

Compound 1051 is prepared analogously to the procedure described in Example 70 replacing 23d with 3-pyridylboronic acid (Aldrich). Purification by preparative HPLC provides compound 1051.

Example 73

Preparation of Compound 1052

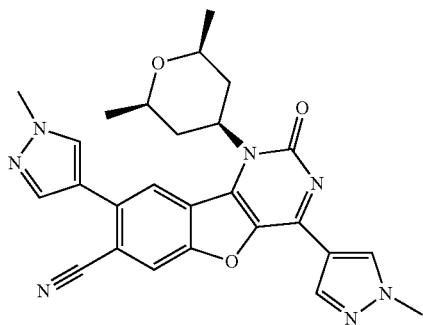 [SMILES: C[C@@H]1C[C@H](n2c(=O)nc(-c3cnn(C)c3)c3oc4cc(C#N)c(-c5cnn(C)c5)cc4c32)C[C@H](C)O1]

Compound 1052 is prepared analogously to the procedure described in Example 70 replacing 3e with 5a. Purification by preparative HPLC provides compound 1052.

Example 74

Preparation of Compound 1053

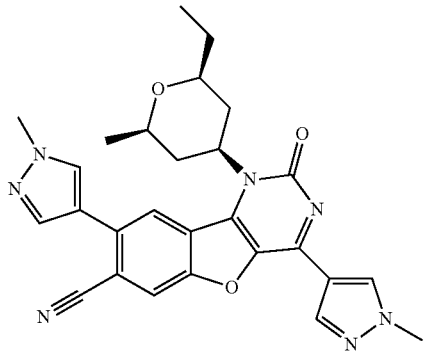 [SMILES: CC[C@H]1C[C@@H](n2c(=O)nc(-c3cnn(C)c3)c3oc4cc(C#N)c(-c5cnn(C)c5)cc4c32)C[C@@H](C)O1]

Compound 1053 is prepared analogously to the procedure described in Example 70 replacing 3e with 6a. Purification by preparative HPLC provides compound 1053.

Example 75

Preparation of Compound 1054

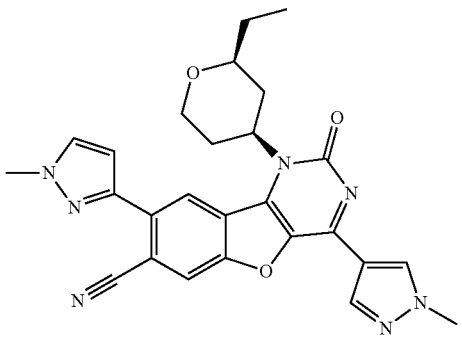

Compound 1054 is prepared analogously to the procedure described in Example 70 replacing 23d with 25a (Milestone). Purification by preparative HPLC provides compound 1054.

Example 76

Preparation of Compound 1055

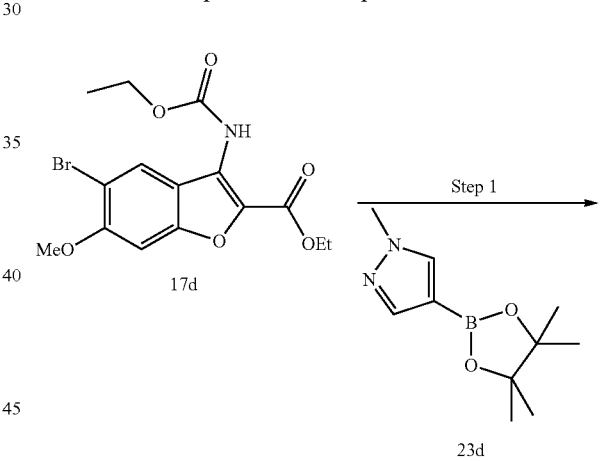

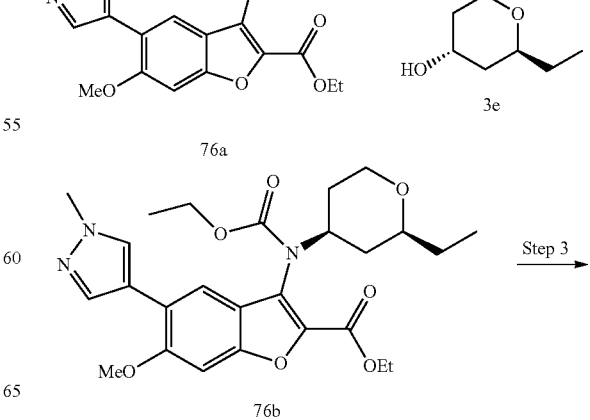

89
-continued

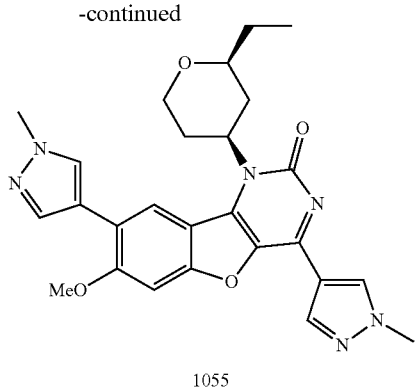

1055

Step 1

According to general procedure D1, arylbromide 17d (1.8 g, 4.66 mmol) is treated with 23d (Frontier) (1.94 g, 9.32 mmol), NaHCO₃ (1.18 g, 13.98 mmol) and PdCl₂dppf (380.6 mg, 0.47 mmol) in a degassed mixture of dioxane (24 mL) and H₂O (6 mL). The solution is heated at 80° C. for 3 h and then 90° C. for 1 h. Standard workup and purification by flash chromatography affords pyrazole 76a.

Step 2

According to general procedure A, carbamate 76a (500 mg, 1.29 mmol) is treated with PPh₃ (1.02 g, 3.87 mmol), alcohol 3e (369.7 mg, 2.84 mmol) and DIAD (0.76 mL, 3.87 mmol) in THF (18 mL). Work-up and purification by flash chromatography affords a crude alkylated product. In order to remove inseparable starting material, this intermediate is treated according to general procedure G with 51a (376 mg, 1.94 mmol) and Cs₂CO₃ (841.1 mg, 2.58 mmol) in DMSO (5 mL). Workup and purification affords 76b contaminated with PPh₃O.

Step 3

Ester 76b is elaborated to compound 1055 analogously to the procedure described in Example 23 (Steps 2, 3, 5 and 6). Purification by preparative HPLC affords compound 1055.

90

Example 77

Preparation of Compound 1056

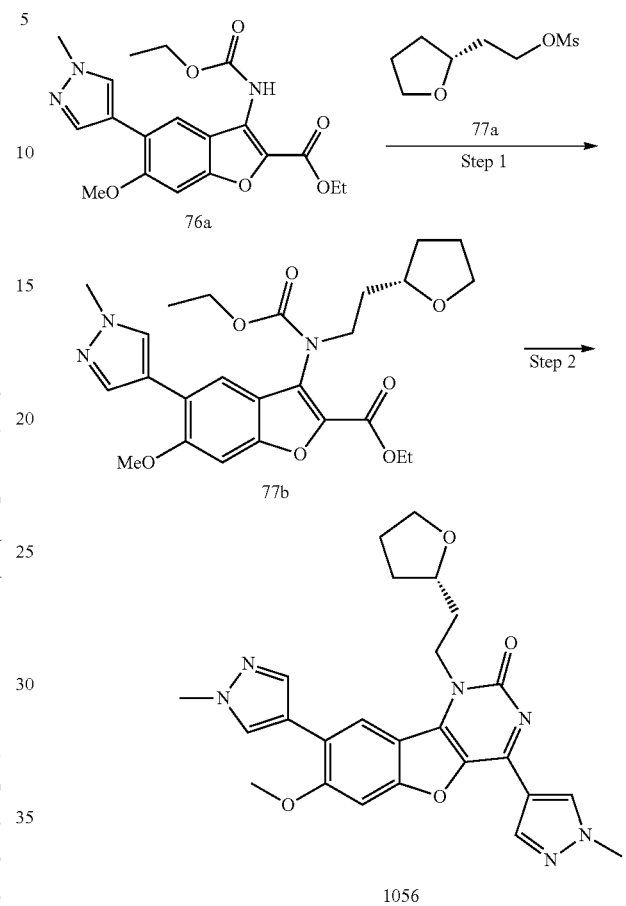

Step 1

According to general procedure G, carbamate 76a (150 mg, 0.39 mmol) is treated with 77a (prepared analogously to the procedure described in Example 51 (Step 1) substituting 2a with 1d) and Cs₂CO₃ in DMSO (2 mL). Standard workup and purification by flash chromatography affords 77b.

Step 2

Ester 77b is elaborated to compound 1056 analogously to the procedure described in Example 23 (Steps 2, 3, 5 and 6).

Example 78

Preparation of Compound 1057

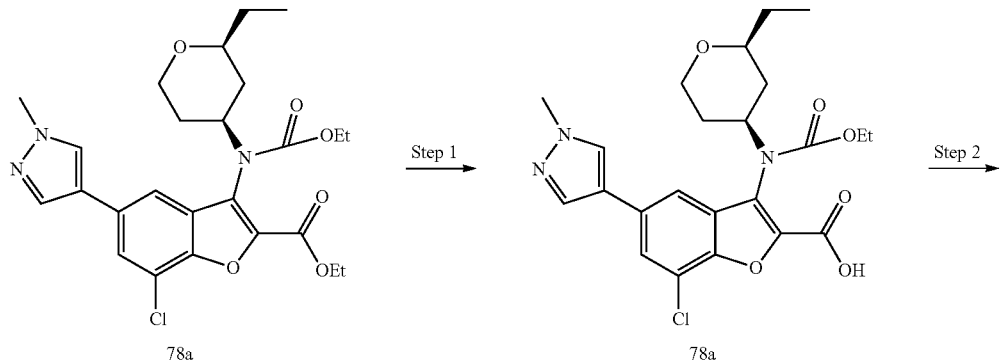

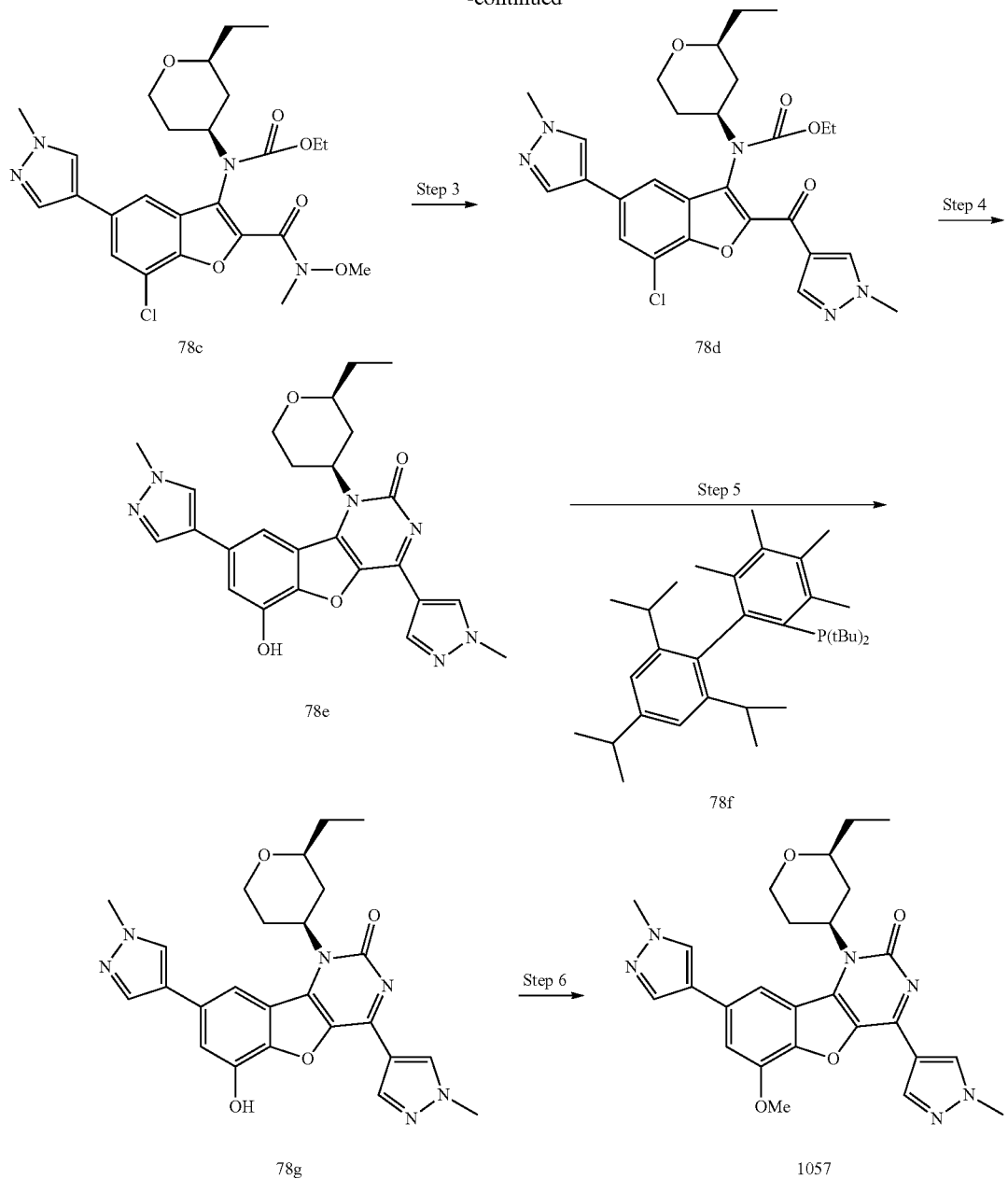

Step 1

According to general procedure B, ester 78a (0.80 g, 1.58 mmol) is hydrolysed to afford crude acid 78b, which is used as such in the next step.

Ester 78a is prepared analogously to the procedure described in Example 59 (Steps 1 and 2), replacing 12d with 15d.

Step 2

According to general procedure C, crude acid 78b (0.62 g, 1.30 mmol) is converted to Weinreb amide 78c. Purification is by flash chromatography (70 to 100% EtOAc in hexanes).

Step 3

According to general procedure E, Weinreb amide 78c (200 mg, 0.39 mmol) is converted to ketone 78d. Purification is by flash chromatography (0 to 100% EtOAc in hex).

Step 4

According to general procedure F, ketone 78d (85 mg, 0.16 mg) is cyclized to afford crude arylchloride 78e. After aqueous workup, the crude arylchloride 78e is used as such in subsequent steps.

Step 5

A mixture of $Pd_2(dba)_3$ (14 mg, 0.015 mmol), ligand 78f (29.5 mg, 0.061 mmol, Aldrich), KOH (52 mg, 0.93 mmol) and arylchloride 78e (75.8 mg, 0.15 mmol) is dissolved in dioxane (1.3 mL), and water (0.63 mL). The solution is degassed (bubbling Ar) and heated to 100° C. in an oil bath for 16 h. The mixture is neutralized with HCl (1N) and diluted with water. The mixture is extracted with DCM (3×) and EtOAc (3×). The organic layers are combined, washed with brine, dried ($Na_2SO_4$), filtered and concentrated. The residue is purified by preparative HPLC to afford phenol 78g.

Step 6

Phenol 78g (23 mg, 0.048 mmol) is dissolved in anhydrous DMF (2 mL) and the solution is treated with $K_2CO_3$ (20 mg, 0.145 mmol) and MeI (15 μL, 0.24 mmol). The mixture is stirred at RT for 2 h, then taken up in EtOAc and washed with brine (4×). The organic layer is dried ($Na_2SO_4$), filtered and concentrated. The residue is purified by preparative HPLC to afford compound 1057.

Example 79

Preparation of Compound 1058

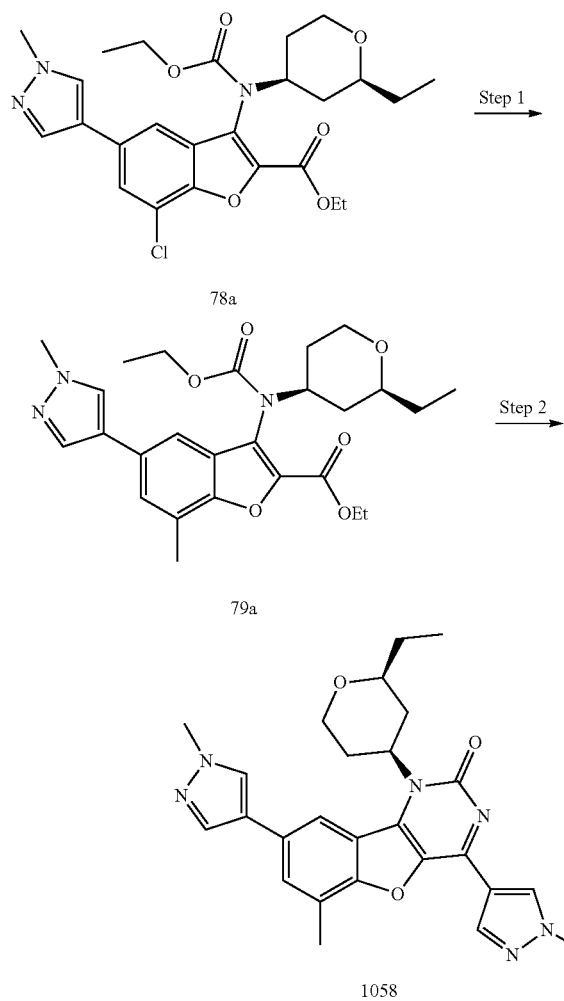

Step 1

Arylchloride 78a (400 mg, 0.79 mmol) is treated with MeB(OH)$_2$ (284 mg, 4.74 mmol), CsF (360 mg, 2.37 mmol) and Pd(PtBu$_3$)$_2$ (202 mg, 0.40 mmol, Strem) in degassed DMA (20 mL). The solution is heated in the microwave for 30 min at 150° C. The mixture is diluted with EtOAc, washed with brine, dried ($Na_2SO_4$), filtered and concentrated. Purification by preparative HPLC affords 79a.

Step 2

Ester 79a is elaborated to compound 1058 analogously to the procedure described in Example 59 (steps 3 and 4).

Example 80

Preparation of Compound 1059

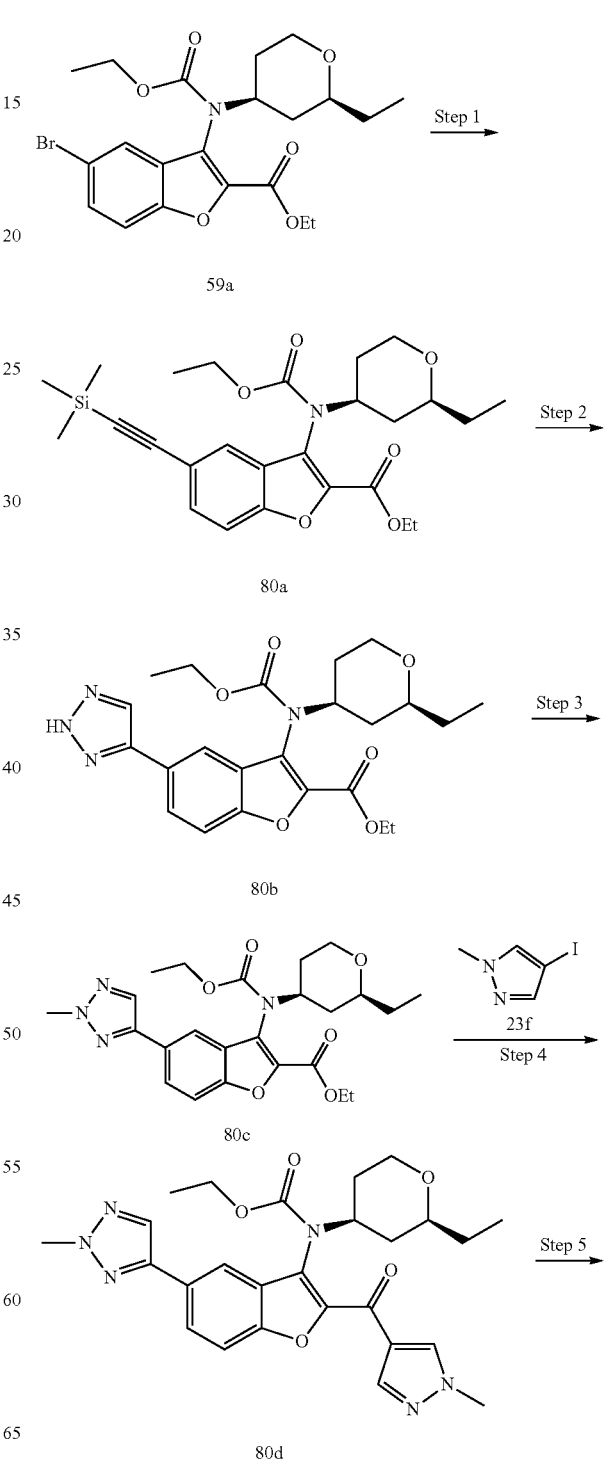

Example 81

Preparation of Compound 1060

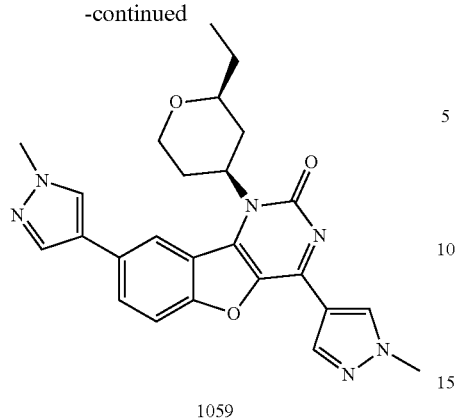

1059

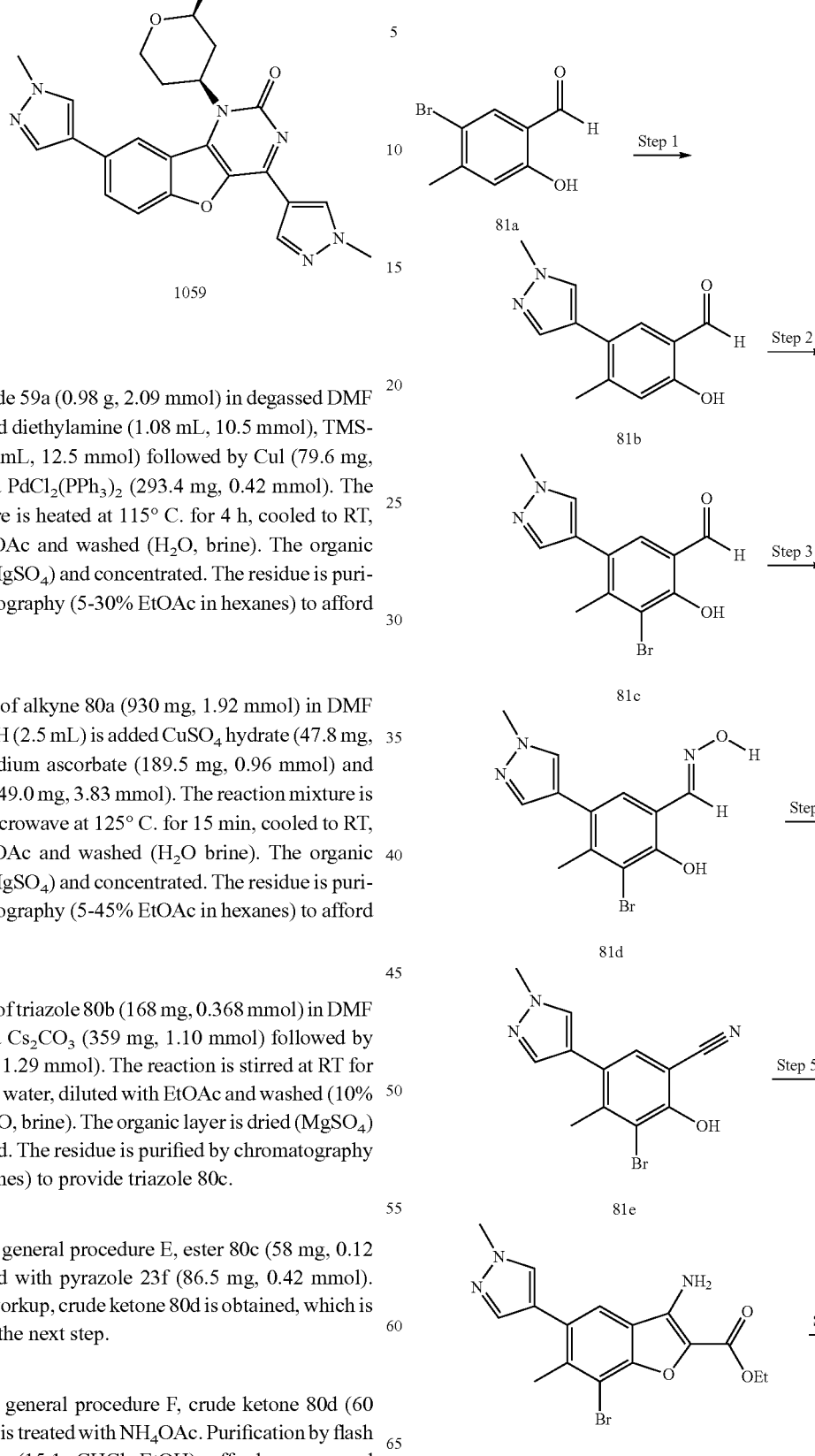

Step 1

To arylbromide 59a (0.98 g, 2.09 mmol) in degassed DMF (20 mL) is added diethylamine (1.08 mL, 10.5 mmol), TMS-acetylene (1.77 mL, 12.5 mmol) followed by CuI (79.6 mg, 0.42 mmol) and PdCl$_2$(PPh$_3$)$_2$ (293.4 mg, 0.42 mmol). The resulting mixture is heated at 115° C. for 4 h, cooled to RT, poured into EtOAc and washed (H$_2$O, brine). The organic layer is dried (MgSO$_4$) and concentrated. The residue is purified by chromatography (5-30% EtOAc in hexanes) to afford alkyne 80a.

Step 2

To a solution of alkyne 80a (930 mg, 1.92 mmol) in DMF (5 mL) and EtOH (2.5 mL) is added CuSO$_4$ hydrate (47.8 mg, 0.19 mmol), sodium ascorbate (189.5 mg, 0.96 mmol) and sodium azide (249.0 mg, 3.83 mmol). The reaction mixture is heated in the microwave at 125° C. for 15 min, cooled to RT, poured into EtOAc and washed (H$_2$O brine). The organic layer is dried (MgSO$_4$) and concentrated. The residue is purified by chromatography (5-45% EtOAc in hexanes) to afford triazole 80b.

Step 3

To a solution of triazole 80b (168 mg, 0.368 mmol) in DMF (8 mL) is added Cs$_2$CO$_3$ (359 mg, 1.10 mmol) followed by MeI (0.080 mL, 1.29 mmol). The reaction is stirred at RT for 3 h, diluted with water, diluted with EtOAc and washed (10% aq Na$_2$S$_2$O$_4$, H$_2$O, brine). The organic layer is dried (MgSO$_4$) and concentrated. The residue is purified by chromatography (EtOAc in hexanes) to provide triazole 80c.

Step 4

According to general procedure E, ester 80c (58 mg, 0.12 mmol) is treated with pyrazole 23f (86.5 mg, 0.42 mmol). After aqueous workup, crude ketone 80d is obtained, which is used as such in the next step.

Step 5

According to general procedure F, crude ketone 80d (60 mg, 0.12 mmol) is treated with NH$_4$OAc. Purification by flash chromatography (15:1 CHCl$_3$:EtOH) affords compound 1059.

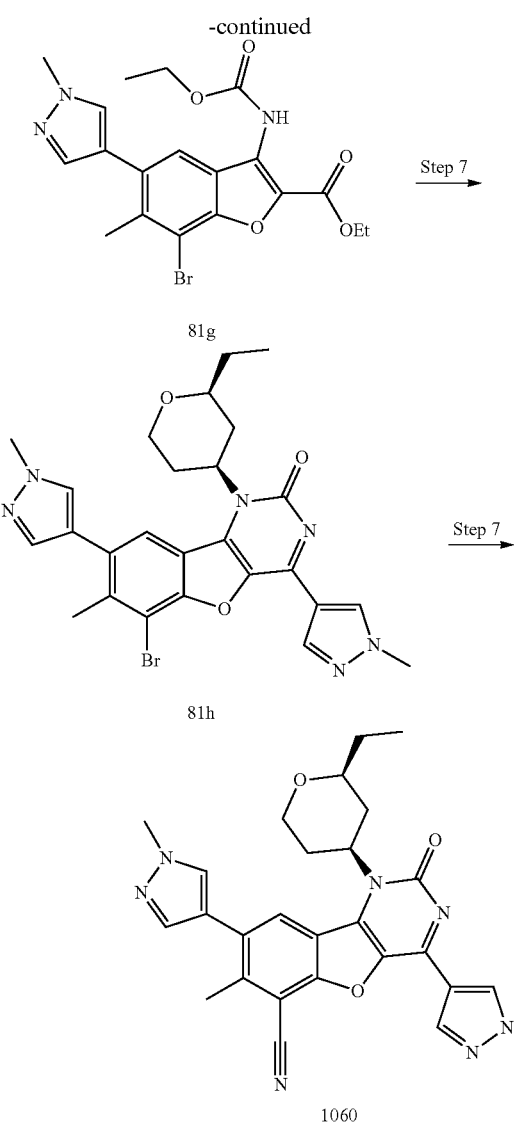

portionwise to this mixture, which is then stirred for 1 h at RT. Water and EtOAc are added to the mixture and the layers are separated. The aqueous layer is extracted with EtOAc (2×) and the combined organic layers are washed with brine, dried ($Na_2SO_4$), filtered and concentrated to afford crude nitrile 81e, which is used as such in the next step.

Step 5

A solution of crude phenol 81e (540 mg, 1.85 mmol) in acetone (10 mL) is treated with ethylbromo acetate (0.21 mL, 1.87 mmol) and heated at reflux overnight. The solution is poured into HCl (1 M) and extracted with EtOAc. The combined organic extracts are washed with brine, dried ($Na_2SO_4$) and concentrated. The residue is dissolved in EtOH (10 mL) and NaOEt/EtOH (21%, 0.2 mL) is added. The mixture is heated at 90° C. for 30 min. The solution is concentrated (approximately ⅓ of its volume) and filtered to give aryl 81f.

Step 6

A suspension of amine 81f (435 mg, 1.15 mmol) in toluene (10 mL) is treated with $EtCO_2Cl$ (0.55 mL, 5.75 mmol) and heated at 110° C. overnight. The solution is concentrated and the residue is triturated with hexanes and filtered to give carbamate 81g, which is used as such in the next step.

Step 7

Carbamate 81g is elaborated to cyclized aryl 81h analogously to the procedure described in Example 78 (steps 1 to 4).

Step 8

Bromide 81h (60 mg, 0.11 mmol) is combined with $Zn(CN)_2$ (63.9 mg, 0.54 mmol) and $Pd(PtBu_3)_2$ (27.8 mg, 0.054 mmol) in degassed DMA (3 mL). The mixture is heated in the microwave (120° C., 20 min). The mixture is quenched with AcOH and TFA, then the diluted with MeOH and filtered (Acrodisk). The solution is purified by preparative HPLC to afford compound 1060.

Example 82

Preparation of Compound 1061

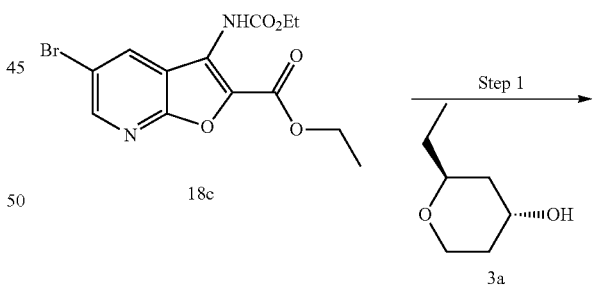

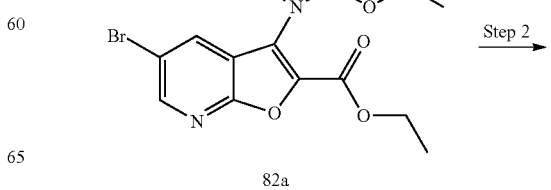

Step 1

According to General Procedure D1, a mixture of bromophenol 81a (900 mg, 4.18 mmol, Oakwood), boronate 23d (1.74 g, 8.37 mmol, Aldrich) and $NaHCO_3$ (1.05 g, 12.55 mmol) in 4:1 dioxane/$H_2O$ (45 mL) is degassed and Pd(dppf)$Cl_2$-DCM complex (342 mg, 0.42 mmol) is added. The mixture is heated at 80° C. for 18 h, then diluted with EtOAc (200 mL), washed (water, brine), dried ($Na_2SO_4$), filtered and concentrated. The residue is purified by flash chromatography to provide pyrazole 81 b.

Step 2

To a solution of aryl 81b (536 mg, 2.47 mmol) in AcOH (10 mL) at RT is added $Br_2$ (127 μL, 2.47 mmol). The solution is stirred at RT for 45 min and then diluted with EtOAc (150 mL), washed (water, brine), dried ($Na_2SO_4$), filtered and concentrated. The residue is purified by flash chromatography to provide arylbromide 81c.

Step 3

To solution of aldehyde 81c in iPr-OH (16 mL) is added hydroxylamine hydrochloride (522 mg, 7.51 mL). The solution is heated to reflux for 1 h, cooled to 0° C. and filtered.

The filtrate is concentrated, triturated twice with cold iPr-OH and filtered to provide oxime 81d.

Step 4

Cyanuric chloride is added in portions to DMF at 0° C. and the mixture is stirred for 1 h at RT. Oxime 81d is added

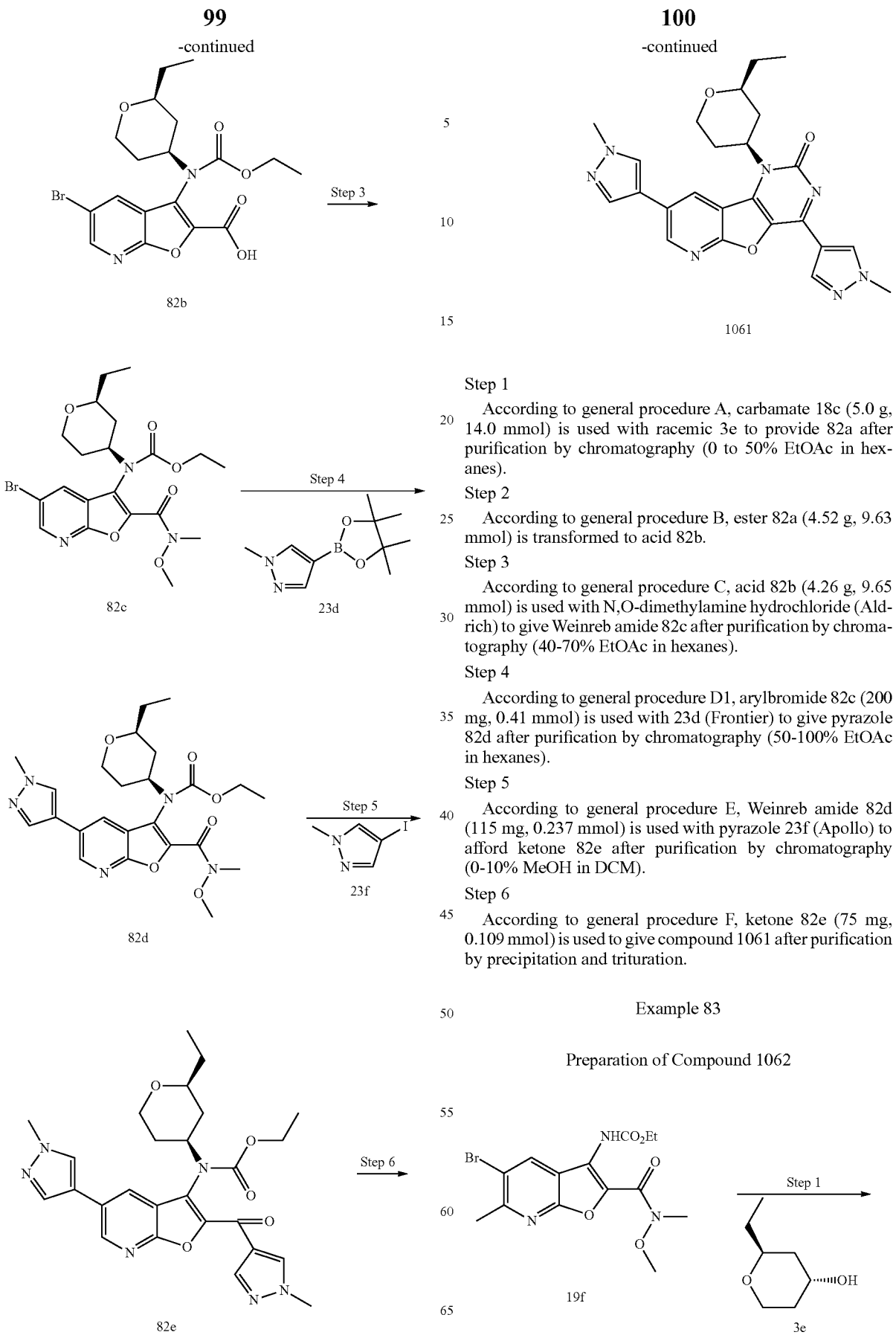

Step 1

According to general procedure A, carbamate 18c (5.0 g, 14.0 mmol) is used with racemic 3e to provide 82a after purification by chromatography (0 to 50% EtOAc in hexanes).

Step 2

According to general procedure B, ester 82a (4.52 g, 9.63 mmol) is transformed to acid 82b.

Step 3

According to general procedure C, acid 82b (4.26 g, 9.65 mmol) is used with N,O-dimethylamine hydrochloride (Aldrich) to give Weinreb amide 82c after purification by chromatography (40-70% EtOAc in hexanes).

Step 4

According to general procedure D1, arylbromide 82c (200 mg, 0.41 mmol) is used with 23d (Frontier) to give pyrazole 82d after purification by chromatography (50-100% EtOAc in hexanes).

Step 5

According to general procedure E, Weinreb amide 82d (115 mg, 0.237 mmol) is used with pyrazole 23f (Apollo) to afford ketone 82e after purification by chromatography (0-10% MeOH in DCM).

Step 6

According to general procedure F, ketone 82e (75 mg, 0.109 mmol) is used to give compound 1061 after purification by precipitation and trituration.

Example 83

Preparation of Compound 1062

-continued

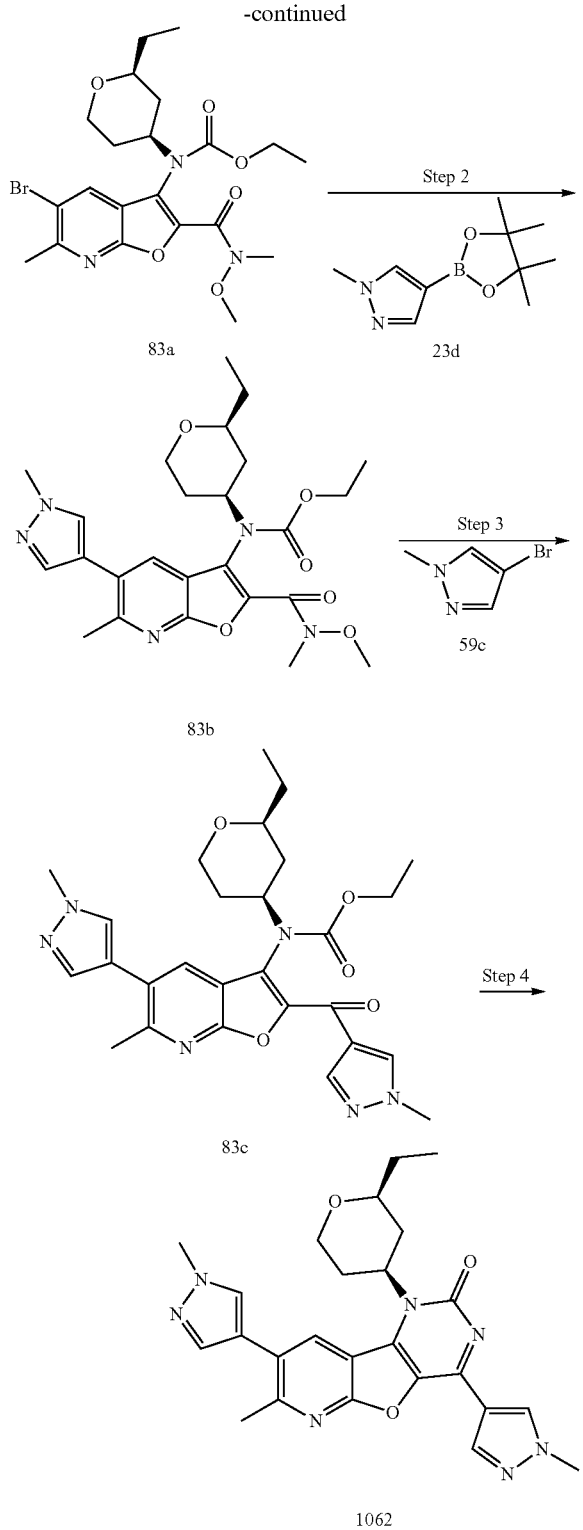

83a

23d

83b

59c

83c

1062

Step 1
According to general procedure A, carbamate 19f (3.3 g, 8.62 mmol) is used with 3e to give 83a after purification by chromatography (10 to 50% EtOAc in hexanes).

Step 2
According to general procedure D1, arylbromide 83a (2.50 g, 5.02 mmol) is used with boronate ester 23d (Frontier) to give pyrazole 83b after purification by chromatography (50-100% EtOAc in hexanes).

Step 3
According to general procedure E, Weinreb amide 83b (1.00 g, 2.00 mmol) is used with pyrazole 59c (Aldrich) to afford ketone 83c after purification by chromatography (0-2% MeOH in DCM).

Step 4
According to general procedure F, ketone 83c (936 mg, 1.80 mmol) is transformed to compound 1062 after purification by precipitation and trituration.

Example 84

Preparation of Compound 1063

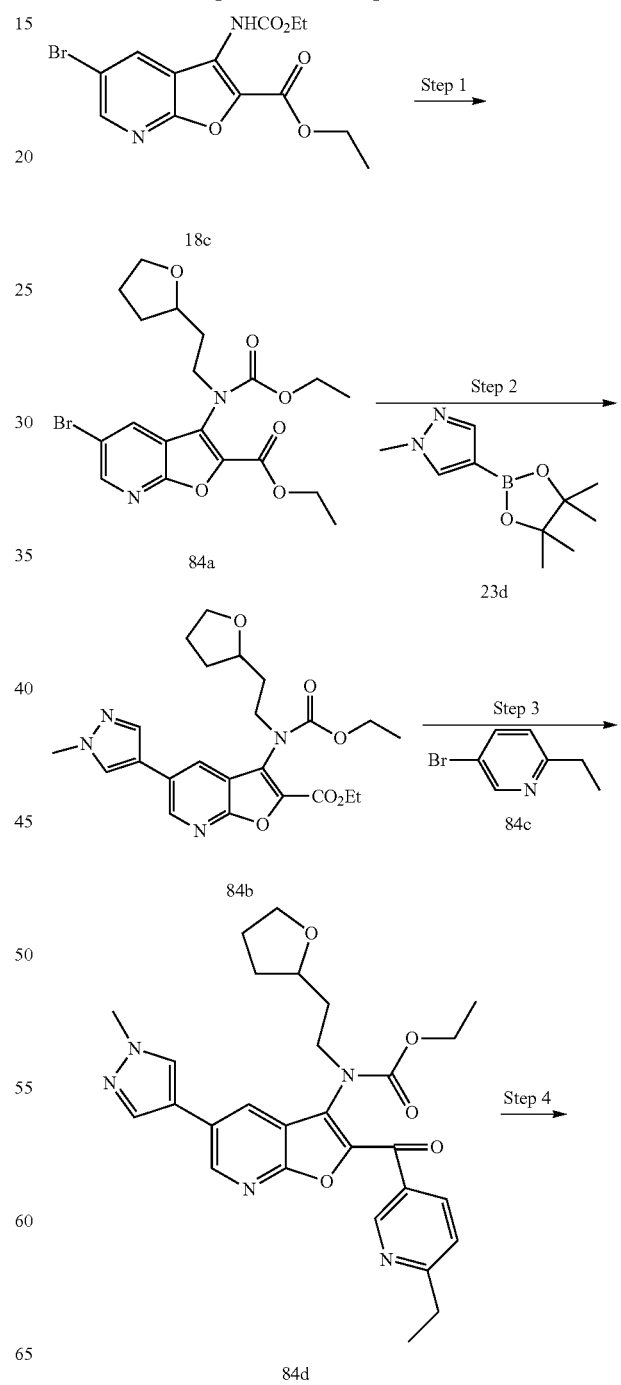

18c

84a

23d

84b

84c

84d

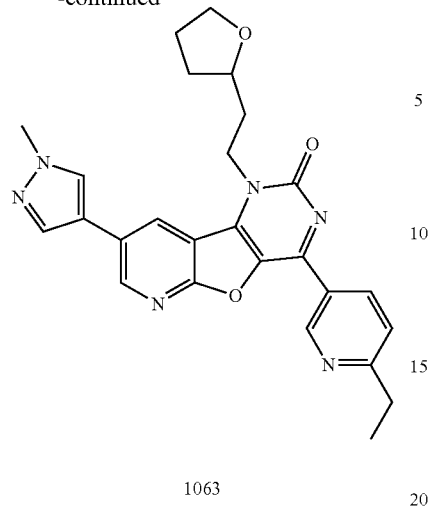

1063

Step 1
According to general procedure G, carbamate 18c (12 g, 33.6 mmol) is used with 2a to provide 84a after purification by chromatography (0-50% EtOAc in hexanes).

Step 2
According to general procedure D1, arylbromide 84a (6 g, 13.2 mmol) is used with boronate ester 23d to provide pyrazole 84b after purification by chromatography (50-100% EtOAc in hexanes).

Step 3
According to general procedure E, ester 84b (70 mg, 0.153 mmol) is used with 3-bromo-6-ethylpyridine 84c to give ketone 84d after purification by chromatography (50-100% EtOAc in hexanes).

Preparation of 84c

A solution of diethylzinc (7.05 mL, 7.05 mmol) is added to THF (12 mL) in a flame dried flask under nitrogen. The flask is charged with 3-bromo-6-iodopyridine (Maybridge, 2.00 g, 7.05 mmol) followed by Pd(PPh$_3$)$_4$ (407.1 mg, 0.35 mmol). The solution is stirred for 1 h and poured into 60 mL of saturated NaHCO$_3$ solution and extracted with EtOAc (2×). The combined organic phases are dried (MgSO$_4$), filtered and concentrated. The residue is purified by flash chromatography (10-50% EtOAc in hexanes) to afford 84c.

Step 4
According to general procedure F, ketone 84d (58 mg, 0.112 mmol) is converted to compound 1063 after purification by preparative HPLC. The obtained product is isolated as a TFA salt.

Example 85

Preparation of Compound 1064

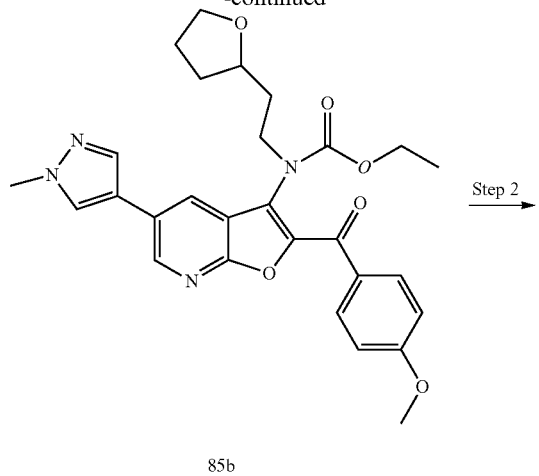

85b

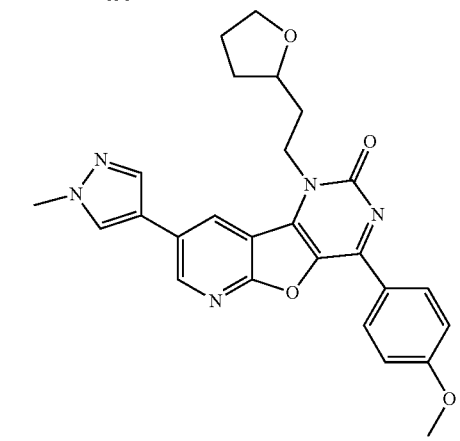

1064

Step 1
According to general procedure E, ester 84b (124 mg, 0.272 mmol) is used with 4-bromoanisole 85a (Aldrich) to afford ketone 85b, but by pre-forming the anion at −78° C. prior to the addition of ester 84b. Purification is by chromatography (70-100% EtOAc in hexanes).

Step 2
According to general procedure F, ketone 85b (140 mg, 0.270 mmol) is used to afford compound 1064 with purification by preparative HPLC.

Example 86

Preparation of Compound 1065

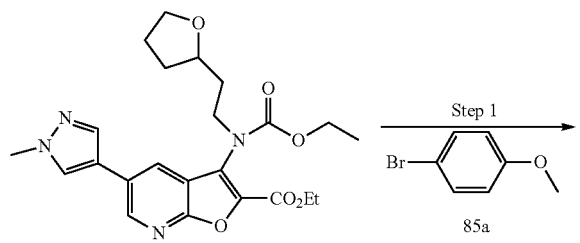

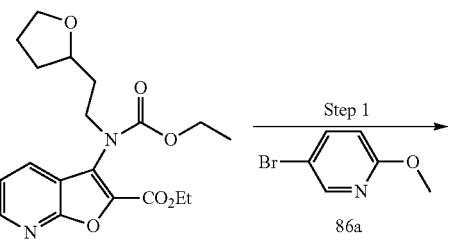

105

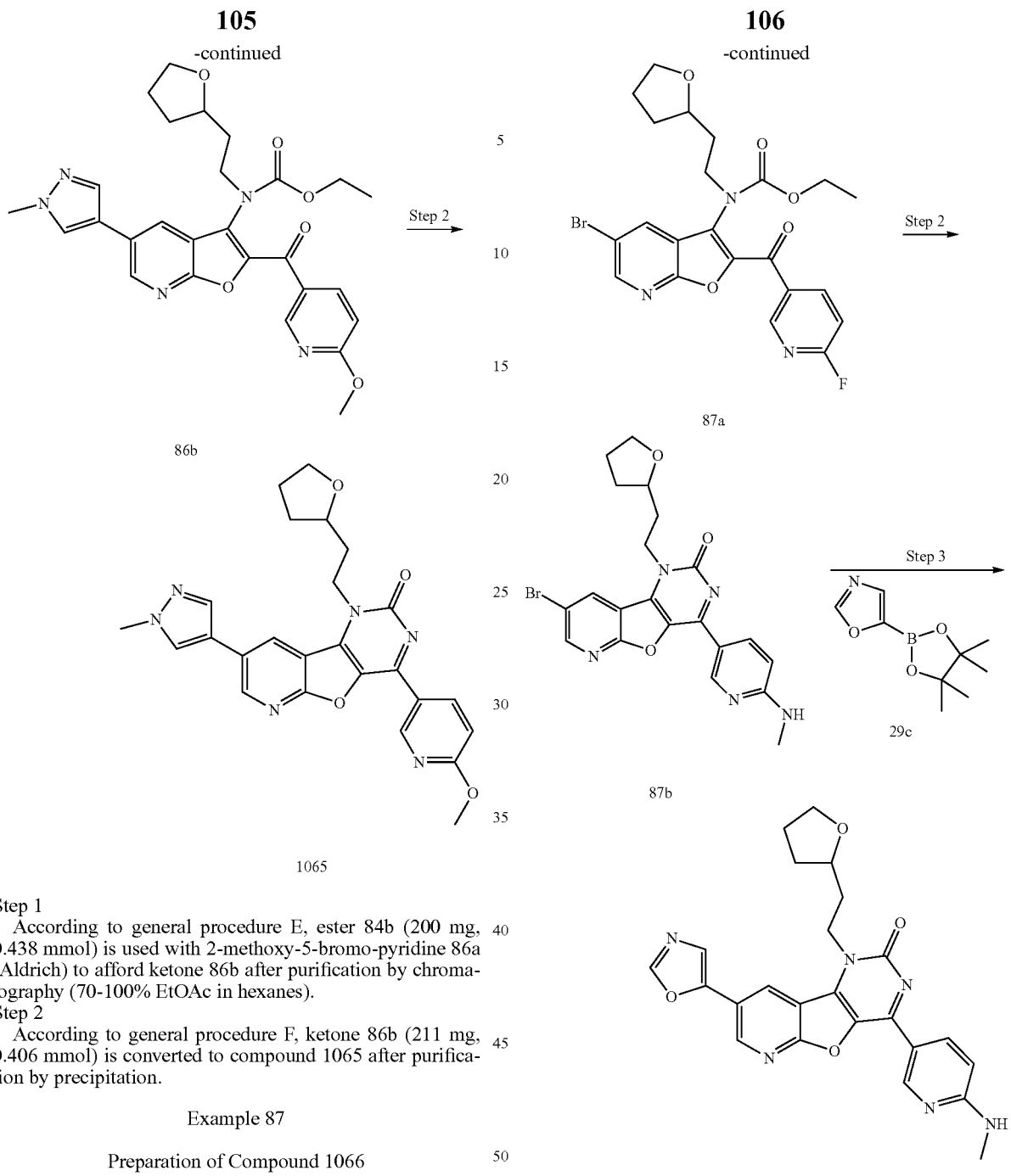

86b

1065

Step 1
According to general procedure E, ester 84b (200 mg, 0.438 mmol) is used with 2-methoxy-5-bromo-pyridine 86a (Aldrich) to afford ketone 86b after purification by chromatography (70-100% EtOAc in hexanes).

Step 2
According to general procedure F, ketone 86b (211 mg, 0.406 mmol) is converted to compound 1065 after purification by precipitation.

Example 87

Preparation of Compound 1066

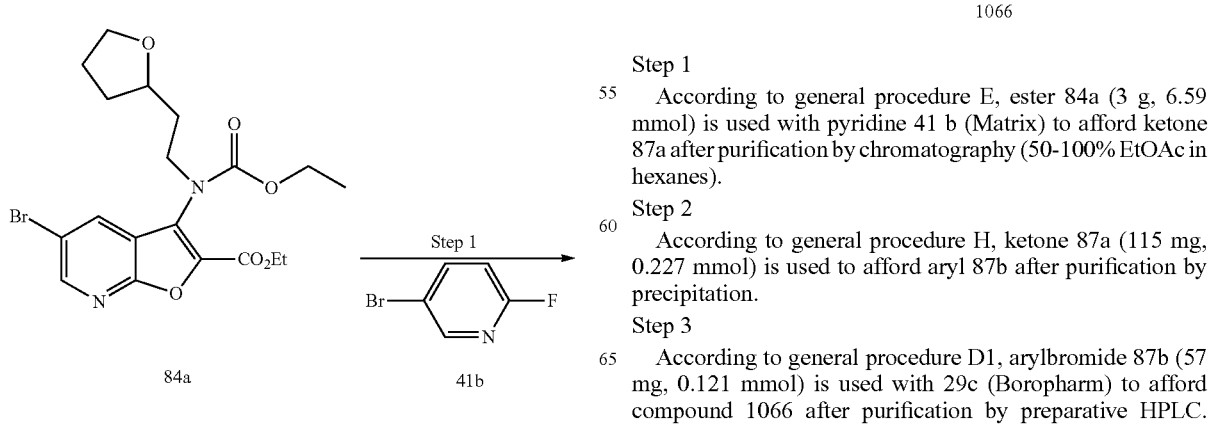

84a     41b

106

87a

87b

29c

1066

Step 1
According to general procedure E, ester 84a (3 g, 6.59 mmol) is used with pyridine 41b (Matrix) to afford ketone 87a after purification by chromatography (50-100% EtOAc in hexanes).

Step 2
According to general procedure H, ketone 87a (115 mg, 0.227 mmol) is used to afford aryl 87b after purification by precipitation.

Step 3
According to general procedure D1, arylbromide 87b (57 mg, 0.121 mmol) is used with 29c (Boropharm) to afford compound 1066 after purification by preparative HPLC.

Example 88

Preparation of Compound 1067

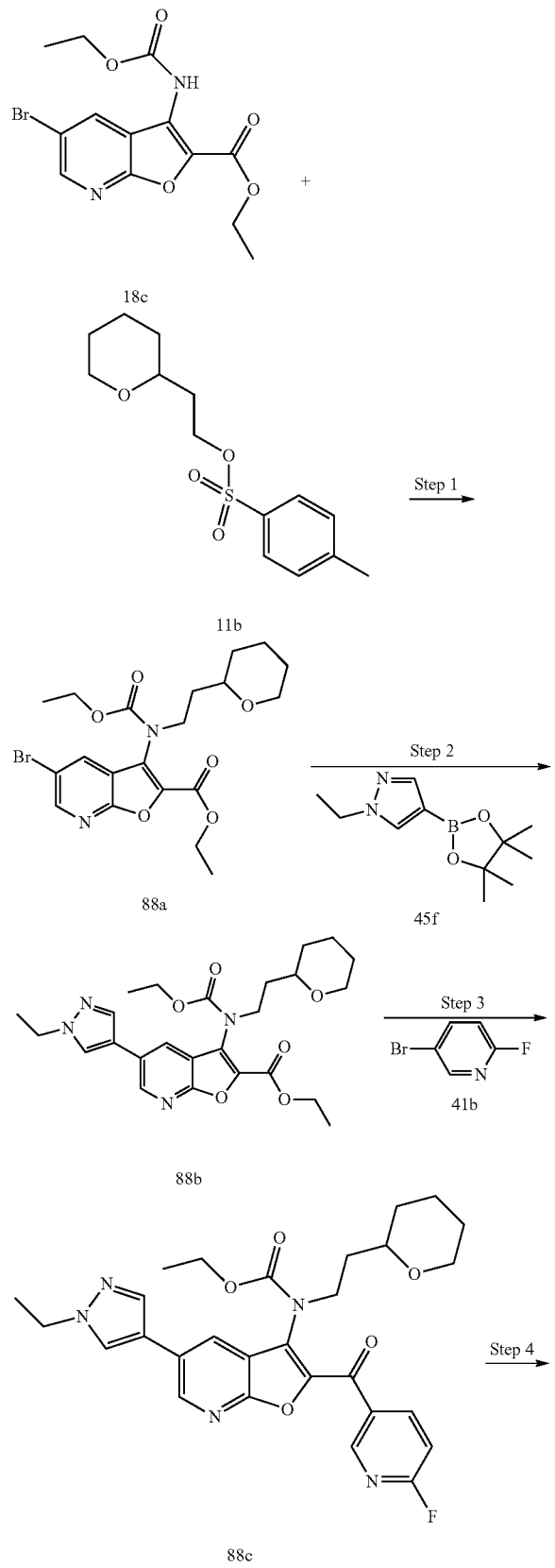

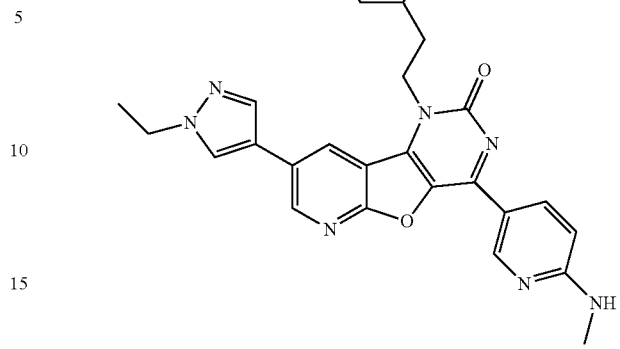

Step 1

According to general procedure G, carbamate 18c (1.92 g, 5.37 mmol) is used with 11 b to afford 88a after purification by chromatography (0-40% EtOAc in hexanes).

Step 2

According to general procedure D2, arylbromide 88a (1.25 g, 2.66 mmol) is used with boronate ester 45f to afford pyrazole 88b after purification by chromatography (60-100% EtOAc in hexanes).

Step 3

According to general procedure E, ester 88b (410 mg, 0.846 mmol) is used with pyridine 41b (Matrix) to afford ketone 88c after purification by chromatography (60-100% EtOAc in hexanes).

Step 4

According to general procedure H, ketone 88c (50 mg, 0.096 mmol) is transformed to compound 1067 after purification by preparative HPLC.

Example 89

Preparation of Compound 1068

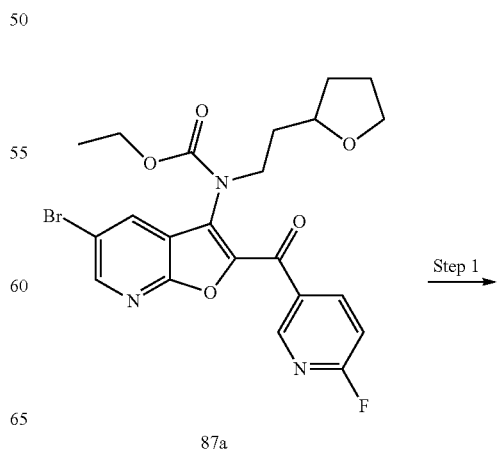

109

-continued

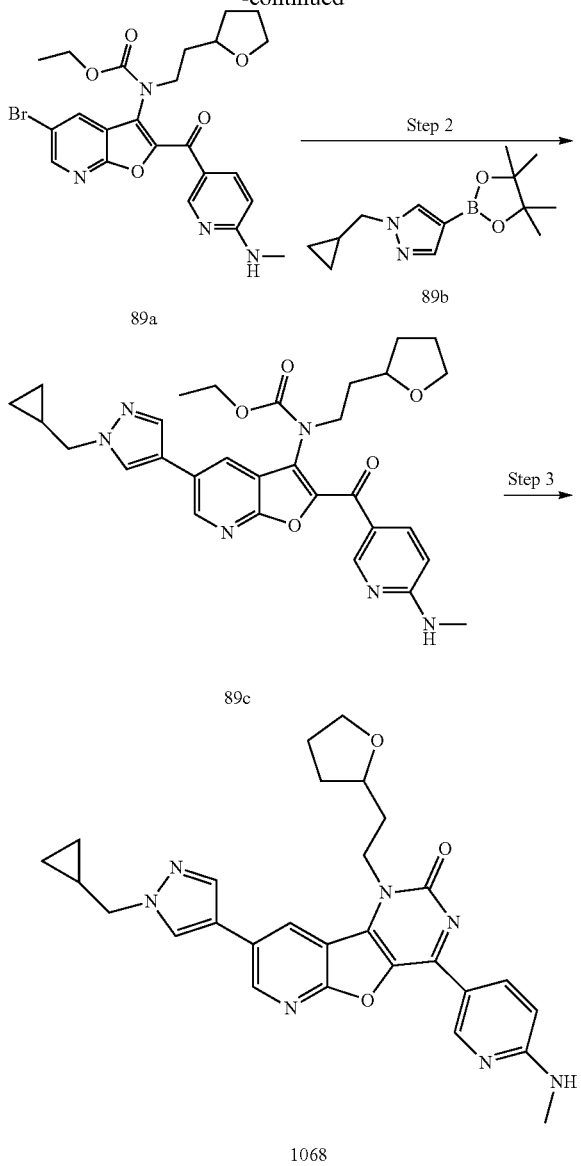

Step 1

To a solution of 87a (1 g, 1.98 mmol) in DMSO (1.5 mL) is added methylamine (5.55 mL, 2.0 M in THF). The mixture is heated at 50° C. in a sealed tube for 1 h. The mixture is cooled to RT, diluted with water and extracted with EtOAc, The combined organic extracts are washed with water, brine, dried (Na$_2$SO$_4$) and concentrated to afford amine 89a.

Step 2

According to general procedure D2, arylbromide 89a (50 mg, 0.097 mmol) is used with boronate ester 89b (prepared analogously to the procedure described in Example 45 Step 5, replacing ethyliodide with (bromomethyl)cyclopropane, Matrix) to afford pyrazole 89c after purification by chromatography (0 to 5% MeOH in DCM).

Step 3

According to general procedure F, ketone 89c (17 mg, 0.030 mmol) is used to afford compound 1068 after purification by precipitation.

110

Example 90

Preparation of Compound 1069

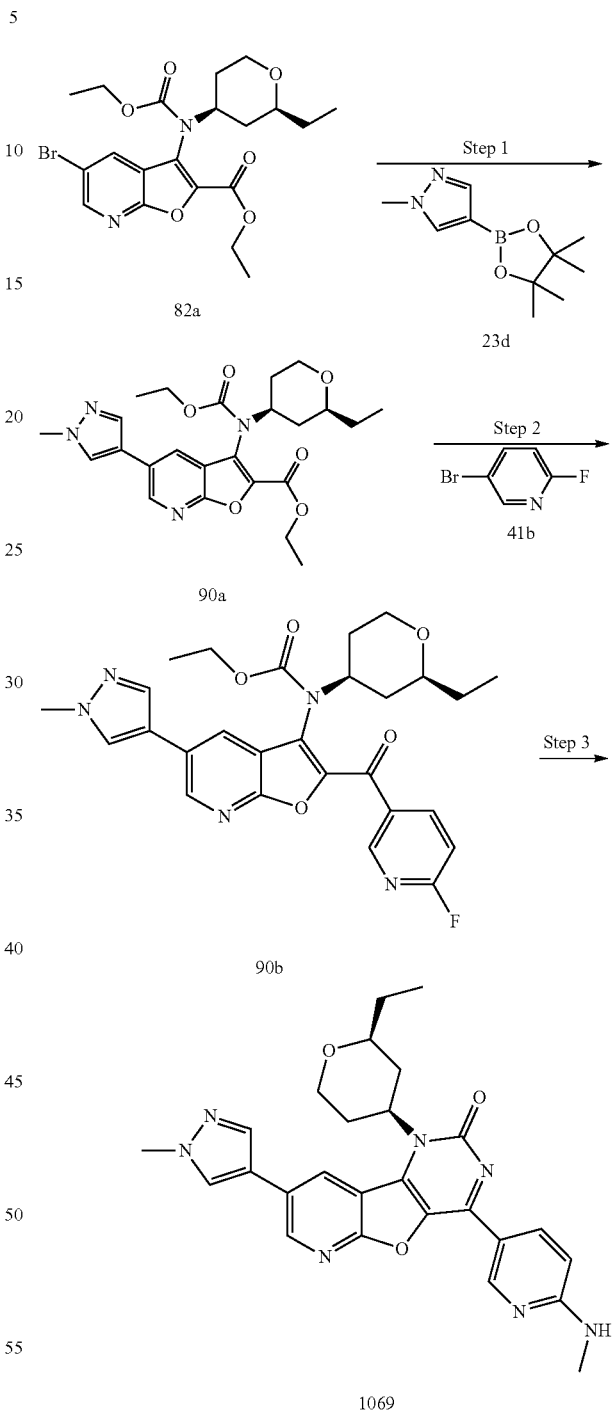

Step 1

According to general procedure D1, arylbromide 82a (720 mg, 1.54 mmol) is used with boronate ester 23d (Frontier) to afford pyrazole 90a after purification by chromatography (0-100% EtOAc in hexanes).

Step 2

According to general procedure E, ester 90a (365 mg, 0.776 mmol) is used with pyridine 41b (Matrix) to afford ketone 90b after purification by chromatography (0-100% EtOAc in hexanes).

Step 3

According to general procedure H, ketone 90b (370 mg, 0.709 mmol) is transformed to compound 1069 after purification by preparative HPLC.

Example 91

Preparation of Compound 1070

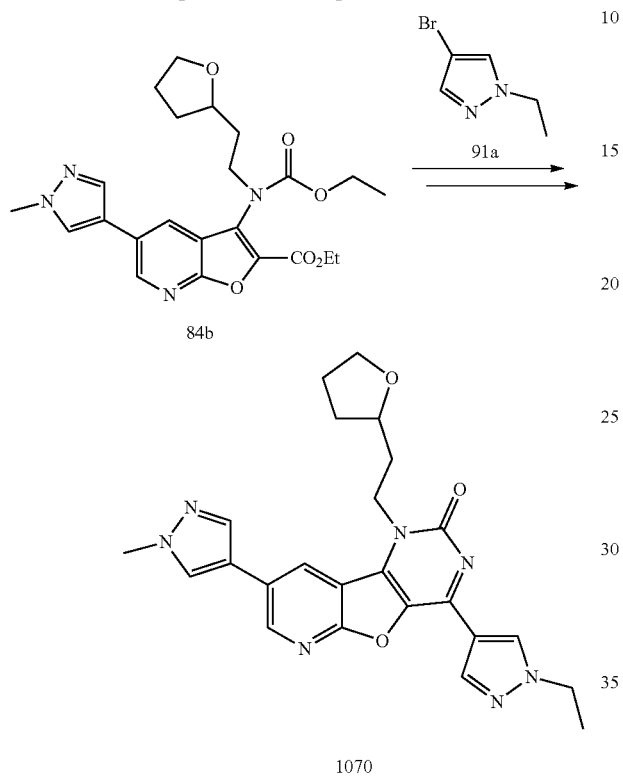

According to general procedure E, ester 84b (prepared analogously to the procedure described in Example 51 replacing 51a with 1e) (75 mg, 0.164 mmol) is used with pyrazole 91a (Aldrich). The resulting intermediate is used without further purification and submitted to general procedure F to obtain compound 1070 after purification by preparative HPLC.

Example 92

Preparation of Compound 1071

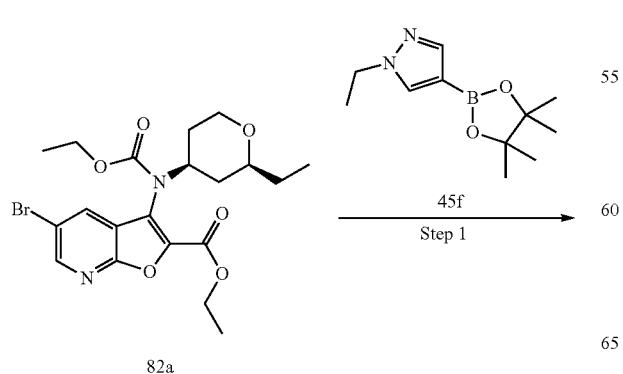

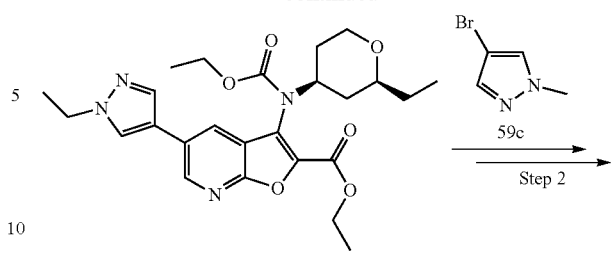

Step 1

According to general procedure D1, arylbromide 82a (250 mg, 0.533 mmol) is used with boronate ester 45f to afford pyrazole 92a after purification by chromatography (0-100% EtOAc in hexanes).

Step 2

According to general procedure E, ester 92a (98 mg, 0.202 mmol) is treated with pyrazole 59c (Aldrich). The resulting intermediate is used without further purification and submitted to general procedure F to obtain compound 1071 after purification by preparative HPLC.

Example 93

Preparation of Compound 1072

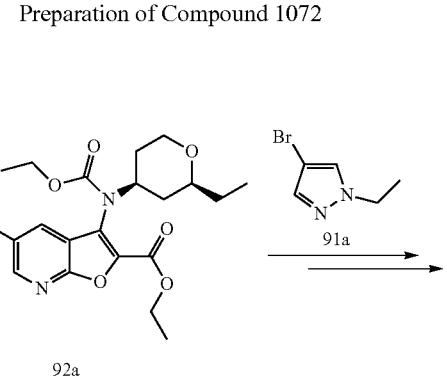

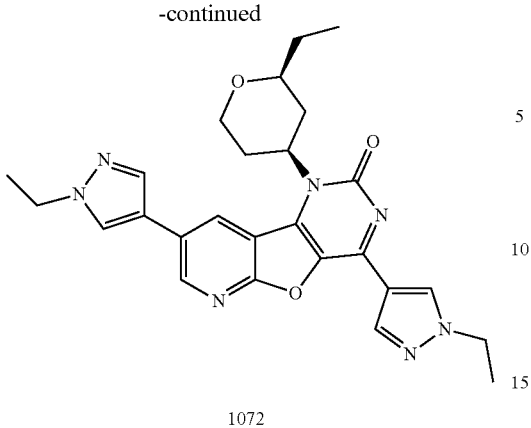

1072

According to general procedure E, ester 92a (98 mg, 0.202 mmol) is treated with pyrazole 91a (Aldrich). The resulting intermediate is used without further purification and submitted to general procedure F to obtain compound 1072 after purification by preparative HPLC.

Example 94

Preparation of Compound 1073

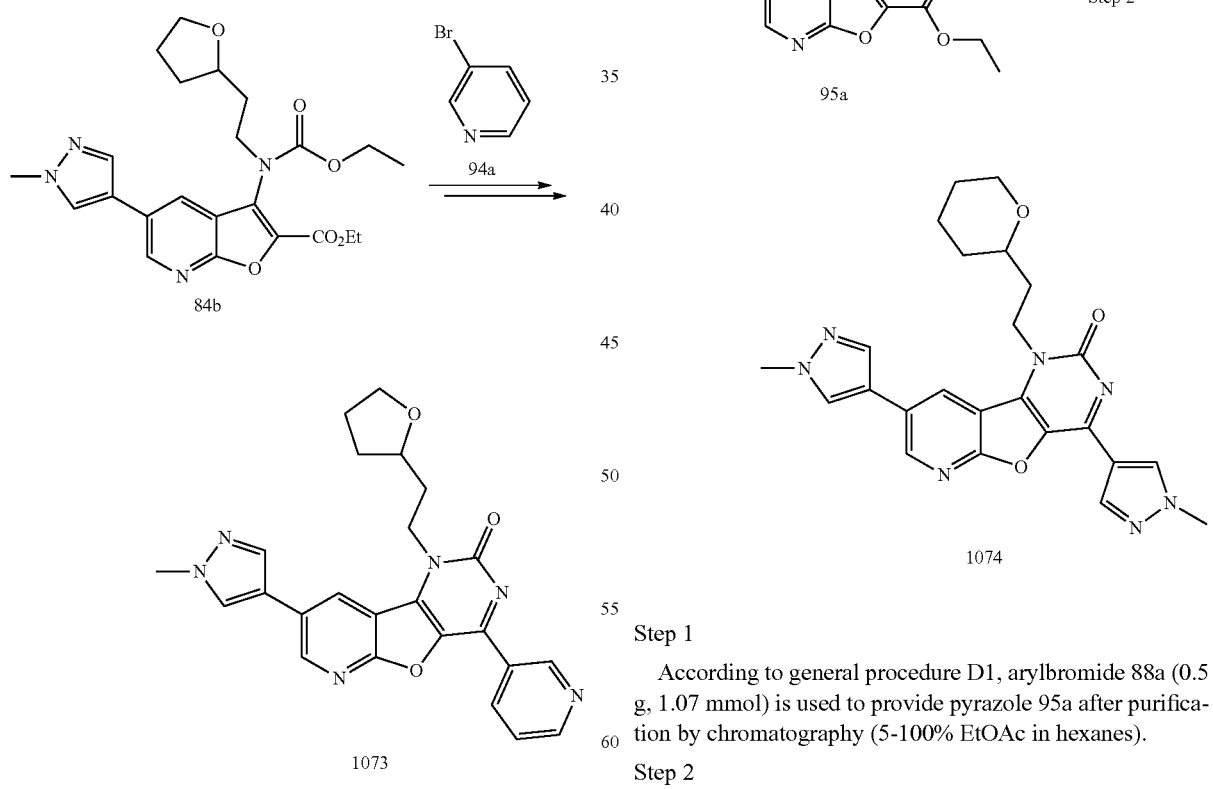

1073

According to general procedure E, ester 84b (prepared analogously to the procedure described in Example 51 replacing 51a with 1e) (86 mg, 0.188 mmol) is used with pyridyl 94a. The resulting intermediate is used without further purification and submitted to general procedure F to afford compound 1073 after purification by preparative HPLC.

Example 95

Preparation of Compound 1074

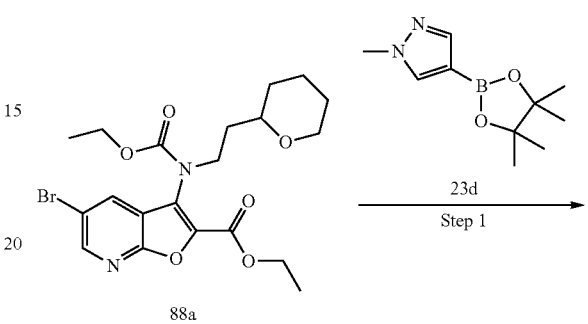

88a

95a

1074

Step 1

According to general procedure D1, arylbromide 88a (0.5 g, 1.07 mmol) is used to provide pyrazole 95a after purification by chromatography (5-100% EtOAc in hexanes).

Step 2

According to general procedure E, ester 95a (100 mg, 0.213 mmol) is used with pyrazole 59c (Aldrich). The resulting intermediate is used without further purification and submitted to general procedure F to provide compound 1074 after purification by preparative HPLC.

Example 96

Preparation of Compound 1075

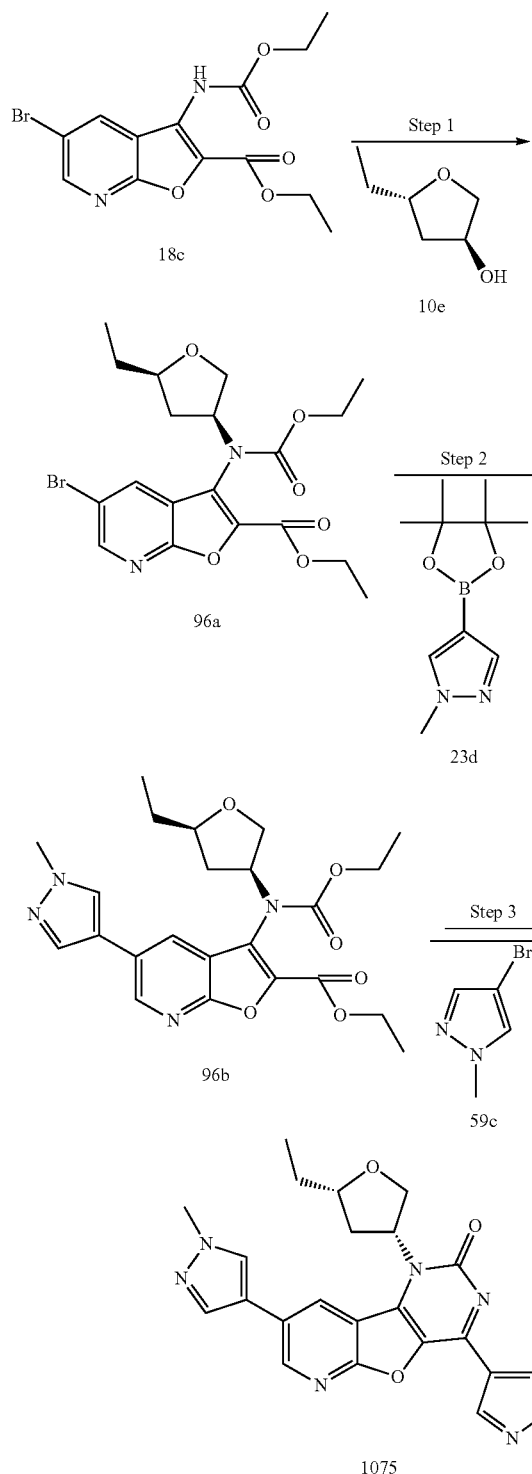

Step 1

According to general procedure A, carbamate 18c (263 mg, 2.26 mmol) is used with racemic 10e to provide 96a after purification by chromatography (0 to 100% EtOAc in hexanes).

Step 2

According to general procedure D1, arylbromide 96a (600 mg, 1.33 mmol) is used with boronate ester 23d (Frontier) to provide pyrazole 96b after purification by chromatography (40-100% EtOAc in hexanes).

Step 3

According to general procedure E, ester 96b (100 mg, 0.219 mmol) is used with pyrazole 59c (Aldrich). The resulting intermediate is used without further purification and submitted to general procedure F to provide compound 1075 after purification by preparative HPLC.

Example 97

Preparation of Compound 1076

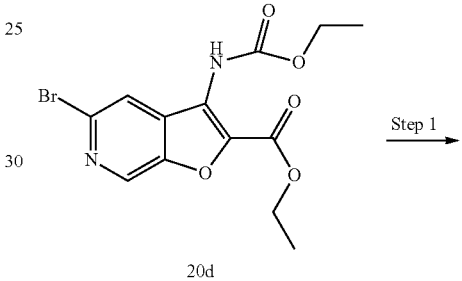

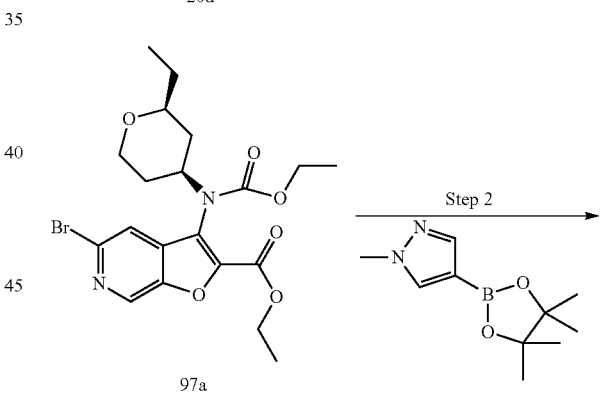

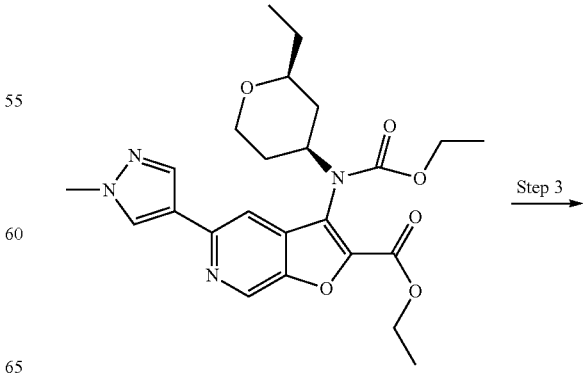

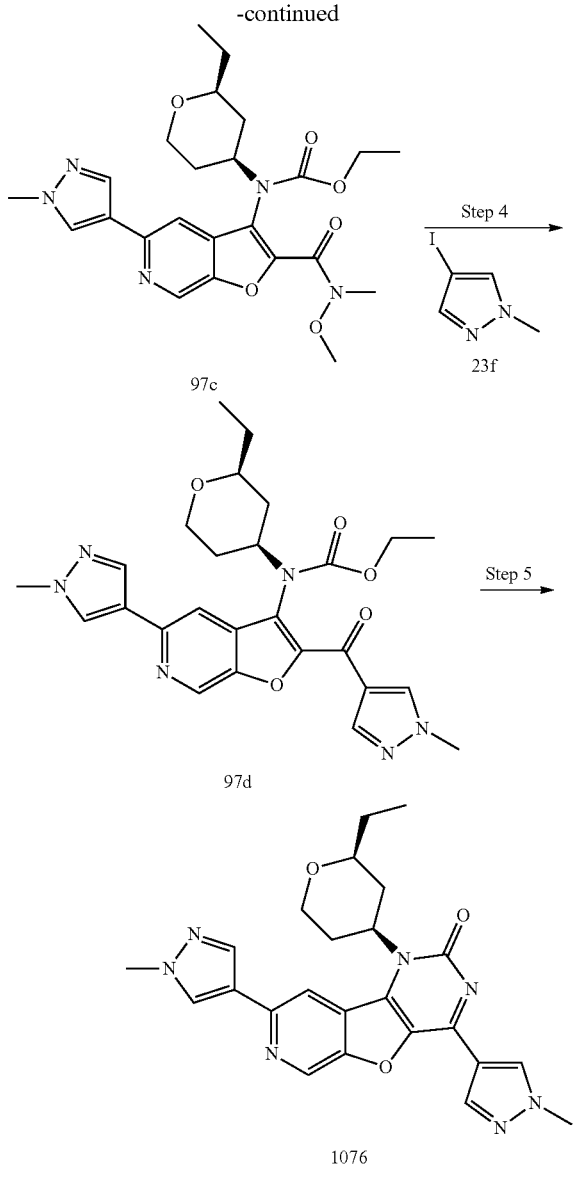

Step 3
According to general procedure I, ester 97b (23.0 g, 48.9 mmol) is used to give Weinreb amide 97c after purification by chromatography (0-100% EtOAc in hexanes to 10% MeOH in EtOAc).

Step 4
According to general procedure E, Weinreb amide 97c (17.0 g, 35.0 mmol) is used to give ketone 97d after purification by chromatography (0-100% EtOAc in hexanes to 10% MeOH in EtOAc.

Step 5
Ketone 97d (16.8 g, 33.2 mmol) is charged with ammonium acetate (158 g, 2.56 mol), and NMP (168 mL) and degassed with $N_2$ for 10 min. The solution is heated at 130° C. until no more fumes from the reaction mixture. $NH_3$ is then bubbled to the reaction at 130° C. for 2-4 h until complete conversion. The reaction mixture is cooled to RT and diluted with water and DCM. The aqueous layer is extracted with DCM and the combined organic extracts are washed with water, brine and concentrated. EtOAc is added to the slurry and further concentrated until a precipitate is formed. The solution is filtered. The obtained cake is washed with EtOAc and triturated at reflux with $MeOH/H_2O$ for 2 h. The suspension is filtered, the cake washed with water and dried to provide compound 1076.

Example 98

Preparation of Compound 1077

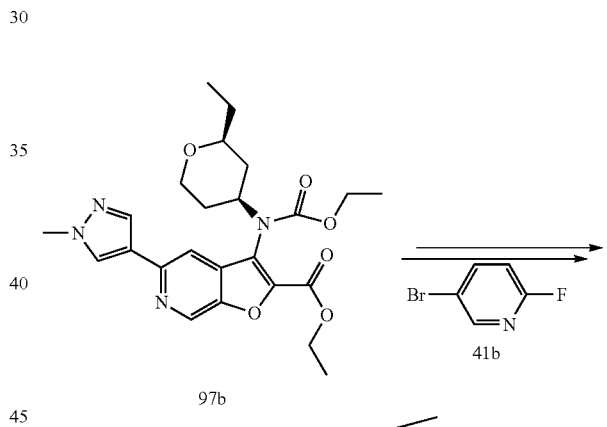

Step 1
To a solution of carbamate 20d (52.5 g, 147 mmol), $PPh_3$ (77.6 g, 294 mmol) and 7c (23 g, 176.4 mmol) in degassed THF (2000 mL) at 0° C. is added DIAD (59.4 g, 294 mmol) over 30-40 min while keeping an internal temperature <5° C. The solution is stirred at RT for 18 h, then concentrated to dryness, charged with MTBE (150 mL), and concentrated again to dryness. The solution is charged with MTBE (140 mL), methylcyclohexane (150 mL), and heptane (150 mL) and stirred for 1 h at RT. The suspension is filtered and the filter cake rinsed sequentially with a mixed solvent (45 mL methylcyclohexane and 5 mL MTBE) followed by (50 mL methylcyclohexane and 50 mL MTBE). The filtrate is concentrated to dryness. The residue is purified by chromatography to provide 97a.

Step 2
According to general procedure D1, arylbromide 97a (52.5 g, 100.6 mmol) is used with boronate ester 23d to give pyrazole 97b after purification by chromatography (0-100% EtOAc in hexanes).

According to general procedure E, ester 97b (150 mg, 0.319 mmol) is used with pyridine 41 b (Matrix). The resulting intermediate is used without further purification and submitted to general procedure H to provide compound 1077 after purification by preparative HPLC.

Example 99

Preparation of Compound 1078

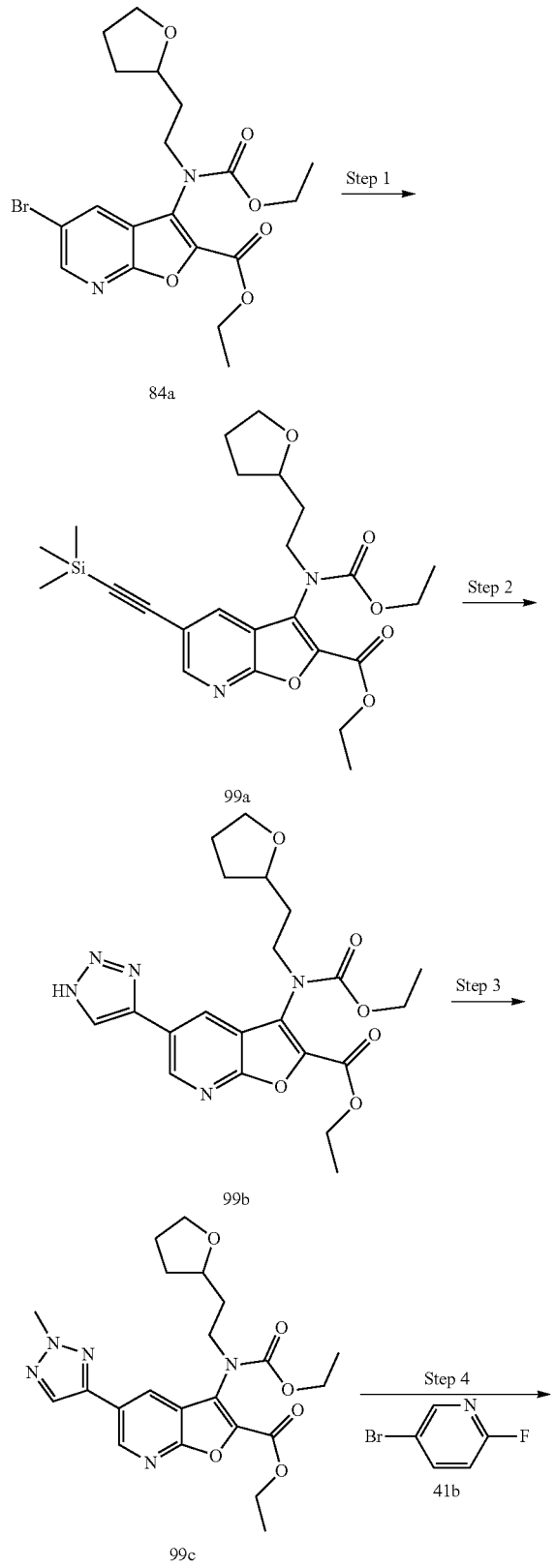 [SMILES: CCOC(=O)c1oc2ncc(Br)cc2c1N(CCC1CCCO1)C(=O)OCC ; CCOC(=O)c1oc2ncc(C#C[Si](C)(C)C)cc2c1N(CCC1CCCO1)C(=O)OCC ; CCOC(=O)c1oc2ncc(-c3c[nH]nn3)cc2c1N(CCC1CCCO1)C(=O)OCC ; CCOC(=O)c1oc2ncc(-c3cnn(C)n3)cc2c1N(CCC1CCCO1)C(=O)OCC ; Fc1ccc(Br)cn1]
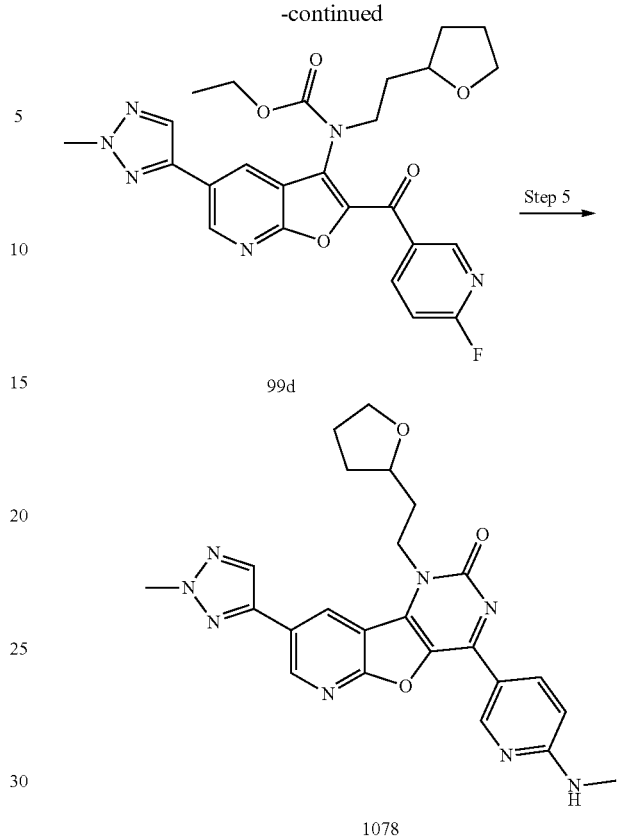

Step 1

To a solution of 84a (1 g, 2.20 mmol) in degassed DMF (25 mL) is added N,N-diethylamine (1.1 mL, 11 mmol), TMS-acetylene (Farchan, 1.87 mL, 13.2 mmol) followed by CuI (84 mg, 0.440 mmol) and $PdCl_2(PPh_3)_2$ (309 mg, 0.440 mmol). The mixture is heated at 120° C. for 4 h, cooled to RT, diluted with $H_2O$ and extracted with EtOAc. The combined organic extracts are washed with brine, dried ($Na_2SO_4$) and concentrated. The residue is purified by chromatography (20-100% EtOAc in hexanes) to provide alkyne 99a.

Step 2

To a solution of alkyne 99a (800 mg, 1.69 mmol) in DMF (10 mL) and EtOH (5 mL) is added $CuSO_4$ hydrate (42 mg, 0.170 mmol), sodium ascorbate (168 mg, 0.850 mmol) and sodium azide (221 mg, 3.40 mmol). The mixture is heated in the microwave at 125° C. for 25 min, diluted with water and extracted with EtOAc. The combined organic extracts are washed with brine, dried ($Na_2SO_4$) and concentrated. The residue is purified by chromatography (EtOAc in hexanes) to provide triazole 99b.

Step 3

To a solution of triazole 99b (215 mg, 0.485 mmol) in DMF (6 mL) is added $Cs_2CO_3$ (400 mg, 1.23 mmol) followed by MeI (0.078 mL, 0.980 mmol). The mixture is stirred at RT for 3 h, diluted with water and extracted with EtOAc. The combined organic extracts are washed with brine, dried ($Na_2SO_4$) and concentrated. The residue is purified by chromatography (EtOAc in hexanes) to provide triazole 99c.

Step 4

According to general procedure E, ester 99c (50 mg, 0.109 mmol) is used with pyridine 41b (Matrix) to provide ketone 99d after purification by chromatography (50-100% EtOAc in hexanes).

Step 5

According to general procedure H, ketone 99d (40 mg, 0.079 mmol) is transformed to compound 1078 after purification by precipitation.

Example 100

Preparation of Compound 1079

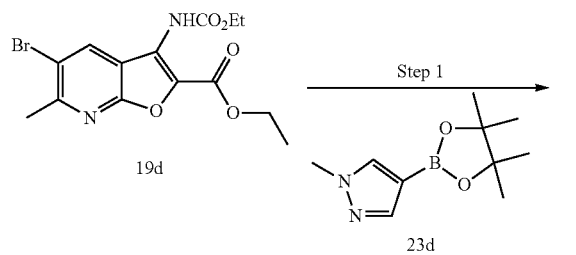

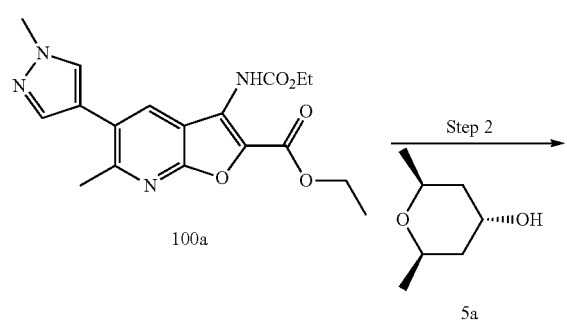

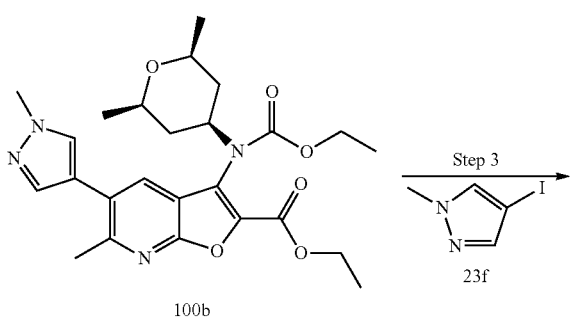

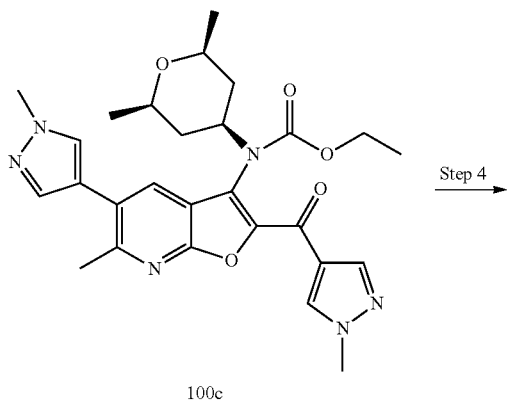

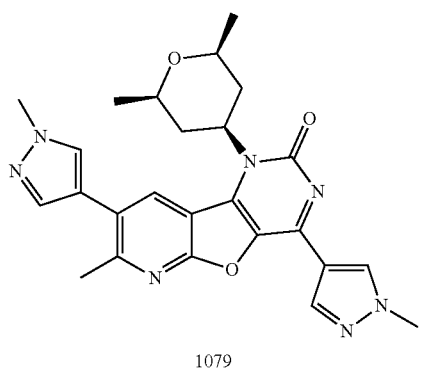

1079

Step 1

According to general procedure D1, arylbromide 19d (4.0 g, 10.8 mmol) is used with boronate ester 23d to afford pyrazole 100a after purification by chromatography (0-100% EtOAc in hexanes).

Step 2

According to general procedure A, carbamate 100a (250 mg, 0.67 mmol) is used with 5a to afford crude 100b, which is used as such in the next step. Purification is by chromatography (0-100% EtOAc in hexanes).

Step 3

According to general procedure E, crude ester 100b (250 mg, 0.53 mmol) is used with pyrazole 23f (Aldrich) to afford crude ketone 100c, which is used as such for the next step.

Step 4

According to general procedure F, crude ketone 100c (250 mg, 0.48 mmol) is transformed to compound 1079 after purification by neutralization with NaOH 5N followed by purification by preparative HPLC.

Example 101

Preparation of Compound 1080

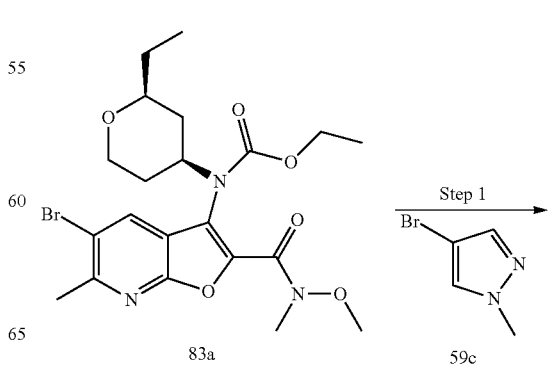

-continued

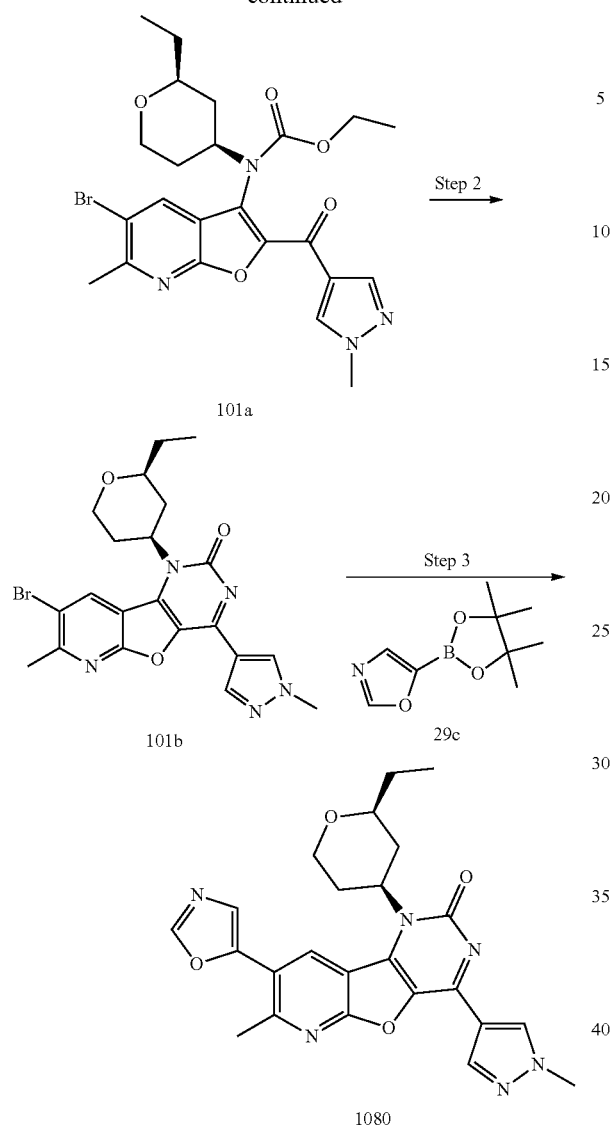

101a

101b

1080

Step 1

To a solution of pyrazole 59c (435 μL, 4.27 mmol) in THF (30 mL) cooled to −78° C. is added a solution of n-BuLi (4.14 mmol) dropwise. This suspension is stirred at −78° C. for 10 min and is then added via cannula to a solution of Weinreb amide 83a (1.3 g, 2.67 mmol) in THF (10 mL) at −78° C. The mixture is quenched with AcOH in THF (10%), then warmed to RT, silica gel is added and the volatiles are evaporated. The residue is purified by chromatography (20-50% EtOAc in hexanes) to provide ketone 101a.

Step 2

According to general procedure F, ketone 101a (480 mg, 0.92 mmol) is transformed to aryl 101 b after purification by precipitation in water with the addition of NaOH 10 N until basic pH is achieved.

Step 3

According to general procedure D2, arylbromide 101 b (50 mg, 0.11 mmol) is used with boronate ester 29c (Synthonix) to afford compound 1080 after purification by preparative HPLC.

Example 102

Preparation of Compound 1081

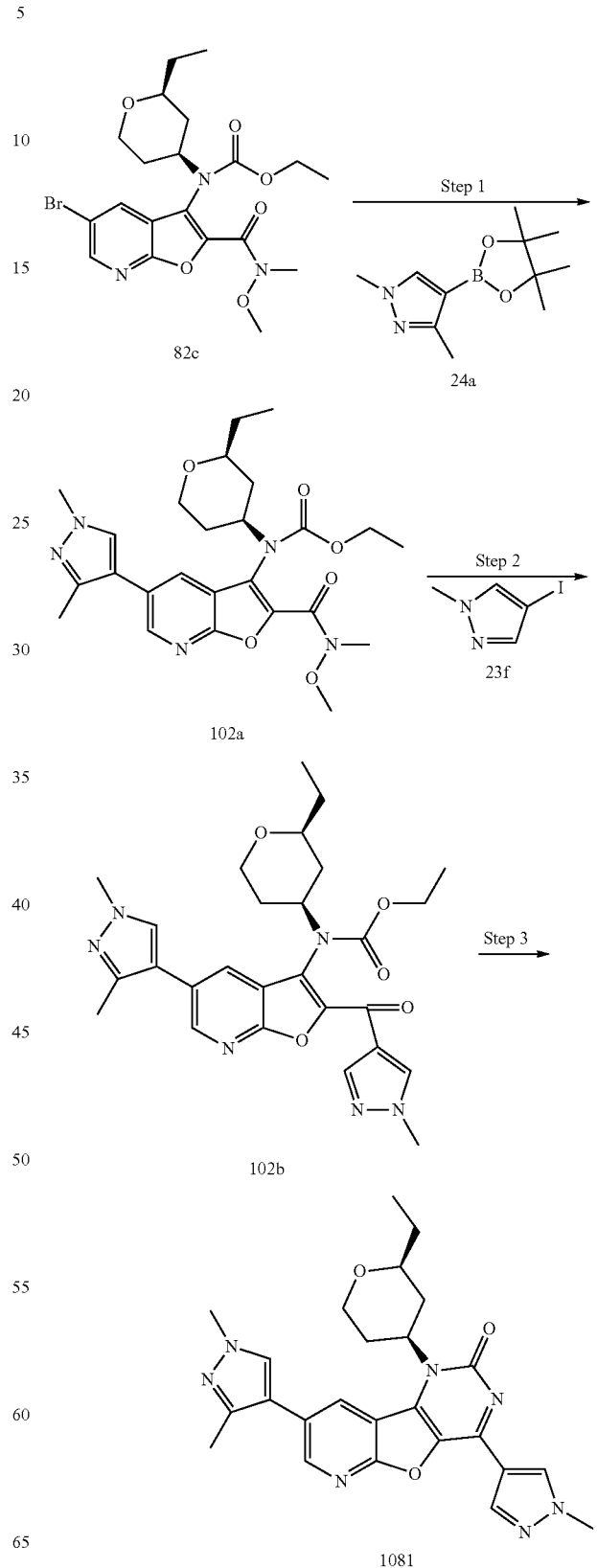

82c

24a

102a

23f

102b

1081

125

Step 1

According to general procedure D2, arylbromide 82c (768 mg, 1.58 mmol) is used with boronate ester 24a to provide pyrazole 102a after purification by chromatography (30-100% EtOAc in hexanes).

Step 2 According to general procedure E, Weinreb amide 102a (643 mg, 1.29 mmol) is used with pyrazole 23f (Aldrich) to provide ketone 102b after purification by chromatography (0-10% MeOH in DCM).

Step 3

According to general procedure F, ketone 102b (700 mg, 1.34 mmol) is transformed to compound 1081 after purification by precipitation and trituration and treatment with activated carbon (Darco G60).

Example 103

Preparation of Compound 1082

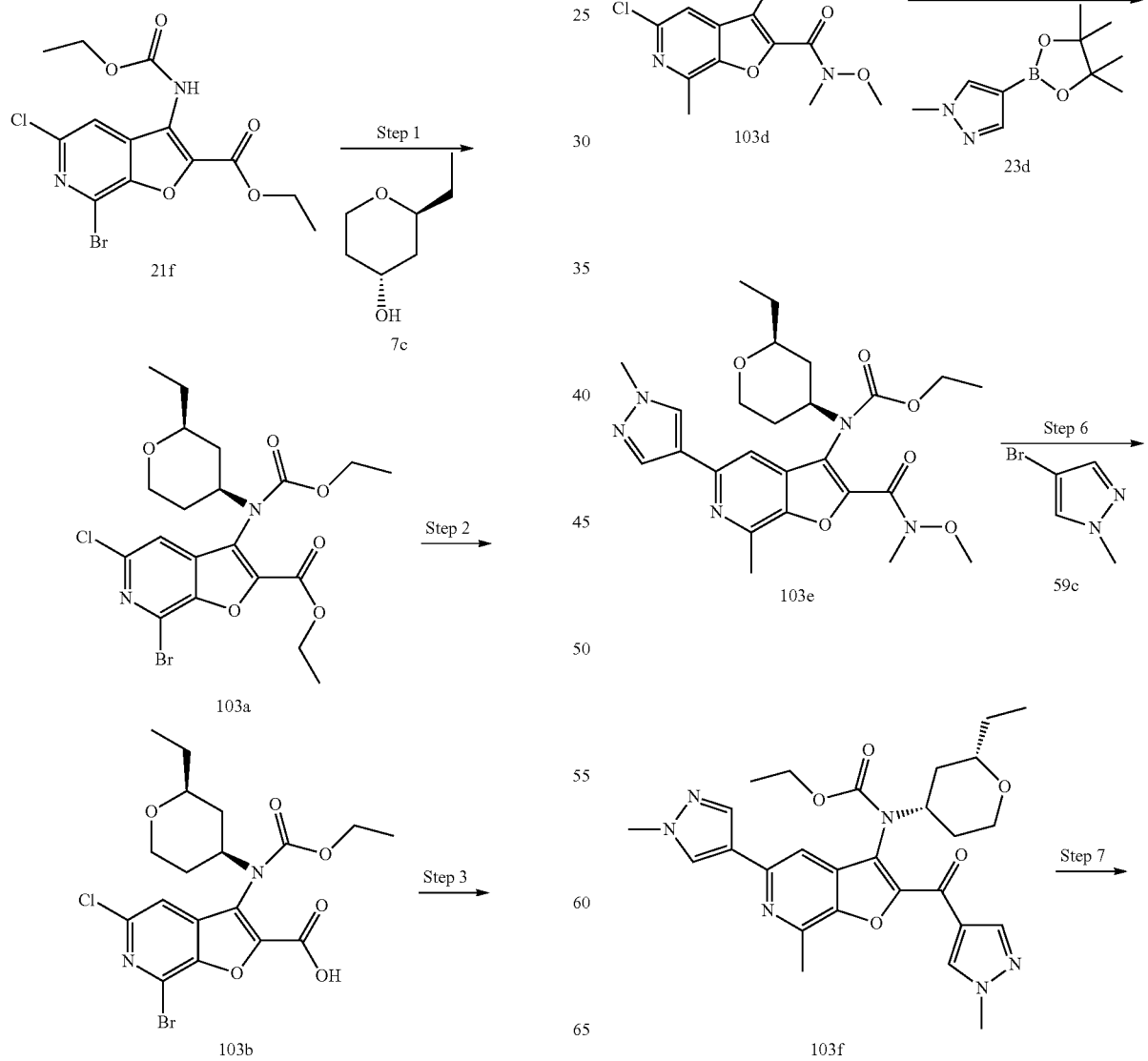

-continued

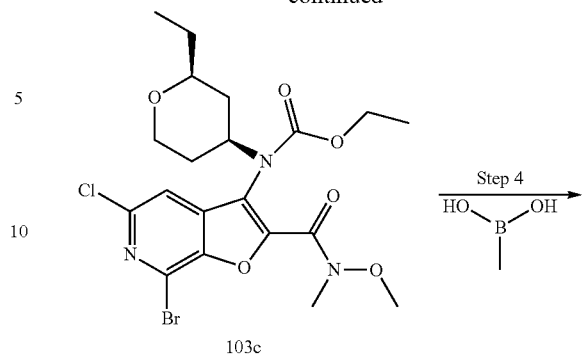

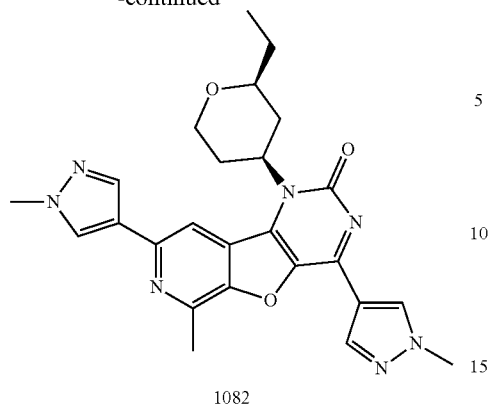

1082

Step 1
According to general procedure A, carbamate 21f (400 mg, 1.02 mmol) is used with 7c to give 103a after purification by chromatography (0-100% EtOAc in hexanes).

Step 2
According to general procedure B, ester 103a (300 mg, 0.596 mmol) is transformed to acid 103b.

Step 3
According to general procedure C, acid 103b (283 mg, 0.600 mmol) is transformed to Weinreb amide 103c after purification by chromatography (10-50% EtOAc in hexanes).

Step 4
According to general procedure D1, arylbromide 103c (265 mg, 0.511 mmol) is used with methylboronic acid (Aldrich) to provide 103d after purification by chromatography (10-60% EtOAc in hexanes).

Step 5
According to general procedure D2, arylchloride 103d (50 mg, 0.110 mmol) is used with boronate ester 23d (Frontier) to afford crude pyrazole 103e after purification by chromatography (0 to 5% MeOH in DCM).

Step 6
According to general procedure E, crude Weinreb amide 103e (55 mg, 0.110 mmol) is used with pyrazole 59c (Aldrich) to afford ketone 103f after purification by chromatography (0 to 10% MeOH in DCM).

Step 7
According to general procedure F, ketone 103f (24 mg, 0.046 mmol) is transformed to compound 1082 after purification by preparative HPLC.

Example 104

Preparation of Compound 1083

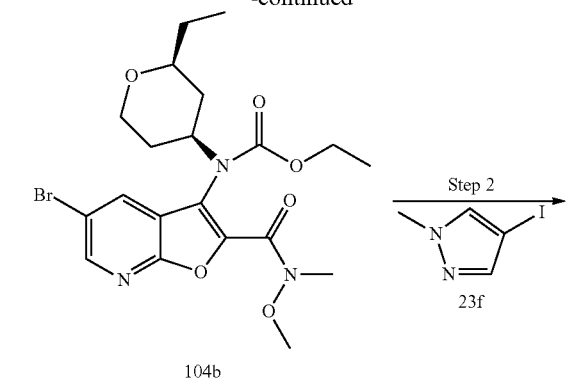

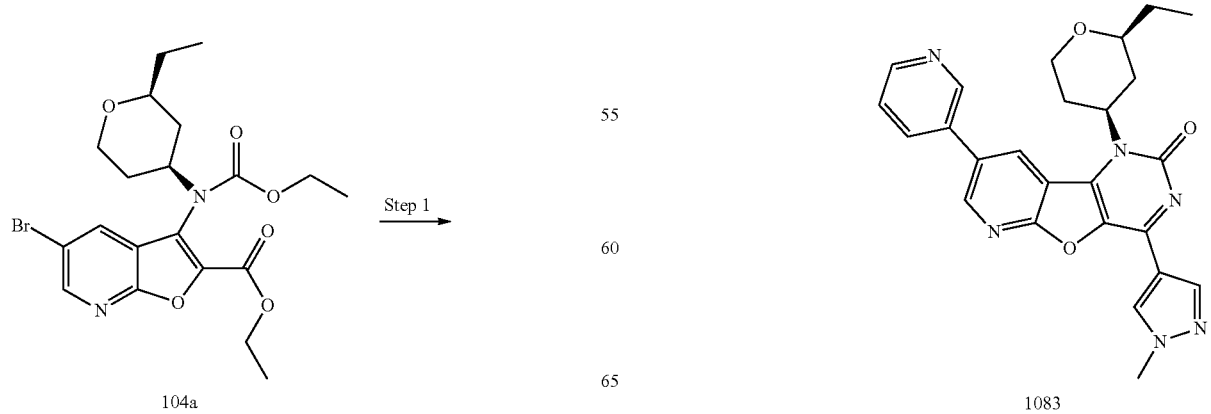

Step 1

According to general procedure I, ester 104a (800 mg, 1.70 mmol, prepared analogously to the procedure described in Example 82 substituting 7c for racemic 3e) is used to give Weinreb amide 104b after purification by chromatography (80-100% EtOAc in hexanes).

Step 2

According to general procedure E, Weinreb amide 104b (440 mg, 0.91 mmol) is used with pyrazole 23f (Aldrich) to provide ketone 104c after purification by chromatography (80-100% EtOAc in hexanes).

Step 3

According to general procedure F, ketone 104c (502 mg, 0.99 mmol) is transformed to aryl 104d after purification by dilution with H₂O, basification (10 M NaOH, pH 10) and filtration.

Step 4

According to general procedure D2, arylbromide 104d (80 mg, 0.17 mmol) is used with 3-pyridylboronic acid (Aldrich) to provide compound 1083 after purification by preparative HPLC.

Example 105

Preparation of Compound 1084

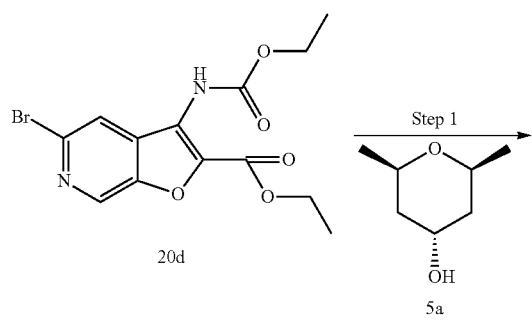

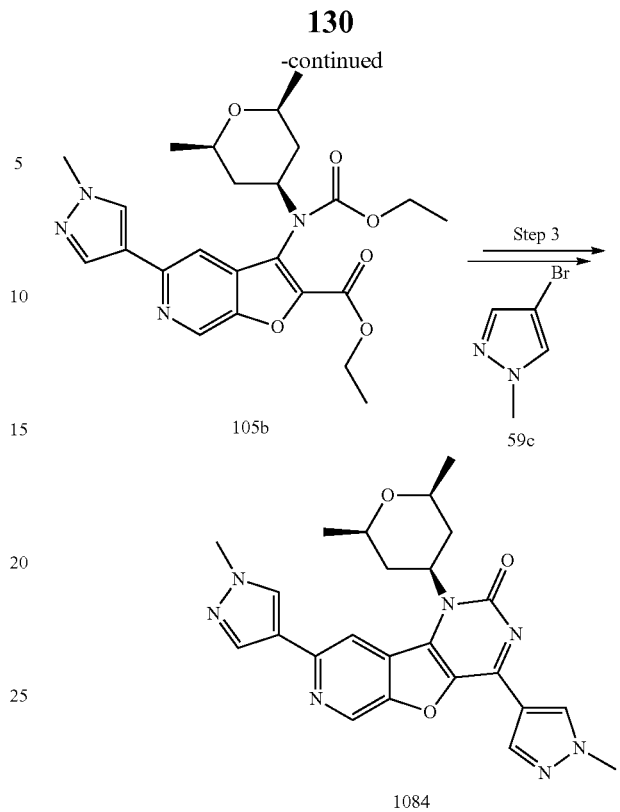

Step 1

According to general procedure A, 20d (250 mg, 0.700 mmol) is used with 5a to provide crude 105a after purification by chromatography (0-50% EtOAc in hexanes).

Step 2

According to general procedure D1, crude arylbromide 105a (329 mg, 0.700 mmol) is used with boronate ester 23d (Frontier) to afford pyrazole 105b after purification by chromatography (0-100% EtOAc in hexanes).

Step 3

According to general procedure E, ester 105b (114 mg, 0.243 mmol) is treated with pyrazole 59c (Aldrich). The resulting intermediate is used without further purification and submitted to general procedure F to obtain compound 1084 after purification by preparative HPLC.

Example 106

Preparation of Compound 1085

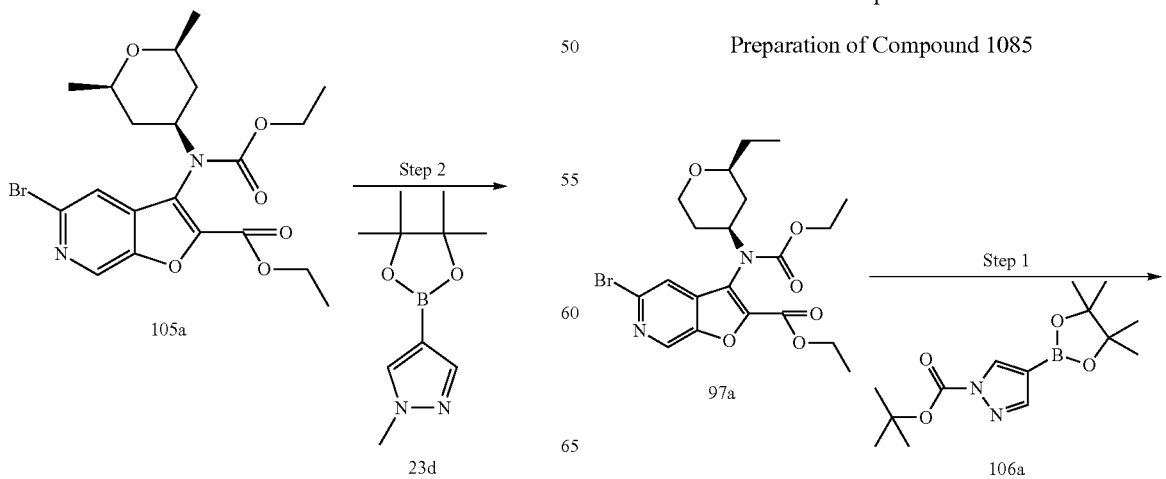

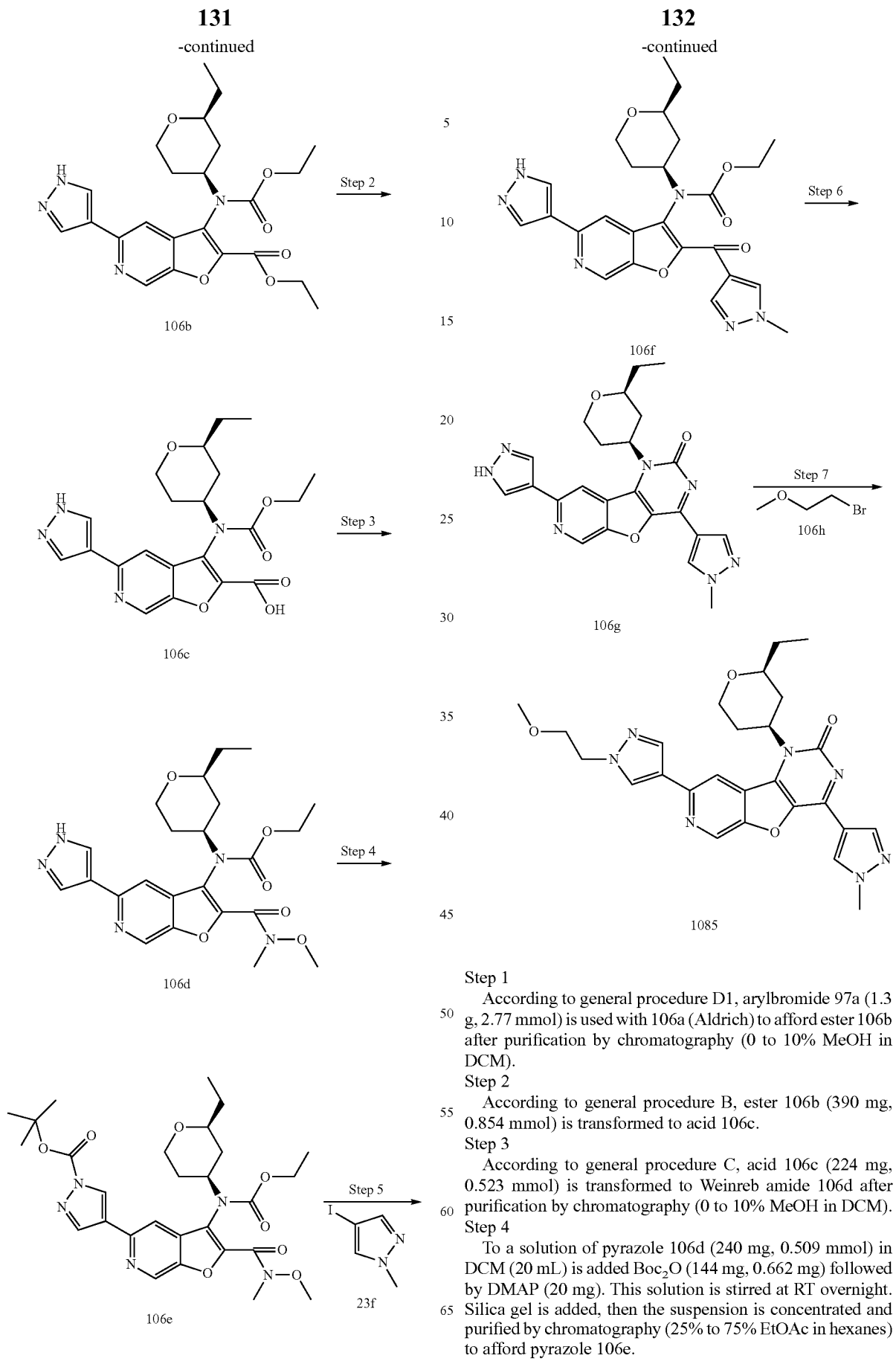

Step 1

According to general procedure D1, arylbromide 97a (1.3 g, 2.77 mmol) is used with 106a (Aldrich) to afford ester 106b after purification by chromatography (0 to 10% MeOH in DCM).

Step 2

According to general procedure B, ester 106b (390 mg, 0.854 mmol) is transformed to acid 106c.

Step 3

According to general procedure C, acid 106c (224 mg, 0.523 mmol) is transformed to Weinreb amide 106d after purification by chromatography (0 to 10% MeOH in DCM).

Step 4

To a solution of pyrazole 106d (240 mg, 0.509 mmol) in DCM (20 mL) is added Boc$_2$O (144 mg, 0.662 mg) followed by DMAP (20 mg). This solution is stirred at RT overnight. Silica gel is added, then the suspension is concentrated and purified by chromatography (25% to 75% EtOAc in hexanes) to afford pyrazole 106e.

Step 5

According to general procedure E, Weinreb amide 106e (150 mg, 0.262 mmol) is used with pyrazole 23f (Aldrich) to afford ketone 106f after purification by chromatography (0 to 10% MeOH in DCM).

Step 6

According to general procedure F, ketone 106f (80 mg, 0.162 mmol) is transformed to aryl 106g after purification by precipitation with the addition of water and trituration in water/MeCN.

Step 7

To a solution of pyrazole 106g (20 mg, 0.037 mmol) in DMF (1 mL) is added bromide 106h (0.010 mL, 0.111 mmol) followed by NaH (6 mg, 60% in oil, 0.148 mmol). The mixture is stirred at RT overnight, and then quenched with AcOH. Purification by preparative HPLC affords compound 1085.

Example 107

Preparation of Compound 1086

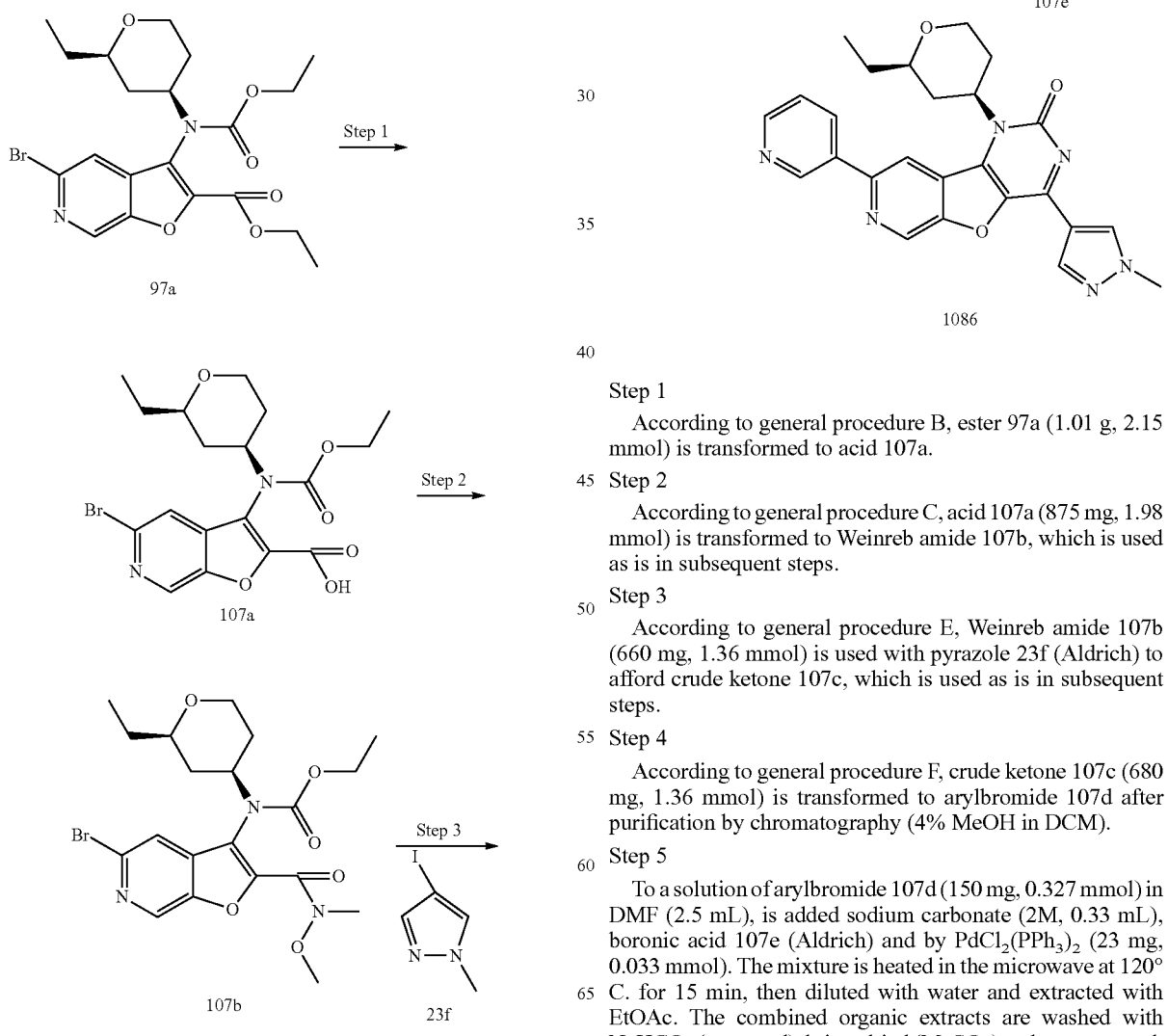

Step 1

According to general procedure B, ester 97a (1.01 g, 2.15 mmol) is transformed to acid 107a.

Step 2

According to general procedure C, acid 107a (875 mg, 1.98 mmol) is transformed to Weinreb amide 107b, which is used as is in subsequent steps.

Step 3

According to general procedure E, Weinreb amide 107b (660 mg, 1.36 mmol) is used with pyrazole 23f (Aldrich) to afford crude ketone 107c, which is used as is in subsequent steps.

Step 4

According to general procedure F, crude ketone 107c (680 mg, 1.36 mmol) is transformed to arylbromide 107d after purification by chromatography (4% MeOH in DCM).

Step 5

To a solution of arylbromide 107d (150 mg, 0.327 mmol) in DMF (2.5 mL), is added sodium carbonate (2M, 0.33 mL), boronic acid 107e (Aldrich) and by $PdCl_2(PPh_3)_2$ (23 mg, 0.033 mmol). The mixture is heated in the microwave at 120° C. for 15 min, then diluted with water and extracted with EtOAc. The combined organic extracts are washed with $NaHCO_3$ (saturated), brine, dried ($MgSO_4$) and concentrated.

The residue is purified by chromatography (1% EtOH in DCM) to afford compound 1086.

Example 108

Preparation of Compound 1087

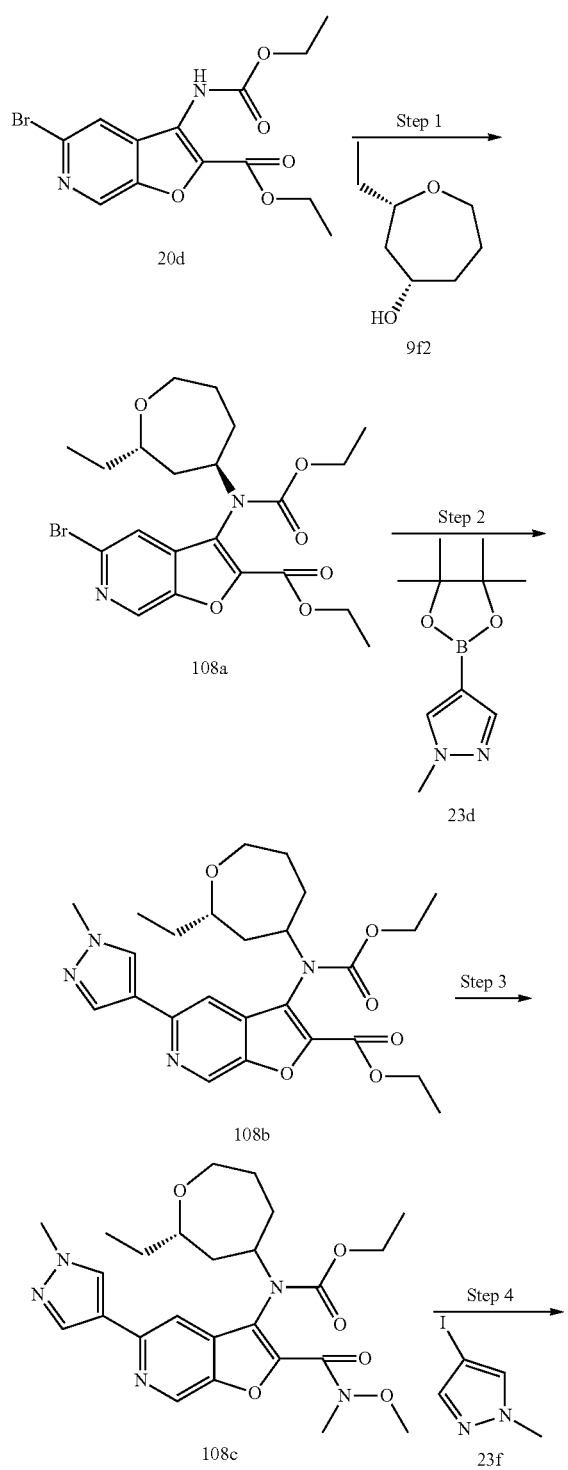

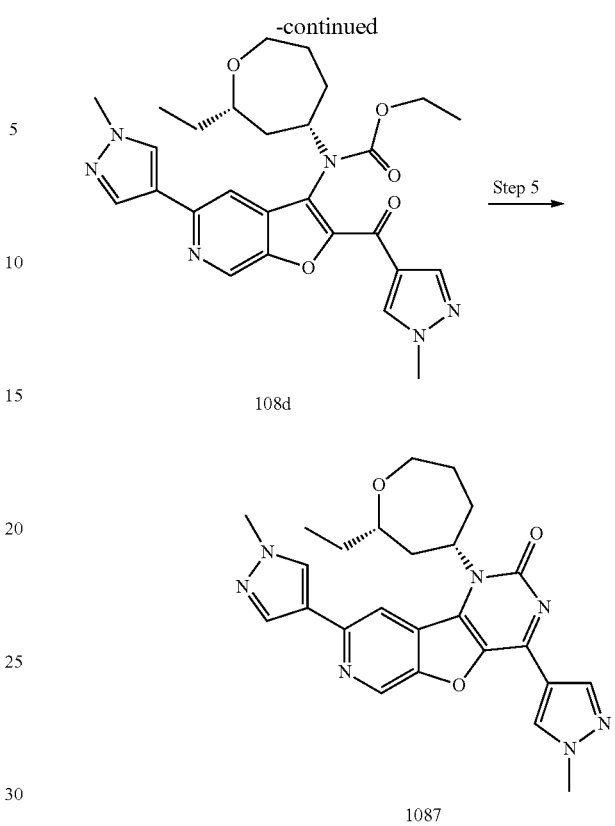

Step 1

According to general procedure A, carbamate 20d (286 mg, 1.39 mmol) is used with 9f2 to provide crude 108a. Purification is by chromatography (10-100% EtOAc in hexanes).

Step 2

According to general procedure D1, arylbromide 108a (310 mg, 0.641 mmol) is used with boronate ester 23d (Frontier) to afford pyrazole 108b after purification by chromatography (40-100% EtOAc in hexanes).

Step 3

According to general procedure I, ester 108b (185 mg, 0.382 mmol) is used to give Weinreb amide 108c after purification by chromatography (50-100% EtOAc in hexanes).

Step 4

According to general procedure E, Weinreb amide 108c (194 mg, 0.388 mmol) is used with pyrazole 23f to afford ketone 108d after purification by chromatography (0-10% MeOH in DCM).

Step 5

According to general procedure F, ketone 108d (202 mg, 0.388 mmol) is used to provide compound 1087 after purification by preparative HPLC followed by chromatography (0-3% MeOH in DCM).

Example 109

Preparation of Compound 1088

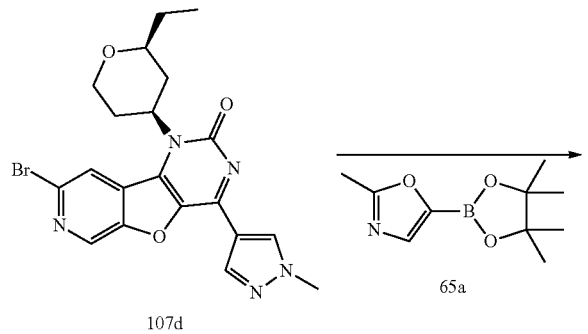

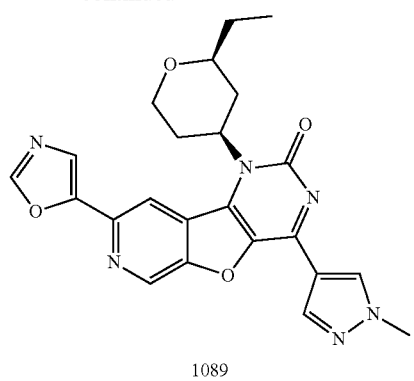

According to general procedure D3, arylbromide 107d (95 mg, 0.207 mmol) is used with boronate ester 65a (Synthonix) to afford compound 1088 after purification by preparative HPLC.

Example 110

Preparation of Compound 1089

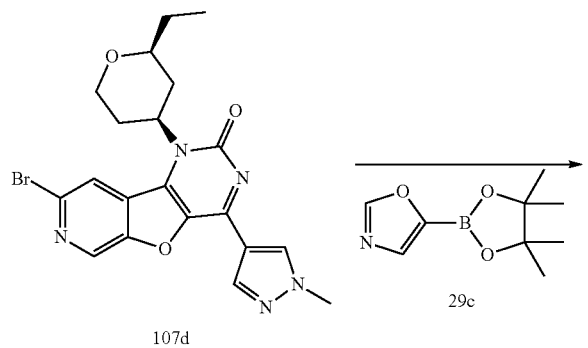

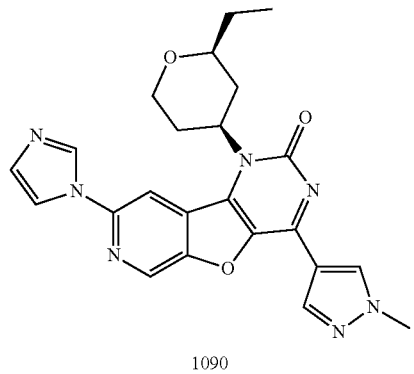

According to general procedure D3, arylbromide 107d (95 mg, 0.207 mmol) is used with boronate ester 29c (Synthonix) to after compound 1089 after purification by preparative HPLC.

Example 111

Preparation of Compound 1090

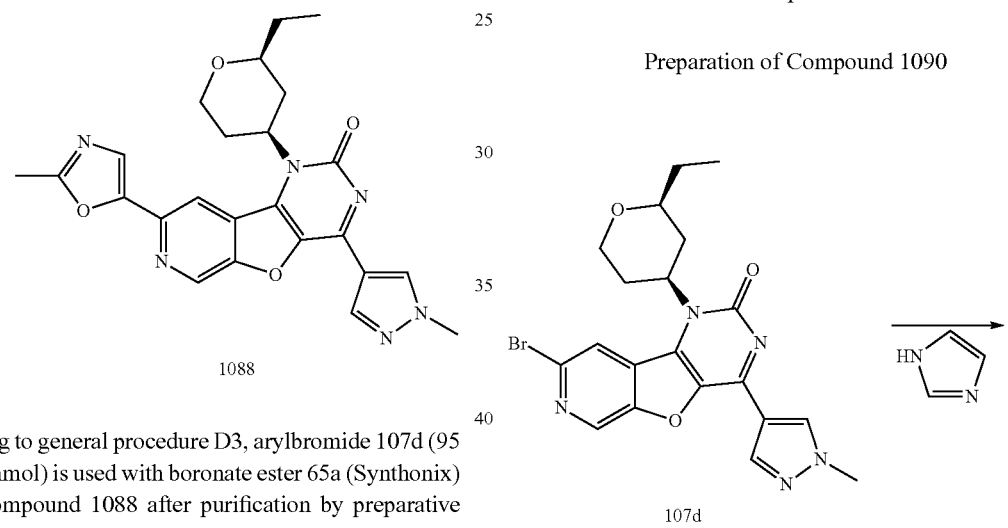

To a solution of MeONa (0.037 mL, 25% in MeOH) in DMSO (3 mL) is added CuI (2 mg, 0.011 mmol) followed by N-hydroxysuccinimide (2.5 mg, 0.022 mmol). This mixture is stirred at RT for 30 min. Arylbromide 107d (50 mg, 0.109 mmol) and imidazole (Aldrich) (7.4 mmol, 0.109 mmol) are added and the solution heated at 120° C. for 24 h. The mixture is purified by preparative HPLC to afford compound 1090.

Example 112

Preparation of Compound 1091

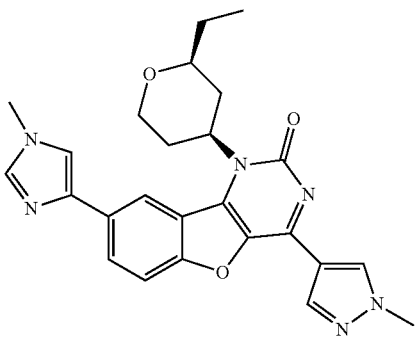 [SMILES: CC[C@H]1C[C@@H](n2c(=O)nc(-c3cnn(C)c3)c3oc4ccc(-c5cn(C)cn5)cc4c32)CCO1]

Compound 112 is prepared analogously to the procedure described in Example 104 substituting 1-methyl-4-tributyl-stannylimidazole (Aldrich) for 3-pyridylboronic acid. The starting carbamate is prepared analogously to the method used for 104a, replacing 18c with 12d according to general procedure A.

Example 113

Preparation of N-ethylimizadolestanane 113c

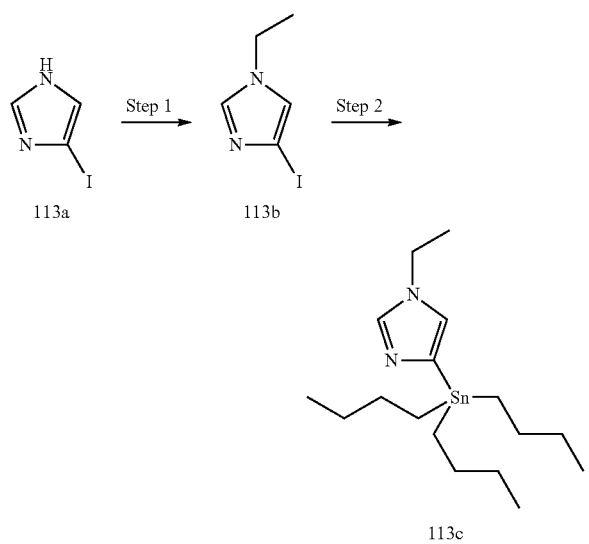

Step 1

To a solution of 113a (Synthonix, 5.0 g, 25.8 mmol) in THF (100 mL) at 0° C. is added portionwise NaH (60% in oil, 1.13 g, 28.3 mmol). The reaction is warmed to RT for 30 min and then cooled to 0° C. EtBr is added and the reaction is stirred for 1 h at 0° C., and then warmed to RT. The reaction is diluted ammonium chloride (10 mL) and NaHCO$_3$ (saturated) is added. The aqueous phase is extracted with EtOAc (100 mL). The organic layer is washed with water (2×20 mL), brine, dried (MgSO$_4$), filtered and concentrated under reduced pressure. Purification by chromatography (40-100% EtOAc/Hexanes) affords imidazole 113b.

Step 2

A solution of EtMgBr (1.98 mL, 3M in Et$_2$O) is added dropwise to a solution of imidazole 113b (1.10 g, 4.95 mmol) in DCM (50 mL) under a nitrogen atmosphere at RT. The resulting mixture is stirred for 30 min. Tributyltin chloride (1.94 g, 5.95 mmol) is added, and this mixture is stirred for 18 h. The mixture is quenched with NH$_4$Cl and extracted with DCM, dried (MgSO$_4$), filtered and concentrated under reduced pressure. The residue is purified by chromatography (MeOH/DCM 0-10%) to afford imidazole 113c, which is contaminated with the corresponding destanylated side-product.

Example 114

Preparation of Intermediate 114b

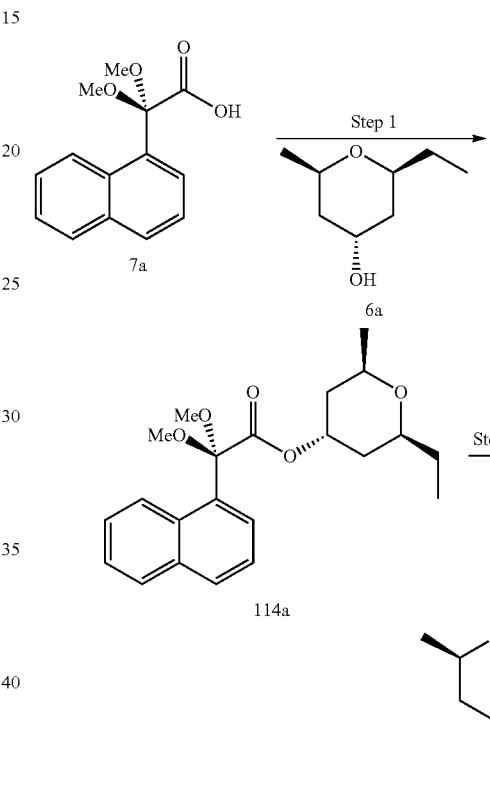

Intermediate 114b is prepared analogously to the procedure described in Example 7 wherein 3e is replaced with 6a in Step 1.

Example 115

Preparation of Compound 1092

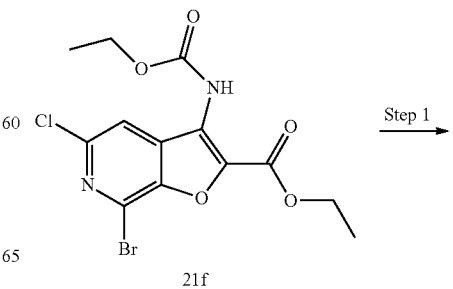

-continued

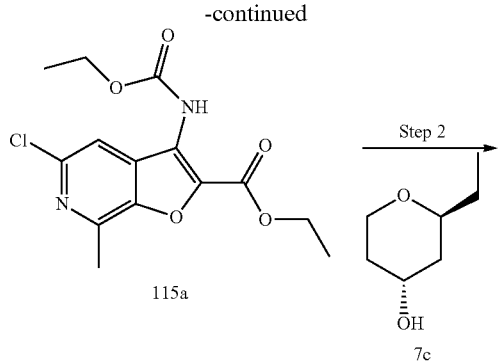

115a

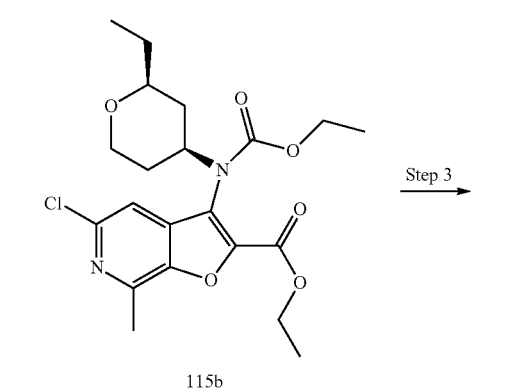

115b

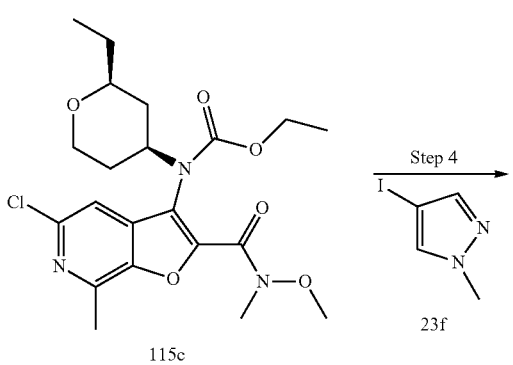

115c

115d

-continued

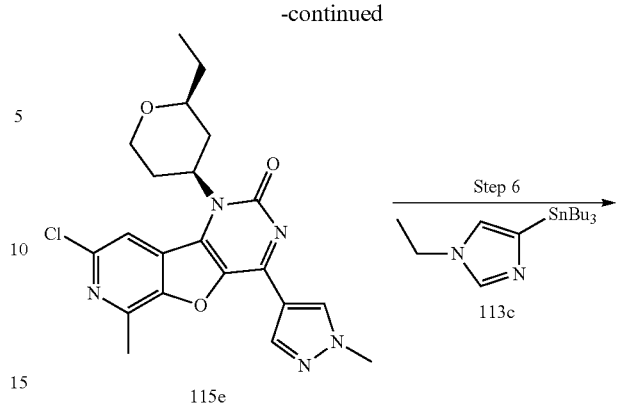

115e

1092

Step 1

To a suspension of 21f (1.50 g, 3.83 mmol) and trans-dichlorobis(triphenylphosphine) palladium (II) (287 mg, 0.383 mmol) in anhydrous, argon-degassed dioxane (45 mL) is added a solution of trimethylaluminum (7.66 mL, 2M in heptane). The reaction mixture is stirred at 60° C. for 10 min in an oil bath. The cooled reaction mixture is added to a stirred 10% solution of citric acid. EtOAc is added to the solution and the two layers are separated. The aqueous layer is extracted with EtOAc (2×) and the combined organic layers are washed with brine, dried ($Na_2SO_4$), filtered and concentrated. The crude product is preadsorbed on silica gel and purified by chromatography (10-50% EtOAc/Hex) to give aryl 115a.

Step 2

According to general procedure A, carbamate 115a (1.39 g, 4.25 mmol) is used with 7c to give 115b after purification by chromatography (0-30% EtOAc in hexanes).

Step 3

According to general procedure I, ester 115b (1.11 g, 2.53 mmol) is used to give Weinreb amide 115c after purification by chromatography (20-50% EtOAc in hexanes).

Step 4

According to general procedure E, Weinreb amide 115c (689 mg, 1.52 mmol) is used to give ketone 115d after purification by chromatography (50-100% EtOAc in hexanes).

Step 5

According to general procedure F, ketone 115d (462 mg, 0.973 mmol) is transformed to aryl 115e after purification by precipitation in water with the addition of NaOH 10 N until basic pH is achieved.

Step 6
According to general procedure D4, aryl 115e (150 mg, 0.351 mmol) and 113c is transformed to compound 1092 after purification by preparative HPLC.
Example 116
Preparation of compounds 1093 and 1094
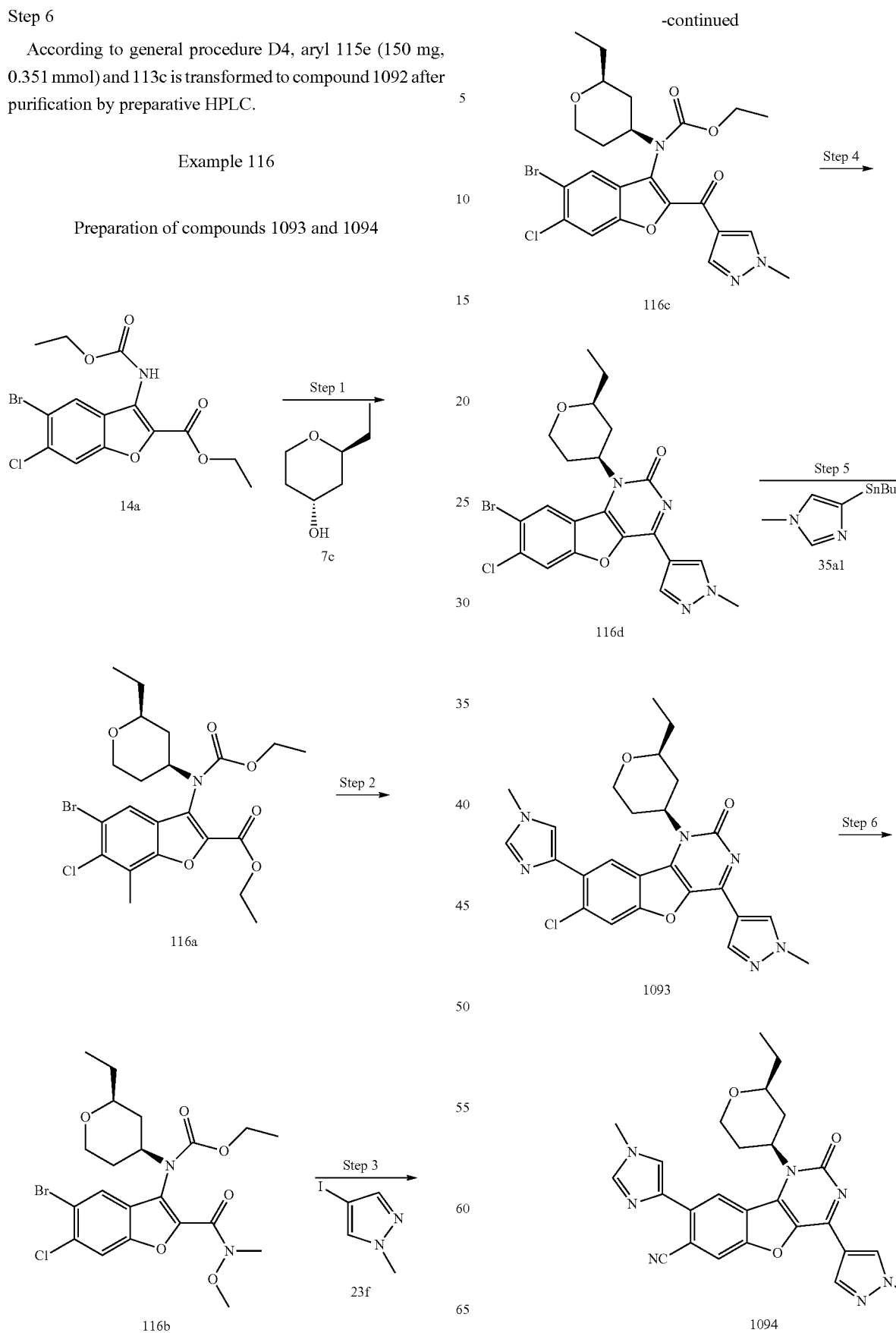

145

Step 1
According to general procedure A, carbamate 14a (2.50 g, 8.32 mmol) is used with 7c to give 116a after purification by chromatography (10-100% EtOAc in hexanes).
Step 2
According to general procedure I, ester 116a (2.10 g, 4.18 mmol) is used to give Weinreb amide 116b.
Step 3
According to general procedure E, Weinreb amide 116b (3.51 g, 6.78 mmol) is used to give ketone 116c after purification by chromatography (0-10% MeOH in $CH_2Cl_2$).
Step 4
According to general procedure F, ketone 116c (2.94 g, 5.46 mmol) is transformed to aryl 116d after purification by precipitation in water with the addition of NaOH 10 N until basic pH is achieved.
Step 5
According to general procedure D4, 116d (50 mg, 0.102 mmol) and stanane 35a1 is transformed to compound 1093 after purification by preparative HPLC.
Step 6
To a solution of compound 1093 (80 mg, 0.162 mmol) in DMF (2 mL) is added CuCN (87 mg, 0.974 mmol). The solution is stirred at 160° C. for 80 min in a microwave. The reaction mixture is quenched with HCl (1 N) and washed with DCM. The solution is then basified with NaOH until neutral pH, and then extracted with DCM. The organic layer is dried ($MgSO_4$), filtered and concentrated. The resulting residue is purified by preparative HPLC to afford compound 1094.

Example 117

Preparation of Compound 1095

146

Step 1
According to general procedure A, carbamate 22e (900 mg, 2.88 mmol) is used with intermediate 114b to give 117a. Purification is by chromatography (0 to 50% EtOAc in hexanes).

Step 2
According to general procedure I, ester 117a (1.07 g, 2.44 mmol) is used to give Weinreb amide 117b.

Step 3
According to general procedure E, Weinreb amide 117b (720 mg, 1.59 mmol) is used to give ketone 117c after purification by chromatography (0-5% MeOH in $CH_2Cl_2$).

Step 4
According to general procedure F, ketone 117c (475 mg, 1.00 mmol) is transformed to aryl 117d after purification by precipitation in water with the addition of NaOH 10 N until basic pH is achieved.

Step 5
According to general procedure D4, 117d (100 mg, 0.234 mmol) and stanane 35a1 is transformed to compound 1095 after purification by chromatography using MeOH in DCM (0 to 20%) and preparative HPLC.

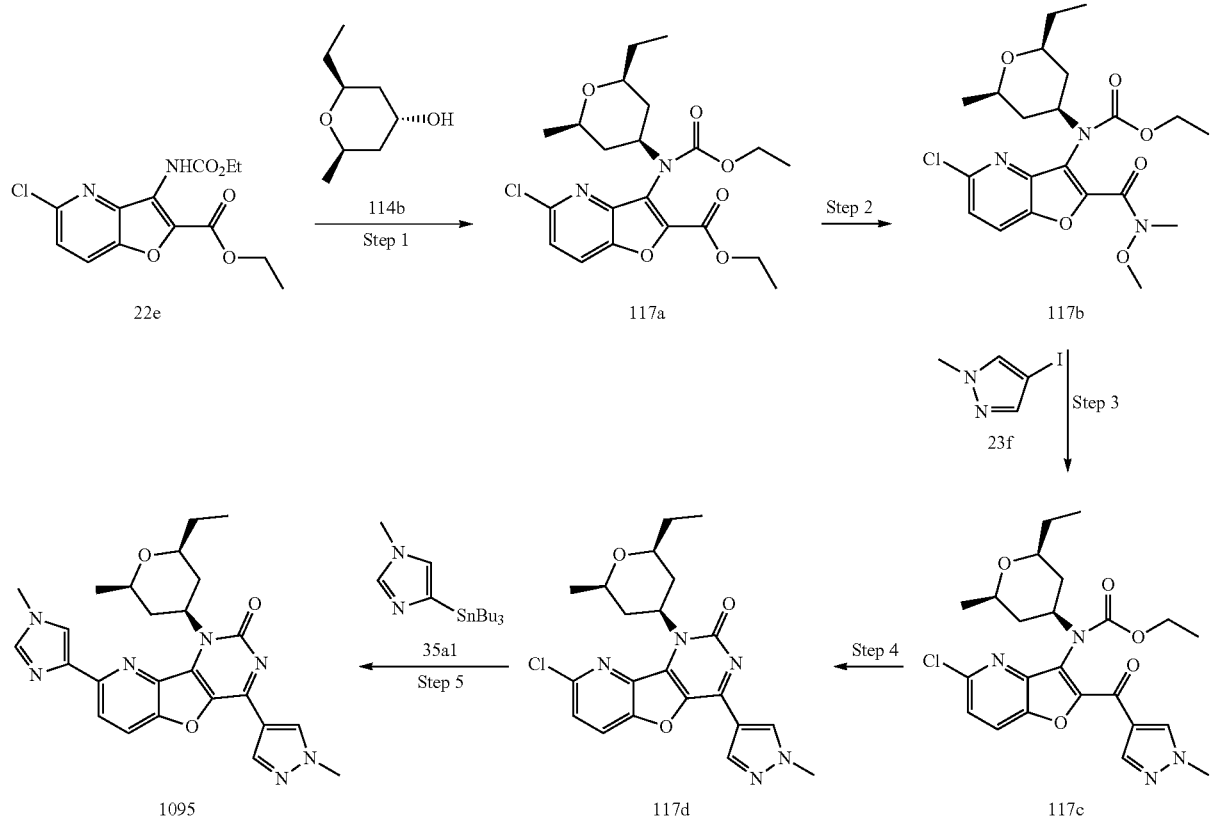

147
Example 118
Preparation of Compound 1096
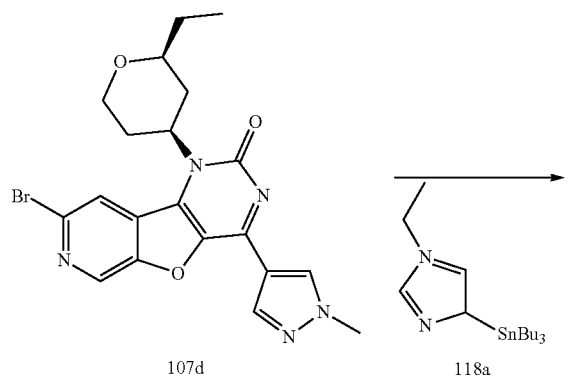
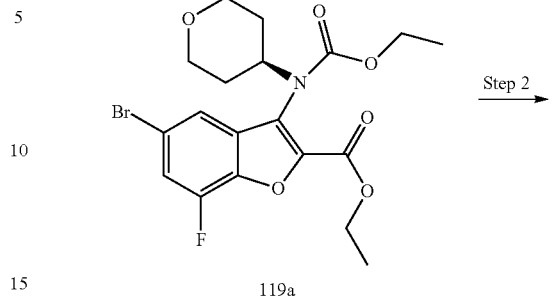
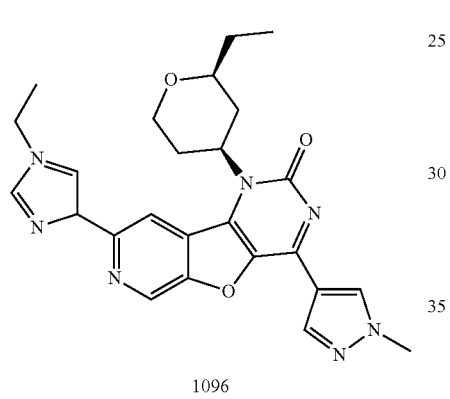
According to general procedure D4, arylbromide 107d (91 mg, 0.199 mmol) and stanane 118a is transformed to compound 1096 after purification by preparative HPLC.
Example 119
Preparation of Compound 1097
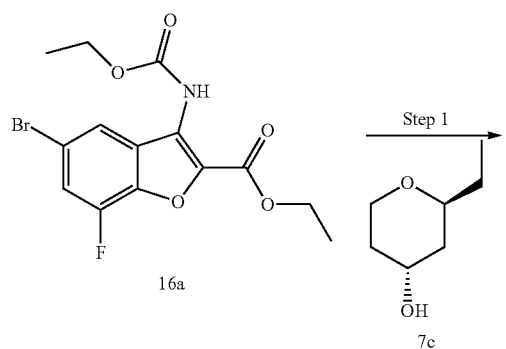
148
-continued
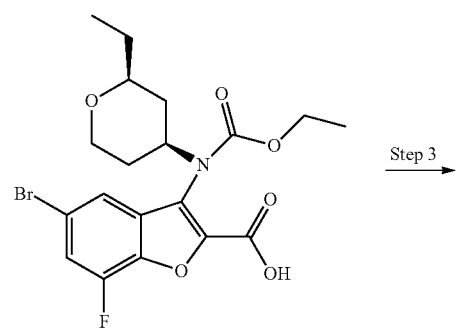
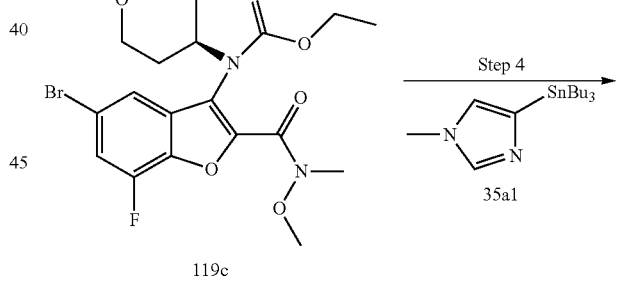
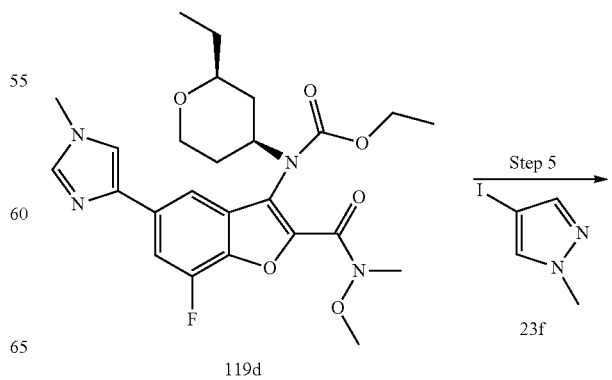

-continued

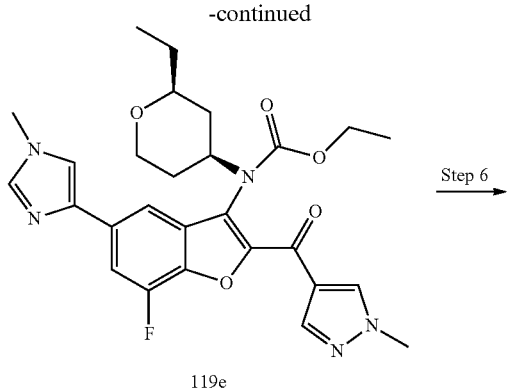

119e

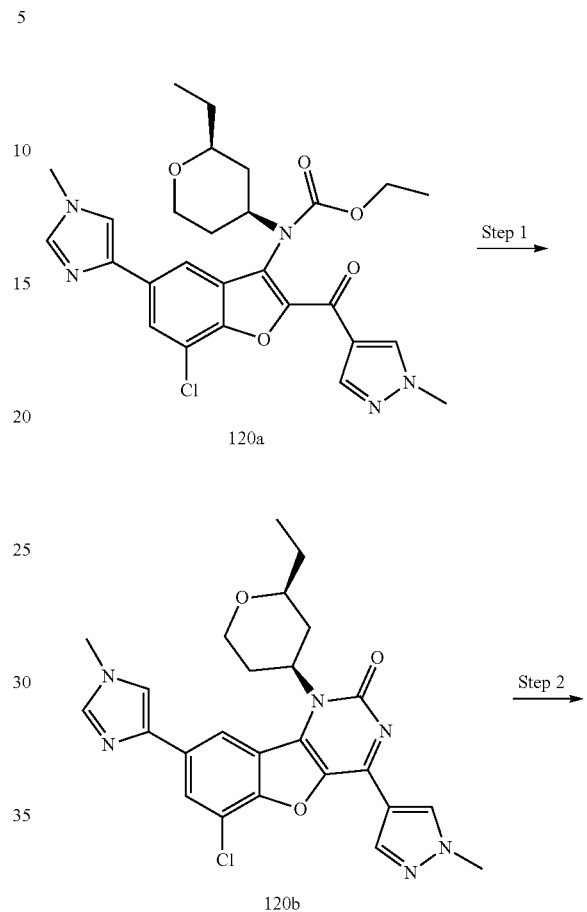

Example 120

Preparation of Compound 1098

Step 1

According to general procedure A, carbamate 16a (1.00 g, 2.67 mmol) is used with intermediate 7c to give 119a after purification by chromatography (0-30% EtOAc in hexanes).

Step 2

According to general procedure B, ester 119a (1.00 g, 2.67 mmol) is saponified to give 119b.

Step 3

According to general procedure C, acid 119b (523 g, 1.08 mmol) is used to give Weinreb amide 119c.

Step 4

According to general procedure D4, 119c (440 mg, 0.878 mmol) and stanane 35a1 is transformed to aryl 119d after purification by chromatography using MeOH in DCM (0 to 5%).

Step 5

According to general procedure E, Weinreb amide 119d (381 mg, 0.758 mmol) is used to give ketone 119e after purification by chromatography (0-10% MeOH in $CH_2Cl_2$).

Step 6

According to general procedure F, ketone 119e (269 mg, 0.514 mmol) is transformed to compound 1097 after partition between DCM and water followed by DCM extractions and purification by preparative HPLC.

Ketone 120a is prepared analogously to the procedure described in Example 119 (Steps 1 to 5), replacing 16a with 15d.

Step 1

According to general procedure F, ketone 120a (430 mg, 0.796 mmol) is transformed to aryl 120b after neutralization with NaOH (5 or 10 N) and extractions with DCM.

Step 2

To a solution of aryl 120b (100 mg, 0.203 mmol) and $Zn(CN)_2$ (119 mg, 1.01 mmol) in degassed DMA (4 mL) is added $(tBu_3P)_2Pd$ (52 mg, 0.101 mmol). The mixture is heated in a microwave at 150° C. for 30 min. The resulting mixture is filtered. The residue is collected and dissolved in $H_2O$/TFA. The resulting solution is filtered over an acrosdisk. The aqueous solution is neutralized with NaOH 1N and extracted with DCM. The combined organic extracts are washed with brine, dried ($Na_2SO_4$) and concentrated to afford compound 1098 (Note: HCN may be produced during the work-up).

Example 121

Preparation of Compound 1099

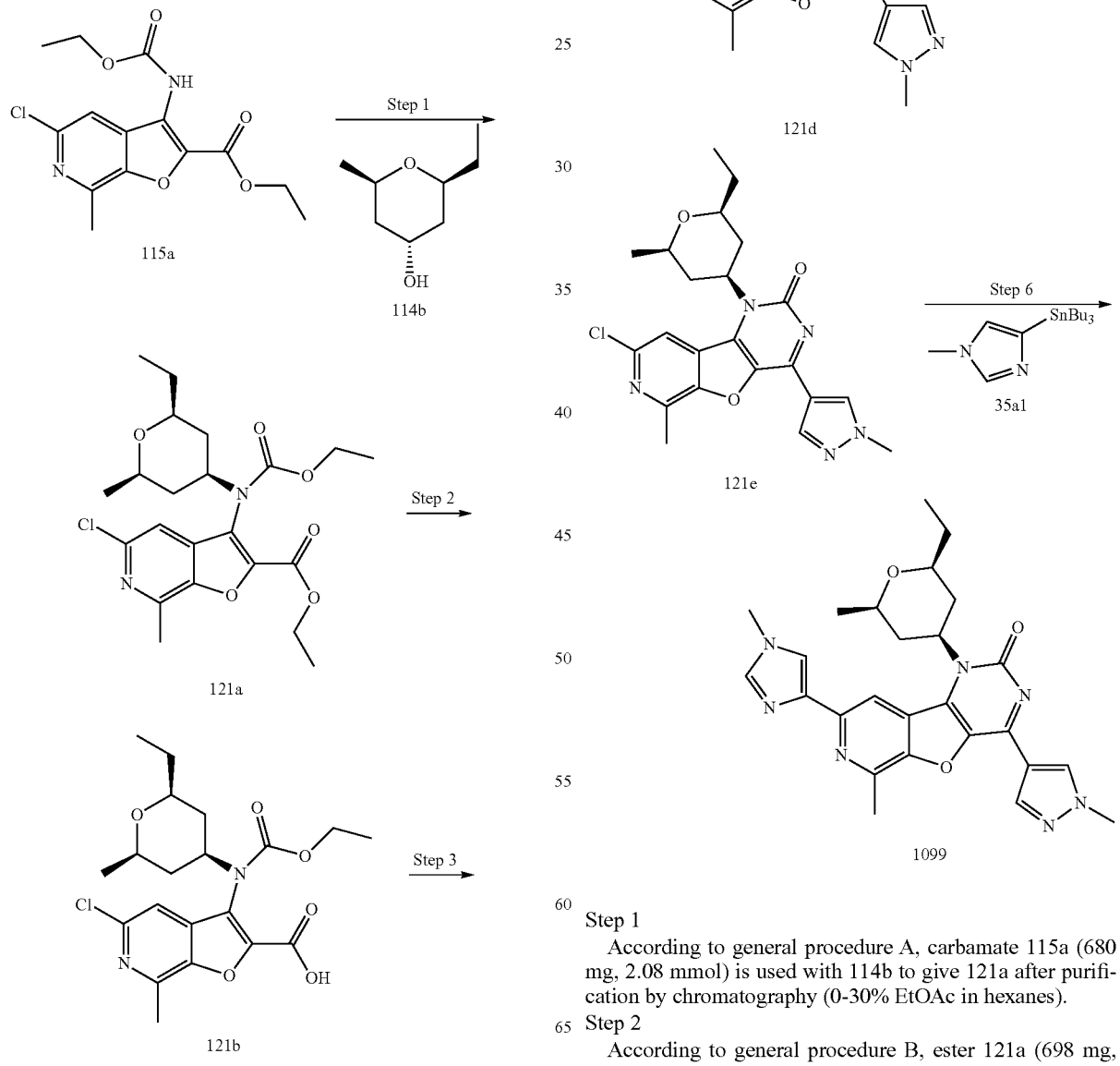

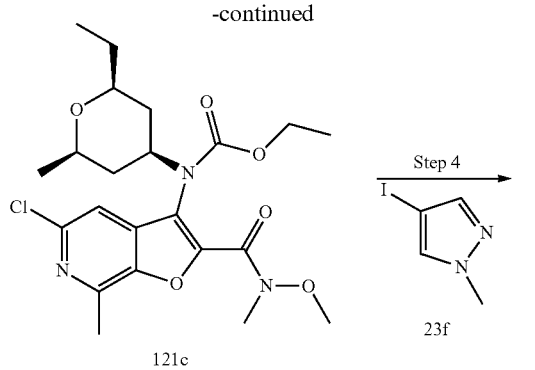

Step 1
According to general procedure A, carbamate 115a (680 mg, 2.08 mmol) is used with 114b to give 121a after purification by chromatography (0-30% EtOAc in hexanes).

Step 2
According to general procedure B, ester 121a (698 mg, 1.54 mmol) is converted to acid 121b.

Step 3

According to general procedure C, acid 121b (650 mg, 1.53 mmol) is used to give Weinreb amide 121c after purification by chromatography (30-50% EtOAc in hexanes).

Step 4

According to general procedure E, Weinreb amide 121c (718 mg, 1.53 mmol) is used to give ketone 121d after purification by chromatography (50-100% EtOAc in hexanes).

Step 5

According to general procedure F, ketone 121d (350 mg, 0.716 mmol) is transformed to aryl 121e after purification by precipitation in water.

Step 6

According to general procedure D4, aryl 121e (100 mg, 0.226 mmol) and 35a1 is transformed to compound 1099 after purification by preparative HPLC.

Example 122

Preparation of Compound 1100

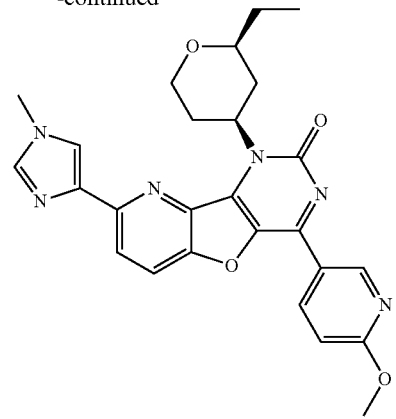

1100

Ketone 122a is prepared analogously to the procedure described in Example 29, replacing pyrazole 23f with 5-bromo-2-methoxypyridine (Aldrich) in Step 1.

Step 1

According to general procedure F, ketone 122a (222 mg, 0.455 mmol) is transformed to aryl 122b after purification by chromatography (0-10% MeOH in DCM).

Step 2

According to general procedure D4, aryl 122b (150 mg, 0.340 mmol) and 35a1 is transformed to compound 1100 after purification by preparative HPLC.

Example 123

Preparation of Compound 1101

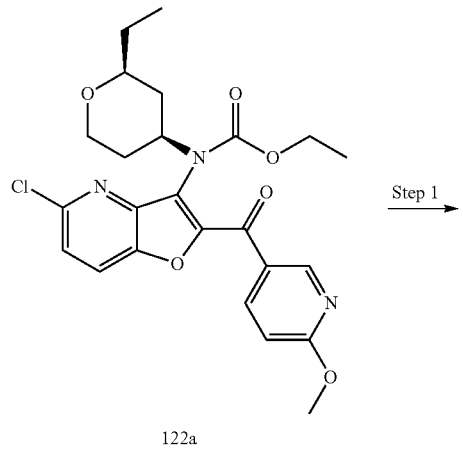

122a

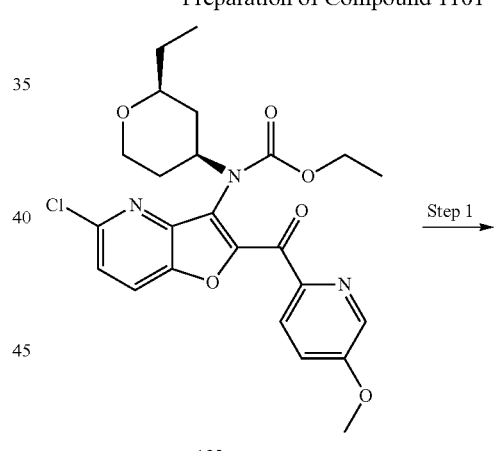

123a

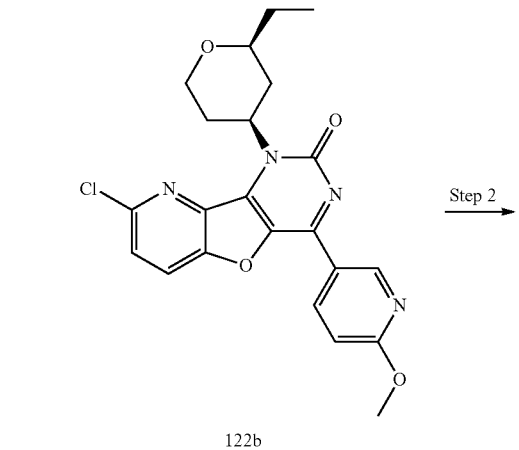

122b

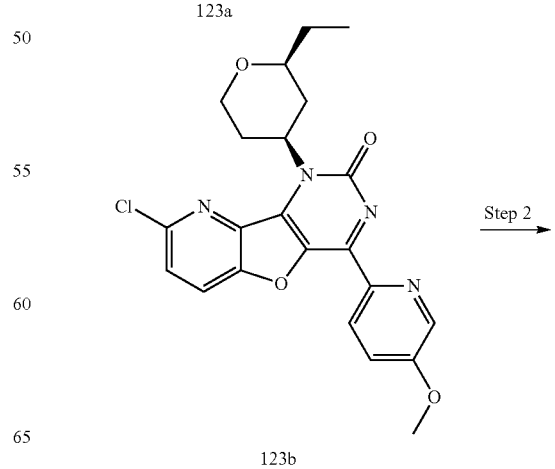

123b

-continued

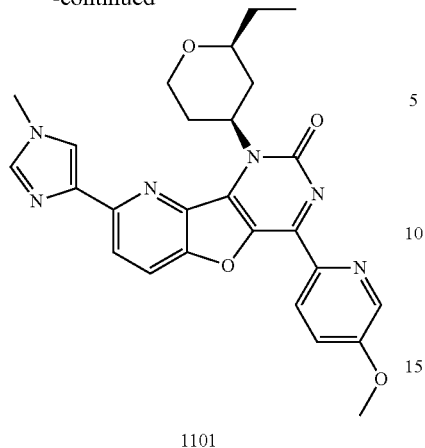

1101

Ketone 123a is prepared analogously to the procedure described in Example 29, replacing pyrazole 23f with 2-bromo-5-methoxypyridine (Synthonix) in Step 1.
Step 1 According to general procedure F, ketone 123a (222 mg, 0.455 mmol) is transformed to aryl 123b after purification by chromatography (0-10% MeOH in DCM).
Step 2
According to general procedure D4, aryl 123b (150 mg, 0.340 mmol) and 35a1 is transformed to compound 1101 after purification by preparative HPLC.

Example 124

Preparation of Compound 1102

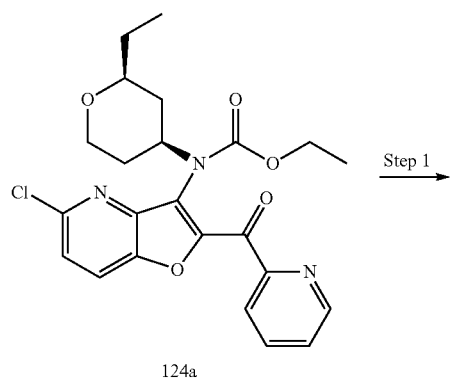

124a

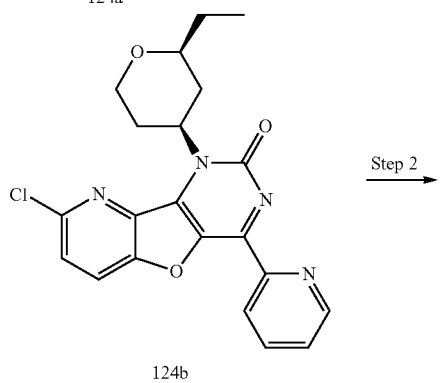

124b

-continued

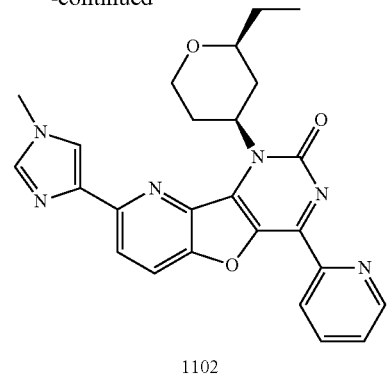

1102

Ketone 124a is prepared analogously to the procedure described in Example 29, replacing pyrazole 23f with 3-iodopyridine (TCI-JP) in Step 1.
Step 1
According to general procedure F, ketone 124a (222 mg, 0.455 mmol) is transformed to aryl 124b after purification by chromatography (0-10% MeOH in DCM) and preparative HPLC.
Step 2
According to general procedure D4, aryl 124b (28 mg, 0.068 mmol) and 35a1 is transformed to compound 1102 after purification by preparative HPLC.

Example 125

Preparation of Compound 1103

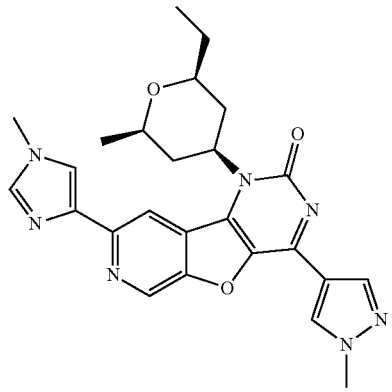 [SMILES: CC[C@H]1C[C@@H](n2c(=O)nc(-c3cnn(C)c3)c3oc4cnc(-c5cn(C)cn5)cc4c32)C[C@@H](C)O1]

Compound 1103 is prepared analogously to the procedure described in Example 117 (Steps 1 to 5), replacing 22e with 20d.

Table 1 lists the UPLC or HPLC retention time and M+ peak for compounds 1001-1103. Retention times ($t_R$) for each compound are measured using the standard analytical UPLC or HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different UPLC or HPLC instruments. Even when measured on the same instrument, the values may vary when measured, for example, using different individual UPLC or HPLC columns, or, when measured on the same instrument and the same individual column, the values may vary, for example, between individual measurements taken on different occasions.

TABLE 1

| CMPD # | $t_R$ (min) | $(M + H)^+$ |
|---|---|---|
| 1001 | 1.03 | 460.1 |
| 1002 | 4.64 | 474.1 |
| 1003 | 1.05 | 460.1 |
| 1004 | 0.90 | 458.1 |
| 1005 | 0.74 | 455.1 |
| 1006 | 3.1 | 457.1 |
| 1007 | 0.99 | 447.1 |
| 1008 | 4.32 | 460.0 |
| 1009 | 4.68 | 474.0 |
| 1010 | 1.9 | 461.3 |
| 1011 | 0.92 | 461.1 |
| 1012 | 1.16 | 446.1 |
| 1013 | 0.94 | 447.1 |
| 1014 | 0.71 | 460.3 |
| 1015 | 1.08 | 485.1 |
| 1016 | 1.03 | 485.0 |
| 1017 | 1.17 | 499.0 |
| 1018 | 5.27 | 499.1 |
| 1019 | 4.19 | 482.2 |
| 1020 | 0.9 | 511.1 |
| 1021 | 4.81 | 474.2 |
| 1022 | 1.13 | 494.0 |
| 1023 | 1.02 | 490.1 |
| 1024 | 1.13 | 485.3 |
| 1025 | 1.02 | 499.2 |
| 1026 | 1.97 | 527.2 |
| 1027 | 1.8 | 458.1 |
| 1028 | 0.9 | 474.2 |
| 1029 | 3.6 | 476.2 |
| 1030 | 2.8 | 489.1 |
| 1031 | 4.68 | 545.2 |
| 1032 | 3.89 | 489.3 |
| 1033 | 3.98 | 515.3 |
| 1034 | 4.0 | 503.3 |
| 1035 | 2.02 | 488.1 |
| 1036 | 0.92 | 485.2 |
| 1037 | 0.84 | 471.3 |
| 1038 | 0.99 | 459.1 |
| 1039 | 4.26 | 459.0 |
| 1040 | 0.74 | 456.1 |
| 1041 | 4.84 | 473.3 |
| 1042 | 1.07 | 477.2 |
| 1043 | 1.1 | 474.1 |
| 1044 | 1.09 | 478.1 |
| 1045 | 0.74 | 504.1 |
| 1046 | 0.79 | 518.1 |
| 1047 | 3.98 | 551.0 |
| 1048 | 1.15 | 493.3/495.3 |
| 1049 | 1.03 | 484.1 |
| 1050 | 1.05 | 473.3 |
| 1051 | 4.58 | 481.0 |
| 1052 | 0.98 | 484.1 |
| 1053 | 1.10 | 498.1 |
| 1054 | 4.81 | 484.1 |
| 1055 | 0.97 | 489.1 |
| 1056 | 0.9 | 475.2 |
| 1057 | 1.02 | 489.2 |
| 1058 | 1.92 | 473.3 |
| 1059 | 4.63 | 460.2 |
| 1060 | 1.07 | 498.1 |
| 1061 | 4.34 | 460.4 |
| 1062 | 0.92 | 474.2 |
| 1063 | 3.59 | 471.2 |
| 1064 | 1.83 | 472.3 |
| 1065 | 1.08 | 473.2 |
| 1066 | 0.73 | 459.0 |
| 1067 | 0.9 | 500.3 |
| 1068 | 0.93 | 512.3 |
| 1069 | 3.64 | 486.3 |
| 1070 | 4.29 | 460.3 |
| 1071 | 4.54 | 474.4 |
| 1072 | 4.81 | 488.4 |
| 1073 | 3.49 | 443.3 |
| 1074 | 0.96 | 460.3 |
| 1075 | 0.9 | 446.3 |
| 1076 | 4.28 | 460.1 |
| 1077 | 4.0 | 486.4 |
| 1078 | 3.65 | 473.4 |
| 1079 | 4.19 | 474.2 |
| 1080 | 0.93 | 461.0 |
| 1081 | 0.92 | 474.1 |
| 1082 | 0.95 | 474.0 |
| 1083 | 0.69 | 457.1 |
| 1084 | 4.12 | 460.0 |
| 1085 | 0.93 | 504.1 |
| 1086 | 0.71 | 457.1 |
| 1087 | 0.96 | 474.1 |
| 1088 | 1.73 | 461.1 |
| 1089 | 1.63 | 447.2 |
| 1090 | 2.81 | 446.2 |
| 1091 | 0.69 | 459.3 |
| 1092 | 0.77 | 488.3 |
| 1093 | 0.74 | 493.2 |
| 1094 | 0.73 | 484.3 |
| 1095 | 1.84 | 474.4 |
| 1096 | 3.33 | 474.3 |
| 1097 | 0.74 | 477.2 |
| 1098 | 0.75 | 484.3 |
| 1099 | 0.76 | 488.3 |
| 1100 | 0.89 | 487.3 |
| 1101 | 1.08 | 487.3 |
| 1102 | 0.64 | 457.3 |
| 1103 | 0.72 | 474.3 |

Table 2 lists the $^1$H-NMR for compounds 1001-1103 or a salt thereof, as indicated. Chemical shifts are reported in parts per million from tetramethylsilane with the solvent resonance as the internal standard. Data are reported as follows: chemical shift, multiplicity (s=singlet, d=doublet, t=triplet, q=quartet, qn=quintet, S=septuplet, m=multiplet and b or br=broad), integration and coupling constant in Hz.

TABLE 2

| Cmpd # | Salt | $^1$H NMR |
|---|---|---|
| 1001 | MsOH | 1H NMR (400 MHz, DMSO-d$_6$) δ ppm 8.76 (s, 1 H), 8.45 (s, 1 H), 8.34 (s, 1 H), 8.31 (d, J = 9.0 Hz, 1 H), 8.22 (s, 1 H), 8.04 (d, J = 9.0 Hz, 1 H), 5.77 (br. s, 1 H), 4.15 (dd, J = 11.9, 4.5 Hz, 1 H), 4.01 (s, 3 H), 3.93 (s, 3 H), 3.61 (t, J = 11.0 Hz, 1 H), 3.39-3.50 (m, 1 H), 2.99-3.14 (m, 1 H), 2.70-2.85 (m, 1 H), 2.30 (s, 3 H), 1.80 (d, J = 12.1 Hz, 1 H), 1.70 (d, J = 11.7 Hz, 1 H), 1.45-1.64 (m, 2 H), 0.92 (t, J = 7.4 Hz, 3 H) |
| 1002 | MsOH | 1H NMR (400 MHz, DMSO-d$_6$) δ ppm 8.76 (s, 1 H), 8.39 (s, 1 H), 8.34 (s, 1 H), 8.32 (d, J = 9.0 Hz, 1 H), 7.98 (d, J = 9.0 Hz, 1 H), 5.93-6.02 (m, 1 H), 4.09 (dd, J = 11.0, 4.4 Hz, 1H), 4.01 (s, 3 H), 3.84 (s, 3 H), 3.52 (t, J = 12.0 Hz, 1 H), 3.32-3.39 (m, 1 H), 2.99 (dq, J = 9, 4.4 Hz, 1 H), 2.70 (dt, J = 6.0, 5.1, Hz 1 H), 2.61 (s, 3 H), 2.30 (s, 3 H), 1.85 (d, J = 12.1 Hz, 1 H), 1.74 (d, J = 12.3 Hz, 1 H), 1.43-1.59 (m, 2 H), 0.90 (t, J = 7.5 Hz, 3 H) |

TABLE 2-continued

| Cmpd # | Salt | $^1$H NMR |
|---|---|---|
| 1003 | TFA | 1H NMR (400 MHz, DMSO-d$_6$) δ ppm 8.70 (s, 1 H), 8.25-8.28 (m, 2 H), 8.21 (d, J = 9.0 Hz, 1 H), 7.80 (d, J = 2.2 Hz, 1 H), 7.01 (br. s., 1 H), 5.69-5.81 (m, 1 H), 4.08 (dd, J = 11.6, 3.6 Hz, 1 H), 3.95 (s, 3 H), 3.89 (s, 3 H), 3.52 (dd, J = 12.1, 1.8 Hz, 2 H), 2.92-3.05 (m, 1 H), 2.66-2.78 (m, 1 H), 1.74 (d, J = 11.0 Hz, 1 H), 1.65 (d, J = 11.0 Hz, 1 H), 1.47-1.57 (m, 1 H), 1.35-1.47 (m, 1 H), 0.84 (t, J = 7.5 Hz, 3 H) |
| 1004 | TFA | 1H NMR (400 MHz, DMSO-d$_6$) δ ppm 9.68 (s, 2 H), 9.31 (s, 1 H), 8.78 (s, 1 H), 8.58 (d, J = 9.0 Hz, 1 H), 8.54 (d, J = 9.0 Hz, 1 H), 8.36 (d, J = 0.7 Hz, 1 H), 5.78 (br. s., 1 H), 4.15 (dd, J = 11.4, 4.4 Hz, 1 H), 4.02 (s, 3 H), 3.58 (dd, J = 11.7, 10.8 Hz, 1 H), 3.38-3.46 (m, 1 H), 2.95-3.07 (m, 1 H), 2.70-2.85 (m, 1 H), 1.85 (d, J = 11.0 Hz, 1 H), 1.75 (d, J = 13.0 Hz, 1 H), 1.53-1.61 (m, 1 H), 1.45-1.53 (m, 1 H), 0.90 (t, J = 7.5 Hz, 3 H) |
| 1005 | MsOH | 1H NMR (400 MHz, DMSO-d$_6$) δ ppm 9.43 (br. s., 1 H), 8.86 (br. s., 1 H), 8.78 (s, 1 H), 8.52 (d, J = 1.8 Hz, 2 H), 8.36 (d, J = 0.7 Hz, 1 H), 7.74 (br. s., 1 H), 5.83 (br. s., 1 H), 4.16 (dd, J = 11.2, 4.4 Hz, 1 H), 4.02 (s, 3 H), 3.37-3.49 (m, 2 H), 3.03 (br. s., 1 H), 2.71-2.81 (m, 1 H), 2.66 (s, 3 H), 2.29 (s, 3 H), 1.85 (d, J = 12.3 Hz, 1 H), 1.76 (d, J = 11.7 Hz, 1 H), 1.44-1.63 (m, 2 H), 0.90 (br. s., 3 H) |
| 1006 | MsOH | 1H NMR (400 MHz, DMSO-d$_6$) δ ppm 9.56 (br. s., 1 H), 8.96 (d, J = 5.5 Hz, 1 H), 8.84 (d, J = 3.9 Hz, 1 H), 8.78 (s, 1 H), 8.49-8.62 (m, 2 H), 8.36 (s, 1 H), 7.88 (dd, J = 8.0, 5.3 Hz, 1 H), 5.81 (br. s., 1 H), 4.16 (dd, J = 11.3, 3.9 Hz, 2 H), 3.60 (t, J = 11.2 Hz, 1 H), 3.39-3.50 (m, 1 H), 3.02 (br. s., 1 H), 2.67-2.84 (m, 1 H), 2.32 (s, 3 H), 1.81-1.91 (m, 1 H), 1.72-1.81 (m, 1 H), 1.42-1.63 (m, 2 H), 0.90 (t, J = 7.4 Hz, 3 H) |
| 1007 | TFA | 1H NMR (400 MHz, DMSO-d$_6$) δ ppm 8.76 (s, 1 H), 8.65 (s, 1 H), 8.45 (d, J = 8.8 Hz, 1 H), 8.34 (d, J = 0.7 Hz, 1 H), 8.13 (d, J = 8.8 Hz, 1 H), 7.99 (s, 1 H), 5.76 (br. s., 1 H), 4.13 (dd, J = 11.1, 4.5 Hz, 1 H), 4.01 (s, 3 H), 3.59 (ddd, J = 11.9, 1.8 Hz, 1 H), 3.39-3.47 (m, 1 H), 2.91-3.03 (m, 1 H), 2.66-2.77 (m, 1 H), 1.80 (dd, J = 11.9, 3.5 Hz, 1 H), 1.71 (dd, J = 10.8, 3.1 Hz, 1 H), 1.53-1.62 (m, 1 H), 1.45-1.53 (m, 1 H), 0.91 (t, J = 7.5 Hz, 3 H) |
| 1008 | MsOH | 1H NMR (400 MHz, DMSO-d$_6$) δ ppm 8.76 (s, 1 H), 8.47 (br. s., 1 H), 8.34 (s, 1 H), 8.31 (d, J = 9.0 Hz, 1 H), 8.22-8.28 (m, 1 H), 8.04 (d, J = 9.0 Hz, 1 H), 4.01 (s, 3 H), 3.93 (s, 3 H), 3.87-3.92 (m, 1 H), 3.64-3.83 (m, 2 H), 2.67-2.83 (m, 2 H), 2.30 (s, 3 H), 1.75 (d, J = 10.2 Hz, 2 H), 1.21 (d, J = 5.9 Hz, 6 H) |
| 1009 | MsOH | 1H NMR (400 MHz, DMSO-d$_6$) δ ppm 8.75 (s, 1 H), 8.48 (br. s., 1 H), 8.33 (s, 1 H), 8.30 (d, J = 9.0 Hz, 1 H), 8.22-8.28 (m, 1 H), 8.03 (d, J = 9.0 Hz, 1 H), 4.01 (s, 3 H), 3.92 (s, 3 H), 3.66-3.77 (m, 2 H), 3.43-3.54 (m, 2 H), 2.70-2.86 (m, 1 H), 2.29 (s, 3 H), 1.76 (d, J = 11.7 Hz, 2 H), 1.44-1.63 (m, 2 H), 1.22 (d, J = 5.9 Hz, 3 H), 0.91 (t, J = 7.4 Hz, 3 H) |
| 1010 | MsOH | 1H NMR (400 MHz, DMSO-d$_6$) δ ppm 8.78 (s, 1 H), 8.46 (s, 1 H), 8.43 (d, J = 8.8 Hz, 1 H), 8.36 (s, 1 H), 8.26 (d, J = 8.8 Hz, 1 H), 5.73 (br. s., 1 H), 4.28 (s, 3 H), 4.16 (dd, J = 11.3, 4.1 Hz, 1 H), 4.02 (s, 3 H), 3.59-3.67 (m, 1 H), 3.43-3.49 (m, 1 H), 3.02-3.12 (m, 1 H), 2.73-2.84 (m, 1 H), 2.30 (s, 3 H), 1.77-1.84 (m, 1 H), 1.67-1.75 (m, 1 H), 1.43-1.61 (m, 2 H), 0.91 (t, J = 7.5 Hz, 3 H) |
| 1011 | MsOH | 1H NMR (400 MHz, DMSO-d$_6$) δ ppm 8.78 (s, 1 H), 8.66 (s, 1 H), 8.43 (s, 2 H), 8.35 (s, 1 H), 5.91 (br. s., 1 H), 4.19 (s, 3 H), 4.02 (s, 3 H), 2.29 (s, 3 H), 1.72-1.84 (m, 2 H), 1.22 (d, J = 6.3 Hz, 6 H) |
| 1012 | MsOH | 1H NMR (400 MHz, DMSO-d$_6$) δ ppm 8.87 (br. s., 1 H), 8.81 (s, 1 H), 8.52 (d, J = 9.2 Hz, 1 H), 8.38 (s, 1 H), 8.34 (d, J = 9.2 Hz, 1 H), 7.92-7.94 (m, 1 H), 6.72 (dd, J = 2.4, 1.8 Hz, 1 H), 5.52-5.67 (m, 1 H), 4.16 (dd, J = 11.3, 4.1 Hz, 1 H), 4.02 (s, 3 H), 3.62 (dt, J = 11.8, 1.8 Hz, 1 H), 3.42-3.50 (m, 1 H), 2.95-3.07 (m, 1 H), 2.68-2.79 (m, 1 H), 2.32 (s, 3 H), 1.77-1.86 (m, 1 H), 1.68-1.77 (m, 1 H), 1.44-1.62 (m, 2 H), 0.91 (t, J = 7.5 Hz, 3 H) |
| 1013 | MsOH | 1H NMR (400 MHz, DMSO-d$_6$) δ ppm 9.54 (s, 1 H), 8.81 (s, 1 H), 8.61 (d, J = 9.4 Hz, 1 H), 8.42 (s, 1 H), 8.38 (s, 1 H), 8.27 (d, J = 9.0 Hz, 1 H), 5.59 (br. s., 1 H), 4.17 (dd, J = 11.5, 4.5 Hz, 1 H), 4.02 (s, 3 H), 3.61-3.70 (m, 1 H), 3.46-3.53 (m, 1 H), 2.96-3.05 (m, 1 H), 2.69-2.77 (m, 1 H), 2.31 (s, 3 H), 1.78-1.85 (m, 1 H), 1.68-1.75 (m, 1 H), 1.44-1.60 (m, 2 H), 0.91 (t, J = 7.4 Hz, 3 H) |

TABLE 2-continued

| Cmpd # | Salt | ¹H NMR |
|---|---|---|
| 1014 | MsOH | 1H NMR (400 MHz, DMSO-d6) δ ppm 8.82 (br.s, 1H), 8.77 (s, 1 H), 8.48 (d, J = 9.0 Hz, 1 H), 8.35 (s, 1 H), 8.23 (d, J = 9.0 Hz, 1 H), 8.19 (br. s., 1 H), 5.77 (br. s., 1 H), 4.07-4.17 (m, 1 H), 4.01 (s, 3 H), 3.91 (s, 3 H), 3.69 (t, 1 H), 3.50 (d, J = 11.0 Hz, 1 H), 2.90-3.02 (m, 1 H), 2.66-2.77 (m, 1 H), 2.30 (s, 3 H), 1.68-1.84 (m, 2 H), 1.43-1.62 (m, 2 H), 0.92 (t, J = 7.4 Hz, 3 H) |
| 1015 | MsOH | 1H NMR (400 MHz, DMSO-d₆) δ ppm 8.97 (s, 1 H), 8.74 (s, 1 H), 8.62 (s, 1 H), 8.37 (s, 1H), 8.34 (s, 1H), 5.57-5.70 (m, 1 H), 4.15 (dd, J = 11.0, 4.3 Hz, 1 H), 4.02 (s, 3 H), 3.99 (s, 3 H), 3.59 (t, J = 11.2 Hz, 1 H), 3.36-3.49 (m, 1 H), 2.90-3.06 (m, 1 H), 2.69 (q, J = 11.3 Hz, 1 H), 2.33 (s, 3 H), 1.81 (d, J = 12.1 Hz, 1 H), 1.71 (d, J = 12.1 Hz, 1 H), 1.44-1.61 (m, 2 H), 0.91 (t, J = 7.4 Hz, 3 H) |
| 1016 | MsOH | 1H NMR (400 MHz, DMSO-d₆) δ ppm 8.97 (s, 1 H), 8.75 (s, 1 H), 8.66 (br. s., 1 H), 8.43 (br. s., 1 H), 8.35 (s, 1 H), 5.67 (br. s., 1 H), 4.02 (s, 3 H), 4.01-3.96 (m, 1 H), 3.99 (s, 3H), 3.72 (br. s., 2 H), 2.59-2.65 (m, 2 H), 2.29 (s, 3 H), 1.77 (d, J = 13.7 Hz, 2 H), 1.21 (d, J = 5.9 Hz, 6 H) |
| 1017 | MsOH | 1H NMR (400 MHz, DMSO-d₆) δ ppm 8.97 (s, 1 H), 8.75 (s, 1 H), 8.68 (br. s., 1 H), 8.42 (br. s., 1 H), 8.35 (s, 1 H), 5.65 (br. s., 1 H), 4.02 (s, 3 H), 3.98 (s, 3 H), 3.66-3.74 (m, 2 H), 3.44-3.56 (m, 1 H), 2.30 (s, 3 H), 1.78 (d, J = 12.1 Hz, 2 H), 1.57-1.62 (m, 1 H), 1.37-1.50 (m, 1 H), 1.22 (d, J = 6.3 Hz, 3 H), 0.91 (t, J = 7.4 Hz, 3 H) |
| 1018 | MsOH | 1H NMR (400 MHz, DMSO-d₆) δ ppm 8.98 (s, 1 H), 8.75 (s, 1 H), 8.63 (s, 1 H), 8.38 (br. s., 1 H), 8.35 (s, 1 H), 4.08-4.17 (m, 1 H), 4.02 (s, 3 H), 3.99 (s, 3 H), 3.48-3.63 (m, 2 H), 2.93-3.04 (m, 1 H), 2.31 (s, 3 H), 1.80 (d, J = 12.9 Hz, 1 H), 1.67-1.76 (m, 2 H), 1.48-1.65 (m, 2 H), 1.34-1.46 (m, 2 H), 1.25 (d, J = 13.3 Hz, 1 H), 0.88 (t, J = 7.0 Hz, 3 H) |
| 1019 | MsOH | 1H NMR (400 MHz, DMSO-d₆) δ ppm 9.48 (d, J = 1.6 Hz, 1 H), 9.12 (s, 1 H), 8.90 (dd, J = 5.1, 1.6 Hz, 1 H), 8.66 (ddd, J = 8.2, 2.0, 1.6 Hz, 1 H), 8.63 (s, 1 H), 8.37 (s, 1 H), 7.76 (ddd, J = 8.2, 4.7, 0.8 Hz, 1 H), 5.75 (br. s., 1 H), 4.18 (dd, J = 11.0, 4.3 Hz, 1 H), 4.00 (s, 3 H), 3.59-3.62 (m, 1H, obscured by water signal), 3.45 (dt, J = 11.0, 5.5 Hz, 1 H), 3.01 (dd, J = 12.3, 4.5 Hz, 1 H), 2.73 (q, J = 11.7 Hz, 1 H), 2.31 (s, 3 H), 1.85 (d, J = 11.3 Hz., 1 H), 1.77 (d, J = 11.3 Hz, 1 H), 1.44-1.63 (m, 2 H), 0.92 (t, J = 7.4 Hz, 3 H) |
| 1020 | MsOH | 1H NMR (400 MHz, DMSO-d₆) δ ppm 9.05 (s, 2 H), 8.62 (s, 1 H), 8.41 (d, J = 8.6 Hz, 1 H), 8.37 (s, 1 H), 6.88 (d, J = 9.0 Hz, 1 H), 5.69 (br. s., 1 H), 4.16 (dd, J = 11.3, 4.3 Hz, 1 H), 3.99 (s, 3 H), 3.60 (t, J = 11.2 Hz, 2 H), 3.43 (dt, J = 10.7, 5.4 Hz, 1 H), 3.02-2.91 (m, 1 H), 2.98 (s, 3 H), 2.71 (d, J = 11.7 Hz, 1 H), 2.32 (s, 3 H), 1.82 (d, J = 11.3 Hz, 1 H), 1.72 (d, J = 11.7 Hz, 1 H), 1.43-1.66 (m, 2 H), 0.92 (t, J = 7.4 Hz, 3 H) |
| 1021 | MsOH | 1H NMR (400 MHz, DMSO-d₆) δ ppm 8.78 (s, 1 H), 8.43 (br. s., 1 H), 8.37 (s, 1 H), 8.24 (br. s., 1 H), 8.21 (s, 1 H), 5.77 (br. s., 1 H), 4.15 (dd, J = 11.1, 3.9 Hz, 1 H), 4.02 (s, 3 H), 3.94 (s, 3 H), 3.36-3.46 (m, 1 H), 2.97-3.12 (m, 1 H), 2.74-2.88 (m, 1 H), 2.70 (s, 3 H), 2.32 (s, 3 H), 1.82 (d, J = 11.4 Hz, 1 H), 1.71 (d, J = 10.8 Hz, 1 H), 1.53-1.63 (m, 1 H), 1.43-1.53 (m, 1 H), 0.91 (t, J = 7.4 Hz, 3 H) |
| 1022 | MsOH | 1H NMR (400 MHz, DMSO-d₆) δ ppm 8.72 (s, 1 H), 8.68 (s, 1 H), 8.62 (s, 1 H), 8.37 (br. s., 1 H), 8.33 (s, 1 H), 5.61-5.72 (m, 1 H), 4.01 (s, 3 H), 3.95 (s, 3 H), 3.50-3.64 (m, 1 H), 3.36-3.48 (m, 1 H), 2.91-3.09 (m, 1 H), 2.69-2.80 (m, 1 H), 2.50-2.57 (m, 1 H), 2.31 (s, 3 H), 2.30-2.33 (m, 1H), 1.76-1.85 (m, 1 H), 1.67-1.76 (m, 1 H), 1.52 (qd, 2 H), 0.91 (t, J = 7.4 Hz, 3 H) |
| 1023 | MsOH | 1H NMR (400 MHz, DMSO-d₆) δ ppm 8.72 (s, 1 H), 8.48 (s, 1 H), 8.34-8.35 (br. s., 1 H), 8.33 (s, 1 H), 8.01 (s, 1 H), 5.61-5.77 (m, 1 H), 4.12-4.20 (m, 1 H) 4.13 (s, 3 H), 4.01 (s, 3 H), 3.93 (s, 3 H), 3.53-3.67 (m, 1 H), 3.37-3.50 (m, 1 H), 2.99-3.20 (m, 1 H), 2.70-2.88 (m, 1 H), 2.49-2.54 (m, 1 H) 2.29 (s, 3 H), 1.79 (dd, J = 13.7, 3.9 Hz, 1 H), 1.64-1.74 (m, 1 H), 1.53 (qd, 2 H), 0.91 (t, J = 7.4 Hz, 3 H) |
| 1024 | MsOH | 1H NMR (400 MHz, DMSO-d₆) δ ppm 9.05 (br. s., 1 H), 8.44-8.52 (m, 1 H) 8.42 (s, 1 H), 8.26 (s, 1 H), 8.02 (dd, J = 8.6, 1.6 Hz, 1 H), 7.97 (s, 1 H), 7.89 (d, J = 9.0 Hz, 1 H), 6.87-6.97 (m, 1H), 4.48-4.56 (m, 2 H), 4.20 (q, J = 7.4 Hz, 2 H), 3.95-4.04 (m, 1 H), 3.83-3.90 (m, 1 H), 3.68-3.76 (m, 1 H), 2.98 (s, 3 H), 2.49-2.58 (m, 1H) 2.30 (s, 3 H), 2.01-2.16 (m, 2 H), 1.82-1.98 (m, 4 H), 1.48-1.55 (m, 1 H), 1.44 (t, J = 7.2 Hz, 3 H) |

TABLE 2-continued

| Cmpd # | Salt | ¹H NMR |
|---|---|---|
| 1025 | MsOH | 1H NMR (400 MHz, DMSO-d$_6$) δ ppm 9.06 (br. s., 1 H), 8.47 (d, J = 9.4 Hz, 1 H), 8.41 (d, J = 1.2 Hz, 1 H), 8.29 (s, 1 H), 8.03 (dd, J = 9.0, 1.6 Hz, 1 H), 7.97 (s, 1 H), 7.89 (d, J = 9.0 Hz, 1 H), 6.90 (d, J = 10.2 Hz, 1 H), 4.44-4.62 (m, 3 H), 3.96-4.07 (m, 3 H), 3.82-3.93 (m, 1 H), 3.65-3.79 (m, 1 H), 2.98 (s, 3 H), 2.30 (s, 3 H), 2.01-2.10 (m, 2 H), 1.83-1.99 (m, 3 H), 1.51-1.56 (m, 1 H), 1.48 (d, J = 6.7 Hz, 6 H) |
| 1026 | MsOH | 1H NMR (400 MHz, DMSO-d$_6$) δ ppm 9.25 (d, J = 2.2 Hz, 1 H), 8.47 (dd, J = 9.1, 2.5 Hz, 1 H), 8.41 (d, J = 1.5 Hz, 1 H), 8.20 (s, 1 H), 7.99 (dd, J = 9.0, 1.8 Hz, 1 H), 7.95 (d, J = 0.7 Hz, 1 H), 7.92 (d, J = 8.8 Hz, 1 H), 7.08 (d, J = 9.2 Hz, 1 H), 4.48-4.54 (m, 2 H), 3.96-4.06 (m, 2 H), 3.91 (s, 3 H), 3.86 (dd, J = 7.9, 6.8 Hz, 1 H), 3.69-3.76 (m, 8 H), 2.29 (s, 3 H), 2.08-2.15 (m, 1 H), 2.01-2.08 (m, 1 H), 1.98-1.89 (m, 1 H), 1.86 (dd, J = 7.0 Hz, 2 H), 1.42-1.55 (m, 1 H) |
| 1027 | MsOH | 1H NMR (400 MHz, DMSO-d$_6$) δ ppm 9.11-9.19 (m, 1 H), 8.64 (s, 1 H), 8.57 (s, 1 H), 8.35-8.43 (m, 1 H), 8.16 (d, J = 8.6 Hz, 1 H), 8.04 (d, J = 8.8 Hz, 1 H), 7.78 (s, 1 H), 6.68-6.80 (m, 1 H), 4.40-4.56 (m, 2 H), 3.96-4.02 (m, 1 H), 3.91 (dd, J = 14.7, 7.7 Hz, 2 H), 3.75 (dd, J = 14.4, 7.2 Hz, 3 H), 2.93 (s, 3 H), 2.29 (s, 3 H), 1.98-2.18 (m, 2 H), 1.82-1.96 (m, 2 H), 1.45-1.57 (m, 1 H) |
| 1028 | MsOH | 1H NMR (400 MHz, DMSO-d$_6$) δ ppm 9.16 (s, 1 H), 9.06 (br. s., 1 H), 8.53 (d, J = 1.6 Hz, 1 H), 8.43-8.49 (m, 1 H), 8.40 (s, 1 H), 8.13 (dd, J = 8.8 Hz, 1.8 Hz, 1 H), 7.98 (d, J = 9.0 Hz, 1 H), 6.86-6.95 (m, 1 H), 4.38-4.56 (m, 2 H), 3.92-4.02 (m, 2 H), 3.84-3.92 (m, 2 H), 3.65-3.74 (m, 1 H), 2.97 (s, 3 H), 2.29 (s, 3 H), 2.10-2.16 (m, 1 H), 2.00-2.10 (m, 1 H), 1.80-1.95 (m, 3 H), 1.42-1.56 (m, 1 H) |
| 1029 | — | 1H NMR (400 MHz, DMSO-d$_6$) δ ppm 9.15 (d, J = 2.2 Hz, 1 H), 8.60 (s, 1 H), 8.46 (d, J = 1.1 Hz, 1 H), 8.31 (d, J = 7.3 Hz, 1 H), 8.18 (dd, J = 11.6, 1.2 Hz, 1 H), 7.83 (s, 1 H), 7.59 (br. s., 1 H), 6.68 (d, J = 9.0 Hz, 1 H), 4.40-4.53 (m, 2 H), 3.98 (br. s., 1 H), 3.86-3.95 (m, 1 H), 3.72-3.78 (m, 1 H), 2.91 (d, J = 4.6 Hz, 3 H), 2.07 (s, 2 H), 1.80-1.93 (m, 3 H), 1.49 (dq, J = 12.2, 8.2 Hz, 1 H) |
| 1030 | MsOH | 1H NMR (400 MHz, DMSO-d$_6$) δ ppm 9.09 (br. s., 1 H), 8.40 (br. s., 1 H), 8.25 (br. s., 2 H), 8.00 (d, J = 0.9 Hz, 2 H), 6.82 (br. s., 1 H), 4.43-4.55 (m, 2 H), 4.01 (br. s., 2 H), 3.92 (s, 3 H), 3.83-3.90 (m, 1 H), 3.68-3.77 (m, 1 H), 3.68-3.77 (m, 1 H), 2.96 (br. s., 2 H), 2.30 (s, 3 H), 2.01-2.15 (m, 2 H), 1.86 (t, J = 6.9 Hz, 3 H), 1.45-1.55 (m, 1 H) |
| 1031 | MsOH | 1H NMR (400 MHz, DMSO-d$_6$) δ ppm 9.19 (d, J = 2.4 Hz, 1 H), 8.44 (dd, J = 9.0, 2.4 Hz, 1 H), 8.23 (br. s., 1 H), 7.98 (br. s., 1 H), 7.09 (d, J = 8.6 Hz, 1 H), 4.48 (br. s., 2 H), 4.01 (br. s., 4 H), 3.90 (s, 3 H), 3.85 (br. s., 2 H), 3.71 (d, J = 2.0 Hz, 7 H), 2.29 (s, 3 H), 2.06 (ddd, J = 19.8, 7.0, 6.7 Hz, 2 H), 1.82-1.93 (m, 1 H), 1.86 (d, J = 7.0 Hz, 2 H), 1.44-1.56 (m, 1 H) |
| 1032 | MsOH | 1H NMR (400 MHz, DMSO-d$_6$) δ ppm 9.07 (br. s, 1 H), 8.53 (d, J = 7.4 Hz, 1 H), 8.40 (br. s, 1 H), 8.18 (d, J = 2.7 Hz, 1 H), 7.98 (d, J = 11.0 Hz, 1H), 7.96 (s, 1 H), 6.84 (br. s, 1 H), 4.52-4.48 (m, 2 H), 3.96-4.02 (m, 1 H), 3.94 (s, 3H), 3.85 (q, J = 7.8 Hz, 1 H), 3.70 (q, J = 7.8 Hz, 1 H), 2.96 (br. s, 3 H), 2.30 (s, 3 H), 2.10-2.15 (m, 1 H), 2.01-2.07 (m, 1 H), 1.82-1.95 (m, 3 H), 1.49 (dq, J = 11.7, 7.8 Hz, 1 H) |
| 1033 | MsOH | 1H NMR (400 MHz, DMSO-d$_6$) δ ppm 9.10 (s, 1 H), 8.53 (d, J = 6.6 Hz, 1 H), 8.45 (d, J = 7.2 Hz, 1 H), 8.18 (s, 1 H), 7.99 (d, J = 11 Hz, 1 H), 7.95 (s, 1 H), 6.64 (d, J = 9.4 Hz, 1 H), 4.53-4.46 (m, 2 H), 4.19 (t, J = 7 Hz, 4 H), 3.96-4.01 (m, 1 H), 3.94 (s, 3 H), 3.84 (q, J = 7.2 Hz, 1 H), 3.70 (q, J = 7 Hz, 1 H), 2.30 (s, 3H), 2.00-2.16 (m, 2H), 1.82-1.97 (m, 3H), 1.49 (dq, J = 11.7, 7.8 Hz, 1H). Signals obscured by water peak |
| 1034 | MsOH | 1H NMR (400 MHz, DMSO-d$_6$) δ ppm 9.18 (d, J = 2.3 Hz, 1 H), 8.51 (d, J = 7.4 Hz, 1 H), 8.42 (dd, J = 9.4, 2.3 Hz, 1 H), 8.17 (d, J = 2.3 Hz, 1 H), 7.99 (d, J = 10.6 Hz, 1 H), 7.95 (s, 1H), 6.93 (d, J = 9.4 Hz, 1 H), 4.44-4.53 (m, 2 H), 3.96-4.02 (m, 1 H), 3.92 (s, 3 H), 3.85 (q, J = 7.4 Hz, 1 H), 3.70 (q, J = 7.5 HZ, 1 H), 3.21 (s, 6 H), 2.29 (s, 3H), 2.01-2.12 (m, 2 H), 1.82-1.95 (m, 3 H), 1.49 (dq, J = 11.7, 7.8 Hz, 1 H) |
| 1035 | TFA | 1H NMR (400 MHz, DMSO-d$_6$) δ ppm 9.22 (d, J = 2.0 Hz, 1 H), 9.17 (s, 1 H), 8.51 (d, J = 1.8 Hz, 1 H), 8.45 (dd, J = 9.4, 2.0 Hz, 1 H), 8.39 (s, 1 H), 8.12 (dd, J = 9.0, 1.8 Hz, 1 H), 8.00 (d, J = 9.0 Hz, 1 H), 6.92 (d, J = 9.4 Hz, 1 H), 4.52-4.46 (m, 2H), 3.98 (m, 1 H), 3.97-3.87 (m, 1 H), 3.73-3.68 (m, 1 H), 3.20 (s, 6 H), 2.14-2.00 (m, 2 H), 1.93-1.82 (m, 3 H), 1.53-1.48 (m, 1 H) |

TABLE 2-continued

| Cmpd # | Salt | ¹H NMR |
|---|---|---|
| 1036 | MsOH | 1H NMR (400 MHz, DMSO-d₆) δ ppm 9.03 (s, 1 H), 8.44-8.53 (m, 1 H), 8.42 (s, 1 H), 8.19 (s, 1 H), 8.00 (dd, J = 8.6, 1.6 Hz, 1 H), 7.95 (s, 1 H), 7.88 (d, J = 9.0 Hz, 1 H), 6.88-6.99 (m, 1 H), 4.41-4.60 (m, 2 H), 3.95 (d, J = 9.8 Hz, 2 H), 3.91 (s, 3 H), 3.46-3.55 (m, 1 H), 3.33-3.42 (m, 1 H), 2.99 (s, 3 H), 2.31 (s, 3H), 1.96-2.05 (m, 1 H), 1.85-1.96 (m, 1 H), 1.74-1.82 (m, 1 H), 1.62 (d, J = 11.7 Hz, 1 H), 1.44-1.57 (m, 3 H), 1.22-1.37 (m, 1 H) |
| 1037 | MsOH | 1H NMR (400 MHz, DMSO-d₆) δ ppm 9.08 (s, 1 H), 8.65 (s, 1 H), 8.39-8.53 (m, 1 H), 8.23 (s, 1 H), 8.00 (s, 1 H), 8.00 (dd, J = 8.8, 1.5 Hz, 1 H), 7.89 (d, J = 8.8 Hz, 1 H), 6.82-6.91 (m, 1 H), 5.96-6.10 (m, 1 H), 4.30 (dd, J = 8.8, 6.2 Hz, 1 H), 4.17 (t, J = 9.6 Hz, 1 H), 4.01-4.10 (m, 1 H), 3.91 (s, 3 H), 2.97 (s, 3 H), 2.34-2.42 (m, 1 H), 2.30 (s, 3 H), 2.20-2.27 (m, 1 H), 1.65-1.84 (m, 2 H), 1.01 (t, J = 7.5 Hz, 3 H) |
| 1038 | — | 1H NMR (400 MHz, DMSO-d₆) δ ppm 8.85 (s, 1 H), 8.42 (s, 1 H), 8.25 (s, 2 H), 8.05 (dd, J = 8.8, 1.4 Hz, 1 H), 7.99 (s, 1 H), 7.92 (d, J = 8.6 Hz, 1 H), 4.08-4.19 (m, 1 H), 4.03 (s, 3 H), 3.92 (s, 3 H), 3.74 (t, J = 11.0 Hz, 1 H), 3.54-3.62 (m, 2 H), 2.70-2.81 (m, 1 H), 2.63-2.69 (m, 1 H), 1.89 (dd, J = 28.6, 11.3 Hz, 2 H), 1.46-1.62 (m, 2 H), 0.93 (t, J = 7.4 Hz, 3 H) |
| 1039 | — | 1H NMR (400 MHz, DMSO-d₆) δ ppm 8.77 (s, 1 H), 8.35 (s, 1 H), 8.26 (s, 2 H), 7.97-8.08 (m, 2 H), 7.90 (d, J = 8.6 Hz, 1 H), 4.02 (s, 3 H), 3.92 (s, 3 H), 3.78-3.89 (m, 4 H), 2.54 (br. s., 1 H), 1.89 (d, J = 14.1 Hz, 2 H), 1.22 (d, J = 6.3 Hz, 6 H) |
| 1040 | TFA | 1H NMR (400 MHz, DMSO-d₆) δ ppm 9.10 (d, J = 2.2 Hz, 1 H), 8.78 (s, 1 H), 8.72 (dd, J = 5.0, 1.4 Hz, 1 H), 8.44 (br. s., 1 H), 8.37-8.40 (m, 1 H), 8.35 (d, J = 0.7 Hz, 1 H), 8.17 (dd, J = 8.8, 1.8 Hz, 1 H), 8.06 (d, J = 8.8 Hz, 1 H), 7.71 (dd, J = 8.1, 4.6 Hz, 1 H), 5.09 (br. s., 1 H), 4.05-4.14 (m, 1 H), 4.02 (s, 3 H), 3.48-3.57 (m, 2 H), 2.73-2.86 (m, 1 H), 1.91 (dd, J = 11.7, 3.5 Hz, 1 H), 1.84 (dd, J = 12.1, 3.7 Hz, 1 H), 1.43-1.59 (m, 2 H), 0.90 (t, J = 7.4 Hz, 3 H) |
| 1041 | — | 1H NMR (400 MHz, DMSO-d₆) δ ppm 8.73 (s, 1 H), 8.29 (d, J = 10.6 Hz, 3 H), 8.01 (d, J = 1.6 Hz, 1 H), 7.98 (s, 1 H), 7.89 (d, J = 8.6 Hz, 1 H), 4.20 (q, J = 7.2 Hz, 2 H), 4.10-4.16 (m, 1 H), 4.01 (s, 3 H), 3.72 (t, J = 11.3 Hz, 1 H), 3.48-3.60 (m, 2 H), 2.70-2.85 (m, 2 H), 1.86 (dd, J = 31.9, 12.3 Hz, 2 H), 1.48-1.62 (m, 2 H), 1.43 (t, J = 7.2 Hz, 3 H), 0.93 (t, J = 7.4 Hz, 3 H) |
| 1042 | — | 1H NMR (400 MHz, DMSO-d₆) δ ppm 8.69 (s, 1 H), 8.32-8.43 (m, 1 H), 8.30 (s, 1 H), 8.20 (d, J = 2.4 Hz, 1 H), 7.97 (s, 1 H), 7.94 (d, J = 10.8 Hz, 1 H), 4.05-4.18 (m, 2 H), 4.00 (s, 3 H), 3.94 (s, 3 H), 3.71 (t, J = 10.9 Hz, 2 H), 3.54 (s, 2 H), 1.85 (dd, J = 32.7, 9.1 Hz, 2 H), 1.39-1.61 (m, 2 H), 0.91 (t, J = 7.5 Hz, 3 H) |
| 1043 | MsOH | 1H NMR (400 MHz, DMSO-d₆) δ ppm 8.74 (s, 1 H), 8.66 (br. s., 1 H), 8.35 (s, 1 H), 7.95 (d, J = 11.0 Hz, 1 H), 7.87 (d, J = 2.0 Hz, 1 H), 6.70 (dd, J = 3.9, 2.0 Hz, 1 H), 4.88-5.11 (m, 1 H), 4.14 (dd, J = 11.5, 4.1 Hz, 1 H), 4.02 (s, 3 H), 3.95 (s, 3 H), 3.57 (dd, J = 12.9, 9.4 Hz, 1 H), 3.40-3.49 (m, 1 H), 2.69-2.83 (m, 1 H), 2.31-2.34 (m, 1 H), 2.31 (s, 3H), 1.78-2.00 (m, 2 H), 1.45-1.68 (m, 2 H), 0.94 (t, J = 7.6 Hz, 3 H) |
| 1044 | MsOH | 1H NMR (400 MHz, DMSO-d₆) δ ppm 8.75 (s, 1 H), 8.47 (br. s., 1 H), 8.35 (s, 1 H), 8.08 (d, J = 10.6 Hz, 1 H), 7.51 (d, J = 4.3 Hz, 1 H), 4.95-5.19 (m, 1 H), 4.14-4.20 (m, 1 H), 4.01 (s, 3 H), 3.59-3.70 (m, 1 H), 3.45-3.56 (m, 1 H), 2.65-2.82 (m, 1 H), 2.54 (s, 3 H), 2.32 (s, 3H), 1.79-1.99 (m, 2 H), 1.44-1.67 (m, 2 H), 0.95 (t, J = 7.4 Hz, 3 H) |
| 1045 | MsOH | 1H NMR (400 MHz, DMSO-d₆) δ ppm 8.80 (s, 1 H), 8.73 (s, 1 H), 8.32 (d, J = 7.4 Hz, 1 H), 8.34 (s, 1 H), 8.17 (d, J = 8.5 Hz, 1 H), 8.06 (d, J = 10.2 Hz, 1 H), 7.70 (d, J = 8.5 Hz, 1 H), 4.93-5.13 (m, 1 H), 4.69 (s, 2 H), 4.03-4.08 (m, 1 H), 4.02 (s, 3 H), 3.62-3.68 (m, 2 H), 3.48 (br. s., 1 H), 2.70-2.81 (m, 1 H), 2.30 (s, 3H), 1.76-1.92 (m, 1 H), 1.40-1.57 (m, 2 H), 0.88 (t, J = 7.4 Hz, 3 H) |
| 1046 | MsOH | 1H NMR (400 MHz, DMSO-d₆) δ ppm 8.83 (s, 1 H), 8.75 (s, 1 H), 8.36 (s, 1 H), 8.34 (br. s., 1 H), 8.24 (d, J = 7.8 Hz, 1 H), 8.07 (d, J = 10.2 Hz, 1 H), 7.80 (d, J = 7.8 Hz, 1 H), 4.94-5.11 (m, 1 H), 4.90 (q, J = 6.4 Hz, 1 H), 4.03-4.09 (m, 1 H), 4.02 (s, 3 H), 3.59-3.70 (m, 1 H), 3.44-3.54 (m, 1 H), 2.70-2.84 (m, 1 H), 2.31 (s, 3H), 1.76-1.93 (m, 2 H), 1.39-1.56 (m, 5 H), 0.88 (t, J = 7.4 Hz, 3 H) |

TABLE 2-continued

| Cmpd # | Salt | ¹H NMR |
|---|---|---|
| 1047 | MsOH | 1H NMR (400 MHz, DMSO-d$_6$) δ ppm 9.02 (s, 1 H), 8.52 (d, J = 8.3 Hz, 1 H), 8.44 (s, 1 H), 8.02 (dd, J = 8.8, 1.2 Hz, 1 H), 7.98 (d, J = 8.8 Hz 1 H), 7.95 (s, 1 H), 7.00 (d, J = 8.6 Hz, 1 H), 4.50 (dd, J = 8.1, 7.7 Hz, 2 H), 3.95-4.01 (m, 1 H), 3.93 (s, 3 H), 3.86-3.92 (m, 1 H), 3.74 (dd, J = 15.0, 6.8 Hz, 1 H), 3.62 (s, J = 14.3, 14.3, 7.3, 7.3 Hz, 1 H), 3.00 (s, 3 H), 2.31 (s, 3 H), 2.00-2.13 (m, 2 H), 1.92-2.00 (m, 1 H), 1.79-1.88 (m, 2 H), 1.50 (dq, J = 11.9, 7.7 Hz, 1 H) |
| 1048 | — | 1H NMR (400 MHz, DMSO-d$_6$) δ ppm 8.64 (s, 1 H), 8.25 (s, 1 H), 8.13-8.18 (m, 2 H), 8.11 (s, 1 H), 7.80 (s, 1 H), 4.83-5.07 (m, 1 H), 3.98-4.07 (m, 2 H), 3.94 (s, 3 H), 3.87 (s, 3 H), 3.57 (t, J = 11.2 Hz, 1 H), 3.36-3.46 (m, 1 H), 2.57-2.71 (m, 2 H), 1.68-1.86 (m, 1 H), 1.36-1.53 (m, 2 H), 0.83 (t, J = 7.4 Hz, 3 H) |
| 1049 | — | 1H NMR (400 MHz, DMSO-d$_6$) δ ppm 8.66 (s, 1 H), 8.48 (s, 1 H), 8.27 (s, 1 H), 8.20-8.25 (m, 2 H), 7.91 (s, 1 H), 4.84-5.03 (m, 1 H), 3.99-4.07 (m, 2 H), 3.94 (s, 3 H), 3.90 (s, 3 H), 3.60 (td, J = 11.8, 1.8 Hz, 2 H), 2.60-2.72 (m, 1 H), 1.81 (dd, J = 10.6, 2.7 Hz, 1 H), 1.74 (dd, J = 13.1, 3.3 Hz, 1 H), 1.37-1.53 (m, 2 H), 0.83 (t, J = 7.4 Hz, 3 H) |
| 1050 | — | 1H NMR (400 MHz, DMSO-d$_6$) δ ppm 8.64 (s, 1 H), 8.22 (s, 1 H), 7.93-8.05 (m, 2 H), 7.74 (s, 1 H), 7.70 (s, 1 H), 3.98-4.08 (m, 1 H), 3.94 (s, 3 H), 3.86 (s, 3 H), 3.48-3.59 (m, 1 H), 3.35-3.44 (m, 2 H), 2.60-2.73 (m, 1 H), 2.50 (s, 3 H), 1.79 (d, J = 14.5 Hz, 1 H), 1.71 (d, J = 14.1 Hz, 1 H), 1.38-1.53 (m, 2 H), 0.83 (t, J = 7.4 Hz, 3 H) |
| 1051 | MsOH | 1H NMR (400 MHz, DMSO-d$_6$) δ ppm 8.99 (s, 1 H), 8.82 (d, J = 4.8 Hz, 1 H), 8.77 (s, 1 H), 8.72 (s, 1 H), 8.41 (s, 1 H), 8.37 (s, 1 H), 8.31 (d, J = 7.0 Hz, 1 H), 7.76 (dd, J = 7.7, 5.1 Hz, 1 H), 4.88-5.02 (m, 2 H, partially hidden by water), 4.03 (s, 3 H), 3.98-4.02 (m, 1 H), 3.63 (t, J = 10.8 Hz, 1 H), 3.45-3.52 (m, 1 H), 2.73-2.81 (m, 1 H), 2.31 (s, 3 H), 1.84 (dd, J = 25.0, 11.6 Hz, 2 H), 1.41-1.55 (m, 2 H), 0.87 (t, J = 7.5 Hz, 3 H) |
| 1052 | — | 1H NMR (400 MHz, DMSO-d$_6$) δ ppm 8.73 (s, 1 H), 8.55 (s, 1 H), 8.34 (s, 1 H), 8.31 (s, 1 H), 8.27 (br. s., 1 H), 8.00 (s, 1 H), 5.01 (br. s., 1 H), 4.02 (s, 3 H), 3.98 (s, 3 H), 3.79 (ddd, J = 10.9, 6.2, 1.7 Hz, 2 H), 2.30-2.45 (m, 3 H), 1.87 (dd, J = 11.7, 3.7 Hz, 1 H), 1.19 (d, J = 6.2 Hz, 6 H) |
| 1053 | — | 1H NMR (400 MHz, DMSO-d$_6$) δ ppm 8.72 (s, 1 H), 8.54 (s, 1 H), 8.27-8.34 (m, 3 H), 7.99 (s, 1 H), 5.03 (br. s., 1 H), 4.01 (s, 3 H), 3.97 (s, 3 H), 3.72-3.82 (m, 1 H), 3.53-3.61 (m, 1 H), 2.34-2.40 (m, 1 H), 1.83-1.92 (m, 2 H), 1.43-1.59 (m, 2 H), 1.20 (d, J = 5.9 Hz, 3 H), 0.89 (t, J = 7.5 Hz, 3 H) |
| 1054 | — | 1H NMR (400 MHz, DMSO-d$_6$) δ ppm 8.74 (s, 1 H), 8.58 (br. s., 1 H), 8.55 (s, 1 H), 8.35 (s, 1 H), 7.92 (d, J = 2.0 Hz, 1 H), 6.88 (d, J = 2.0 Hz, 1 H), 4.91-5.13 (m, 1 H), 4.12 (d, J = 11.3 Hz, 2 H), 4.02 (s, 3 H), 3.96 (s, 3 H), 3.59 (t, J = 11.9 Hz, 2 H), 2.70-2.80 (m, 1 H), 1.92 (d, J = 7.4 Hz, 1 H), 1.81 (d, J = 9.4 Hz, 1 H), 1.45-1.64 (m, 2 H), 0.92 (t, J = 7.4 Hz, 3 H) |
| 1055 | — | 1H NMR (400 MHz, DMSO-d$_6$) δ ppm 8.59 (s, 1 H), 8.20 (s, 1 H), 8.10 (s, 1 H), 7.88 (s, 1 H), 7.50 (s, 1 H), 4.72-5.46 (m, 1 H), 4.02-4.13 (m, 1 H), 3.98 (s, 3 H), 3.93 (s, 3 H), 3.84 (s, 3 H), 3.57-3.67 (m, 1 H), 3.46 (dt, J = 11.0, 5.5 Hz, 1 H), 3.28-3.34 (m, 1 H), 2.56-2.73 (m, 1 H), 2.29-2.40 (m, 1 H), 1.68-1.86 (m, 2 H), 1.46 (qd, J = 14.0, 13.7 Hz, 2 H), 0.85 (t, J = 7.4 Hz, 3 H) |
| 1056 | — | 1H NMR (400 MHz, DMSO-d$_6$) δ ppm 8.57 (s, 1 H), 8.26 (s, 1 H), 8.19 (s, 1 H), 8.06 (s, 1 H), 7.86 (s, 1 H), 7.46 (s, 1 H), 4.28-4.44 (m, 1 H), 3.97 (s, 3 H), 3.92 (s, 3 H), 3.86-3.91 (m, 2 H), 3.84 (s, 3 H), 3.77 (q, J = 7.3 Hz, 1 H), 3.62 (q, J = 7.3 Hz, 1 H), 1.90-2.07 (m, 2 H), 1.73-1.88 (m, 3 H), 1.41 (dq, J = 12.1, 8.2 Hz, 1 H) |
| 1057 | — | 1H NMR (400 MHz, DMSO-d$_6$) δ ppm 8.60 (s, 1 H), 8.28 (s, 1 H), 8.24 (s, 1 H), 8.01 (s, 1 H), 7.78 (br. s., 1 H), 7.57 (s, 1 H), 4.75-5.24 (m, 1 H), 4.10-4.16 (m, 1 H) 4.12 (s, 3 H), 4.01 (s, 3 H), 3.91 (s, 3 H), 3.64-3.76 (m, 1 H), 3.47-3.59 (m, 1 H), 2.69-2.85 (m, 1 H), 2.42-2.54 (m, 1 H), 1.87 (dd, J = 12.1, 3.5 Hz, 1 H), 1.79 (dd, J = 10.6, 3.1 Hz, 1 H), 1.54 (qd, J = 14.3, 7.1, 6.9 Hz, 2 H), 0.92 (t, J = 7.4 Hz, 3 H) |
| 1058 | — | 1H NMR (400 MHz, DMSO-d$_6$) δ ppm 8.69 (s, 1 H), 8.29 (s, 1 H), 8.21 (s, 1 H), 8.07 (br. s., 1 H), 7.95 (s, 1 H), 7.85 (s, 1 H), 4.83-5.26 (m, 1 H), 4.07-4.19 (m, 1 H), 4.02 (s, 3 H), 3.91 (s, 3 H), 3.64-3.78 (m, 1 H), 3.46-3.60 (m, 1 H), 2.71-2.85 (m, 1 H), 2.66 (s, 3 H), 2.44-2.54 (m, 1 H), 1.87 (d, J = 11.3 Hz, 1 H), 1.79 (d, J = 9.4 Hz, 1 H), 1.53 (dq, 2 H), 0.92 (t, J = 7.4 Hz, 3 H) |

TABLE 2-continued

| Cmpd # | Salt | ¹H NMR |
|---|---|---|
| 1059 | MsOH | 1H NMR (400 MHz, DMSO-$d_6$) δ ppm 8.77 (s, 1 H), 8.55 (br. s., 1 H), 8.34 (s, 2 H), 8.24 (dd, J = 8.8, 1.5 Hz, 1 H), 8.00 (d, J = 8.8 Hz, 1 H), 4.24 (s, 3 H), 4.02 (s, 3 H), 3.64-3.77 (m, 1 H), 3.45-3.60 (m, 1 H), 2.29 (s, 3 H), 1.80-1.95 (m, 2 H), 1.45-1.63 (m, 2 H), 0.93 (t, J = 7.4 Hz, 3 H) |
| 1060 | — | 1H NMR (400 MHz, DMSO-$d_6$) δ ppm 8.53 (br. s., 1 H), 8.25 (br. s., 1 H), 8.21 (s, 1 H), 8.06 (s, 1 H), 7.75 (s, 1 H), 4.81-5.05 (m, 1 H), 3.98-4.05 (m, 1 H), 3.95 (s, 3 H), 3.88 (s, 3 H), 3.50-3.61 (m, 1 H), 3.35-3.45 (m, 1 H), 2.67 (s, 3 H), 2.57-2.65 (m, 1 H), 1.66-1.85 (m, 2 H), 1.30-1.52 (m, 2 H), 0.82 (t, J = 7.4 Hz, 3 H) |
| 1061 | MsOH | 1H NMR (400 MHz, DMSO-$d_6$) δ ppm 8.99 (d, J = 2.0 Hz, 1 H), 8.76 (s, 1 H), 8.64 (br. s., 1 H), 8.37 (s, 1 H), 8.28 (s, 1 H), 8.09 (s, 1 H), 4.98 (br. s., 1 H), 4.06-4.14 (m, 1 H), 4.03 (s, 3 H), 3.94 (s, 3 H), 3.75 (t, J = 11.2 Hz, 2 H), 3.57-3.60 (m, 1 H, partially hidden by water), 2.76 (br. s., 1 H), 2.31 (s, 3 H), 1.79-1.93 (m, 2 H), 1.44-1.59 (m, 2 H), 0.92 (t, J = 7.4 Hz, 3 H) |
| 1062 | MsOH | 1H NMR (400 MHz, DMSO-$d_6$) δ ppm 8.77 (s, 1 H), 8.49 (s, 1 H), 8.27 (s, 1 H), 8.15 (s, 1 H), 7.84 (s, 1 H), 4.97 (br. s., 1 H), 4.05-4.13 (m, 1 H), 4.02 (s, 3 H), 3.95 (s, 3 H), 3.62-3.71 (m, 1 H), 3.42-3.57 (m, 1 H), 2.75 (s, 3 H), 2.71 (br. s., 1H), 2.41-2.47 (m, 1 H), 2.30 (s, 3 H), 1.84-1.91 (m, 1 H), 1.76-1.82 (m, 1 H), 1.39-1.59 (m, 2 H), 0.90 (t, J = 7.4 Hz, 3 H) |
| 1063 | TFA | 1H NMR (400 MHz, DMSO-$d_6$) δ ppm 9.33 (br. s., 1 H), 8.78 (s, 1 H), 8.67 (d, J = 9.4 Hz, 1 H), 8.40 (br. s., 1 H), 8.37 (s, 1 H), 8.34 (d, J = 9.0 Hz, 1 H), 7.59 (br. s., 1 H), 5.59 (br. s., 1 H), 4.11-4.19 (m, 1 H), 4.02 (s, 3 H), 3.59-3.66 (m, 1 H), 3.41-3.50 (m, 1 H), 2.92-3.03 (m, 1 H), 2.29 (s, 3 H), 1.79-1.85 (m, 1 H), 1.68-1.76 (m, 1 H), 1.44-1.61 (m, 2 H), 0.90 (t, J = 7.4 Hz, 3 H) |
| 1064 | MsOH | 1H NMR (400 MHz, DMSO-$d_6$) δ ppm 8.99 (d, J = 2.2 Hz, 1 H), 8.85 (d, J = 2.2 Hz, 1 H), 8.38-8.44 (m, 2 H), 8.32 (br. s., 1 H), 8.04 (d, J = 0.4 Hz, 1 H), 7.21-7.26 (m, 2 H), 4.44-4.56 (m, 2 H), 3.96-4.02 (m, 1 H), 3.93 (s, 3 H), 3.90 (s, 3 H), 3.84 (dd, J = 15.0, 7.0 Hz, 1 H), 3.69 (dd, J = 14.3, 7.7 Hz, 1 H), 2.29 (s, 3 H), 2.06-2.16 (m, 1 H), 1.97-2.05 (m, 1 H), 1.90-1.97 (m, 1 H), 1.85 (d, J = 6.8 Hz, 1 H), 1.80-1.90 (m, 1 H), 1.49 (dq, J = 12.1, 7.9 Hz, 1 H) |
| 1065 | MsOH | 1H NMR (400 MHz, DMSO-$d_6$) δ ppm 9.20 (dd, J = 2.4, 0.7 Hz, 1 H), 9.01 (d, J = 2.0 Hz, 1 H), 8.86 (d, J = 2.2 Hz, 1 H), 8.60 (dd, J = 8.8, 2.4 Hz, 1 H), 8.32 (s, 1 H), 8.04 (d, J = 0.7 Hz, 1 H), 7.12 (dd, J = 8.8, 0.7 Hz, 1 H), 4.46-4.57 (m, 1 H), 4.01 (s, 3 H), 3.95-3.98 (m, 1H), 3.93 (s, 3 H), 3.84 (dd, J = 15.0, 7.3 Hz, 1 H), 3.67 (dd, J = 14.5, 7.9 Hz, 1 H), 2.30 (s, 3 H), 2.07-2.16 (m, 1 H), 1.98-2.07 (m, 1 H), 1.90-1.98 (m, 1 H), 1.80-1.89 (m, 2 H), 1.50 (dd, J = 12.1, 7.9 Hz, 1 H) |
| 1066 | MsOH | 1H NMR (400 MHz, DMSO-$d_6$) δ ppm 9.17 (d, J = 2.2 Hz, 1 H), 9.08 (br. s., 1 H), 9.07 (d, J = 2.2 Hz, 1 H), 8.66 (s, 1 H), 8.37-8.45 (m, 1 H), 7.92 (s, 1 H), 6.79-6.86 (m, 1 H), 4.38-4.55 (m, 3 H), 3.94-4.01 (m, 1 H), 3.91 (dd, J = 14.8, 6.6 Hz, 1 H), 3.73 (dd, J = 14.3, 7.7 Hz, 1 H), 2.95 (s, 2 H), 2.29 (s, 3 H), 2.07-2.20 (m, 1 H), 1.98-2.07 (m, 1 H), 1.79-1.93 (m, 2 H), 1.39-1.57 (m, 1 H), 1.23 (s, 1 H) |
| 1067 | MsOH | 1H NMR (400 MHz, DMSO-$d_6$) δ ppm 8.89-8.98 (m, 2 H), 8.78 (d, J = 2.3 Hz, 1 H), 8.35-8.47 (m, 1 H), 8.30 (s, 1 H), 7.97 (s, 1 H), 6.86-6.96 (m, 1 H), 4.30-4.53 (m, 2 H), 4.15 (q, J = 7.2 Hz, 2 H), 3.78 (d, J = 10.6 Hz, 2 H), 3.32-3.43 (m, 1 H), 3.13-3.27 (m, 1 H), 2.93 (s, 3 H), 2.24 (s, 3H), 1.87-2.00 (m, 1 H), 1.74-1.87 (m, 1 H), 1.62-1.74 (m, 1 H), 1.53 (d, J = 12.9 Hz, 1 H), 1.31-1.45 (m, 6 H), 1.17-1.26 (m, 1 H) |
| 1068 | MsOH | 1H NMR (400 MHz, DMSO-$d_6$) δ ppm 9.03 (br. s., 1 H), 9.02 (d, J = 2.2 Hz, 1 H), 8.85 (d, J = 2.2 Hz, 1 H), 8.46 (d, J = 8.1 Hz, 1 H), 8.40 (s, 1 H), 8.05 (s, 1 H), 6.92 (d, J = 8.6 Hz, 1 H), 4.42-4.55 (m, 2 H), 4.06 (d, J = 7.0 Hz, 2 H), 3.94-4.01 (m, 1 H), 3.81-3.88 (m, 1 H), 3.65-3.73 (m, 1 H), 2.98 (s, 3 H), 2.30 (s, 3 H), 2.07-2.15 (m, 1 H), 1.98-2.07 (m, 1 H), 1.89-1.97 (m, 1 H), 1.79-1.89 (m, 2 H), 1.49 (qd, J = 11.9, 8.2 Hz, 1 H), 1.25-1.35 (m, 1 H), 0.54-0.61 (m, 2 H), 0.37-0.48 (m, 2 H) |
| 1069 | MsOH | 1H NMR (400 MHz, DMSO-$d_6$) δ ppm 9.09 (s, 1 H), 8.99 (d, J = 2.0 Hz, 1 H), 8.65 (br. s., 1 H), 8.38 (s, 2 H), 8.09 (s, 1 H), 6.79 (d, J = 8.2 Hz, 1 H), 5.00 (br. s., 1 H), 4.06-4.15 (m, 1 H), 3.94 (s, 3 H), 3.73-3.79 (m, 1 H, partially obscured by H2O peak), 2.94 (br. s., 3 H), 2.44-2.46 (m, 1 H), 2.29 (s, 3H), 1.78-1.94 (m, 2 H), 1.40-1.66 (m, 2 H), 1.24 (br. s., 2 H), 0.93 (t, J = 7.4 Hz, 3 H) |

TABLE 2-continued

| Cmpd # | Salt | $^1$H NMR |
|---|---|---|
| 1070 | MsOH | 1H NMR (400 MHz, DMSO-$d_6$) δ ppm 8.99 (d, J = 2.2 Hz, 1 H), 8.78 (s, 1 H), 8.83 (d, J = 2.2 Hz, 1 H), 8.32 (d, J = 5.7 Hz, 1 H), 8.03 (s, 1 H), 4.42-4.51 (m, 1 H), 4.34 (q, J = 7.4 Hz, 1 H), 3.80-4.00 (m, 8 H), 3.63-3.74 (m, 2 H), 2.30 (s, 2 H), 1.97-2.10 (m, 1 H), 1.81-1.94 (m, 2 H), 1.46 (t, J = 7.3 Hz, 3 H), 1.29-1.38 (m, 1 H) |
| 1071 | MsOH | 1H NMR (400 MHz, DMSO-$d_6$) δ ppm 9.01 (d, J = 2.0 Hz, 1 H), 8.77 (s, 1 H), 8.66 (br. s., 1 H), 8.42 (s, 1 H), 8.30 (s, 1 H), 8.10 (s, 1 H), 4.99 (br. s., 1 H), 4.22 (q, J = 7.0 Hz, 3 H), 4.07-4.13 (m, 1 H), 4.02 (s, 3 H), 3.71-3.80 (m, 1 H), 3.53-3.64 (m, 1 H, partially hidden by water), 2.72-2.76 (m, 1 H), 2.32 (s, 3 H), 1.80-1.93 (m, 2 H), 1.47-1.57 (m, 2 H), 1.44 (t, J = 7.2 Hz, 3 H), 0.92 (t, J = 7.4 Hz, 3 H) |
| 1072 | MsOH | 1H NMR (400 MHz, DMSO-$d_6$) δ ppm 9.02 (d, J = 2.0 Hz, 1 H), 8.82 (s, 1 H), 8.67 (br. s., 1 H), 8.43 (s, 1 H), 8.35 (s, 1 H), 8.10 (s, 1 H), 5.27-5.37 (m, 1 H), 4.35 (q, J = 7.0 Hz, 2 H), 4.23 (q, J = 7.3 Hz, 2 H), 4.07-4.16 (m, 1 H), 3.76 (t, J = 11.0 Hz, 1 H), 3.56-3.65 (m, 1 H), 2.78 (br. s., 1 H), 2.34 (s, 3 H), 1.88 (dd, J = 28.8, 12.7 Hz, 2 H), 1.50-1.58 (m, 2 H), 1.46 (q, J = 7.2 Hz, 7 H), 0.93 (t, J = 7.4 Hz, 3 H) |
| 1073 | MsOH | 1H NMR (400 MHz, DMSO-$d_6$) δ ppm 9.48 (d, J = 1.6 Hz, 1 H), 9.02 (d, J = 2.3 Hz, 1 H), 8.87-8.91 (m, 2 H), 8.73 (dt, J = 8.2, 2.0 Hz, 1 H), 8.33 (s, 1 H), 8.04 (s, 1 H), 7.78 (dd, J = 8.0, 5.3 Hz, 1 H), 4.40-4.57 (m, 2 H), 3.95-4.02 (m, 1 H), 3.93 (s, 3 H), 3.80-3.88 (m, 1 H), 3.65-3.73 (m, 1 H), 2.31 (s, 3 H), 2.12 (d, J = 9.4 Hz, 1 H), 1.90-2.05 (m, 2 H), 1.80-1.89 (m, 2 H), 1.44-1.54 (m, 1 H) |
| 1074 | MsOH | 1H NMR (400 MHz, DMSO-$d_6$) δ ppm 8.99 (d, J = 2.0 Hz, 1 H), 8.83 (d, J = 2.0 Hz, 1 H), 8.77 (s, 1 H), 8.32 (s, 1H), 8.30 (s, 1H), 8.02 (s, 1 H), 4.34-4.55 (m, 2 H), 4.03 (s, 3 H), 3.93 (s, 3 H), 3.89-3.95 (m, 1H), 3.80-3.88 (m, 1 H), 3.39-3.46 (m, 1 H), 3.19-3.29 (m, 1 H), 2.31 (s, 3 H), 1.95-2.05 (m, 1 H), 1.80-1.92 (m, 1 H), 1.67-1.77 (m, 1 H), 1.53-1.61 (m, 1 H), 1.38-1.50 (m, 3 H), 1.19-1.31 (m, 1 H) |
| 1075 | MsOH | 1H NMR (400 MHz, DMSO-$d_6$) δ ppm 9.10 (d, J = 1.8 Hz, 1 H), 8.98 (d, J = 2.0 Hz, 1 H), 8.75 (s, 1 H), 8.33 (s, 1 H), 8.27 (s, 1 H), 8.05 (s, 1 H), 5.92-5.94 (m, 1 H), 4.28 (dd, J = 9.3, 6.0 Hz, 1 H), 4.13 (t, J = 9.5 Hz, 1 H), 4.02 (s, 3H), 4.02-4.07 (m, 1H) 3.92 (s, 3 H), 2.32-2.40 (m, 1 H), 2.30 (s, 4 H), 2.20 (q, J = 10.42 Hz, 1 H), 1.65-1.82 (m, 2 H), 1.00 (t, J = 7.48 Hz, 3 H) |
| 1076 | — | 1H NMR (400 MHz, DMSO-$d_6$) δ ppm 9.21 (s, 1 H), 8.77 (s, 1 H), 8.32 (br. s., 2 H), 8.18 (br. s., 1 H), 8.05 (s, 1 H), 4.99 (br. s., 1 H), 4.11 (br. s., 1 H), 4.01 (s, 3 H), 3.92 (s, 3 H), 3.76 (t, J = 11.2 Hz, 1 H), 3.59 (br. s., 1 H), 2.69 (d, J = 19.2 Hz, 1 H), 2.44 (br. s., 1 H), 1.76-1.93 (m, 2 H), 1.53 (dq, J = 20.5, 6.9 Hz, 2 H), 0.93 (t, J = 7.4 Hz, 3 H) |
| 1077 | MsOH | 1H NMR (400 MHz, DMSO-$d_6$) δ ppm 9.26 (s, 1 H), 9.07 (s, 1 H), 8.42-8.53 (m, 1 H), 8.34 (s, 1 H), 8.21 (br. s., 1 H), 8.08 (s, 1 H), 6.94 (d, J = 9.0 Hz, 1 H), 5.04 (br. s., 1 H), 4.14 (dd, J = 11.1, 4.3 Hz, 1 H), 3.94 (s, 3 H), 3.80 (dd, J = 12.0, 10.2 Hz, 2 H), 2.99 (s, 3 H), 2.77 (br. s., 1 H), 2.32 (s, 3 H), 1.91 (dd, J = 10.5, 3.9 Hz, 1 H), 1.84 (dd, J = 11.8, 3.0 Hz, 1 H), 1.46-1.62 (m, 2 H), 0.95 (t, J = 7.5 Hz, 3 H) |
| 1078 | MsOH | 1H NMR (400 MHz, DMSO-$d_6$) δ ppm 9.20 (d, J = 2.0 Hz, 1 H), 9.17 (d, J = 2.0 Hz, 1 H), 9.00 (br. s., 1 H), 8.49 (m, 1 H), 8.41 (s, 1 H), 6.98 (m, 1 H), 4.41-4.56 (m, 2 H), 4.27 (s, 3 H), 3.92 (dd, J = 14.9, 6.9 Hz, 1 H), 3.88-4.00 (m, 1 H), 3.70 (dd, J = 14.5, 7.7 Hz, 1 H), 3.00 (s, 3 H), 2.31 (s, 3H), 1.99-2.16 (m, 2 H), 1.79-1.95 (m, 2 H), 1.49 (dq, J = 11.9, 8.2 Hz, 1 H), 1.21-1.31 (m, 1 H) |
| 1079 | MsOH | 1H NMR (400 MHz, DMSO-$d_6$) δ ppm 8.76 (s, 1 H), 8.48 (br. s., 1 H), 8.27 (s, 1 H), 8.16 (s, 1 H), 7.86 (s, 1 H), 4.97, br. s., 1H), 4.02 (s, 3 H), 3.95 (s, 3 H), 3.72-3.82 (m, 2 H), 2.75 (s, 3 H), 2.44-2.46 (m, 1 H), 2.35-2.43 (m, 1 H), 2.30 (s, 3 H), 1.85 (dd, J = 11.5, 4.5 Hz, 2 H), 1.18 (d, J = 6.3 Hz, 6 H) |
| 1080 | MsOH | 1H NMR (400 MHz, DMSO-$d_6$) δ ppm 8.79 (s, 1 H), 8.76 (s, 1 H), 8.66 (s, 1 H), 8.26 (s, 1 H), 7.73 (s, 1 H), 4.96 (br. s., 1 H), 4.06-4.12 (m, 1 H), 4.02 (s, 3 H), 3.58-3.70 (m, 1 H), 3.45-3.55 (m, 1 H), 2.82 (s, 3 H), 2.29 (s, 3 H), 1.84-1.92 (m, 1 H), 1.77-1.84 (m, 1 H), 1.46-1.59 (m, 2 H), 0.91 (t, J = 7.4 Hz, 3 H) |
| 1081 | MsOH | 1H NMR (400 MHz, DMSO-$d_6$) δ ppm 8.80 (d, J = 2.0 Hz, 1 H), 8.76 (s, 1 H), 8.59 (d, J = 1.6 Hz, 1 H), 8.29 (s, 1 H), 8.16 (s, 1 H), 4.96-5.03 (m, 1H), 4.08 (dd, J = 11.0, 4.7 Hz, 1 H), 4.03 (s, 3 H), 3.86 (s, 3 H), 3.66 (t, J = 11.2 Hz, 1 H), 3.40-3.56 (m, 1 H), 2.69-2.82 (m, 1 H), 2.48-2.53 (m, 1H), 2.40 (s, 3 H), 2.31 (s, 3 H), 1.91 (d, J = 11.3 Hz, 1 H), 1.82 (d, J = 11.7 Hz, 1 H), 1.41-1.59 (m, 2 H), 0.90 (t, J = 7.4 Hz, 3 H) |

TABLE 2-continued

| Cmpd # | Salt | ¹H NMR |
|---|---|---|
| 1082 | MsOH | 1H NMR (400 MHz, DMSO-$d_6$) δ ppm 8.78 (s, 1 H), 8.34 (s, 1 H), 8.31 (s, 1 H), 8.05 (br. s., 2 H), 4.99 (br. s., 1 H), 4.07-4.17 (m, 1 H), 4.03 (s, 3 H), 3.93 (s, 3 H), 3.71-3.77 (m, 1 H), 3.56-3.65 (m, 1 H), 2.88 (s, 3 H), 2.68-2.78 (m, 1 H), 2.42-2.47 (m, 1 H), 2.30 (s, 3 H), 1.84-1.92 (m, 1 H), 1.77-1.84 (m, 1 H), 1.42-1.62 (m, 2 H), 0.93 (t, J = 7.4 Hz, 3 H) |
| 1083 | MsOH | 1H NMR (400 MHz, DMSO-$d_6$) δ ppm 9.23 (br. s., 1 H), 9.13 (d, J = 2.0 Hz, 1 H), 8.93 (d, J = 2.0 Hz, 1 H), 8.83 (d, J = 4.8 Hz, 1 H), 8.79 (s, 1 H), 8.59 (d, J = 7.5 Hz, 1 H), 8.30 (s, 1 H), 7.86 (dd, J = 7.0, 5.5 Hz, 1 H), 4.98 (br. s., 1 H), 4.08 (d, J = 4.2 Hz, 1 H), 4.04 (s, 3 H), 3.72 (t, J = 11.0 Hz, 1 H), 3.49-3.62 (m, 1 H), 2.78 (dd, J = 12.8, 3.5 Hz, 1 H), 2.31 (s, 3 H), 1.90 (d, J = 11.7 Hz, 1 H), 1.83 (d, J = 11.9 Hz, 1 H), 1.43-1.58 (m, 2 H), 0.90 (t, J = 7.4 Hz, 3 H) |
| 1084 | MsOH | 1H NMR (400 MHz, DMSO-$d_6$) δ ppm 9.23 (s, 1H), 8.79 (s, 1 H), 8.34-8.41 (m, 2 H), 8.22 (br.s., 1H), 8.08 (s, 1 H), 4.02 (s, 3 H), 3.93 (s, 3 H), 3.89 (s, 2 H), 3.77 (d, J = 10.2 Hz, 2 H), 2.61 (br. s., 1 H), 2.30 (s, 3 H), 1.87 (d, J = 9.0 Hz, 2 H), 1.21 (d, J = 5.9 Hz, 6 H) |
| 1085 | MsOH | 1H NMR (400 MHz, DMSO-$d_6$) δ ppm 9.23 (s, 1 H), 8.80 (s, 1 H), 8.35 (s, 1 H), 8.34 (s, 1 H), 8.23 (br. s., 1 H), 8.10 (s, 1 H), 4.95-5.17 (m, 1 H), 4.36 (t, J = 5.3 Hz, 2 H), 4.08-4.16 (m, 1 H), 4.02 (s, 3 H), 3.72-3.78 (m, 3 H), 3.57-3.65 (m, 1 H), 3.26 (s, 3 H), 2.67-2.80 (m, 1 H), 2.31 (s, 3H), 1.77-1.95 (m, 2 H), 1.44-1.63 (m, 2 H), 0.94 (t, J = 7.4 Hz, 3 H) |
| 1086 | MsOH | 1H NMR (400 MHz, DMSO-$d_6$) δ ppm 9.45 (s, 1 H), 9.43 (s, 1 H), 8.82 (s, 1 H), 8.78 (dd, J = 5.1, 1.3 Hz, 1 H), 8.72 (d, J = 7.7 Hz, 1 H), 8.67 (s, 1 H), 8.38 (s, 1 H), 7.79 (dd, J = 7.8, 5.2 Hz, 1 H), 5.07 (br. s., 1 H), 4.07-4.16 (m, 1 H), 4.03 (s, 3 H), 3.71-3.83 (m, 1 H), 3.57-3.69 (m, 1 H), 2.68-2.83 (m, 1 H), 2.30 (s, 3 H), 1.81-1.95 (m, 2 H), 1.44-1.62 (m, 2 H), 0.92 (t, J = 7.5 Hz, 3 H) |
| 1087 | MsOH | 1H NMR (400 MHz, DMSO-$d_6$) δ ppm 9.21 (s, 1 H), 8.90 (br. s., 1 H), 8.81 (s, 1 H), 8.34 (s, 1 H), 8.23 (br. s., 1 H), 8.00-8.15 (m, 1 H), 5.47 (br. s., 1 H), 4.02 (s, 3 H), 3.89-3.98 (m, 5 H), 3.73-3.84 (m, 2 H), 2.67-2.87 (m, 1 H), 2.33 (s, 3 H), 1.98-2.19 (m, 2 H), 1.83-1.94 (m, 1 H), 1.38-1.55 (m, 2 H), 0.85-0.97 (m, 3 H) |
| 1088 | MsOH | 1H NMR (400 MHz, DMSO-$d_6$) δ ppm 9.33 (s, 1 H), 8.81 (s, 1 H), 8.36 (s, 1 H), 8.31 (br. s., 1 H), 7.70 (s, 1 H), 4.90-5.11 (m, 1 H), 4.14 (dd, J = 11.3, 4.3 Hz, 2 H), 4.02 (s, 3 H), 3.68 (t, J = 10.8 Hz, 1 H), 3.54 (d, J = 6.3 Hz, 1 H), 2.63-2.75 (m, 2 H), 2.55 (s, 3 H), 2.31 (s, 3 H), 1.93 (d, J = 3.5 Hz, 1 H), 1.83 (d, J = 12.9 Hz, 1 H), 1.49-1.64 (m, 1 H), 0.95 (t, J = 7.4 Hz, 3 H) |
| 1089 | MsOH | 1H NMR (400 MHz, DMSO-$d_6$) δ ppm 9.36 (s, 1 H), 8.82 (s, 1 H), 8.63 (s, 1 H), 8.40 (br. s., 1 H), 8.37 (s, 1 H), 7.85 (s, 1 H), 4.91-5.12 (m, 1 H), 4.14 (dd, J = 11.3, 4.7 Hz, 1 H), 4.02 (s, 3 H), 3.68 (t, J = 11.0 Hz, 1 H), 3.43-3.60 (m, 1 H), 2.70-2.82 (m, 2 H), 2.31 (s, 3 H), 1.91 (d, J = 11.0 Hz, 1 H), 1.84 (d, J = 13.3 Hz, 1 H), 1.56 (d, J = 6.7 Hz, 2 H), 0.94 (t, J = 7.4 Hz, 3 H) |
| 1090 | MsOH | 1H NMR (400 MHz, DMSO-$d_6$) δ ppm 9.30 (s, 2 H), 8.82 (s, 1 H), 8.39 (s, 2 H), 8.30 (br. s., 1 H), 7.63 (br. s., 1 H), 4.83-4.93 (m, 1 H), 4.02 (s, 3 H), 3.72-3.82 (m, 2 H), 3.48-3.68 (m, 2 H), 2.28 (s, 3 H), 1.78-1.90 (m, 2 H), 1.43-1.61 (m, 2 H), 0.92 (t, J = 7.4 Hz, 3 H) |
| 1091 | MsOH | 1H NMR (400 MHz, DMSO-d6) δ ppm 8.97 (s, br, 1H), 8.75 (s, 1H), 8.34 (s, 1H), 8.11 (dd, J = 1.2, 8.6 Hz, 1H), 8.05 (d, J = 8.6 Hz, 1H), 4.88 (s, br, 1H), 4.10 (dd, J = 4.5, 10.8 Hz, 1H), 4.01 (s, 1H), 3.92 (s, 1H), 3.73 (app t, J = 11.3 Hz, 1H), 3.52-3.56, m, 1H, partially obscured by H$_2$O), 2.79-2.86, m, 1H), 2.60-2.64, m, 1H, partially obscured by solvent), 2.30 (s, 3H, MeSO$_3$H), 1.81-1.89 (m, 2H), 1.46-1.60 (m, 2H), 0.93 (t, J = 7.5 Hz, 3H) |
| 1092 | MsOH | 1H NMR (400 MHz, DMSO-$d_6$) δ ppm 8.98 (br. s., 1 H), 8.80 (s, 1 H), 8.36 (s, 1 H), 8.22-8.33 (m, 2 H), 4.78 (br. s., 1 H), 4.26 (q, J = 7.2 Hz, 2 H), 4.07-4.14 (m, 1 H), 4.04 (s, 3 H), 3.66-3.81 (m, 1 H), 2.94 (s, 3 H), 2.75-2.86 (m, 1 H), 2.55-2.62 (m, 1 H), 2.29 (s, 3 H), 1.76-1.83 (m, 2 H), 1.50 (t, J = 7.2 Hz, 3 H), 1.45-1.61 (m, 2 H), 0.93 (t, J = 7.4 Hz, 3 H) |
| 1093 | MsOH | 1H NMR (400 MHz, DMSO-d6) δ ppm 8.72 (s, 2 H), 8.54 (br. s., 1 H), 8.33 (s, 1 H), 8.26 (s, 1 H), 8.04 (br. s., 1 H), 4.83 (br. s., 1 H), 4.08 (s, 1 H), 4.01 (s, 3 H), 3.89 (s, 3 H), 3.83-3.89 (m, 1H), 3.55-3.70 (m, 1 H), 2.72-2.85 (m, 1 H), 2.55-2.64 (m, 1 H, partially obstructed by DMSO peak), 2.31 (s, 3 H), 1.78-1.85 (m, 2 H), 1.44-1.58 (m, 2 H), 0.90 (t, J = 7.4 Hz, 3 H) |

TABLE 2-continued

| Cmpd # | Salt | $^1$H NMR |
|---|---|---|
| 1094 | MsOH | 1H NMR (400 MHz, DMSO-d6) δ ppm 8.92 (br. s., 1 H), 8.74 (s, 1 H), 8.68 (s, 1 H), 8.48 (s, 1 H), 8.35 (s, 1 H), 8.14 (s, 1 H), 4.83 (br. s., 1 H), 4.07 (br. s., 1 H), 4.01 (s, 3 H), 3.94 (s, 3 H), 3.63-3.66 (m, 2 H, partially obstructed by water peak), 2.69-2.84 (m, 1 H), 2.54-2.61 (m, 1 H), 2.32 (s, 3 H), 1.79-1.90 (m, 2 H), 1.43-1.58 (m, 2 H), 0.90 (t, J = 7.4 Hz, 3 H) |
| 1095 | MsOH | 1H NMR (400 MHz, DMSO-d6) δ ppm 8.77 (s, 1 H), 8.61 (br. s., 1 H), 8.44 (d, J = 9.0 Hz, 1 H), 8.35 (s, 1 H), 8.24 (d, J = 9.0 Hz, 1 H), 8.16 (br. s., 1 H), 5.76 (s, 1 H), 4.02 (s, 3 H), 3.88 (s, 3 H), 3.74-3.8 (m, 2 H), 2.61-2.73 (m, 2 H), 2.30 (s, 3 H), 1.78 (d, J = 8.6 Hz, 2 H), 1.46-1.63 (m, 2 H), 1.23 (d, J = 6.3 Hz, 3 H), 0.93 (t, J = 7.4 Hz, 3 H) |
| 1096 | MsOH | 1H NMR (400 MHz, DMSO-d$_6$) δ ppm 9.38 (s, 1 H), 9.03 (br. s., 1 H), 8.79 (s, 1 H), 8.41 (s, 1 H), 8.33-8.39 (m, 2 H), 4.80 (br. s., 1 H), 4.27 (q, J = 7.3 Hz, 2 H), 4.10 (dd, J = 11.0, 4.3 Hz, 1 H), 4.02 (s, 3 H), 3.71-3.80 (m, 1 H), 3.54-3.62 (m, 2 H), 2.74-2.87 (m, 1 H), 2.54-2.67 (m, 1 H), 2.31 (s, 3 H), 1.80-1.93 (m, 2 H), 1.51 (t, J = 7.2 Hz, 3 H), 1.47-1.60 (m, 1 H), 0.93 (t, J = 7.4 Hz, 3 H) |
| 1097 | MsOH | 1H NMR (400 MHz, DMSO-d$_6$) δ ppm 8.82 (br. s., 1 H), 8.70 (s, 1 H), 8.24-8.27 (m, 1 H), 8.03-8.19 (m, 2 H), 4.85 (br. s., 1 H), 4.10 (dd, J = 11.2, 4.5 Hz, 1 H), 4.02 (s, 3 H), 3.90 (s, 3 H), 3.65-3.77 (m, 2 H), 3.47-3.59 (m, 1 H), 2.75-2.89 (m, 1 H), 2.54-2.64 (m, 1 H), 2.30 (s, 3 H), 1.79-1.91 (m, 2 H), 1.45-1.61 (m, 2 H), 0.92 (t, J = 7.4 Hz, 3 H) |
| 1098 | MsOH | 1H NMR (400 MHz, DMSO-d$_6$) δ ppm 8.60-8.66 (m, 3 H), 8.58 (br. s., 1 H), 8.29 (s, 1 H), 8.07 (s, 1 H), 4.88 (br. s., 1 H), 4.11 (dd, J = 11.5, 4.5 Hz, 1 H), 4.03 (s, 3 H), 3.87 (s, 3 H), 3.61-3.74 (m, 2 H), 2.71-2.87 (m, 1 H), 2.54-2.63 (m, 1 H), 2.30 (s, 3 H), 1.80-1.92 (m, 2 H), 1.44-1.60 (m, 2 H), 0.92 (t, J = 7.4 Hz, 3 H) |
| 1099 | MsOH | 1H NMR (400 MHz, DMSO-d$_6$) δ ppm 9.06 (br. s., 1 H), 8.80 (s, 1 H), 8.36 (s, 1 H), 8.30 (br. s., 1 H), 8.21 (s, 1 H), 4.78 (br. s., 1 H), 4.03 (s, 3 H), 3.94 (s, 3 H), 3.81-3.90 (m, 1 H), 3.59-3.68 (m, 2 H), 2.95 (s, 3 H), 2.30 (s, 3 H), 1.81-1.90 (m, 2 H), 1.46-1.61 (m, 2 H), 1.22 (d, J = 6.3 Hz, 3 H), 0.93 (t, J = 7.4 Hz, 3 H) |
| 1100 | MsOH | 1H NMR (400 MHz, DMSO-d$_6$) δ ppm 9.26 (d, J = 2.3 Hz, 1 H), 8.60 (dd, J = 8.8, 2.5 Hz, 1 H), 8.50 (d, J = 9.0 Hz, 1 H), 8.25 (d, J = 9.0 Hz, 1 H), 8.12 (br. s., 1 H), 7.12 (d, J = 8.6 Hz, 1 H), 5.86 (br. s., 1 H), 4.10-4.20 (m, 1 H), 4.01 (s, 3 H), 3.88 (s, 3 H), 3.45-3.57 (m, 1 H), 2.94-3.06 (m, 1 H), 2.71-2.80 (m, 1 H), 2.54-2.57 (m, 1 H), 2.30 (s, 3 H), 1.72-1.86 (m, 2 H), 1.45-1.63 (m, 2 H), 0.93 (t, J = 7.4 Hz, 3 H) |
| 1101 | MsOH | 1H NMR (400 MHz, DMSO-d$_6$) δ ppm 8.55-8.71 (m, 2 H), 8.51 (d, J = 8.6 Hz, 1 H), 8.37 (d, J = 9.0 Hz, 1 H), 8.23 (d, J = 9.0 Hz, 1 H), 8.14 (br. s., 1 H), 7.68 (dd, J = 9.0, 3.1 Hz, 1 H), 5.92 (br. s., 1 H), 4.11-4.18 (m, 1 H), 3.98 (s, 3 H), 3.90 (s, 3 H), 2.93-3.06 (m, 1 H), 2.69-2.80 (m, 1 H), 2.30 (s, 3 H), 1.73-1.88 (m, 2 H), 1.46-1.63 (m, 2 H), 0.93 (t, J = 7.4 Hz, 3 H) |
| 1102 | MsOH | 1H NMR (400 MHz, DMSO-d$_6$) δ ppm 9.50 (dd, J = 2.3, 0.8 Hz, 1 H), 8.88 (dd, J = 5.1, 1.6 Hz, 1 H), 8.68 (dt, J = 8.1, 2.0 Hz, 1 H), 8.56 (d, J = 9.0 Hz, 1 H), 8.27 (d, J = 9.0 Hz, 1 H), 8.19 (s, 1 H), 7.72-7.76 (m, 1 H), 5.89 (br. s., 1 H), 4.15 (dd, J = 11.0, 3.9 Hz, 1 H), 3.91 (s, 3 H), 3.67-3.76 (m, 2 H), 3.49-3.58 (m, 1 H), 2.94-3.07 (m, 1 H), 2.69-2.81 (m, 1 H), 2.31 (s, 3 H), 1.73-1.88 (m, 2 H), 1.47-1.63 (m, 2 H), 0.93 (t, J = 7.4 Hz, 3 H) |
| 1103 | MsOH | 1H NMR (400 MHz, DMSO-d$_6$) δ ppm 9.39 (s, 1H), 8.90-9.10 (m, 1 H), 8.80 (s, 1H), 8.39 (s, 1 H), 8.37 (s, 1 H), 8.25-8.34 (m, 1 H), 4.75-4.87 (m, 1H), 4.02 (s, 3 H), 3.93 (s, 3 H), 3.82-3.88 (m, 2H), 3.58-3.68 (m, 2H), 2.30 (s, 3 H), 1.72-1.86 (m, 2 H), 1.45-1.63 (m, 2 H), 1.22 (d, J = 6.3 Hz, 3H) 0.93 (t, J = 7.4 Hz, 3 H) |

Example 126

C8166 HIV-1 Luciferase Assay (Ec$_{50}$)

The assay used to measure inhibition of HIV replication is as described in WO 2004/050643, pages 73-75, incorporated herein by reference, with the following modifications:
Preparation of Compounds
Serial dilutions of HIV-1 inhibitors are prepared in complete media from DMSO stock solutions. Eleven serial dilutions of desired concentration are prepared in a 1 mL deep well titer plate (96 wells). The 12th well contains complete media with no inhibitor and serves as the positive control. All samples contain the same concentration of DMSO (<0.1% DMSO). Inhibitor is added, to triplicate wells, of a 96 well tissue culture treated clear view black microtiter plate (Corning Costar catalogue #3904). The total volume per well is 200 μL of media containing the cells and inhibitor. The last row is reserved for uninfected C8166 LTRIuc cells to serve as the background blank control and the first row is media alone.

Infection of Cells

Count C8166 LTRIuc cells and place in a minimal volume of complete RPMI 1640 in a tissue culture flask (ex. 30×106 cells in 10 mL media/25 cm$^2$ flask). Infect cells with HIV-1 at a moi of 0.005. Incubate cells for 1.5 h at 37° C. on a rotating rack in a 5% $CO_2$ incubator. Resuspend cells in complete RPMI to give a final concentration of 25,000-cells/well. Add cells to wells of 96 well microtiter plate containing inhibitors. Add 25,000 uninfected C8166-LTRIuc cells/well in 200 µL complete RPMI to last row for background control. Incubate cells at 37° C. in 5% $CO_2$ incubator for 3 days.

Luciferase Assay

50 µL Steady Glo (luciferase substrate $T_{1⁄2}$=5 hours Promega catalogue # E2520) is added to each well of the 96 well plate. The relative light units (RLU) of luciferase are determined using a luminescence plate reader. The calculated % inhibition values are used to determine $EC_{50}$, slope factor (n) and maximum inhibition ($I_{max}$).

Example 127

Caco-2 Permeability Assay

Caco-2 cells are purchased from Cell Culture Services as frozen instant cells at a concentration of 1*10$^7$ cells/vial. DMEM+glutamax-I culture media is purchased from Gibco (10569). Fetal bovine serum (FBS) is purchased from HyClone (SH30396.03). Pennicilin/Streptomycin antibiotics are purchased from Gibco (15140). MEM non-essential amino acids are purchased from Gibco (11140). Hank's balanced salt solution (HBSS) is purchased from Gibco (14025). Bovine serum albumin (BSA) is purchased from Sigma-Aldrich (A7906). MES low moisture is purchased from Sigma-Aldrich (M3671). HEPES is purchased from Sigma-Aldrich (H3375). Dimethyl Sulfoxide (DMSO) is purchased from EMD (MX1457-6).

Complete DMEM media is prepared by adding 1 L of FBS, 100 mL of pen/strep and 110 mL of MEM non essential amino acids to 10 L of DMEM+glutamax-I.

Apical buffer is prepared by adding 0.25% BSA and 25 mM MES to HBSS and adjusting the pH to 6.0.

Basolateral buffer is prepared by adding 0.25% BSA and 25 mM HEPES to HBSS and adjusting the pH to 7.4.

Caco-2 cells are seeded on HTS transwell 24-well plates purchased from Corning (3397). These polycarbonate membrane plates have a diameter of 6.5 mM and pore size of 0.4 µm. The Caco-2 cells vial is thawed in a 37° C. water bath until only a small ice pellet is left. The vial is then transferred to the laminar flow hood and its exterior is extensively washed with 70% ethanol. The total content of the vial (2 mL) is transferred into a 50 mL tube containing 38 mL of complete DMEM. With this dilution the final cell concentration is now 250 000 cells/mL. The seeding is done by the Hamilton star robotic station which is controlled with the Venus program. Each well will receive 600 µL of complete DMEM on its basolateral side and 200 µL of cells on its apical side. Each well receives 50 000 cells. The 24-well plates are then returned to an automated Liconic STX110 incubator set at 37° C., 5% $CO_2$ and 100% humidity. The culture media for the cells is changed every two days except on weekends. These cells are maintained for a period of two weeks prior to the running of the permeability assay. Permeability assays are usually performed between day 15 and 18 after the initial seeding.

Stock solutions of test compounds are prepared by adding DMSO to a powder of the test compound to achieve a concentration of 5 mM. Controls for the assay are mannitol for tight junction determination and Digoxin for efflux transporter (p-glycoprotein) expression. On the day of the assay, each compound is diluted to 10 µM in the buffer (apical for A to B). 6 µl of the 5 mM DMSO stock is added to 3 mL of the buffer in a 24-well 10 mL deep plate covered with a lid. The plate containing all the diluted compounds is spun for 10 min at 3000 rpm in a Rotanta 46 RSC centrifuge from Hettich to remove unsoluble compound. This dilution is used to add at the start of the incubation. Each compound is tested in duplicate.

On the day of the assay, the culture media of the 24-well plate is removed and replaced with warm HBSS. The HBSS is then also removed and the Apical and Basolatral buffer are added to their respective side of the transwells. These steps are performed by the Hamilton Star robotic station.

The plate is then placed in a 37° C. incubator and is left to equilibrate for 30 min. After 30 min of incubation a background sample (25 µL from each well) is taken from the receiver side (Basolateral for A to B), and replenished with warm buffer. These samples and all others afterwards are kept in a 96-well 1 mL plate. To start the assay, the donor compartment (apical for A to B) is emptied and replaced with new buffer containing the compound at 10 µM. Once the compounds are added, the plate is returned to the 37° C. incubator and the timer is started. In order to determine how much compound is actually added to each well, a 50 µL sample is taken from each compound dilution, this sample is refered to as the load. These steps and the following are performed by the Tecan Freedom EVO robotic station controlled via the Gemini software.

For A-to-B Assay:

Samples (190 µL) are taken from each basolateral (receiver) chamber at time points 0, 60, 120 and 180 min or at time points 0, 30, 60 and 90 min. From the 190 µL taken, 50 µL is transferred to the receiving plate and 140 µL is discarded. After each sample is taken the chamber is replenished with warm buffer (190 µL). After the 180 min or 90 min timepoint is taken, a 25 µL sample will be taken from each donor well to determine how much compound is left after the 3 h of incubation, this sample is refered to as top.

A standard curve for each compound is created by adding 1.8 µL of the 5 mM DMSO stock to the receiving plate and diluting with 450 µL HBSS:MeOH (1:1). From this well, 25 µL is taken and transferred to the next well where 450 µL of HBSS:MeOH (1:1) is again added. From this well, 25 µL is transferred to the final plate and 450 µL of MeOH:$H_2O$ (1:1) is added to the well. Finally a 1:10 dilution is made from this well to another well to create the two point standard curve (5 and 0.5 µM). This curve will be used to determine the starting concentration of the compounds.

Once all the samples are collected, the receiving plate is quenched with 450 µL of MeOH to precipitate the proteins and the plate is spun for 10 min at 3000 rpm in a Rotanta 46 RSC centrifuge from Hettich to pellet the precipitated proteins. After the plate is taken out of the centrifuge, 25 µL of each sample is transferred to a 96-well 2 mL deep well plate and 450 µL of MeOH:$H_2O$ (1:1) is added. The samples are analysed via the API 5000 LC/MS/MS system.

The apparent permeability of each compound is calculated using the following equation:

$$P_{app} = \frac{\text{Net rate of appearance in receiver side}}{\text{Surface} \times 60 \times \text{Load area}} = \text{cm/sec}$$

Surface is 1.12 cm$^2$ 60 is the conversion factor (min to sec)

Load area is the working solution area/ml

For A to B permeability, the donor side is the apical chamber and the receiver is basolateral.

Data for compounds 1001-1103 when tested in the assay described in Example 126 and/or the assay described in Example 127 are provided below in Table 3.

TABLE 3

| Cmpd # | EC$_{50}$ (nM) | P$_{app}$ (cm/sec, *10$^{-6}$) |
|---|---|---|
| 1001 | 4.9 | 20.4 |
| 1002 | 8.6 | 14.5 |
| 1003 | 6.4 | 22.2 |
| 1004 | 21 | 14.1 |
| 1005 | 28 | 20.2 |
| 1006 | 7.4 | 18.1 |
| 1007 | 8.4 | 19.7 |
| 1008 | 73.9 | 18.1 |
| 1009 | 4.6 | 27.6 |
| 1010 | 14 | 20.8 |
| 1011 | 98 | 17.5 |
| 1012 | 15 | 19.2 |
| 1013 | 98 | 16.8 |
| 1014 | 5.2 | 20.7 |
| 1015 | 3 | 20.7 |
| 1016 | 89 | 15.9 |
| 1017 | 22 | 23.6 |
| 1018 | 22 | 19.8 |
| 1019 | 52 | 22.5 |
| 1020 | 7.8 | 9.9 |
| 1021 | 6.6 | 22.3 |
| 1022 | 3.2 | 17.2 |
| 1023 | 2.5 | 7.3 |
| 1024 | 34 | 6.9 |
| 1025 | 350 | 8.1 |
| 1026 | 27.9 | 7.4 |
| 1027 | 54 | 12.4 |
| 1028 | 50 | 19.9 |
| 1029 | 19 | 16.1 |
| 1030 | 10.2 | 6.1 |
| 1031 | 14 | 6.4 |
| 1032 | 11.9 | 7.7 |
| 1033 | 7.6 | 6.9 |
| 1034 | 23 | 6.8 |
| 1035 | 9.4 | 11.5 |
| 1036 | 6.8 | 7.6 |
| 1037 | 10.2 | 8.2 |
| 1038 | 6.6 | 19.5 |
| 1039 | 36 | 16.8 |
| 1040 | 12.8 | 19.2 |
| 1041 | 6.6 | 26.9 |
| 1042 | 6.9 | 23.4 |
| 1043 | 6.5 | 20.4 |
| 1044 | 22 | 12.4 |
| 1045 | 17.3 | 9.4 |
| 1046 | 110 | 17.9 |
| 1047 | 160 | 12.3 |
| 1048 | 6 | 22.1 |
| 1049 | 15.1 | 20.6 |
| 1050 | 7.7 | 19.1 |
| 1051 | 220 | 15.4 |
| 1052 | 150 | 18.2 |
| 1053 | 43 | 22.2 |
| 1054 | 32.2 | 20.3 |
| 1055 | 3.6 | 8.42 |
| 1056 | 8.3 | 6.7 |
| 1057 | 2.2 | 14.9 |
| 1058 | 0.6 | 16.6 |
| 1059 | 43.3 | 21.2 |
| 1060 | 140 | 13 |
| 1061 | 20.3 | 9.3 |
| 1062 | 26 | 8.4 |
| 1063 | 290 | 22.1 |
| 1064 | 130 | 16.4 |
| 1065 | 116 | 18.8 |
| 1066 | 110 | 8.3 |
| 1067 | 40 | 5.3 |
| 1068 | 78 | 8.1 |
| 1069 | 7.8 | 6.2 |
| 1070 | 55 | 8.2 |
| 1071 | 57 | 17.6 |
| 1072 | 110 | 21.4 |
| 1073 | 260 | 14.6 |
| 1074 | 90 | 11 |
| 1075 | 97.4 | 8.9 |
| 1076 | 5.9 | 17.9 |
| 1077 | 6 | 14.7 |
| 1078 | 151 | 15.9 |
| 1079 | 350 | 11.1 |
| 1080 | 120 | 12.4 |
| 1081 | 23.7 | 12.4 |
| 1082 | 3.3 | 18.9 |
| 1083 | 41 | 12.5 |
| 1084 | 120 | 20.5 |
| 1085 | 120 | 19.2 |
| 1086 | 18 | 22.5 |
| 1087 | 9.7 | 23.1 |
| 1088 | 36.2 | 22.9 |
| 1089 | 30 | 18.6 |
| 1090 | 160 | 8.7 |
| 1091 | 15.4 | 7.9 |
| 1092 | 55.5 | 10.7 |
| 1093 |  | 5.2 |
| 1094 | 9.1 | 8.3 |
| 1095 | 8.6 | 39.8 |
| 1096 | 98 | 17.3 |
| 1097 | 3.9 | 37.1 |
| 1098 | 9.9 | 5.3 |
| 1099 | 59 | 15.4 |
| 1100 | 6.2 | 29.3 |
| 1101 | 17 | 32.0 |
| 1102 | 57 | 24.6 |
| 1103 | 56 | 18.5 |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of formula (I) or a racemate, enantiomer, diastereomer or tautomer thereof:

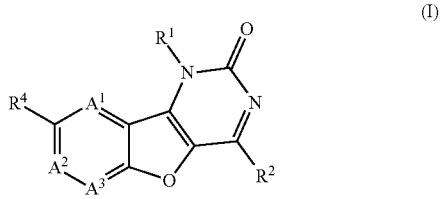

(I)

wherein
R$^1$ is

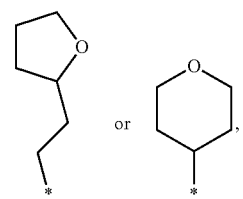 [SMILES: *CCC1CCCO1 ; *C1CCOCC1]

optionally substituted with 1 to 2 substituents each independently selected from —(C$_{1-3}$)alkyl;

$R^2$ is a 5- or 6-membered heteroaryl selected from the group consisting of

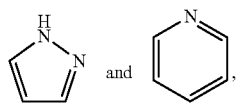

wherein each said heteroaryl is optionally substituted with 1 or 2 substituents independently selected from the group consisting of —$(C_{1-3})$alkyl, halo, —$(C_{1-3})$haloalkyl, —$N(R^{21})(R^{22})$ and —$O(C_{1-3})$alkyl;

$R^{21}$ is H or —$(C_{1-6})$alkyl optionally substituted 1 to 3 times with halo;

$R^{22}$ is H, —$(C_{2-6})$alkenyl or —$(C_{3-7})$cycloalkyl, wherein each said alkyl, alkenyl and cycloalkyl is optionally substituted 1 to 3 times with halo;

$A^1$, $A^2$ and $A^3$ are each independently selected from the group consisting of N and $CR^3$, wherein $R^3$ is independently in each instance selected from the group consisting of H, halo —CN, —$N(R^{21})(R^{22})$, —$O(C_{1-6})$alkyl, —$(C_{3-7})$cycloalkyl and —$(C_{1-6})$alkyl, wherein each said alkyl and cycloalkyl is optionally substituted with 1 to 3 substituents each independently selected from the group consisting of —$O(C_{1-6})$alkyl and halo;

$R^4$ is a 5- or 6-membered heteroaryl selected from the group consisting of

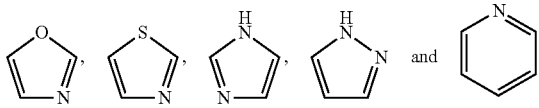

wherein said heteroaryl is optionally substituted with 1 to 2 substituents each independently selected from the group consisting of halo and —$(C_{1-3})$alkyl optionally substituted one time with OH or —$O(C_{1-3})$alkyl;

or a pharmaceutically acceptable salt thereof.

2. The compound according to claim 1, or a pharmaceutically acceptable salt thereof, wherein $A^1$, $A^2$ and $A^3$ are each independently selected from $CR^3$.

3. The compound according to claim 1, or a pharmaceutically acceptable salt thereof, wherein one of $A^1$, $A^2$ and $A^3$ is N and the remaining two of $A^1$, $A^2$ and $A^3$ are each independently selected from $CR^3$.

4. The compound according to claim 1, or a pharmaceutically acceptable salt thereof, wherein $R^3$ is independently in each instance selected from the group consisting of H, halo, —CN, —$O(C_{1-6})$alkyl and —$(C_{1-6})$alkyl optionally substituted with —$O(C_{1-6})$alkyl.

5. The compound according to claim 4, or a pharmaceutically acceptable salt thereof, wherein $R^3$ is independently in each instance selected from the group consisting of H, F, —CN, and —$CH_3$.

6. A pharmaceutical composition comprising a therapeutically effective amount of a compound of formula (I) according to claim 1, or a pharmaceutically acceptable salt thereof; and one or more pharmaceutically acceptable carriers.

7. The pharmaceutical composition according to claim 6, further comprising at least one other antiviral agent.

8. A method of treating an HIV infection in a human being having or at risk of having the infection comprising administering to the patient a therapeutically effective amount of a compound according to claim 1 or a pharmaceutically acceptable salt thereof.

* * * * *